(12) United States Patent
Wan et al.

(10) Patent No.: US 12,371,432 B2
(45) Date of Patent: Jul. 29, 2025

(54) HALOALLYLAMINE COMPOUNDS AND APPLICATION THEREOF

(71) Applicant: TransThera Sciences (Nanjing), Inc., Jiangsu (CN)

(72) Inventors: Zhonghui Wan, Jiangsu (CN); Lin Li, Jiangsu (CN); Frank Wu, Jiangsu (CN)

(73) Assignee: TransThera Sciences (Nanjing), Inc., Jiangsu (CN)

( * ) Notice: Subject to any disclaimer, the term of this patent is extended or adjusted under 35 U.S.C. 154(b) by 1010 days.

(21) Appl. No.: 17/421,428

(22) PCT Filed: Jan. 10, 2020

(86) PCT No.: PCT/CN2020/071405
§ 371 (c)(1),
(2) Date: Jul. 8, 2021

(87) PCT Pub. No.: WO2020/143763
PCT Pub. Date: Jul. 16, 2020

(65) Prior Publication Data
US 2022/0081439 A1    Mar. 17, 2022

(30) Foreign Application Priority Data

Jan. 11, 2019 (CN) .......................... 201910025251.8
Mar. 15, 2019 (CN) .......................... 201910196383.7
May 23, 2019 (CN) .......................... 201910434159.7
Sep. 24, 2019 (CN) .......................... 201910914387.4
Oct. 26, 2019 (CN) .......................... 201911026383.9

(51) Int. Cl.
C07D 471/04 (2006.01)
A61K 31/4025 (2006.01)
A61K 31/4155 (2006.01)
A61K 31/437 (2006.01)
A61K 31/5377 (2006.01)
C07D 207/34 (2006.01)
C07D 209/14 (2006.01)
C07D 231/14 (2006.01)
C07D 401/06 (2006.01)
C07D 403/06 (2006.01)
C07D 487/04 (2006.01)
C07D 498/04 (2006.01)

(52) U.S. Cl.
CPC ........ C07D 471/04 (2013.01); A61K 31/4025 (2013.01); A61K 31/4155 (2013.01); A61K 31/437 (2013.01); A61K 31/5377 (2013.01); C07D 207/34 (2013.01); C07D 209/14 (2013.01); C07D 231/14 (2013.01); C07D 401/06 (2013.01); C07D 403/06 (2013.01); C07D 487/04 (2013.01); C07D 498/04 (2013.01)

(58) Field of Classification Search
None
See application file for complete search history.

(56) References Cited

U.S. PATENT DOCUMENTS

| | | |
|---|---|---|
| 2009/0203764 A1 | 8/2009 | Wang et al. |
| 2010/0298330 A1 | 11/2010 | McDonald et al. |
| 2015/0158813 A1 | 6/2015 | Deodhar et al. |
| 2018/0104198 A1 | 4/2018 | Rippmann et al. |
| 2018/0296560 A1 | 10/2018 | Fan et al. |
| 2018/0297987 A1 | 10/2018 | Coates et al. |
| 2019/0308944 A1 | 10/2019 | Han et al. |
| 2019/0322655 A1 | 10/2019 | Han et al. |
| 2020/0087248 A1 | 3/2020 | Zhu et al. |
| 2020/0377461 A1 | 12/2020 | Gu et al. |

(Continued)

FOREIGN PATENT DOCUMENTS

| | | |
|---|---|---|
| CN | 101917845 A | 12/2010 |
| CN | 109988106 A | 7/2019 |
| JP | 2022-511374 A | 1/2022 |

(Continued)

OTHER PUBLICATIONS

WO2019101086A1—translation (Year: 2019).*
Extended European Search Report issued in European Patent Application No. 20738964.4 on Jan. 12, 2022, 7 pages.
McDonald et al., "A general preparation of fluoroallylamine enzyme inhibitors incorporating a beta-substituted heteroatom", Tetrahedron Letters, 1985, vol. 26, No. 32, pp. 3807-3810.
Office Action issued for Colombia Patent Application No. NC2021/0010493 on Oct. 23, 2023, 5 pages.
International Search Report issue for International Application No. PCT/CN2020/071405 on Apr. 22, 2020, 8 pages.

(Continued)

*Primary Examiner* — Juliet C Switzer
*Assistant Examiner* — Dawanna Shar-Day White
(74) *Attorney, Agent, or Firm* — ROTHWELL, FIGG, ERNST & MANBECK, P.C.

(57) ABSTRACT

The present invention relates to the technical field of pharmaceuticals. Specifically, the present invention relates to a halo-allylamine compound, or a pharmaceutically acceptable salt, an ester, a stereoisomer or a tautomer thereof, and a pharmaceutical formulation and a pharmaceutical composition comprising the compounds, and use in preventing and/or treating a disease related to or mediated by the SSAO/VAP-1 protein,

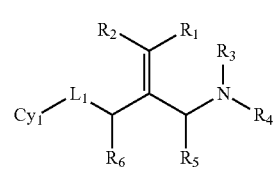

wherein $R_1$, $R_2$, $R_3$, $R_4$, $R_5$, $R_6$, $L_1$ and $Cy_1$ are defined in the specification.

19 Claims, No Drawings

(56) References Cited

U.S. PATENT DOCUMENTS

2021/0070750 A1    3/2021    Wu

FOREIGN PATENT DOCUMENTS

| JP | 7305196 B2 | 7/2023 | |
|---|---|---|---|
| WO | WO-2007120528 A2 * | 10/2007 | ........... A61K 31/137 |
| WO | 2009066152 A2 | 5/2009 | |
| WO | 2013163675 A1 | 11/2013 | |
| WO | 2018028517 A1 | 2/2018 | |
| WO | 2018151985 A1 | 8/2018 | |
| WO | 2018157190 A1 | 9/2018 | |
| WO | 2018196677 A1 | 11/2018 | |
| WO | WO-2019101086 A1 * | 5/2019 | ............. A61K 31/33 |
| WO | 2019129213 A1 | 7/2019 | |
| WO | 2020006177 A1 | 1/2020 | |
| WO | 2020-069330 A2 | 4/2020 | |

* cited by examiner

HALOALLYLAMINE COMPOUNDS AND APPLICATION THEREOF

CROSS-REFERENCE TO RELATED APPLICATION

This application a 35 U.S.C. 371 National Phase Entry Application from PCT/CN2020/071405, filed on Jan. 10, 2020 and designating the United States, which claims the benefit of priorities to Chinese Patent Application Nos. 201910025251.8 filed on Jan. 11, 2019; 201910196383.7 filed on Mar. 15, 2019; 201910434159.7 filed on May 23, 2019; 201910914387.4 filed on Sep. 24, 2019; and 201911026383.9 filed on Oct. 26, 2019, the entire disclosures of which are incorporated herein by reference.

TECHNICAL FIELD

The present invention belongs to the technical field of pharmaceuticals. Specifically, the present invention relates to a halo-allylamine compound or a pharmaceutically acceptable salt, ester, stereoisomer or tautomer thereof, a pharmaceutical formulation and a pharmaceutical composition comprising the compounds, and the use in preventing and/or treating diseases related to or mediated by the SSAO/VAP-1 protein.

BACKGROUND

As a class of amine oxidases particularly sensitive to semicarbazide, semicarbazide-sensitive amine oxidase (SSAO) is widely distributed in vivo, as well as on cell membranes and in plasma. In endothelial cells, SSAO exists in the form of vascular adhesion protein-1 (VAP-1). At present, it is believed that the main in vivo physiological function of SSAO is to participate in the metabolism of amines, catalyze the oxidative deaminization of short-chain primary amines (such as methylamine, aminoacetone and the like) and generate corresponding aldehydes, hydrogen peroxide and ammonia. The SSAO structure contains a bivalent copper ion, with a quinonyl group as a coenzyme. SSAO does not have a specific substrate, and its main substrates are aliphatic and aromatic primary amines.

WO 2013163675A1 discloses a 3-halo-allylamine derivative as an SSAO/VAP-1 inhibitor (shown as formula I) having inhibitory activity on SSAO/VAP-1 enzyme, and specifically discloses a compound 23, also referred to as PXS-4728, the structure of which is as follows:

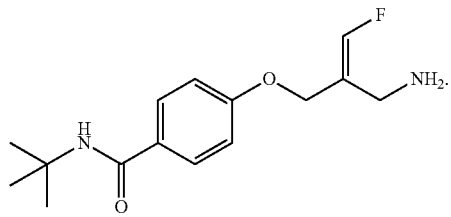 [SMILES: CC(C)(C)NC(=O)c1ccc(OC/C(=C/F)CN)cc1]

At present, no SSAO/VAP-1 inhibitor has been launched yet. The SSAO/VAP-1 inhibitor of the present invention can be used to effectively relieve symptoms and lesions under imbalance condition of a variety of disease conditions that is related to SSAO/VAP-1 overexpression etc., thus having a great application prospect.

SUMMARY OF THE INVENTION

In view of the aforementioned subject in the art, the inventor conducted an in-depth study, and, as a result, developed a novel halo-allylamine compound (hereinafter, sometimes also referred to as "the compound of the present invention") or a pharmaceutically acceptable salt, ester, stereoisomer or tautomer thereof as an SSAO/VAP-1 inhibitor. Such an inhibitor compound exhibits excellent inhibitory activity on the SSAO/VAP-1 protein, so it can be used to prevent and/or treat diseases related to or mediated by the SSAO/VAP-1 protein.

Moreover, the SSAO/VAP-1 inhibitor compound of the present invention shows excellent inhibition on SSAO/VAP-1 protein and shows excellent selectivity against rhAOC1 protein and MAO protein, thus preventing other unnecessary side effects while preventing and/or treating diseases related to or mediated by the SSAO/VAP-1 protein.

In addition, compared with existing drugs, the SSAO/VAP-1 inhibitor compound of the present invention can hardly penetrate the blood-brain barrier, so the compound of the present invention has a very low toxic risk to the nervous system, showing excellent drug safety.

Specifically, the present invention provides the following technical solutions.

Solution 1. A compound shown as formula I below or a pharmaceutically acceptable salt, ester, stereoisomer or tautomer thereof:

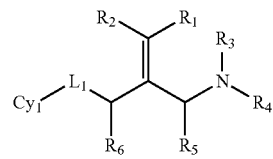

I wherein $R_1$ and $R_2$ are each independently selected from hydrogen and halogen, and $R_1$ and $R_2$ are not both hydrogen;

$R_3$ and $R_4$ are each independently selected from hydrogen and $C_{1-6}$ alkyl optionally substituted by a substituent A, or form a 5-10 membered nitrogen containing heterocyclyl optionally substituted by a substituent A along with an N atom connected thereto;

$R_5$ and $R_6$ are each independently selected from hydrogen and $C_{1-6}$ alkyl optionally substituted by a substituent A;

$L_1$ is a bond or —CR'R"—, —NR'—, —S—, —SO$_2$—, —S(O)—, —SONR'—, —SO$_2$NR'— or —NR'CONR'—, and R' and R" are each independently selected from hydrogen and $C_{1-6}$ alkyl optionally substituted by a substituent A;

$Cy_1$ is a group shown as general formula (A), (a), (b) or (c) below that is unsubstituted or substituted by one or more $R^a$:

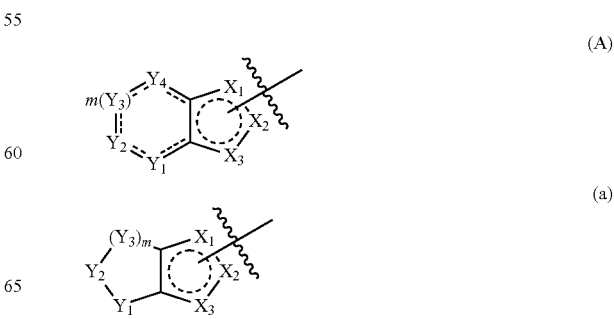

-continued

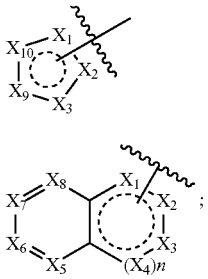

(b)

(c)

m is an integer from 0 to 3, and n is an integer from 0 to 2;

$Y_1$, $Y_2$, $Y_3$ and $Y_4$ are each independently selected from $CR^cR^c$, $NR^d$, O and S;

$X_1$, $X_2$, $X_3$, $X_4$, $X_9$ and $X_{10}$ are each independently selected from $CR^cR^c$, $NR^d$, O and S, $X_5$, $X_6$, $X_7$ and $X_8$ are each independently selected from $CR^cR^c$ and $NR^d$, and at least one of $X_1$, $X_2$ and $X_3$ is $NR^d$;

each $R^a$ is independently selected from hydroxyl, amino, carboxyl, cyano, nitro, halogen, aminocarboxyl, $C_{1-6}$ alkyl optionally substituted by one or more $R^b$, $C_{2-6}$ alkenyl optionally substituted by one or more $R^b$, $C_{2-6}$ alkynyl optionally substituted by one or more $R^b$, $C_{1-6}$ alkoxy optionally substituted by one or more $R^b$, $C_{1-6}$ alkoxy $C_{1-6}$ alkyl optionally substituted by one or more $R^b$, $C_{1-6}$ alkoxy $C_{1-6}$ alkoxy optionally substituted by one or more $R^b$, $C_{1-6}$ alkylthio optionally substituted by one or more $R^b$, $C_{1-6}$ alkylthio $C_{1-6}$ alkyl optionally substituted by one or more $R^b$, $C_{1-6}$ alkylamino optionally substituted by one or more $R^b$, $(C_{1-6}$ alkyl$)_2$ amino optionally substituted by one or more $R^b$, $C_{1-6}$ alkylamino $C_{1-6}$ alkyl optionally substituted by one or more $R^b$, $(C_{1-6}$ alkyl$)_2$ amino $C_{1-6}$ alkyl optionally substituted by one or more $R^b$, $C_{1-6}$ alkylaminocarbonyl optionally substituted by one or more $R^b$, $(C_{1-6}$ alkyl$)_2$ aminocarbonyl optionally substituted by one or more $R^b$, $C_{1-6}$ alkylaminocarbonyl $C_{1-6}$ alkyl optionally substituted by one or more $R^b$, $(C_{1-6}$ alkyl$)_2$ aminocarbonyl $C_{1-6}$ alkyl optionally substituted by one or more $R^b$, $C_{1-6}$ alkylcarbonylamino optionally substituted by one or more $R^b$, $C_{1-6}$ alkylcarbonylamino $C_{1-6}$ alkyl optionally substituted by one or more $R^b$, $C_{1-6}$ alkylcarbonyl optionally substituted by one or more $R^b$, $C_{1-6}$ alkylcarbonyl $C_{1-6}$ alkyl optionally substituted by one or more $R^b$, $C_{1-6}$ alkylaminosulfonyl optionally substituted by one or more $R^b$, $(C_{1-6}$ alkyl$)_2$ aminosulfonyl optionally substituted by one or more $R^b$, $C_{1-6}$ alkylaminosulfonyl $C_{1-6}$ alkyl optionally substituted by one or more $R^b$, $(C_{1-6}$ alkyl$)_2$ aminosulfonyl $C_{1-6}$ alkyl optionally substituted by one or more $R^b$, $C_{1-6}$ alkylsulfonylamino optionally substituted by one or more $R^b$, $C_{1-6}$ alkylsulfonylamino $C_{1-6}$ alkyl optionally substituted by one or more $R^b$, $C_{1-6}$ alkylsulfonyl optionally substituted by one or more $R^b$, $C_{1-6}$ alkylsulfonyl $C_{1-6}$ alkyl optionally substituted by one or more $R^b$, $Cy_2$- optionally substituted by one or more $R^b$, $Cy_2$-$C_{1-6}$ alkyl optionally substituted by one or more $R^b$, $Cy_2$-$C_{1-6}$ alkoxy optionally substituted by one or more $R^b$, $Cy_2$-carbonyl optionally substituted by one or more $R^b$, $Cy_2$-aminocarbonyl optionally substituted by one or more $R^b$ and $Cy_2$-carbonylamino optionally substituted by one or more $R^b$, and $Cy_2$ is each independently selected from 3-12 membered cycloalkyl, 3-12 membered cycloalkenyl, 3-12 membered heterocyclyl, 6-10 membered aryl and 5-14 membered heteroaryl;

each $R^b$ is independently selected from hydroxyl, amino, carboxyl, cyano, nitro, halogen, aminocarbonyl, $C_{1-6}$ alkyl, $C_{2-6}$ alkenyl, $C_{2-6}$ alkynyl, $C_{1-6}$ alkoxy, amino $C_{1-6}$ alkyl, $C_{1-6}$ haloalkyl, $C_{1-6}$ alkoxy $C_{1-6}$ alkyl, $C_{1-6}$ alkoxy $C_{1-6}$ alkoxy, amino $C_{1-6}$ alkoxy, $C_{1-6}$ haloalkoxy, $C_{1-6}$ alkylthio, $C_{1-6}$ alkylamino, $(C_{1-6}$ alkyl$)_2$ amino, $C_{1-6}$ alkylaminocarbonyl, $(C_{1-6}$ alkyl$)_2$ aminocarbonyl, $C_{1-6}$ alkylcarbonylamino, $C_{1-6}$ alkylcarbonyl, $C_{1-6}$ alkylaminosulfonyl, $(C_{1-6}$ alkyl$)_2$ aminosulfonyl, $C_{1-6}$ alkylsulfonylamino and $C_{1-6}$ alkylsulfonyl;

the substituents A are each independently selected from hydroxyl, amino, carboxyl, cyano, nitro, halogen, aminocarbonyl, $C_{1-6}$ alkyl, $C_{2-6}$ alkenyl, $C_{2-6}$ alkynyl, $C_{1-6}$ alkoxy, amino $C_{1-6}$ alkyl, $C_{1-6}$ alkoxy $C_{1-6}$ alkyl, $C_{1-6}$ alkoxy $C_{1-6}$ alkoxy, amino $C_{1-6}$ alkoxy, $C_{1-6}$ alkylamino, $(C_{1-6}$ alkyl$)_2$ amino, $C_{1-6}$ alkylaminocarbonyl, $(C_{1-6}$ alkyl$)_2$ aminocarbonyl, $C_{1-6}$ alkylcarbonylamino, $C_{1-6}$ alkylcarbonyl, $C_{1-6}$ alkylsulfonylamino, $C_{1-6}$ alkylaminosulfonyl, $(C_{1-6}$ alkyl$)_2$ aminosulfonyl, $C_{1-6}$ haloalkyl, $C_{1-6}$ haloalkoxy, $C_{1-6}$ alkylsulfonyl, $C_{1-6}$ alkylthio, 3-12 membered cycloalkyl, 6-10 membered aryl, 3-12 membered heterocyclyl, 5-14 membered heteroaryl and oxo;

$R^c$ is absent, or is each independently selected from hydrogen atom when present; or two $R^c$ form an oxo group together;

$R^d$ is absent, or is each independently selected from hydrogen atom when present;

=== represents a single bond or a double bond;

⋮ represents a double bond optionally present in the ring structure; with the proviso that when $Cy_1$ is formula (c), formula (c) is substituted by one or more $R^a$; and with the proviso that when $Cy_1$ is formula (b), $X_1$, $X_2$, $X_3$, $X_9$ and $X_{10}$ are not C=O.

Solution 2: The compound or the pharmaceutically acceptable salt, ester, stereoisomer or tautomer thereof according to solution 1, wherein $R_1$ and $R_2$ are each independently selected from hydrogen and halogen, and $R_1$ and $R_2$ are not both hydrogen;

$R_3$ and $R_4$ are each independently selected from hydrogen and $C_{1-6}$ alkyl;

$R_5$ and $R_6$ are each independently selected from hydrogen and $C_{1-6}$ alkyl;

$L_1$ is a bond or —CR'R"—, —NR'— or —S—, and R' and R" are each independently selected from hydrogen and $C_{1-6}$ alkyl;

m is an integer from 0 to 3, and n is an integer from 0 to 2;

$Y_1$, $Y_2$, $Y_3$ and $Y_4$ are each independently selected from $CR^cR^c$ and $NR^d$;

$X_1$, $X_2$, $X_3$, $X_4$, $X_9$ and $X_{10}$ are each independently selected from $CR^cR^c$ and $NR^d$, and at least one of $X_1$, $X_2$ and $X_3$ is $NR^d$;

$X_5$, $X_6$, $X_7$ and $X_8$ are each independently selected from $CR^cR^c$ and $NR^d$;

each $R^a$ is independently selected from hydroxyl, amino, carboxyl, cyano, nitro, halogen, aminocarbonyl, $C_{1-6}$ alkyl optionally substituted by one or more $R^b$, $C_{1-6}$ alkoxy optionally substituted by one or more $R^b$, $C_{1-6}$ alkoxy $C_{1-6}$ alkyl optionally substituted by one or more $R^b$, $C_{1-6}$ alkoxy $C_{1-6}$ alkoxy optionally substituted by one or more $R^b$, $C_{1-6}$ alkylthio optionally substituted by one or more $R^b$, $C_{1-6}$ alkylthio $C_{1-6}$ alkyl optionally substituted by one or more $R^b$, $C_{1-6}$ alkylamino optionally substituted by one or more $R^b$, $(C_{1-6}$ alkyl$)_2$ amino optionally substituted by one or more $R^b$, $C_{1-6}$ alkylamino $C_{1-6}$ alkyl optionally substituted by one or more $R^b$, $(C_{1-6}$ alkyl$)_2$ amino $C_{1-6}$ alkyl optionally substituted by one or more $R^b$, $C_{1-6}$ alkylaminocarbonyl optionally substituted by one or more $R^b$, $(C_{1-6}$ alkyl$)_2$ aminocarbonyl optionally substituted by one or more $R^b$, $C_{1-6}$ alkylaminocarbonyl $C_{1-6}$ alkyl optionally substituted by one or more $R^b$, $(C_{1-6}$ alkyl$)_2$ aminocarbonyl $C_{1-6}$ alkyl optionally substituted by one or more $R^b$, $C_{1-6}$ alkylcarbonylamino optionally substituted by one or more $R^b$, $C_{1-6}$ alkylcarbonylamino $C_{1-6}$ alkyl optionally substituted by one or more $R^b$, $C_{1-6}$ alkylcarbonyl optionally substituted by one or more $R^b$, $C_{1-6}$ alkylcarbonyl $C_{1-6}$ alkyl optionally substituted by one or more $R^b$, $Cy_2$- optionally substituted by one or more $R^b$, $Cy_2$-$C_{1-6}$ alkyl optionally substituted by one or more $R^b$, $Cy_2$-$C_{1-6}$ alkoxy optionally substituted by one or more $R^b$, $Cy_2$-carbonyl optionally substituted by one or more $R^b$, $Cy_2$-aminocarbonyl optionally substituted by one or more $R^b$ and $Cy_2$-carbonylamino optionally substituted by one or more $R^b$;

$Cy_2$ is each independently selected from 3-8 membered cycloalkyl, 5-10 membered heterocyclyl, phenyl, naphthyl and 5-10 membered heteroaryl;

each $R^b$ is independently selected from hydroxyl, amino, carboxyl, cyano, nitro, halogen, aminocarbonyl, $C_{1-6}$ alkyl, $C_{1-6}$ alkoxy, amino $C_{1-6}$ alkyl, $C_{1-6}$ haloalkyl, $C_{1-6}$ alkoxy $C_{1-6}$ alkyl, $C_{1-6}$ alkoxy $C_{1-6}$ alkoxy, amino $C_{1-6}$ alkoxy, $C_{1-6}$ haloalkoxy, $C_{1-6}$ alkylthio, $C_{1-6}$ alkylamino, $(C_{1-6}$ alkyl$)_2$ amino, $C_{1-6}$ alkylaminocarbonyl, $(C_{1-6}$ alkyl$)_2$ aminocarbonyl, $C_{1-6}$ alkylcarbonylamino and $C_{1-6}$ alkylcarbonyl;

The substituents A are each independently selected from hydroxyl, amino, carboxyl, cyano, nitro, halogen, $C_{1-6}$ alkyl, $C_{1-6}$ alkoxy, amino $C_{1-6}$ alkyl, $C_{1-6}$ alkoxy $C_{1-6}$ alkyl, $C_{1-6}$ alkoxy $C_{1-6}$ alkoxy, amino $C_{1-6}$ alkoxy, $C_{1-6}$ alkylamino, $(C_{1-6}$ alkyl$)_2$ amino, $C_{1-6}$ alkylaminocarbonyl, $(C_{1-6}$ alkyl$)_2$ aminocarbonyl, $C_{1-6}$ alkylcarbonylamino, $C_{1-6}$ alkylcarbonyl, $C_{1-6}$ haloalkyl, $C_{1-6}$ haloalkoxy, $C_{1-6}$ alkylthio, 3-8 membered cycloalkyl, 5-10 membered heterocyclyl, phenyl, naphthyl, 5-10 membered heteroaryl and oxo;

preferably, each $R^a$ is independently selected from hydroxyl, amino, cyano, halogen, aminocarbonyl, $C_{1-4}$ alkyl optionally substituted by one or more $R^b$, $C_{1-4}$ alkoxy optionally substituted by one or more $R^b$, $C_{1-4}$ alkoxy $C_{1-4}$ alkyl optionally substituted by one or more $R^b$, $C_{1-4}$ alkoxy $C_{1-4}$ alkoxy optionally substituted by one or more $R^b$, $C_{1-4}$ alkylthio optionally substituted by one or more $R^b$, $C_{1-4}$ alkylthio $C_{1-4}$ alkyl optionally substituted by one or more $R^b$, $C_{1-4}$ alkylamino optionally substituted by one or more $R^b$, $(C_{1-4}$ alkyl$)_2$ amino optionally substituted by one or more $R^b$, $C_{1-4}$ alkylamino $C_{1-4}$ alkyl optionally substituted by one or more $R^b$, $(C_{1-4}$ alkyl$)_2$ amino $C_{1-4}$ alkyl optionally substituted by one or more $R^b$, $C_{1-4}$ alkylaminocarbonyl optionally substituted by one or more $R^b$, $(C_{1-4}$ alkyl$)_2$ aminocarbonyl optionally substituted by one or more $R^b$, $C_{1-4}$ alkylaminocarbonyl $C_{1-4}$ alkyl optionally substituted by one or more $R^b$, $(C_{1-4}$ alkyl$)_2$ aminocarbonyl $C_{1-4}$ alkyl optionally substituted by one or more $R^b$, $C_{1-4}$ alkylcarbonylamino optionally substituted by one or more $R^b$, $C_{1-4}$ alkylcarbonylamino $C_{1-4}$ alkyl optionally substituted by one or more $R^b$, $C_{1-4}$ alkylcarbonyl optionally substituted by one or more $R^b$, $C_{1-4}$ alkylcarbonyl $C_{1-4}$ alkyl optionally substituted by one or more $R^b$, $Cy_2$- optionally substituted by one or more $R^b$, $Cy_2$-$C_{1-4}$ alkyl optionally substituted by one or more $R^b$, $Cy_2$-$C_{1-4}$ alkoxy optionally substituted by one or more $R^b$, $Cy_2$-carbonyl optionally substituted by one or more $R^b$, $Cy_2$-aminocarbonyl optionally substituted by one or more $R^b$ and $Cy_2$-carbonylamino optionally substituted by one or more $R^b$;

preferably, each $R^b$ is independently selected from hydroxyl, amino, cyano, halogen, aminocarbonyl, $C_{1-4}$ alkyl, $C_{1-4}$ alkoxy, amino $C_{1-4}$ alkyl, $C_{1-4}$ haloalkyl, $C_{1-4}$ alkoxy $C_{1-4}$ alkyl, $C_{1-4}$ alkoxy $C_{1-4}$ alkoxy, amino $C_{1-4}$ alkoxy, $C_{1-4}$ haloalkoxy, $C_{1-4}$ alkylthio, $C_{1-4}$ alkylamino, $(C_{1-4}$ alkyl$)_2$ amino, $C_{1-4}$ alkylaminocarbonyl, $(C_{1-4}$ alkyl$)_2$ aminocarbonyl, $C_{1-4}$ alkylcarbonylamino and $C_{1-4}$ alkylcarbonyl;

preferably, the substituents A are each independently selected from hydroxyl, amino, carboxyl, cyano, nitro, halogen, $C_{1-4}$ alkyl, $C_{1-4}$ alkoxy, amino $C_{1-4}$ alkyl, $C_{1-4}$ alkoxy $C_{1-4}$ alkyl, $C_{1-4}$ alkoxy $C_{1-4}$ alkoxy, amino $C_{1-4}$ alkoxy, $C_{1-4}$ alkylamino, $(C_{1-4}$ alkyl$)_2$ amino, $C_{1-4}$ alkylaminocarbonyl, $(C_{1-4}$ alkyl$)_2$ aminocarbonyl, $C_{1-4}$ alkylcarbonylamino, $C_{1-4}$ alkylcarbonyl, $C_{1-4}$ haloalkyl, $C_{1-4}$ haloalkoxy, $C_{1-4}$ alkylthio, 3-6 membered cycloalkyl, 5-10 membered heterocyclyl, phenyl, naphthyl, 5-10 membered heteroaryl and oxo;

preferably, at least one of $Y_1$, $Y_2$, $Y_3$ and $Y_4$ is C=O;

preferably, for formula (A), when $R^a$ is present, at least one $R^a$ is connected to any one of $Y_1$, $Y_2$, $Y_3$ and $Y_4$;

preferably, for formula (a), when $R^a$ is present, at least one $R^a$ is connected to any one of $Y_1$, $Y_2$ and $Y_3$;

preferably, for formula (c), at least one $R^a$ is present, and at least one $R^a$ is connected to any one of $X_5$, $X_6$, $X_7$ and $X_8$;

preferably, for formula (A), the $L_1$ group is connected to $X_1$, $X_2$ or $X_3$ in formula (A);

preferably, for formula (A), the $L_1$ group is connected to $X_1$, $X_2$ or $X_3$ in formula (A);

preferably, for formula (c), the $L_1$ group is connected to $X_1$, $X_2$, $X_3$ or $X_4$ in formula (c);

preferably, the $L_1$ group is connected to an N atom.

Solution 3. The compound or the pharmaceutically acceptable salt, ester, stereoisomer or tautomer thereof according to solution 1 or solution 2:

wherein $Cy_1$ is a group shown as general formula (A-1), (A-2), (A-3), (a), (b) or (c) below that is unsubstituted or substituted by one or more $R^a$:

(A-1)

(A-2)

(A-3)

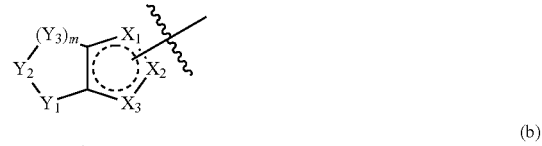

(a)

(b)

(c)

[chemical structure showing ring with X1-X8 and (X4)n]

Solution 4. The compound or the pharmaceutically acceptable salt, ester, stereoisomer or tautomer thereof according to any one of solutions 1-3, wherein $Cy_1$ is a group shown as general formula (A-11), (a-1), (a-2), (b-1), (c-1) or (c-2) below that is unsubstituted or substituted by one or more $R^a$:

(A-11)

[chemical structure]

(a-1)

[chemical structure]

(a-2)

[chemical structure]

(b-1)

[chemical structure]

(c-1)

[chemical structure]

(c-2)

[chemical structure]

wherein m is an integer that is 1 or 2;

$Y_1$, $Y_2$ and $Y_3$ are each independently selected from $CH_2$, NH, CH and N;

$X_1$, $X_2$, $X_3$, $X_4$ and $X_9$ are each independently selected from $CH_2$, CH, N, NH and C=O, and at least one of $X_1$, $X_2$ and $X_3$ is N or NH;

with the proviso that when $Cy_1$ is formula (c-1) or (c-2), formula (c-1) or (c-2) is substituted by one or more $R^a$, and with the proviso that when $Cy_1$ is formula (b-1), $X_1$, $X_2$, $X_3$ and $X_9$ are not C=O;

preferably, for formula (A-11), when $R^a$ is present, at least one $R^a$ is connected to $Y_2$;

preferably, for formula (a-1), when $R^a$ is present, at least one $R^a$ is connected to $Y_2$;

preferably, for formula (a-2), when $R^a$ is present, at least one $R^a$ is connected to $Y_1$;

preferably, for formula (b-1), when $R^a$ is present, at least one $R^a$ is connected to a cyclic carbon atom;

preferably, for formulas (c-1) and (c-2), at least one $R^a$ is present, and at least one $R^a$ is connected to a benzene ring group.

Solution 5. The compound or the pharmaceutically acceptable salt, ester, stereoisomer or tautomer thereof according to any one of solutions 1-4, wherein $Cy_1$ is a group shown as general formula (A-11) or (a-1) below that is unsubstituted or substituted by one or more $R^a$:

(A-11)

[chemical structure]

(a-1)

[chemical structure]

m is an integer that is 1 or 2;

$Y_2$ and $Y_3$ are each independently selected from $CH_2$, NH, CH and N;

$X_1$, $X_2$ and $X_3$ are each independently selected from $CH_2$, CH, N, NH and C=O, and at least one of $X_1$, $X_2$ and $X_3$ is N or NH;

each $R^a$ is independently selected from hydroxyl, amino, carboxyl, cyano, nitro, halogen, aminocarbonyl, $C_{1-6}$ alkyl optionally substituted by one or more $R^b$, $C_{1-6}$ alkoxy optionally substituted by one or more $R^b$, $C_{1-6}$ alkoxy $C_{1-6}$ alkyl optionally substituted by one or more $R^b$, $C_{1-6}$ alkoxy $C_{1-6}$ alkoxy optionally substituted by one or more $R^b$, $C_{1-6}$ alkylamino optionally substituted by one or more $R^b$, $(C_{1-6}$ alkyl$)_2$ amino optionally substituted by one or more $R^b$, $C_{1-6}$ alkylamino $C_{1-6}$ alkyl optionally substituted by one or more $R^b$, $(C_{1-6}$ alkyl$)_2$ amino $C_{1-6}$ alkyl optionally substituted by one or more $R^b$, $C_{1-6}$ alkylaminocarbonyl optionally substituted by one or more $R^b$, $(C_{1-6}$ alkyl$)_2$ aminocarbonyl optionally substituted by one or more $R^b$, $C_{1-6}$ alkylaminocarbonyl $C_{1-6}$ alkyl optionally substituted by one or more $R^b$, $(C_{1-6}$ alkyl$)_2$ aminocarbonyl $C_{1-6}$ alkyl optionally substituted by one or more $R^b$, $C_{1-6}$ alkylcarbonylamino optionally substituted by one or more $R^b$, $C_{1-6}$ alkylcarbonylamino $C_{1-6}$ alkyl optionally substituted by one or more $R^b$, $C_{1-6}$ alkylcarbonyl optionally substituted by one or more $R^b$, $C_{1-6}$ alkylcarbonyl $C_{1-6}$ alkyl optionally substituted by one or more $R^b$, $Cy_2$- optionally substituted by one or more $R^b$, $Cy_2$-$C_{1-6}$ alkyl optionally substituted by one or more $R^b$, $Cy_2$-$C_{1-6}$ alkoxy optionally substituted by one or more $R^b$, $Cy_2$-carbonyl optionally substituted by one or more $R^b$, and $Cy_2$-aminocarbonyl optionally substituted by one or more $R^b$;

$Cy_2$ is each independently selected from 3-8 membered cycloalkyl, 5-10 membered heterocyclyl, phenyl, naphthyl and 5-10 membered heteroaryl; each $R^b$ is independently selected from hydroxyl, amino, carboxyl, cyano, nitro, halogen, aminocarbonyl, $C_{1-6}$ alkyl, $C_{1-6}$ alkoxy, amino $C_{1-6}$ alkyl, $C_{1-6}$ haloalkyl, $C_{1-6}$ alkoxy $C_{1-6}$ alkyl, $C_{1-6}$ alkoxy $C_{1-6}$ alkoxy, amino $C_{1-6}$ alkoxy, $C_{1-6}$ haloalkoxy, $C_{1-6}$ alkylthio, $C_{1-6}$ alkylamino, $(C_{1-6}$ alkyl$)_2$ amino, $C_{1-6}$ alkylaminocarbonyl, $(C_{1-6}$ alkyl$)_2$ aminocarbonyl, $C_{1-6}$ alkylcarbonylamino and $C_{1-6}$ alkylcarbonyl;

preferably, $Cy_2$ is each independently selected from 3-6 membered cycloalkyl, 5-6 membered heterocyclyl, phenyl, naphthyl and 5-6 membered heteroaryl;

preferably, $R^a$ is each independently selected from halogen, cyano, $C_{1-6}$ alkyl optionally substituted by at least one of halogen, $C_{1-6}$ alkyl, $C_{1-6}$ alkoxy and 3-6 membered cycloalkyl, 3-8 membered cycloalkyl optionally substituted by at least one of halogen, $C_{1-6}$ alkyl and $C_{1-6}$ alkoxy, phenyl optionally substituted by at least one of halogen, $C_{1-6}$ alkyl and $C_{1-6}$ alkoxy, and 5-6 membered heteroaryl optionally substituted by at least one of halogen, $C_{1-6}$ alkyl and $C_{1-6}$ alkoxy;

more preferably, $R^a$ is each independently selected from halogen, cyano, $C_{1-4}$ alkyl optionally substituted by at least one of halogen, $C_{1-6}$ alkyl, $C_{1-6}$ alkoxy and 3-5 membered cycloalkyl, 3-5 membered cycloalkyl optionally substituted by at least one of halogen, $C_{1-6}$ alkyl and $C_{1-6}$ alkoxy, phenyl optionally substituted by at least one of halogen, $C_{1-6}$ alkyl and $C_{1-6}$ alkoxy, and 5-6 membered nitrogen heteroaryl optionally substituted by at least one of halogen, $C_{1-6}$ alkyl and $C_{1-6}$ alkoxy;

preferably, in formula (A-11), $X_1$ and $X_2$ are each independently selected from $CH_2$, CH, N and NH;

preferably, in formula (a-1), $X_1$ and $X_2$ are each independently selected from $CH_2$, CH, N and NH;

preferably, in formulas (A-11) and (a-1), $Y_2$ is NH;

preferably, in formulas (A-11) and (a-1), $Y_3$ is $CH_2$ or CH;

preferably, in formulas (A-11) and (a-1), when $R^a$ is present, at least one $R^a$ is connected to the position of $Y_2$;

preferably, in formulas (A-11) and (a-1), the $L_1$ group is connected to $X_1$, $X_2$ or $X_3$;

preferably, in formulas (A-11) and (a-1), the $L_1$ group is connected to an N atom.

Solution 6. The compound or the pharmaceutically acceptable salt, ester, stereoisomer or tautomer thereof according to solution 5, wherein $R_1$ and $R_2$ are each independently selected from hydrogen and halogen, and $R_1$ and $R_2$ are not both hydrogen;

$R_3$ and $R_4$ are each independently selected from hydrogen and $C_{1-6}$ alkyl;

$R_5$ and $R_6$ are each independently selected from hydrogen and $C_{1-6}$ alkyl;

$L_1$ is a bond;

$Cy_1$ is one of the following groups unsubstituted or substituted by one or more $R^a$:

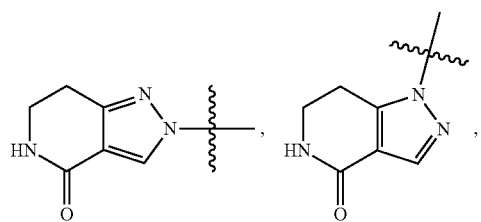

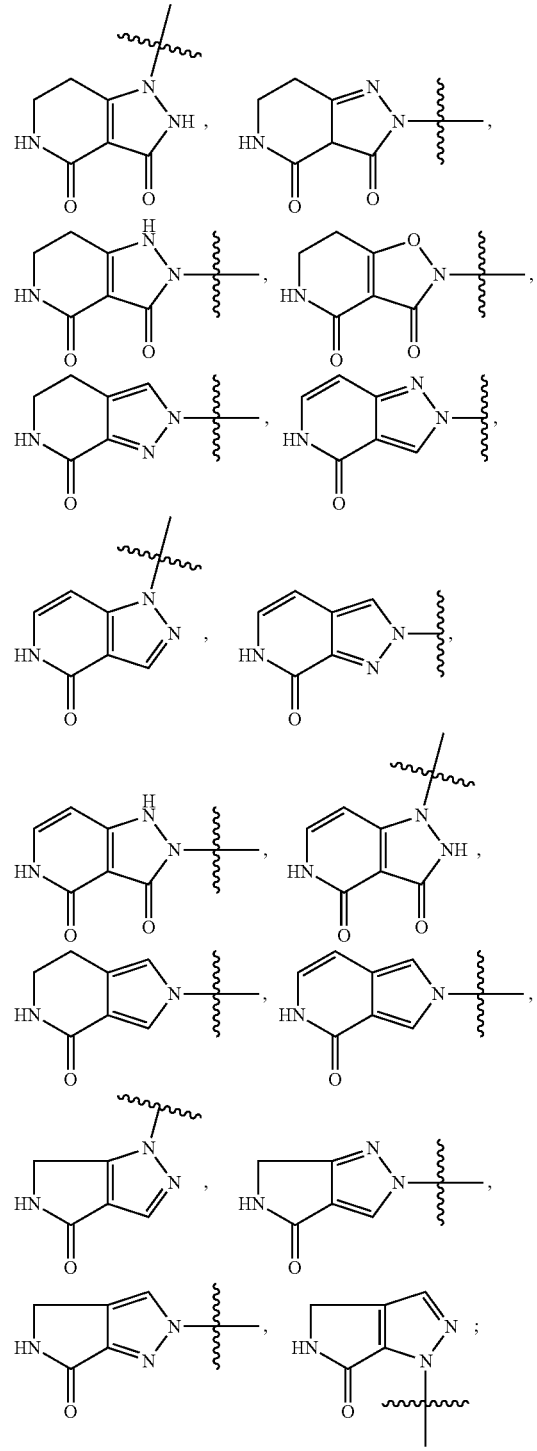

each $R^a$ is independently selected from hydroxyl, amino, carboxyl, cyano, nitro, halogen, aminocarbonyl, $C_{1-6}$ alkyl optionally substituted by one or more $R^b$, $C_{1-6}$ alkoxy optionally substituted by one or more $R^b$, $C_{1-6}$ alkoxy $C_{1-6}$ alkyl optionally substituted by one or more $R^b$, $C_{1-6}$ alkoxy $C_{1-6}$ alkoxy optionally substituted by one or more $R^b$, $C_{1-6}$ alkylamino optionally substituted by one or more $R^b$, $C_{1-6}$ alkylamino $C_{1-6}$ alkyl optionally substituted by one or more $R^b$, $C_{1-6}$ alkylaminocarbonyl optionally substituted by one or more $R^b$, $C_{1-6}$ alkylaminocarbonyl $C_{1-6}$ alkyl optionally substituted by one or more $R^b$, $C_{1-6}$ alkylcarbonylamino optionally substituted by one or more $R^b$, $C_{1-6}$ alkylcarbonylamino $C_{1-6}$ alkyl optionally substituted by one or more $R^b$, $C_{1-6}$ alkylcarbonyl optionally substituted by one or more $R^b$, $C_{1-6}$ alkylcarbonyl $C_{1-6}$ alkyl optionally substituted by one or more $R^b$, $Cy_2$- optionally substituted by one or more $R^b$, $Cy_2$-$C_{1-6}$ alkyl optionally substituted by one or more $R^b$, $Cy_2$-$C_{1-6}$ alkoxy optionally substituted by one or more $R^b$, $Cy_2$-carbonyl optionally substituted by one or more $R^b$ and $Cy_2$-aminocarbonyl optionally substituted by one or more $R^b$;

$Cy_2$ is each independently selected from 3-8 membered cycloalkyl, 5-10 membered heterocyclyl, phenyl, naphthyl and 5-10 membered heteroaryl; each $R^b$ is independently selected from hydroxyl, amino, carboxyl, cyano, nitro, halogen, aminocarbonyl, $C_{1-6}$ alkyl, $C_{1-6}$ alkoxy, amino $C_{1-6}$ alkyl, $C_{1-6}$ haloalkyl, $C_{1-6}$ alkoxy $C_{1-6}$ alkyl, $C_{1-6}$ alkoxy $C_{1-6}$ alkoxy, amino $C_{1-6}$ alkoxy, $C_{1-6}$ haloalkoxy, $C_{1-6}$ alkylthio, $C_{1-6}$ alkylamino, $C_{1-6}$ alkylaminocarbonyl, $C_{1-6}$ alkylcarbonylamino and $C_{1-6}$ alkylcarbonyl;

preferably, $Cy_2$ is each independently selected from 3-6 membered cycloalkyl, 5-6 membered heterocyclyl, phenyl and 5-6 membered heteroaryl;

preferably, $R^a$ is each independently selected from halogen, cyano, $C_{1-6}$ alkyl optionally substituted by at least one of halogen, $C_{1-6}$ alkyl, $C_{1-6}$ alkoxy and 3-6 membered cycloalkyl, 3-8 membered cycloalkyl optionally substituted by at least one of halogen, $C_{1-6}$ alkyl and $C_{1-6}$ alkoxy, phenyl optionally substituted by at least one of halogen, $C_{1-6}$ alkyl and $C_{1-6}$ alkoxy, and 5-6 membered heteroaryl optionally substituted by at least one of halogen, $C_{1-6}$ alkyl and $C_{1-6}$ alkoxy.

More preferably, $R^a$ is each independently selected from fluorine; chlorine; bromine; cyano; methyl, ethyl, propyl, isopropyl, butyl, isobutyl, sec-butyl and tert-butyl optionally substituted by at least one of halogen, $C_{1-6}$ alkyl, $C_{1-6}$ alkoxy and 3-5 membered cycloalkyl; cyclopropyl, cyclobutyl and cyclopentyl optionally substituted by at least one of halogen and $C_{1-6}$ alkyl; phenyl optionally substituted by at least one of halogen and $C_{1-6}$ alkyl; and pyrrolyl, imidazolyl, pyrazolyl, oxazolyl and thiazolyl optionally substituted by at least one of halogen and $C_{1-6}$ alkyl.

Solution 7. The compound or the pharmaceutically acceptable salt, ester, stereoisomer or tautomer thereof according to any one of solutions 1-4, wherein $Cy_1$ is a group shown as general formula (b-1) below that is unsubstituted or substituted by one or more $R^a$:

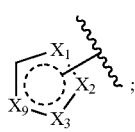
(b-1)

$X_1$, $X_2$, $X_3$ and $X_9$ are each independently selected from $CH_2$, CH, N and NH, and at least one of $X_1$, $X_2$ and $X_3$ is N or NH;

each $R^a$ is independently selected from hydroxyl, amino, carboxyl, cyano, nitro, halogen, aminocarbonyl, $C_{1-6}$ alkyl optionally substituted by one or more $R^b$, $C_{1-6}$ alkoxy optionally substituted by one or more $R^b$, $C_{1-6}$ alkoxy $C_{1-6}$ alkyl optionally substituted by one or more $R^b$, $C_{1-6}$ alkoxy $C_{1-6}$ alkoxy optionally substituted by one or more $R^b$, $C_{1-6}$ alkylamino optionally substituted by one or more $R^b$, ($C_{1-6}$ alkyl)$_2$ amino optionally substituted by one or more $R^b$, $C_{1-6}$ alkylamino $C_{1-6}$ alkyl optionally substituted by one or more $R^b$, ($C_{1-6}$ alkyl)$_2$ amino $C_{1-6}$ alkyl optionally substituted by one or more $R^b$, $C_{1-6}$ alkylaminocarbonyl optionally substituted by one or more $R^b$, ($C_{1-6}$ alkyl)$_2$ aminocarbonyl optionally substituted by one or more $R^b$, $C_{1-6}$ alkylaminocarbonyl $C_{1-6}$ alkyl optionally substituted by one or more $R^b$, ($C_{1-6}$ alkyl)$_2$ aminocarbonyl $C_{1-6}$ alkyl optionally substituted by one or more $R^b$, $C_{1-6}$ alkylcarbonylamino optionally substituted by one or more $R^b$, $C_{1-6}$ alkylcarbonylamino $C_{1-6}$ alkyl optionally substituted by one or more $R^b$, $C_{1-6}$ alkylcarbonyl optionally substituted by one or more $R^b$, $C_{1-6}$ alkylcarbonyl $C_{1-6}$ alkyl optionally substituted by one or more $R^b$, $Cy_2$- optionally substituted by one or more $R^b$, $Cy_2$-$C_{1-6}$ alkyl optionally substituted by one or more $R^b$, $Cy_2$-$C_{1-6}$ alkoxy optionally substituted by one or more $R^b$, $Cy_2$-carbonyl optionally substituted by one or more $R^b$, $Cy_2$-aminocarbonyl optionally substituted by one or more $R^b$, and $Cy_2$-carbonylamino optionally substituted by one or more $R^b$;

$Cy_2$ is each independently selected from 3-8 membered cycloalkyl, 5-10 membered heterocyclyl, phenyl, naphthyl and 5-10 membered heteroaryl;

each $R^b$ is independently selected from hydroxyl, amino, carboxyl, cyano, nitro, halogen, aminocarbonyl, $C_{1-6}$ alkyl, $C_{1-6}$ alkoxy, amino $C_{1-6}$ alkyl, $C_{1-6}$ haloalkyl, $C_{1-6}$ alkoxy $C_{1-6}$ alkyl, $C_{1-6}$ alkoxy $C_{1-6}$ alkoxy, amino $C_{1-6}$ alkoxy, $C_{1-6}$ haloalkoxy, $C_{1-6}$ alkylthio, $C_{1-6}$ alkylamino, ($C_{1-6}$ alkyl)$_2$ amino, $C_{1-6}$ alkylaminocarbonyl, ($C_{1-6}$ alkyl)$_2$ aminocarbonyl, $C_{1-6}$ alkylcarbonylamino and $C_{1-6}$ alkylcarbonyl;

preferably, $Cy_2$ is each independently selected from 3-6 membered cycloalkyl, 5-6 membered heterocyclyl, phenyl and 5-6 membered heteroaryl;

preferably, $R^a$ is each independently selected from $C_{1-6}$ alkyl optionally substituted by halogen; halogen; aminocarbonyl; $C_{1-6}$ alkylaminocarbonyl optionally substituted by halogen; ($C_{1-6}$ alkyl)$_2$ aminocarbonyl optionally substituted by halogen; 3-8 membered cycloalkylaminocarbonyl optionally substituted by at least one of halogen, $C_{1-6}$ alkyl and $C_{1-6}$ alkoxy; phenylaminocarbonyl optionally substituted by at least one of halogen, $C_{1-6}$ alkyl and $C_{1-6}$ alkoxy; 5-6 membered heteroarylaminocarbonyl optionally substituted by at least one of halogen, $C_{1-6}$ alkyl and $C_{1-6}$ alkoxy; and 5-10 membered heterocyclylcarbonyl optionally substituted by at least one of halogen, $C_{1-6}$ alkyl and $C_{1-6}$ alkoxy;

more preferably, $R^a$ is each independently selected from aminocarbonyl, $C_{1-4}$ alkylaminocarbonyl optionally substituted by halogen, ($C_{1-4}$ alkyl)$_2$ aminocarbonyl optionally substituted by halogen, 3-5 membered cycloalkylaminocarbonyl optionally substituted by at least one of halogen, $C_{1-6}$ alkyl and $C_{1-6}$ alkoxy, phenylaminocarbonyl optionally substituted by at least one of halogen, $C_{1-6}$ alkyl and $C_{1-6}$ alkoxy and 5-6 membered nitrogen containing heterocyclylcarbonyl optionally substituted by at least one of halogen, $C_{1-6}$ alkyl and $C_{1-6}$ alkoxy.

Preferably, in formula (b-1), the $L_1$ group is connected to the N atom in formula (b-1); and preferably, in formula (b-1), when $R^a$ is present, at least one $R^a$ is connected to the carbon atom of formula (b-1).

Solution 8. The compound or the pharmaceutically acceptable salt, ester, stereoisomer or tautomer thereof according to solution 7, wherein $R_1$ and $R_2$ are each independently selected from hydrogen and halogen, and $R_1$ and $R_2$ are not both hydrogen;

$R_3$ and $R_4$ are each independently selected from hydrogen and $C_{1-6}$ alkyl;

$R_5$ and $R_6$ are each independently selected from hydrogen and $C_{1-6}$ alkyl;

$L_1$ is a bond;

$Cy_1$ is one of the following groups unsubstituted or substituted by one or more $R^a$:

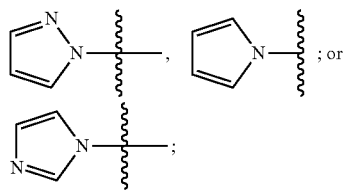

each $R^a$ is independently selected from hydroxyl, amino, carboxyl, cyano, nitro, halogen, aminocarbonyl, $C_{1-6}$ alkyl optionally substituted by one or more $R^b$, $C_{1-6}$ alkoxy optionally substituted by one or more $R^b$, $C_{1-6}$ alkoxy $C_{1-6}$ alkyl optionally substituted by one or more $R^b$, $C_{1-6}$ alkoxy $C_{1-6}$ alkoxy optionally substituted by one or more $R^b$, $C_{1-6}$ alkylamino optionally substituted by one or more $R^b$, $(C_{1-6}$ alkyl$)_2$ amino optionally substituted by one or more $R^b$, $C_{1-6}$ alkylamino $C_{1-6}$ alkyl optionally substituted by one or more $R^b$, $(C_{1-6}$ alkyl$)_2$ amino $C_{1-6}$ alkyl optionally substituted by one or more $R^b$, $C_{1-6}$ alkylaminocarbonyl optionally substituted by one or more $R^b$, $(C_{1-6}$ alkyl$)_2$ aminocarbonyl optionally substituted by one or more $R^b$, $C_{1-6}$ alkylaminocarbonyl $C_{1-6}$ alkyl optionally substituted by one or more $R^b$, $(C_{1-6}$ alkyl$)_2$ aminocarbonyl $C_{1-6}$ alkyl optionally substituted by one or more $R^b$, $C_{1-6}$ alkylcarbonylamino optionally substituted by one or more $R^b$, $C_{1-6}$ alkylcarbonylamino $C_{1-6}$ alkyl optionally substituted by one or more $R^b$, $C_{1-6}$ alkylcarbonyl optionally substituted by one or more $R^b$, $C_{1-6}$ alkylcarbonyl $C_{1-6}$ alkyl optionally substituted by one or more $R^b$, $Cy_2$- optionally substituted by one or more $R^b$, $Cy_2$-$C_{1-6}$ alkyl optionally substituted by one or more $R^b$, $Cy_2$-$C_{1-6}$ alkoxy optionally substituted by one or more $R^b$, $Cy_2$-carbonyl optionally substituted by one or more $R^b$, $Cy_2$-aminocarbonyl optionally substituted by one or more $R^b$, and $Cy_2$-carbonylamino optionally substituted by one or more $R^b$;

$Cy_2$ is each independently selected from 3-8 membered cycloalkyl, 5-10 membered heterocyclyl, phenyl and 5-10 membered heteroaryl;

each $R^b$ is independently selected from hydroxyl, amino, carboxyl, cyano, nitro, halogen, aminocarbonyl, $C_{1-6}$ alkyl, $C_{1-6}$ alkoxy, amino $C_{1-6}$ alkyl, $C_{1-6}$ haloalkyl, $C_{1-6}$ alkoxy $C_{1-6}$ alkyl, $C_{1-6}$ alkoxy $C_{1-6}$ alkoxy, amino $C_{1-6}$ alkoxy, $C_{1-6}$ haloalkoxy, $C_{1-6}$ alkylthio, $C_{1-6}$ alkylamino, $(C_{1-6}$ alkyl$)_2$ amino, $C_{1-6}$ alkylaminocarbonyl, $(C_{1-6}$ alkyl$)_2$ aminocarbonyl, $C_{1-6}$ alkylcarbonylamino and $C_{1-6}$ alkylcarbonyl;

preferably, $Cy_2$ is each independently selected from 3-6 membered cycloalkyl, 5-6 membered heterocyclyl, phenyl and 5-6 membered heteroaryl;

preferably, $R^a$ is each independently selected from $C_{1-6}$ alkyl optionally substituted by halogen; halogen; aminocarbonyl; $C_{1-6}$ alkylaminocarbonyl optionally substituted by halogen; $(C_{1-6}$ alkyl$)_2$ aminocarbonyl optionally substituted by halogen; 3-8 membered cycloalkylaminocarbonyl optionally substituted by at least one of halogen, $C_{1-6}$ alkyl and $C_{1-6}$ alkoxy; phenylaminocarbonyl optionally substituted by at least one of halogen, $C_{1-6}$ alkyl and $C_{1-6}$ alkoxy; 5-6 membered heteroarylaminocarbonyl optionally substituted by at least one of halogen, $C_{1-6}$ alkyl and $C_{1-6}$ alkoxy; and 5-10 membered heterocyclylcarbonyl optionally substituted by at least one of halogen, $C_{1-6}$ alkyl and $C_{1-6}$ alkoxy;

more preferably, $R^a$ is each independently selected from aminocarbonyl, methylaminocarbonyl optionally substituted by halogen, ethylaminocarbonyl optionally substituted by halogen, propylaminocarbonyl optionally substituted by halogen, isopropylaminocarbonyl optionally substituted by halogen, n-aminocarbonyl optionally substituted by halogen, isobutylaminocarbonyl optionally substituted by halogen, sec-butylaminocarbonyl optionally substituted by halogen, tert-butylaminocarbonyl optionally substituted by halogen, cyclopropylaminocarbonyl optionally substituted by at least one of halogen and $C_{1-6}$ alkyl, cyclobutylaminocarbonyl optionally substituted by at least one of halogen and $C_{1-6}$ alkyl, cyclopentylaminocarbonyl optionally substituted by at least one of halogen and $C_{1-6}$ alkyl, phenylaminocarbonyl optionally substituted by at least one of halogen and $C_{1-6}$ alkyl, pyrrolidinylcarbonyl optionally substituted by at least one of halogen and $C_{1-6}$ alkyl, piperidylcarbonyl optionally substituted by at least one of halogen and $C_{1-6}$ alkyl and piperazinylcarbonyl optionally substituted by at least one of halogen and $C_{1-6}$ alkyl.

Solution 9. The compound or the pharmaceutically acceptable salt, ester, stereoisomer or tautomer thereof according to any one of solutions 1-4, wherein $Cy_1$ is a group shown as general formula (c-1) below that is substituted by one or more $R^a$:

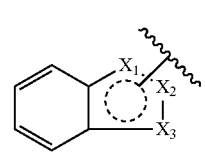

(c-1)

$X_1$, $X_2$ and $X_3$ are each independently selected from $CH_2$, CH, N, NH and C=O, and at least one of $X_1$, $X_2$ and $X_3$ is N or NH;

each $R^a$ is independently selected from hydroxyl, amino, carboxyl, cyano, nitro, halogen, aminocarbonyl, $C_{1-6}$ alkyl optionally substituted by one or more $R^b$, $C_{1-6}$ alkoxy optionally substituted by one or more $R^b$, $C_{1-6}$ alkoxy $C_{1-6}$ alkyl optionally substituted by one or more $R^b$, $C_{1-6}$ alkoxy $C_{1-6}$ alkoxy optionally substituted by one or more $R^b$, $C_{1-6}$ alkylamino optionally substituted by one or more $R^b$, $(C_{1-6}$ alkyl$)_2$ amino optionally substituted by one or more $R^b$, $C_{1-6}$ alkylamino $C_{1-6}$ alkyl optionally substituted by one or more $R^b$, $(C_{1-6}$ alkyl$)_2$ amino $C_{1-6}$ alkyl optionally substituted by one or more $R^b$, $C_{1-6}$ alkylaminocarbonyl optionally substituted by one or more $R^b$, $(C_{1-6}$ alkyl$)_2$ aminocarbonyl optionally substituted by one or more $R^b$, $C_{1-6}$ alkylaminocarbonyl $C_{1-6}$ alkyl optionally substituted by one or more $R^b$, $(C_{1-6}$ alkyl$)_2$ aminocarbonyl $C_{1-6}$ alkyl optionally substituted by one or more $R^b$, $C_{1-6}$ alkylcarbonylamino optionally substituted by one or more $R^b$, $C_{1-6}$ alkylcarbonylamino $C_{1-6}$ alkyl optionally substituted by one or more $R^b$, $C_{1-6}$ alkylcarbonyl optionally substituted by one or more $R^b$, $C_{1-6}$ alkylcarbonyl $C_{1-6}$ alkyl optionally substituted by one or more $R^b$, $Cy_2$- optionally substituted by one or more $R^b$, $Cy_2$-$C_{1-6}$ alkyl optionally substituted by one or more $R^b$, $Cy_2$-$C_{1-6}$ alkoxy optionally substituted by one or more $R^b$, $Cy_2$-carbonyl optionally substituted by one or more $R^b$, $Cy_2$-aminocarbonyl optionally substituted by one or more $R^b$, and $Cy_2$-carbonylamino optionally substituted by one or more $R^b$;

$Cy_2$ is each independently selected from 3-8 membered cycloalkyl, 5-10 membered heterocyclyl, phenyl, naphthyl and 5-10 membered heteroaryl;

each $R^b$ is independently selected from hydroxyl, amino, carboxyl, cyano, nitro, halogen, aminocarbonyl, $C_{1-6}$ alkyl, $C_{1-6}$ alkoxy, amino $C_{1-6}$ alkyl, $C_{1-6}$ haloalkyl, $C_{1-6}$ alkoxy $C_{1-6}$ alkyl, $C_{1-6}$ alkoxy $C_{1-6}$ alkyl, amino $C_{1-6}$ alkoxy, $C_{1-6}$ haloalkoxy, $C_{1-6}$ alkylthio, $C_{1-6}$ alkylamino, $(C_{1-6}$ alkyl$)_2$ amino, $C_{1-6}$ alkylaminocarbonyl, $(C_{1-6}$ alkyl$)_2$ aminocarbonyl, $C_{1-6}$ alkylcarbonylamino and $C_{1-6}$ alkylcarbonyl;

preferably, $Cy_2$ is each independently selected from 3-6 membered cycloalkyl, 5-6 membered heterocyclyl, phenyl and 5-6 membered heteroaryl; preferably, $R^a$ is each independently selected from $C_{1-6}$ alkyl optionally substituted by halogen; halogen; aminocarbonyl; $C_{1-6}$ alkylaminocarbonyl optionally substituted by halogen; $(C_{1-6}$ alkyl$)_2$ aminocarbonyl optionally substituted by halogen; 3-8 membered cycloalkylaminocarbonyl optionally substituted by at least one of halogen, $C_{1-6}$ alkyl and $C_{1-6}$ alkoxy; phenylaminocarbonyl optionally substituted by at least one of halogen, $C_{1-6}$ alkyl and $C_{1-6}$ alkoxy; 5-6 membered heteroarylaminocarbonyl optionally substituted by at least one of halogen, $C_{1-6}$ alkyl and $C_{1-6}$ alkoxy; and 5-10 membered heterocyclylcarbonyl optionally substituted by at least one of halogen, $C_{1-6}$ alkyl and $C_{1-6}$ alkoxy;

more preferably, $R^a$ is each independently selected from aminocarbonyl, $C_{1-4}$ alkylaminocarbonyl optionally substituted by halogen, $(C_{1-4}$ alkyl$)_2$ aminocarbonyl optionally substituted by halogen, 3-5 membered cycloalkylaminocarbonyl optionally substituted by at least one of halogen, $C_{1-6}$ alkyl and $C_{1-6}$ alkoxy, phenylaminocarbonyl optionally substituted by at least one of halogen, $C_{1-6}$ alkyl and $C_{1-6}$ alkoxy and 5-6 membered nitrogen containing heterocyclylcarbonyl optionally substituted by at least one of halogen, $C_{1-6}$ alkyl and $C_{1-6}$ alkoxy;

preferably, in formula (c-1), at least one $R^a$ is connected to the benzene ring moiety in formula (c-1);

preferably, in formula (c-1), the $L_1$ group is connected to $X_1$, $X_2$ or $X_3$; preferably, in formula (c-1), the $L_1$ group is connected to the N atom in formula (c-1).

Solution 10. The compound or the pharmaceutically acceptable salt, ester, stereoisomer or tautomer thereof according to solution 9, wherein $R_1$ and $R_2$ are each independently selected from hydrogen and halogen, and $R_1$ and $R_2$ are not both hydrogen;

$R_3$ and $R_4$ are each independently selected from hydrogen and $C_{1-6}$ alkyl;

$R_5$ and $R_0$ are each selected from hydrogen and $C_{1-6}$ alkyl;

$L_1$ is a bond;

$Cy_1$ is the following group substituted by one or more substituent $R^a$:

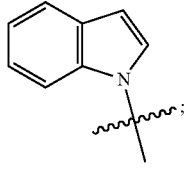 [SMILES: *n1ccc2ccccc21]

each $R^a$ is independently selected from hydroxyl, amino, carboxyl, cyano, nitro, halogen, aminocarbonyl, $C_{1-6}$ alkyl optionally substituted by one or more $R^b$, $C_{1-6}$ alkoxy optionally substituted by one or more $R^b$, $C_{1-6}$ alkoxy $C_{1-6}$ alkyl optionally substituted by one or more $R^b$, $C_{1-6}$ alkoxy $C_{1-6}$ alkoxy optionally substituted by one or more $R^b$, $C_{1-6}$ alkylamino optionally substituted by one or more $R^b$, $(C_{1-6}$ alkyl$)_2$ amino optionally substituted by one or more $R^b$, $C_{1-6}$ alkylamino $C_{1-6}$ alkyl optionally substituted by one or more $R^b$, $(C_{1-6}$ alkyl$)_2$ amino $C_{1-6}$ alkyl optionally substituted by one or more $R^b$, $C_{1-6}$ alkylaminocarbonyl optionally substituted by one or more $R^b$, $(C_{1-6}$ alkyl$)_2$ aminocarbonyl optionally substituted by one or more $R^b$, $C_{1-6}$ alkylaminocarbonyl $C_{1-6}$ alkyl optionally substituted by one or more $R^b$, $(C_{1-6}$ alkyl$)_2$ aminocarbonyl $C_{1-6}$ alkyl optionally substituted by one or more $R^b$, $C_{1-6}$ alkylcarbonylamino optionally substituted by one or more $R^b$, $C_{1-6}$ alkylcarbonylamino $C_{1-6}$ alkyl optionally substituted by one or more $R^b$, $C_{1-6}$ alkylcarbonyl optionally substituted by one or more $R^b$, $C_{1-6}$ alkylcarbonyl $C_{1-6}$ alkyl optionally substituted by one or more $R^b$, $Cy_2$- optionally substituted by one or more $R^b$, $Cy_2$-$C_{1-6}$ alkyl optionally substituted by one or more $R^b$, $Cy_2$-$C_{1-6}$ alkoxy optionally substituted by one or more $R^b$, $Cy_2$-carbonyl optionally substituted by one or more $R^b$, $Cy_2$-aminocarbonyl optionally substituted by one or more $R^b$, and $Cy_2$-carbonylamino optionally substituted by one or more $R^b$;

$Cy_2$ is each independently selected from 3-8 membered cycloalkyl, 5-10 membered heterocyclyl, phenyl and 5-10 membered heteroaryl;

each $R^b$ is independently selected from hydroxyl, amino, carboxyl, cyano, nitro, halogen, aminocarbonyl, $C_{1-6}$ alkyl, $C_{1-6}$ alkoxy, amino $C_{1-6}$ alkyl, $C_{1-6}$ haloalkyl, $C_{1-6}$ alkoxy $C_{1-6}$ alkyl, $C_{1-6}$ alkoxy $C_{1-6}$ alkoxy, amino $C_{1-6}$ alkoxy, $C_{1-6}$ haloalkoxy, $C_{1-6}$ alkylthio, $C_{1-6}$ alkylamino, $(C_{1-6}$ alkyl$)_2$ amino, $C_{1-6}$ alkylaminocarbonyl, $(C_{1-6}$ alkyl$)_2$ aminocarbonyl, $C_{1-6}$ alkylcarbonylamino and $C_{1-6}$ alkylcarbonyl;

preferably, $Cy_2$ is each independently selected from 3-6 membered cycloalkyl, 5-6 membered heterocyclyl, phenyl and 5-6 membered heteroaryl;

preferably, $R^a$ is each independently selected from $C_{1-6}$ alkyl optionally substituted by halogen; halogen; aminocarbonyl; $C_{1-6}$ alkylaminocarbonyl optionally substituted by halogen; $(C_{1-6}$ alkyl$)_2$ aminocarbonyl optionally substituted by halogen; 3-8 membered cycloalkylaminocarbonyl optionally substituted by at least one of halogen, $C_{1-6}$ alkyl and $C_{1-6}$ alkoxy; phenylaminocarbonyl optionally substituted by at least one of halogen, $C_{1-6}$ alkyl and $C_{1-6}$ alkoxy; 5-6 membered heteroarylaminocarbonyl optionally substituted by at least one of halogen, $C_{1-6}$ alkyl and $C_{1-6}$ alkoxy; and 5-10 membered heterocyclylcarbonyl optionally substituted by at least one of halogen, $C_{1-6}$ alkyl and $C_{1-6}$ alkoxy;

preferably, $R^a$ is each independently selected from aminocarbonyl, methylaminocarbonyl optionally substituted by halogen, ethylaminocarbonyl optionally substituted by halogen, propylaminocarbonyl optionally substituted by halogen, isopropylaminocarbonyl optionally substituted by halogen, n-aminocarbonyl optionally substituted by halogen, isobutylaminocarbonyl optionally substituted by halogen, sec-butylaminocarbonyl optionally substituted by halogen, tert-butylaminocarbonyl optionally substituted by halogen, cyclopropylaminocarbonyl optionally substituted by at least one of halogen, $C_{1-6}$ alkyl and $C_{1-6}$ alkoxy, cyclobutylaminocarbonyl optionally substituted by at least one of halogen, $C_{1-6}$ alkyl and $C_{1-6}$ alkoxy, cyclopentylaminocarbonyl optionally substituted by at least one of halogen, $C_{1-6}$ alkyl and $C_{1-6}$ alkoxy; phenylaminocarbonyl optionally substituted by at least one of halogen, $C_{1-6}$ alkyl and $C_{1-6}$ alkoxy; azetidinylcarbonyl optionally substituted by at least one of halogen, $C_{1-6}$ alkyl and $C_{1-6}$ alkoxy, pyrrolidinylcarbonyl optionally substituted by at least one of halogen, $C_{1-6}$ alkyl and $C_{1-6}$ alkoxy, piperidylcarbonyl optionally substituted by at least one of halogen, $C_{1-6}$ alkyl and $C_{1-6}$ alkoxy, piperazinylcarbonyl optionally substituted by at least one of halogen, $C_{1-6}$ alkyl and $C_{1-6}$ alkoxy, and morpholinylcarbonyl optionally substituted by at least one of halogen, $C_{1-6}$ alkyl and $C_{1-6}$ alkoxy.

Solution 11. The compound or the pharmaceutically acceptable salt, ester, stereoisomer or tautomer thereof according to solution 1. The compound is selected from:

| Serial number | Structural formula |
|---|---|
| A1 | |
| A2 | |
| A3 | |
| A4 | |
| A5 | |
| A6 | |
| A7 | |
| A9 | |
| A10 | |
| A11 | |
| A12 | |
| A13 | |
| A14 | |
| A15 | |

| Serial number | Structural formula |
|---|---|
| A16 | (4-chlorophenyl-substituted tetrahydropyrazolo[4,3-c]pyridin-4-one with N-CH2-C(=CHF)-CH2NH2 side chain) |
| A17 | (1-methylpyrazol-4-yl-substituted tetrahydropyrazolo[4,3-c]pyridin-4-one with N-CH2-C(=CHF)-CH2NH2 side chain) |
| A18 | (5-cyclopropyl tetrahydroisoxazolo[4,3-c]pyridine-3,4-dione with N-CH2-C(=CHF)-CH2NH2 side chain) |
| A19 | (5-cyclopropyl-2-(3-fluorophenyl) tetrahydropyrazolo[4,3-c]pyridine-3,4-dione with N-CH2-C(=CHF)-CH2NH2 side chain) |
| A20 | (5-cyclopropyl-1-(3-fluorophenyl) tetrahydropyrazolo[4,3-c]pyridine-3,4-dione with N-CH2-C(=CHF)-CH2NH2 side chain) |
| A21 | (5-tert-butyl tetrahydropyrazolo[3,4-c]pyridin-4-one with N-CH2-C(=CHF)-CH2NH2 side chain) |

| Serial number | Structural formula |
|---|---|
| A22 | (5-cyclopropyl tetrahydropyrrolo[3,4-c]pyridin-4-one with N-CH2-C(=CHF)-CH2NH2 side chain) |
| A23 | (NH tetrahydropyrazolo[4,3-c]pyridin-4-one with N-CH2-C(=CHF)-CH2NH2 side chain) |
| A24 | (5-methyl tetrahydropyrazolo[4,3-c]pyridin-4-one with N-CH2-C(=CHF)-CH2NH2 side chain) |
| A25 | (5-ethyl tetrahydropyrrolo[3,4-c]pyridin-4-one with N-CH2-C(=CHF)-CH2NH2 side chain) |
| A26 | (5-tert-butyl dihydropyrrolo[3,4-c]pyrazol-4-one with N-CH2-C(=CHF)-CH2NH2 side chain) |
| A27 | (5-isopropyl tetrahydropyrazolo[4,3-c]pyridin-4-one with N-CH2-C(=CHF)-CH2NH2 side chain) |
| A28 | (5-ethyl pyrazolo[4,3-c]pyridin-4-one with N-CH2-C(=CHF)-CH2NH2 side chain) |
| A29 | (5-ethyl pyrazolo[3,4-c]pyridin-4-one with N-CH2-C(=CHF)-CH2NH2 side chain) |

| Serial number | Structural formula |
|---|---|
| A30 | 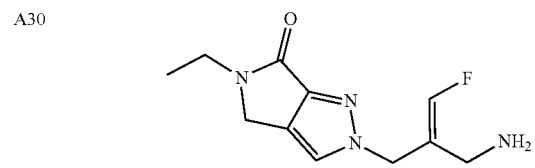 |
| A31 | 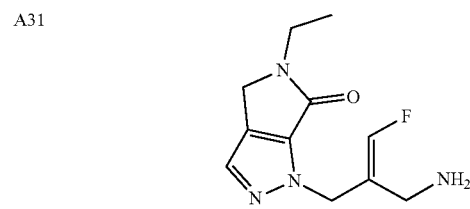 |
| A32 | 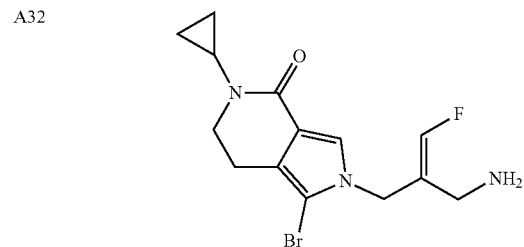 |
| A33 | 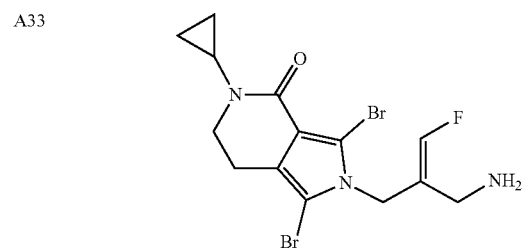 |
| A34 | 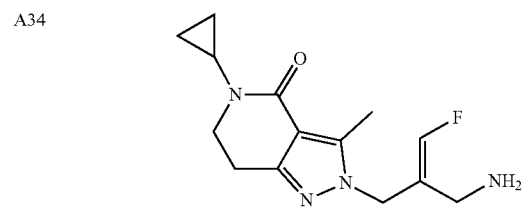 |
| A35 | 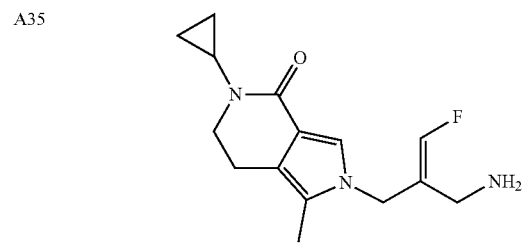 |
| A36 | 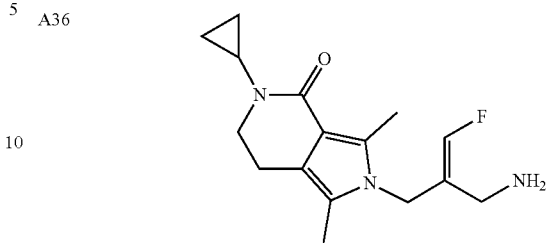 |
| A37 | 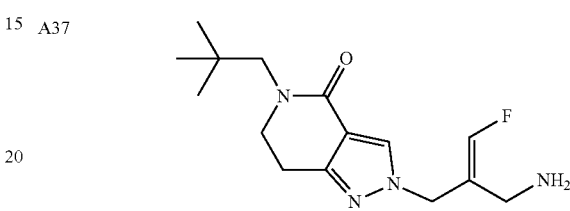 |
| A38 | 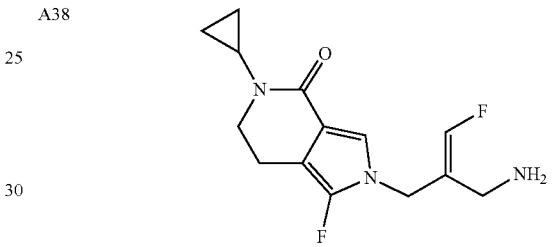 |
| A39 | 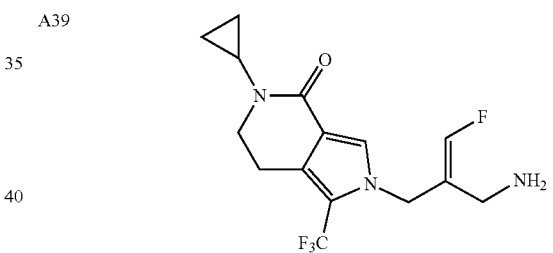 |
| A40 | 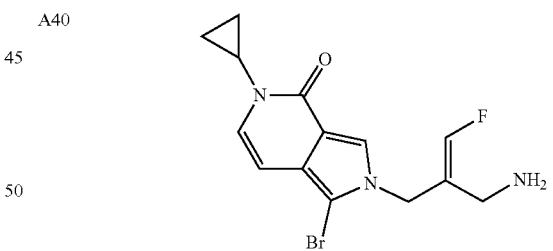 |
| A41 | 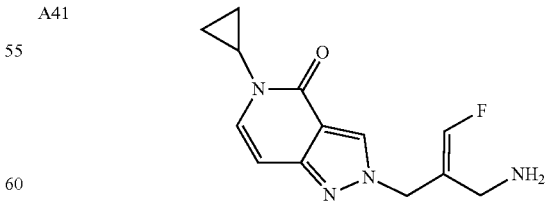 |
| A42 | 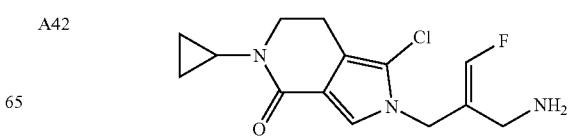 |

| Serial number | Structural formula |
|---|---|
| A44 | 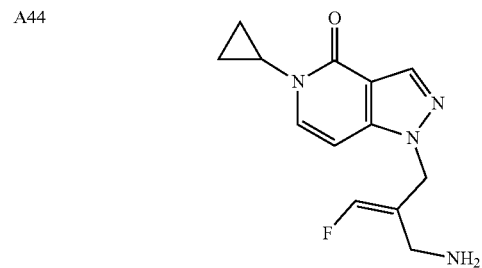 |
| A45 | 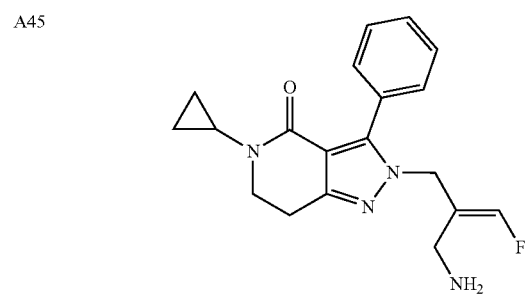 |
| A46 | 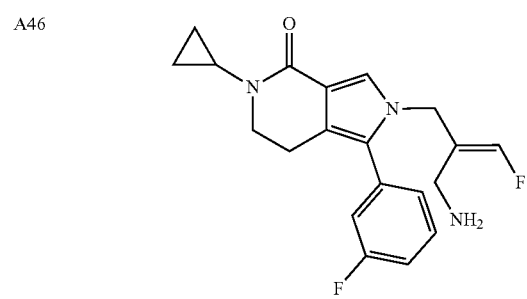 |
| A47 | 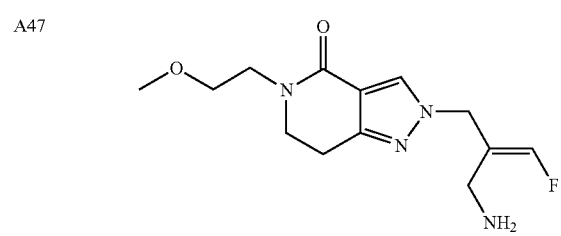 |
| A48 | 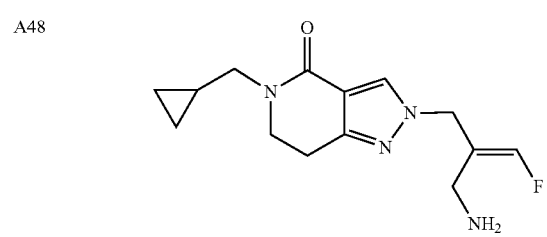 |
| A49 | 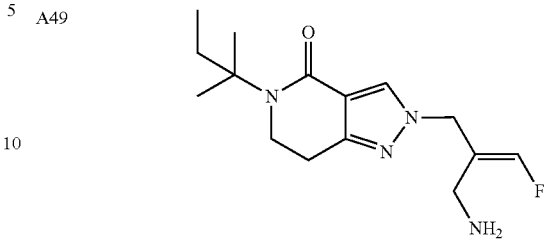 |
| A50 | 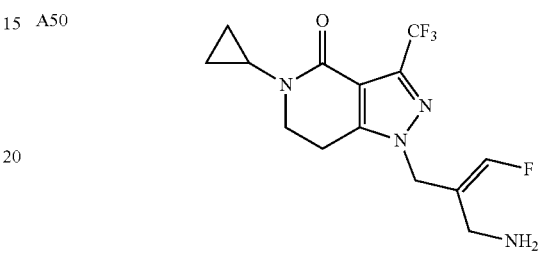 |
| A51 | 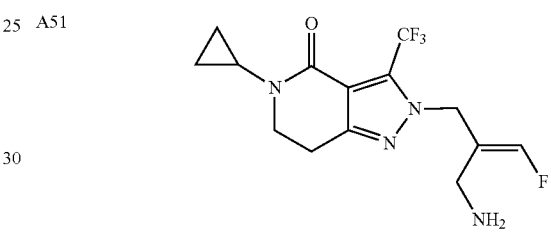 |
| A52 | 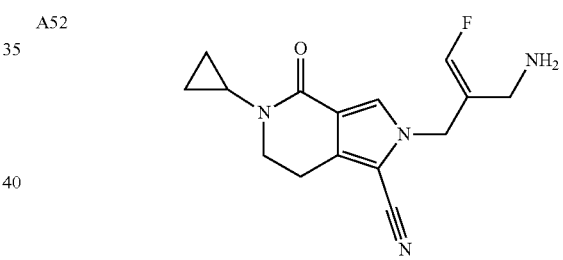 |
| B1 | 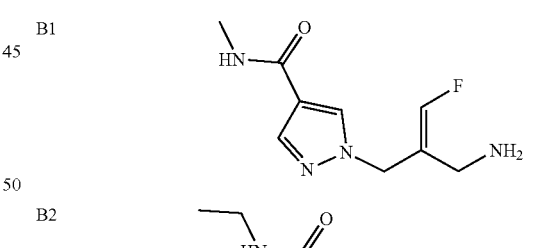 |
| B2 | 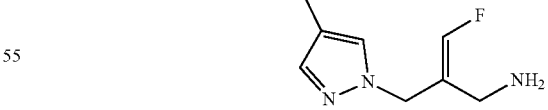 |
| B3 | 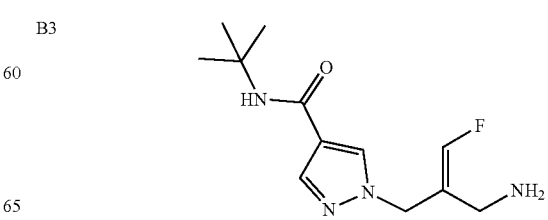 |

-continued
| Serial number | Structural formula |
|---|---|
| B4 | |
| B5 | |
| B6 | |
| B7 | |
| B8 | |
| B9 | |
| B10 | |
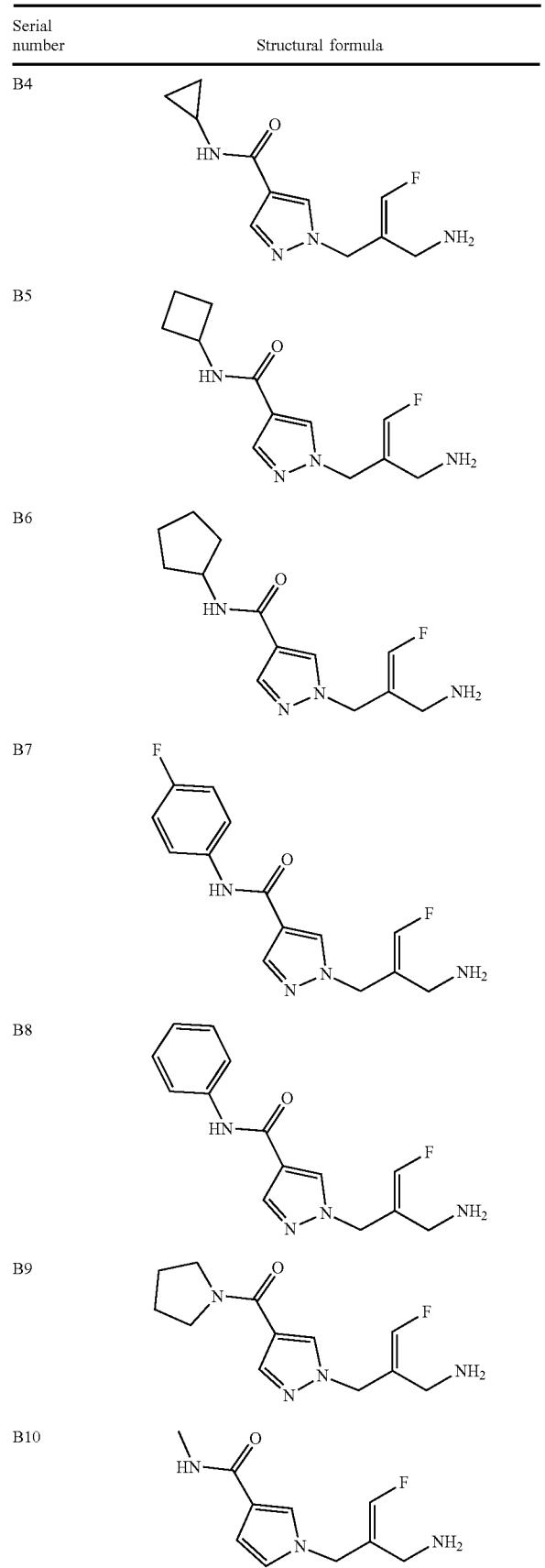
-continued
| Serial number | Structural formula |
|---|---|
| B11 | |
| B12 | |
| B13 | |
| B14 | |
| B15 | |
| B16 | |
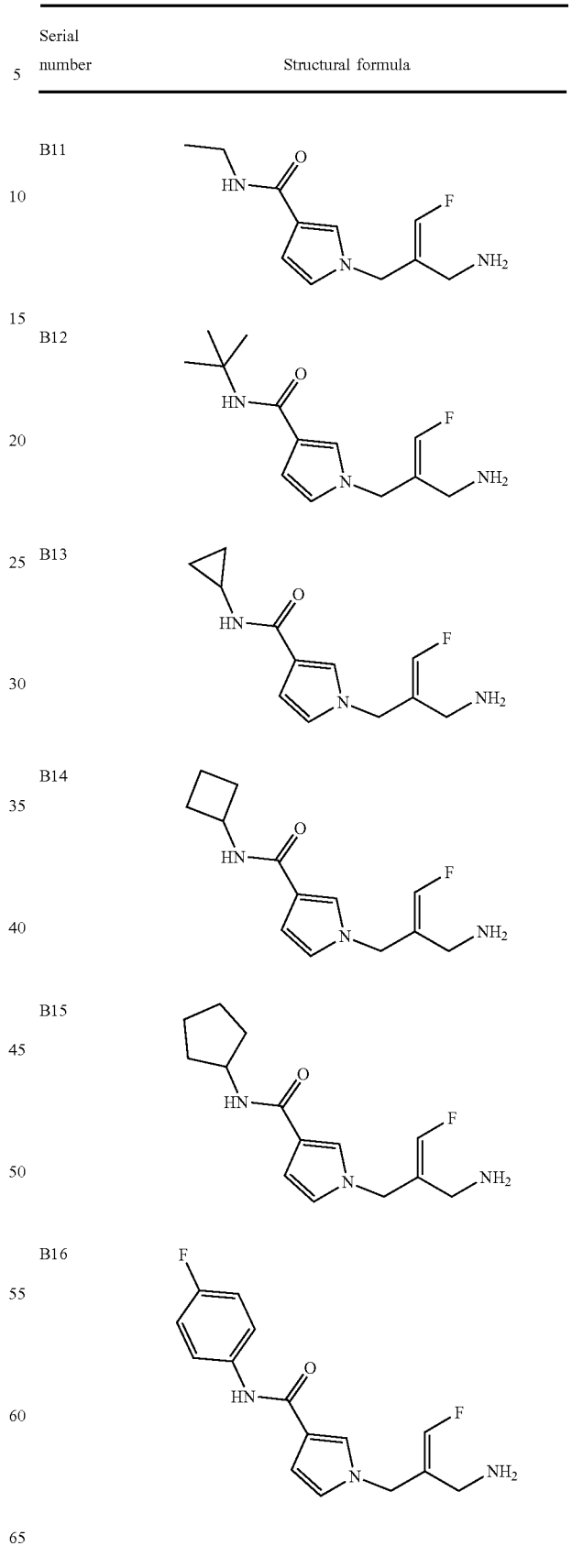

| Serial number | Structural formula |
|---|---|
| B17 | 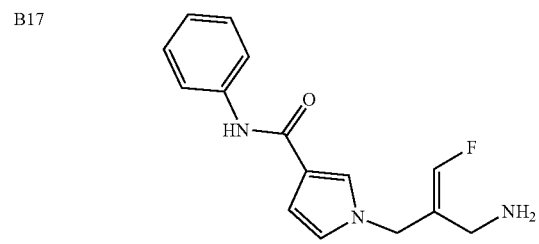 |
| B18 | 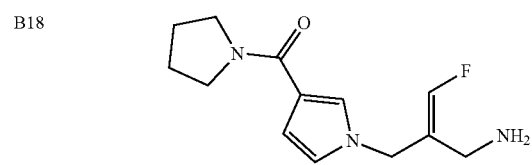 |
| B19 | 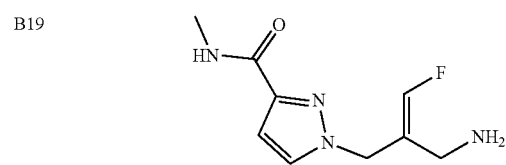 |
| B20 | 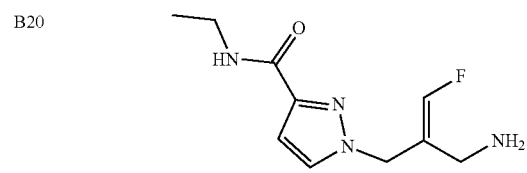 |
| B21 | 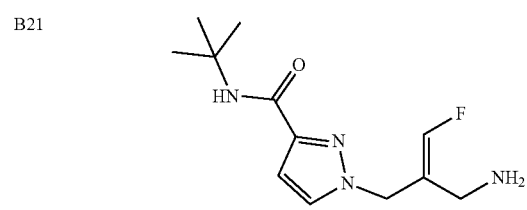 |
| B22 | 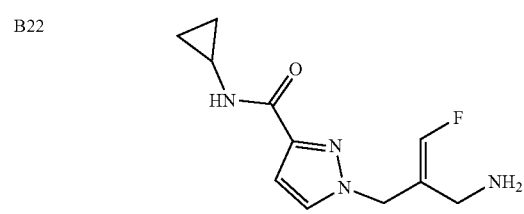 |
| B23 | 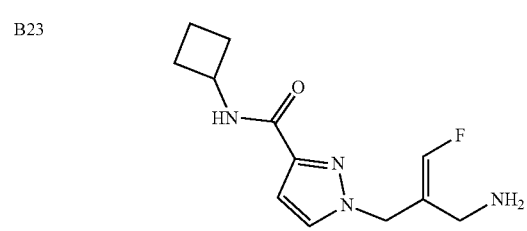 |
| Serial number | Structural formula |
|---|---|
| B24 | 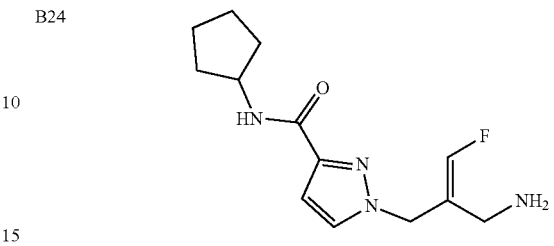 |
| B25 | 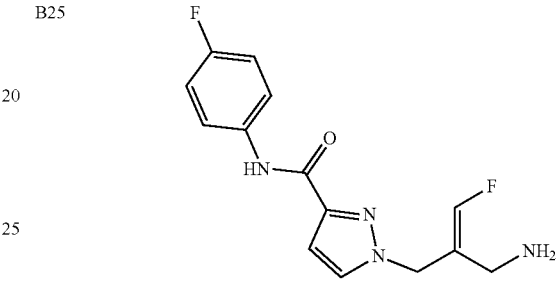 |
| B26 | 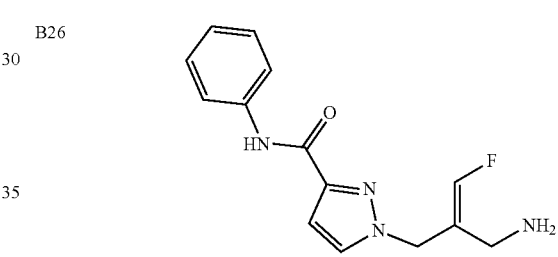 |
| B27 | 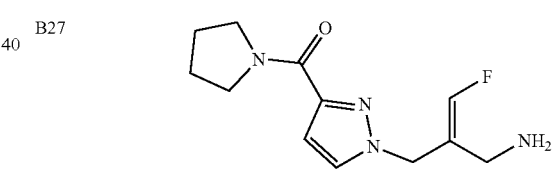 |
| B28 | 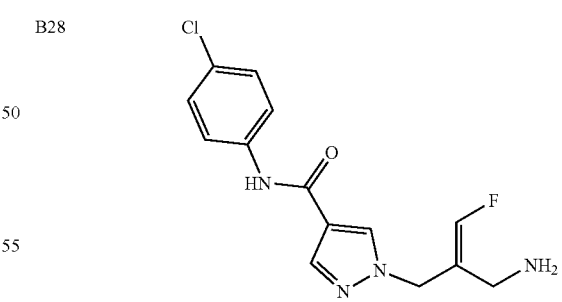 |
| B29 | 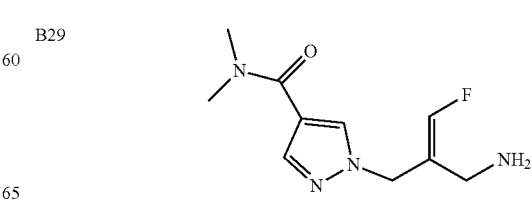 |

| Serial number | Structural formula |
|---|---|
| B30 | |
| B31 | |
| C1 | |
| C2 | |
| C4 | |
| C5 | |
| C6 | |
| C7 | |
| C8 | |
| C9 | |
| C10 | |
| C11 | |
| C12 | |
| C13 | |

| Serial number | Structural formula |
|---|---|
| C14 | 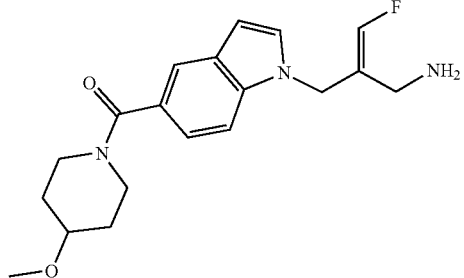 [SMILES: COC1CCN(C(=O)c2ccc3c(ccn3C/C(=C/F)CN)c2)CC1] |
| C15 | 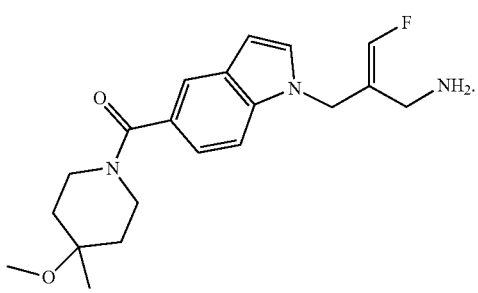 [SMILES: COC1(C)CCN(C(=O)c2ccc3c(ccn3C/C(=C/F)CN)c2)CC1] |

Solution 12. A pharmaceutical composition comprising the compound or the pharmaceutically acceptable salt, ester, stereoisomer or tautomer thereof according to any one of solutions 1-11, wherein the pharmaceutical composition optionally comprises one or more pharmaceutically acceptable carriers.

Solution 13. Use of the compound or the pharmaceutically acceptable salt, ester, stereoisomer or tautomer thereof according to any one of solutions 1-11 or the pharmaceutical composition according to solution 12 in the manufacture of a medicament for preventing and/or treating diseases related to or mediated by the SSAO/VAP-1 protein.

Effect of the Invention

The present invention provides a novel halo-allylamine compound, which is effective in preventing and/or treating diseases related to or mediated by the SSAO/VAP-1 protein. Specifically, the compound shown as formula I and the pharmaceutically acceptable salt, ester, stereoisomer or tautomer thereof of the present invention exhibits excellent inhibitory activity against the SSAO/VAP-1 protein, and thus can be used to prevent and/or treat diseases related to or mediated by the SSAO/VAP-1 protein.

Moreover, the compound of the present invention shows excellent inhibition on the SSAO/VAP-1 protein and shows excellent selectivity against the rhAOC1 protein and the MAO protein. Therefore, the compound of the present invention avoids other undesired side effects while preventing and/or treating diseases related to or mediated by the SSAO/VAP-1 protein.

In addition, compared with existing drugs, the compound of the present invention can hardly penetrate the blood-brain barrier. Therefore, the compound of the present invention has a very low toxic risk to the nervous system, showing excellent drug safety.

Therefore, the present invention can provide a highly safe compound or a pharmaceutically acceptable salt, ester, stereoisomer or tautomer thereof that can prevent and/or treat diseases related to or mediated by the SSAO/VAP-1 protein.

DETAILED DESCRIPTION OF THE INVENTION

The embodiments of the present invention will be described in more detail in conjunction with specific implementations below, but those skilled in the art will understand that the specific implementations described below are only used to illustrate the present invention and should not be regarded as limiting the protection scope of the present invention. On the contrary, the present invention is intended to encompass all alternatives, modifications and equivalents that can be included within the scope of the invention as defined by the claims. Unless otherwise specified, the various embodiments of the present invention can be combined in any manner, and the conversions, modifications, and changes of the technical solutions thus obtained are also included in the scope of the present invention.

Definition

In the present invention, the expression of "$C_{a-b}$ group" (a and b represent an integer $\geq 1$, and a<b) means that the "group" has a to b carbon atoms, for example, $C_{1-6}$ alkyl represents alkyl with 1-6 carbon atoms, $C_{1-6}$ alkoxy represents alkoxy with 1-6 carbon atoms, $C_{3-8}$ cycloalkyl represents cycloalkyl with 3-8 carbon atoms, and $C_{1-6}$ alkoxy $C_{1-6}$ alkyl represents a group formed by bonding alkoxy having 1-6 carbon atoms with alkyl having 1-6 carbon atoms. In addition, in the present invention, the expression of "group" may also refer to a group containing two or more subgroups, and at this point, the expression of "$C_a$-b" defines the number of carbon atoms of the entire group containing the two or more subgroups. For example, the expression of "$C_{7-12}$ alkylaryl" means that the total number of carbon atoms of an alkylaryl group comprising an alkyl moiety and an aryl moiety is 7-10, that is, it can be decomposed into, but is not limited to, $C_{1-6}$ alkylphenyl or $C_{1-2}$ alkylnaphthyl.

In the present invention, "group" represents a monovalent group or a divalent or higher group meeting the valence as required. For example, "cycloalkyl" (also expressed as cycloalkyl group) includes a monovalent group obtained by removing a hydrogen atom from cycloalkane, as well as a divalent or higher group obtained by removing two or more hydrogen atoms from the same carbon atom or two or more different carbon atoms of cycloalkane. For example, when "cycloalkyl" serves as a terminal group, it is connected to other parts of the compound structure in the form of a monovalent group when not carrying substituents; and when it carries substituents, cycloalkyl shows a corresponding valence number (substituent number+1) according to the number of the substituents carried. Those skilled in the art can unambiguously determine the valence a "group". In addition, in the present invention, if a "group" represents a divalent or higher group, it is preferred to connect these bonds to different atoms (such as but not limited to carbon atoms, nitrogen atoms, etc.) in the group.

"Halogen" or "halogen atom" described in the present invention refers to fluorine, chlorine, bromine, and iodine, preferably fluorine and chlorine.

"$C_{1-6}$ alkyl" described in the present invention refers to a linear or branched alkyl group derived by removing a hydrogen atom from an alkane moiety containing 1 to 6 carbon atoms, and includes linear $C_{1-6}$ alkyl and branched $C_{1-6}$ alkyl. In fact, it is well-known by those skilled in the art that C$_{1-6}$ alkyl has at least three carbon atoms when having a branch chain (branched C$_{1-6}$ alkyl). Examples of "C$_{1-6}$ alkyl" may include, for example, methyl, ethyl, n-propyl, isopropyl, n-butyl, isobutyl, sec-butyl, ten-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1-methyl-2-methylpropyl, etc. The "C$_{1-4}$ alkyl" refers to the aforementioned examples containing 1 to 4 carbon atoms.

"C$_{2-6}$ alkenyl" described in the present invention refers to a linear or branched alkenyl group derived by removing a hydrogen atom from alkene that contains 2 to 6 carbon atoms and at least one carbon-carbon double bond, for example, vinyl, 1-propenyl, 2-propenyl, 1-butenyl, 2-butenyl, 1,3-butadiene-1-yl, 1-pentene-3-yl, 2-pentene-1-yl, 3-pentene-1-yl, 3-pentene-2-yl, 1,3-pentadiene-1-yl, 1,4-pentadiene-3-yl, 1-hexene-3-yl, 1,4-hexadiene-1-yl, etc. Preferably, "C$_{2-6}$ alkenyl" contains a carbon-carbon double bond.

"C$_{2-6}$ alkynyl" described in the present invention refers to a linear or branched alkynyl group derived by removing a hydrogen atom from alkyne that contains 2 to 6 carbon atoms and at least one carbon-carbon triple bond, for example, ethynyl, propynyl, 2-butyn-1-yl, 2-pentyn-1-yl, 3-pentyn-1-yl, 4-methyl-2-pentyn-1-yl, 2-hexyn-1-yl, 3-hexyn-2-yl, 3-hexyn-1-yl, 3-hexyn-2-yl, etc. Preferably, "C$_{2-6}$ alkynyl" contains a carbon-carbon triple bond.

"C$_{1-6}$ alkoxy" described in the present invention refers to a group derived by connecting "C$_{1-6}$ alkyl" defined above to other parts of the chemical structural formula through oxygen atoms, i.e. a "C$_{1-6}$ alkyl-O—" group, such as groups obtained by bonding the groups enumerated regarding the aforementioned "C$_{1-6}$ alkyl" to —O—, including, but not limited to, methoxy, ethoxy, propoxy, isopropoxy, n-butoxy, tert-butoxy, n-pentyloxy, neopentyloxy, n-hexyloxy, etc. The "C$_{1-4}$ alkoxy" refers to the aforementioned examples containing 1 to 4 carbon atoms, i.e. a "C$_{1-4}$ alkyl-O—" group.

The "C$_{1-6}$ alkoxy C$_{1-6}$ alkoxy" refers to a group formed by substituting one or more hydrogen atoms on C$_{1-6}$ alkoxy with C$_{1-6}$ alkoxy.

"C$_{1-6}$ alkylamino (C$_{1-6}$ alkylamino)", "(C$_{1-6}$ alkyl)$_2$ amino", "C$_{1-6}$ alkylcarbonylamino", "C$_{1-6}$ alkylaminocarbonyl", "C$_{1-6}$ alkylcarbonyl", "C$_{1-6}$ alkylaminosulfonyl", "C$_{1-6}$ alkylsulfonylamino", "C$_{1-6}$ alkylsulfonyl", "C$_{1-6}$ alkylthio (C$_{1-6}$ alkylthio)", etc., described in the present invention refer to groups formed by respectively connecting C$_{1-6}$ alkyl to corresponding groups such as —NH$_2$, —CO—NH$_2$—, —NH$_2$—CO—, —CO—, —NH$_2$SO$_2$—, —SO$_2$NH$_2$—, —SO$_2$—, and —S—.

"C$_{1-6}$ alkoxy C$_{1-6}$ alkyl", "C$_{1-6}$ alkylthio C$_{1-6}$ alkyl", "C$_{1-6}$ alkylamino C$_{1-6}$ alkyl", "C$_{1-6}$ alkylaminocarbonyl C$_{1-6}$ alkyl", "C$_{1-6}$ alkylcarbonylamino C$_{1-6}$ alkyl", "C$_{1-6}$ alkylcarbonyl C$_{1-6}$ alkyl", "C$_{1-6}$ alkylaminosulfonyl C$_{1-6}$ alkyl", "C$_{1-6}$ alkylsulfonylamino C$_{1-6}$ alkyl", "C$_{1-6}$ alkylsulfonyl C$_{1-6}$ alkyl", etc., described in the present invention refer to groups formed by substituting one or more hydrogen atoms on C$_{1-6}$ alkyl with C$_{1-6}$ alkoxy, C$_{1-6}$ alkylthio, C$_{1-6}$ alkylamino, C$_{1-6}$ alkylaminocarbonyl, C$_{1-6}$ alkylcarbonylamino, C$_{1-6}$ alkylcarbonyl, C$_{1-6}$ alkylaminosulfonyl, C$_{1-6}$ alkylsulfonylamino and C$_{1-6}$ alkylsulfonyl.

The "polycyclic ring" in the present invention refers to a multi-ring system structure formed by two or more ring structures connected by an ortho-fused, spiro- or bridged linkage. The ortho-fused ring refers to a polycyclic structure formed by two or more ring structures sharing two adjacent ring atoms (i.e., sharing a bond) with each other. The bridged ring refers to a polycyclic structure formed by two or more ring structures sharing two non-adjacent ring atoms with each other. The spiro-ring refers to a polycyclic structure formed by two or more ring structures sharing a ring atom with each other.

The "cycloalkyl" described in the present invention refers to a monovalent group or a bivalent group (as required) derived from cycloalkane, and the cycloalkane includes monocyclic cycloalkane or polycyclic cycloalkane, and may have 3, 4, 5, 6, 7, 8, 9, 10, 11 or 12 carbon atoms. Unless otherwise specified, a certain membered cycloalkyl includes all possibly formed monocyclic and polycyclic (including fused in the form of ortho-, spiro- or bridged) cases. Cycloalkyl may be a 3-12 membered monovalent, divalent or higher (as required) group, a 3-10 membered monovalent, divalent or higher (as required) group, a 3-8 membered monovalent, divalent or higher (as required) group, a 3-6 membered monovalent, divalent or higher (as required) group, a 4-6 membered monovalent, divalent or higher (as required) group, or a 5-7 membered monovalent, divalent or higher (as required) group.

(Monovalent, divalent or higher) monocyclic cycloalkyl may be 3-12 membered cycloalkyl, 3-10 membered cycloalkyl, 3-8 membered cycloalkyl, 3-6 membered cycloalkyl, 4-6 membered cycloalkyl or 5-7 membered cycloalkyl, examples of which include, but are not limited to, cyclopropyl, cyclobutyl, cyclopentyl, cyclohexyl, cycloheptyl, cyclooctyl, cyclopentyl-1,3-diyl, cyclohexyl-1,4-diyl, cycloheptyl-1,4-diyl, etc.

(Monovalent, divalent or higher) polycyclic cycloalkyl includes ortho-fused cycloalkyl, bridged cycloalkyl and spiro-cycloalkyl.

(Monovalent, divalent or higher) ortho-fused cycloalkyl may be 6-12 membered ortho-fused cycloalkyl or 7-10 membered ortho-fused cycloalkyl, examples of which include, but are not limited to, bicyclo[3.1.1]heptyl, bicyclo[2.2.1]heptyl, bicyclo[2.2.2]octanyl, bicyclo[3.2.2]nonyl, bicyclo[3.3.1]nonyl and bicyclo[4.2.1]nonyl.

"Cycloalkenyl" described in the present invention refers to a group obtained by having at least one carbon-carbon double bond (preferably having a carbon-carbon double bond) in the aforementioned cycloalkyl group.

"Cycloalkyl" and "cycloalkenyl" may also be monovalent groups obtained by removing a hydrogen atom from 6-12 membered spiro-ring or 7-11 membered spiro-ring or divalent groups (as required) obtained by removing a hydrogen atom each from two different carbon atoms. Examples of spiro-ring include but are not limited to:

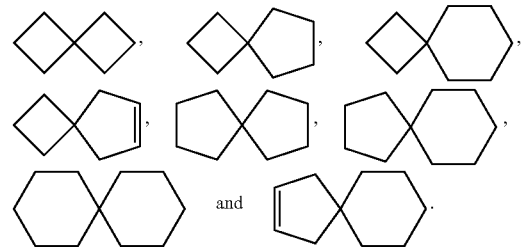

"Cycloalkyl" and "cycloalkenyl" may also be monovalent groups obtained by removing a hydrogen atom from 6-12 membered bridged ring or 7-11 membered bridged ring or divalent groups (as required) obtained by removing a hydrogen atom each from two different carbon atoms. Examples of the bridge ring include but are not limited to:

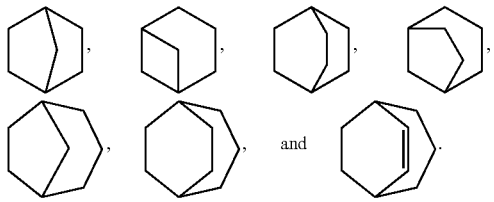

Therefore, unless otherwise specified, "3-12 membered cycloalkenyl" described in the present invention includes all possibly formed monocyclic and polycyclic (including fused in the form of ortho-, spiro- or bridged) cases. It is a group that has at least one carbon-carbon double bond in the 3-12 membered monovalent, divalent or higher (as required) cycloalkyl group enumerated above. For example, it may be a monovalent or bivalent group derived from 3-8 membered cycloalkenyl, 7-11 membered spiro-cycloalkenyl, 7-11 membered ortho-fused cycloalkenyl, 6-11 membered bridged cycloalkenyl or the like. Examples include cyclobutenyl, cyclopentenyl, cyclohexenyl, 1,4-cyclohexadienyl, cycloheptenyl, 1,4-cycloheptadienyl, cyclooctenyl and 1,5-cyclooctadienyl.

"Heterocyclyl" described in the present invention refers to a nonaromatic monovalent or bivalent cyclic group formed by substituting at least one cyclic carbon atom of the aforementioned cycloalkyl with a heteroatom selected from O, S and N, preferably not having or having a carbon-carbon double bond. Preferably, it is a heterocyclyl obtained by substituting the ring-forming carbon atoms of the aforementioned ring-forming alkyl with 1 to 3 heteroatoms selected from O, S and N. In addition, the heterocyclyl described in the present invention further includes the case of the carbon atoms or sulfur atoms as ring-forming atoms being substituted by oxygen or nitrogen, for example, the ring-forming carbon atoms are substituted by C(=O), S(=O), S(=O)$_2$ and S(=O)(=NH).

Specifically, the "heterocyclyl" of the present invention may be a group with 3, 4, 5, 6, 7, 8, 9, 10, 11 and 12 ring-forming atoms. It may be 3-14 membered heterocyclyl, 3-12 membered heterocyclyl, 3-10 membered heterocyclyl, 4-10 membered heterocyclyl, 3-8 membered heterocyclyl, 4-12 membered heterocyclyl, 4-8 membered heterocyclyl, 4-6 membered heterocyclyl or 5-10 membered heterocyclyl.

In addition, "heterocyclyl" further includes a monovalent, bivalent or higher (as required) monocyclic heterocyclyl system or a monovalent, bivalent or higher (as required) polycyclic heterocyclyl system (also referred to as a polycyclic system), and includes a saturated or unsaturated heterocyclyl group, and it is not aromatic as a whole. Unless otherwise specified, it includes all possibly formed monocyclic, polycyclic (including fused in the form of ortho-, spiro- or bridged), saturated and unsaturated cases, and it is not aromatic as a whole.

Monovalent, bivalent or higher (as required) monocyclic heterocyclyl may be 3-14 membered heterocyclyl, 3-12 membered heterocyclyl, 3-10 membered heterocyclyl, 4-10 membered heterocyclyl, 3-8 membered heterocyclyl, 4-12 membered heterocyclyl, 4-8 membered heterocyclyl, 4-6 membered heterocyclyl, 5-10 membered heterocyclyl, 3-8 membered saturated heterocyclyl, 3-6 membered heterocyclyl, 4-12 membered heterocyclyl, 4-7 membered heterocyclyl, 4-6 membered heterocyclyl, 5-10 membered heterocyclyl, 5-7 membered heterocyclyl, 5-6 membered heterocyclyl, 5-6 membered oxygen containing heterocyclyl, 5-6 membered nitrogen containing heterocyclyl, 5-6 membered saturated heterocyclyl, 5-7 membered saturated heterocyclyl or the like, which may be saturated, partially saturated or unsaturated but nonaromatic. Its examples include but are not limited to: azacyclopropyl, 2H-azacyclopropyl, diazacyclopropyl, 3H-diazacyclopropyl, azetidinyl, 1,4-dioxacyclohexyl, 1,3-dioxacyclohexyl, 1,3-dioxacyclopentyl, 1,4-dioxacyclohexadienyl, tetrahydrofuryl, dihydropyrrolyl, pyrrolidinyl, imidazolidinyl, 4,5-dihydroimidazolyl, pyrazolidinyl, 4,5-dihydropyrazolyl, 2,5-dihydrothienyl, tetrahydrothienyl, 4,5-dihydrothiazolyl, piperidyl, piperazinyl, morpholinyl, hexahydropyrimidinyl, hexahydropyridazinyl, 4,5-dihydroxazolyl, 4,5-dihydroisoxazolyl, 2,3-dihydroisoxazolyl, 2H-1,2-oxazinyl, 6H-1,3-oxazinyl, 4H-1,3-thiazinyl, 6H-1,3-thiazinyl, 2H-pyranyl, 2H-pyran-2-one, 3,4-dihydro-2H-pyranyl, 1,1-dioxotetrahydrothiapyranyl, 1,1-dioxotetrahydrothienyl, 1-imino-1-oxo-tetrahydrothiobutylcyclyl, 1-imino-1-oxo-tetrahydrothienyl, 1-imino-1-oxo-hexahydrothiapyranyl, etc.

The monovalent, divalent or higher (as required) polycyclic heterocyclyl includes ortho-fused heterocyclyl, spiro-heterocyclyl and bridged heterocyclyl, which may be saturated, partially saturated or unsaturated, but nonaromatic. The ortho-fused heterocyclyl may be a 6-12 membered ortho-fused heterocyclyl, 7-10 membered ortho-fused heterocyclyl, 6-10 membered ortho-fused cyclyl, 6-12 membered saturated ortho-fused heterocyclyl, 7-8 membered saturated ortho-fused heterocyclyl or 8 membered saturated ortho-fused heterocyclyl, and its examples include, but are not limited to: 3-azabicyclo[3.1.0]hexyl, 3,6-diazabicyclo[3.2.0]heptyl, 3,8-diazabicyclo[4.2.0]octyl, 3,7-diazabicyclo[4.2.0]octyl, octahydropyrrolo[3,4-c]pyrrolyl, octahydropyrrolo [3,4-&]pyrrolyl, octahydropyrrolo[3,4-b][1,4] oxazinyl, octahydro-1H-pyrrolo [3,4-c]pyridyl, 2,3-dihydrobenzofuran-2-yl, 2,3-dihydrobenzofuryl-3-yl, indolin-1-yl, indolin-2-yl, indolin 3-yl, 2,3-dihydrobenzothiophen-2-yl, octahydro-1H-indolyl, octahydrobenzofuryl, octahydrocyclopenta[c]pyrrolyl, hexahydrocyclopenta [c]furyl, 2,2-dioxohexahydrocyclopenta[c]thienyl and 2-imino-2-oxo-octahydrocyclopenta[c]thienyl.

The spiro-heterocyclyl may be a monovalent group obtained by removing a hydrogen atom from 6-12 membered spiro heterocyclic ring, 7-11 membered spiro heterocyclic ring, 6-12 membered saturated spiro heterocyclic ring or 7 membered saturated spiro heterocyclic ring, or a bivalent group (as required) obtained by removing a hydrogen atom each from two different carbon atoms, and the examples of the spiro heterocyclyl include but are not limited to:

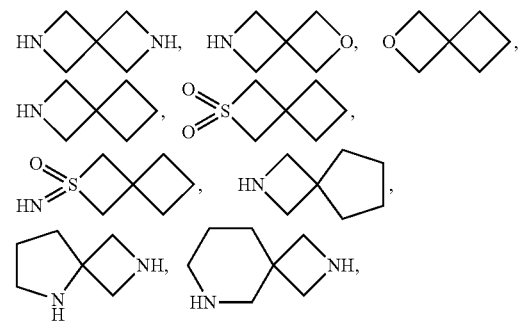

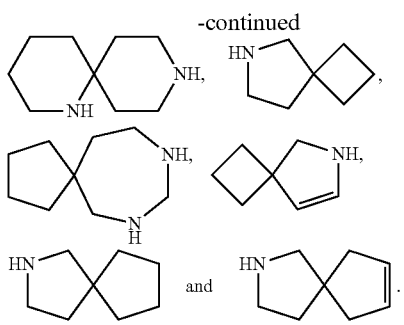

The bridged heterocyclyl may be a monovalent group obtained by removing a hydrogen atom from 6-12 membered bridged heterocyclic ring, 7-11 membered bridged heterocyclic ring, 6-12 membered saturated bridged heterocyclic ring or 7-8 membered saturated bridged heterocyclic ring, or a bivalent group (as required) obtained by removing a hydrogen atom each from two different carbon atoms, and the examples of the bridged heterocyclyl include but are not limited to:

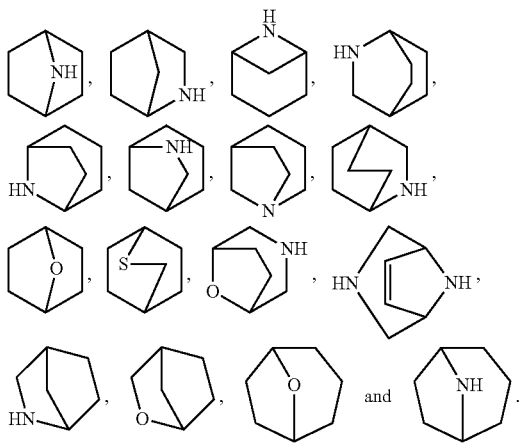

"Aryl" described in the present invention refers to a monovalent group or a bivalent or higher group as required derived from aromatic carbocyclic hydrocarbon, and the aromatic carbocyclic hydrocarbon includes 6-8 membered monocyclic aromatic hydrocarbon and 8-14 membered polycyclic aromatic hydrocarbon. The 6-8 membered monocyclic aryl is, for example, phenyl. The 8-14 membered polycyclic aryl is, for example, naphthyl, phenanthryl, anthryl and the like. Divalent aryl may include, for example, phenylene, naphthylene and the like.

"Heteroaryl" described in the present invention may be 5-14 membered heteroaryl, 5-10 membered heteroaryl or 5-6 membered heteroaryl, and refers to an aromatic monovalent or divalent cyclic group with 5, 6, 7, 8, 9, 10, 11, 12, 13 or 14 ring-forming atoms that has at least one heteroatom selected from O, S and N. Preferably, it has 1 to 3 ring-forming heteroatoms. In addition, heteroaryl further includes the case of the carbon atoms or sulfur atoms as ring-forming atoms being substituted by oxygen or nitrogen, such as the case of the carbon atoms being substituted by C(=O), S(=O), S(=O)$_2$ and S(=O)(=NH). The heteroaromatic ring described in the present invention may be a monocyclic system or a polycyclic system (fused in the form of ortho-, spiro- or bridged). Heteroaryl includes monocyclic heteroaryl and polycyclic heteroaryl. Unless otherwise specified, a certain membered heteroaryl includes all possibly formed monocyclic, polycyclic, fully aromatic and partially aromatic cases. Monocyclic heteroaryl may be, for example, 5-7 membered heteroaryl or 5-6 membered heteroaryl, examples of which include, but are not limited to, furyl, imidazolyl, isoxazolyl, thiazolyl, isothiazolyl, oxadiazolyl, oxazolyl, isoxazolyl, pyridyl, pyridonyl, pyridazinyl, pyrimidinyl, pyrazinyl, pyrazolyl, pyrrolyl, tetrazolyl, thiadiazolyl, thiazolyl, thienyl, triazolyl and triazinyl. Polycyclic heteroaryl may be 8-12 membered ortho-fused heteroaryl or 9-10 membered ortho-fused heteroaryl, examples of which include, but are not limited to, benzimidazolyl, benzofuryl, isobenzofuryl, benzothienyl, benzothienyl, benzooxadiazolyl, benzothiazolyl, cinnolinyl, indazolyl, indolyl, isoindolyl, isoquinolinyl, naphthyridinyl, purinyl, quinolinyl, quinoxalinyl and quinazolinyl. The heteroaryl may also be divalent groups derived from the above groups.

In the present invention, "heteroatom" means an atom selected from S, O and N. In addition, in some cases, the cases of S or O being oxidized or nitridized are also included.

The "3-6 membered ring", "3-8 membered ring", "4-6 membered ring" and "4-7 membered ring" described in the present invention refer to chemically feasible ring structures with 3-6 ring atoms, 3-8 ring atoms, 4-6 ring atoms and 4-7 ring atoms; the ring atoms may be optionally selected from C, N, O, S, C(=O), S(=O), S(=O)$_2$ and S(=O)(=NH), and the formed ring structures may be monocyclic, fused polycyclic, saturated, partially saturated or aromatic. Specifically, examples may be the aforementioned groups enumerated as cycloalkyl, cycloalkenyl, heterocyclyl, aryl and heteroaryl.

In "amino" or a group containing "amino" described in the present invention, a group/subgroup with the amino as the terminal can be represented by —N(R$^e$)$_2$, wherein R$^e$ is each independently selected from hydrogen, the aforementioned C$_{1-6}$ alkyl optionally substituted by the substituent A of the present invention, the aforementioned C$_{2-6}$ alkenyl optionally substituted by the substituent A of the present invention, the aforementioned C$_{2-6}$ alkynyl optionally substituted by the substituent A of the present invention, the aforementioned cycloalkyl optionally substituted by the substituent A of the present invention, the aforementioned cycloalkenyl optionally substituted by the substituent A of the present invention, the aforementioned aryl optionally substituted by the substituent A of the present invention, the aforementioned heteroaryl optionally substituted by the substituent A of the present invention, the aforementioned heterocyclyl optionally substituted by the substituent A of the present invention, the aforementioned Cy$_2$ of the present invention optionally substituted by the substituent A of the present invention and other groups (including but not limited to carbonyl, sulfonyl, etc.) connected to an amino in the group containing "amino" in the present invention. In the present invention, a group/subgroup with an amino as a terminal in a group containing an "amino" means that the amino is bonded with two R$^e$ and then connected to other groups. For example, for "(C$_{1-6}$ alkyl)$_2$ amino", it corresponds to the case of a group with an amino as a terminal in a group containing "amino"; for "C$_{1-6}$ alkylamino", it corresponds to the case of a group with an amino as a terminal in a group containing "amino", in which one R$^e$ has already represented "C$_{1-6}$ alkyl" and the other R$^e$ represents the group enumerated above; for "(C$_{1-6}$ alkyl)$_2$ amino C$_{1-6}$ alkyl", the "(C$_{1-6}$ alkyl)$_2$ amino" therein corresponds to the case of a subgroup with an amino as a terminal in a group containing "amino", that is, the amino is bonded with two $C_{1-6}$ alkyl (corresponding to $R^e$) first and then $C_{1-6}$ alkyl; for "$(C_{1-6}$ alkyl$)_2$ aminocarbonyl", the "$(C_{1-6}$ alkyl$)_2$ amino" therein corresponds to the case of a subgroup with an amino as a terminal in a group containing "amino", that is, the amino is bonded with two $C_{1-6}$ alkyl (corresponding to $R^e$) first and then a carbonyl; for "$C_{1-6}$ alkylaminocarbonyl", the "$C_{1-6}$ alkylamino" therein corresponds to the case of a subgroup with an amino as a terminal in a group containing "amino", that is, the amino is bonded with a $C_{1-6}$ alkyl (corresponding to $R^e$) first and then a carbonyl, and one $R^e$ in the group has already represented "$C_{1-6}$ alkyl", and the other $R^e$ represents the group enumerated above; for "amino $C_{1-6}$ alkyl", the "amino" therein corresponds to the case of a subgroup with an amino as a terminal in a group containing "amino", and the amino in the group may be represented as —$N(R^e)_2$, that is, the group may be represented as "$N(R^e)_2$—$C_{1-6}$ alkyl". In sum, N in the amino in the present invention is trivalent

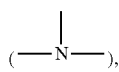

the two bonds in which may be bonded with $R^e$. In addition, in the present invention, the two $R^e$ in "—$N(R^e)_2$", along with an N atom, may form an nitrogen containing heterocyclyl having the definition described above in the present invention.

In the present invention, the term "optionally substituted" or "optionally substituted by" means that any portion of the moiety known to those skilled in the art to be available for being substituted may be unsubstituted or substituted by a substituent described in the present invention, wherein if one or more substituents are present, each substituent may be independently selected. In terms of substitution, the number of substituents is determined according to the number of positions capable of being substituted on a substituted group, and there may be 1 substitution, 2 substitutions, 3 substitutions, 4 substitutions, 5 substitutions, 6 substitutions, 7 substitutions, 8 substitutions or more as long as the number of the positions capable of being substituted on the substituted group is not exceeded. Under the existence of substituents, "one or more" substituents indicate that no less than one substituents are present, and the specific number of substituents varies according to a substituted group, and there may be 1 substitution, 2 substitutions, 3 substitutions, 4 substitutions, 5 substitutions, 6 substitutions, 7 substitutions, 8 substitutions or more as long as the number of the positions capable of being substituted on the substituted group is not exceeded.

In the present invention, "optionally substituted" added before a group or "optionally substituted by" added after a group indicates that all subgroups in the group can be optionally substituted. For example, for "$C_{7-12}$ alkylaryl optionally substituted by halogen", the alkyl moiety may be substituted by halogen, the aryl moiety may be substituted by halogen, or both the alkyl moiety and the aryl moiety may be substituted by halogen.

In the present invention, ⌒ in the ring structure represents a double bond optionally existing in the ring, and there may be 1, 2 or 3 double bonds, limited to the maximum number of double bonds that may exist in the ring. For example, in a 5 membered ring, one or two double bonds may exist; and in a 6 membered ring, one, two or three double bonds may exist.

In the present invention, ═══ represents a single bond or a double bond.

In the present invention, the "absence" of a certain group may mean that the group itself is absent; for example, for the definition of "$R^d$ is absent", when the ring-forming N atom is connected to adjacent atoms with single bonds and double bonds in a ring, $R^d$ is absent in the definition of "$NR^d$". In addition, it may also mean that the group is a bond; for example, for the definition of "$L_1$ is absent" in the present invention, it means that $L_1$ is a bond enabling the $Cy_1$ group to directly bond to a carbon atom connected with a $R_6$ group.

In the present invention, the substituent in "optionally substituted by substituents" may be the "substituent A" described in the present invention. The number of substituents is determined according to the number of positions capable of being substituted on a substituted group, and there may be 1 substitution, 2 substitutions, 3 substitutions, 4 substitutions, 5 substitutions, 6 substitutions, 7 substitutions, 8 substitutions or more.

In the present invention, the valences of all groups, substituents, chemical bonding sites, atoms, etc., do not violate the common knowledge in the chemical field. For example, carbon atoms are tetravalent, nitrogen atoms are trivalent, oxygen atoms are bivalent, and hydrogen atoms are monovalent.

Specifically, the present invention provides a compound shown as formula (I) below or a pharmaceutically acceptable salt, ester, stereoisomer or tautomer thereof:

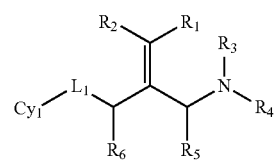

wherein $R_1$ and $R_2$ are each independently selected from hydrogen and halogen, and $R_1$ and $R_2$ are not both hydrogen;

$R_3$ and $R_4$ are each independently selected from hydrogen and $C_{1-6}$ alkyl optionally substituted by a substituent A, or form a 5-10 membered nitrogen containing heterocyclyl optionally substituted by a substituent A along with an N atom connected thereto;

$R_5$ and $R_6$ are each independently selected from hydrogen and $C_{1-6}$ alkyl optionally substituted by a substituent A;

$L_1$ is a bond or —CR'R"—, —NR'—, —S—, —SO$_2$—, —S(O)—, —SONR'—, —SO$_2$NR'— or —NR'CONR'—, and R' and R" are each independently selected from hydrogen and $C_{1-6}$ alkyl optionally substituted by a substituent A;

$Cy_1$ is a group shown as general formula (A), (a), (b) or (c) below that is unsubstituted or substituted by one or more $R^a$:

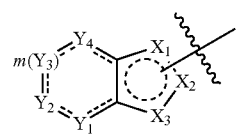

-continued

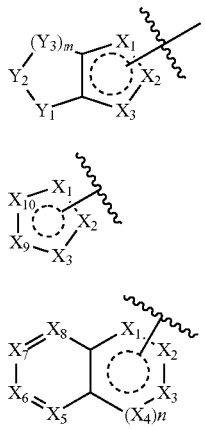

m is an integer from 0 to 3, and n is an integer from 0 to 2;

$Y_1$, $Y_2$, $Y_3$ and $Y_4$ are each independently selected from $CR^cR^c$, $NR^d$, O and S;

$X_1$, $X_2$, $X_3$, $X_4$, $X_9$ and $X_{10}$ are each independently selected from $CR^cR^c$, $NR^d$, O and S, $X_5$, $X_6$, $X_7$ and $X_8$ are each independently selected from $CR^cR^c$ and $NR^d$, and at least one of $X_1$, $X_2$ and $X_3$ is $NR^d$;

each $R^a$ is independently selected from hydroxyl, amino, carboxyl, cyano, nitro, halogen, aminocarboxyl, $C_{1-6}$ alkyl optionally substituted by one or more $R^b$, $C_{2-6}$ alkenyl optionally substituted by one or more $R^b$, $C_{2-6}$ alkynyl optionally substituted by one or more $R^b$, $C_{1-6}$ alkoxy optionally substituted by one or more $R^b$, $C_{1-6}$ alkoxy $C_{1-6}$ alkyl optionally substituted by one or more $R^b$, $C_{1-6}$ alkoxy $C_{1-6}$ alkoxy optionally substituted by one or more $R^b$, $C_{1-6}$ alkylthio optionally substituted by one or more $R^b$, $C_{1-6}$ alkylthio $C_{1-6}$ alkyl optionally substituted by one or more $R^b$, $C_{1-6}$ alkylamino optionally substituted by one or more $R^b$, $(C_{1-6}$ alkyl$)_2$ amino optionally substituted by one or more $R^b$, $C_{1-6}$ alkylamino $C_{1-6}$ alkyl optionally substituted by one or more $R^b$, $(C_{1-6}$ alkyl$)_2$ amino $C_{1-6}$ alkyl optionally substituted by one or more $R^b$, $C_{1-6}$ alkylaminocarbonyl optionally substituted by one or more $R^b$, $(C_{1-6}$ alkyl$)_2$ aminocarbonyl optionally substituted by one or more $R^b$, $C_{1-6}$ alkylaminocarbonyl $C_{1-6}$ alkyl optionally substituted by one or more $R^b$, $(C_{1-6}$ alkyl$)_2$ aminocarbonyl $C_{1-6}$ alkyl optionally substituted by one or more $R^b$, $C_{1-6}$ alkylcarbonylamino optionally substituted by one or more $R^b$, $C_{1-6}$ alkylcarbonylamino $C_{1-6}$ alkyl optionally substituted by one or more $R^b$, $C_{1-6}$ alkylcarbonyl optionally substituted by one or more $R^b$, $C_{1-6}$ alkylcarbonyl $C_{1-6}$ alkyl optionally substituted by one or more $R^b$, $C_{1-6}$ alkylaminosulfonyl optionally substituted by one or more $R^b$, $(C_{1-6}$ alkyl$)_2$ aminosulfonyl optionally substituted by one or more $R^b$, $C_{1-6}$ alkylaminosulfonyl $C_{1-6}$ alkyl optionally substituted by one or more $R^b$, $(C_{1-6}$ alkyl$)_2$ aminosulfonyl $C_{1-6}$ alkyl optionally substituted by one or more $R^b$, $C_{1-6}$ alkylsulfonylamino optionally substituted by one or more $R^b$, $C_{1-6}$ alkylsulfonylamino $C_{1-6}$ alkyl optionally substituted by one or more $R^b$, $C_{1-6}$ alkylsulfonyl optionally substituted by one or more $R^b$, $C_{1-6}$ alkylsulfonyl $C_{1-6}$ alkyl optionally substituted by one or more $R^b$, $Cy_2$ optionally substituted by one or more $R^b$, $Cy_2$-$C_{1-6}$ alkyl optionally substituted by one or more $R^b$, $Cy_2$-$C_{1-6}$ alkoxy optionally substituted by one or more $R^b$, $Cy_2$-carbonyl optionally substituted by one or more $R^b$, $Cy_2$-aminocarbonyl optionally substituted by one or more $R^b$ and $Cy_2$-carbonylamino optionally substituted by one or more $R^b$, and $Cy_2$ is each independently selected from 3-12 membered cycloalkyl, 3-12 membered cycloalkenyl, 3-12 membered heterocyclyl, 6-10 membered aryl and 5-14 membered heteroaryl;

each $R^b$ is independently selected from hydroxyl, amino, carboxyl, cyano, nitro, halogen, aminocarbonyl, $C_{1-6}$ alkyl, $C_{2-6}$ alkenyl, $C_{2-6}$ alkynyl, $C_{1-6}$ alkoxy, amino $C_{1-6}$ alkyl, $C_{1-6}$ haloalkyl, $C_{1-6}$ alkoxy $C_{1-6}$ alkyl, $C_{1-6}$ alkoxy $C_{1-6}$ alkoxy, amino $C_{1-6}$ alkoxy, $C_{1-6}$ haloalkoxy, $C_{1-6}$ alkylthio, $C_{1-6}$ alkylamino, $(C_{1-6}$ alkyl$)_2$ amino, $C_{1-6}$ alkylaminocarbonyl, $(C_{1-6}$ alkyl$)_2$ aminocarbonyl, $C_{1-6}$ alkylcarbonylamino, $C_{1-6}$ alkylcarbonyl, $C_{1-6}$ alkylaminosulfonyl, $(C_{1-6}$ alkyl$)_2$ aminosulfonyl, $C_{1-6}$ alkylsulfonylamino and $C_{1-6}$ alkylsulfonyl;

the substituents A are each independently selected from hydroxyl, amino, carboxyl, cyano, nitro, halogen, aminocarbonyl, $C_{1-6}$ alkyl, $C_{2-6}$ alkenyl, $C_{2-6}$ alkynyl, $C_{1-6}$ alkoxy, amino $C_{1-6}$ alkyl, $C_{1-6}$ alkoxy $C_{1-6}$ alkyl, $C_{1-6}$ alkoxy $C_{1-6}$ alkoxy, amino $C_{1-6}$ alkoxy, $C_{1-6}$ alkylamino, $(C_{1-6}$ alkyl$)_2$ amino, $C_{1-6}$ alkylaminocarbonyl, $(C_{1-6}$ alkyl$)_2$ aminocarbonyl, $C_{1-6}$ alkylcarbonylamino, $C_{1-6}$ alkylcarbonyl, $C_{1-6}$ alkylsulfonylamino, $C_{1-6}$ alkylaminosulfonyl, $(C_{1-6}$ alkyl$)_2$ aminosulfonyl, $C_{1-6}$ haloalkyl, $C_{1-6}$ haloalkoxy, $C_{1-6}$ alkylsulfonyl, $C_{1-6}$ alkylthio, 3-12 membered cycloalkyl, 6-10 membered aryl, 3-12 membered heterocyclyl, 5-14 membered heteroaryl and oxo;

$R^c$ is absent, or is each independently selected from hydrogen atom when present; or two $R^c$ form an oxo group together;

$R^d$ is absent, or is each independently selected from hydrogen atom when present;

=== represents a single bond or a double bond;

⋯ represents a double bond optionally present in the ring structure; with the proviso that when $Cy_1$ is formula (c), formula (c) is substituted by one or more $R^a$; and with the proviso that when $Cy_1$ is formula (b), $X_1$, $X_2$, $X_3$, $X_9$ and $X_{10}$ are not C=O.

In one embodiment of the present invention, $R_1$ and $R_2$ are each independently selected from hydrogen and halogen, and $R_1$ and $R_2$ are not both hydrogen. In one embodiment of the present invention, $R_1$ and $R_2$ are each independently selected from hydrogen, fluorine, chlorine, bromine and iodine, and $R_1$ and $R_2$ are not both hydrogen. In one embodiment of the present invention, $R_1$ and $R_2$ are each independently selected from hydrogen, fluorine and chlorine, and $R_1$ and $R_2$ are not both hydrogen. In one embodiment of the present invention, $R_1$ is hydrogen, and $R_2$ is fluorine. In one embodiment of the present invention, $R_1$ and $R_2$ form 5-8 nitrogen containing heterocyclyl along with N atoms connected thereto.

In one embodiment of the present invention, $R_3$ and $R_4$ are each independently selected from hydrogen and $C_{1-6}$ alkyl. In one embodiment of the present invention, $R_3$ and $R_4$ are each independently selected from hydrogen and $C_{1-4}$ alkyl. In one embodiment of the present invention, $R_3$ and $R_4$ are each independently selected from hydrogen, methyl, ethyl, propyl, isopropyl, butyl, sec-butyl and tert-butyl. In one embodiment of the present invention, $R_3$ and $R_4$ are hydrogen. In one embodiment of the present invention, $R_3$ and $R_4$ form 5-6 membered nitrogen containing heterocyclyl along with N atoms connected thereto. In one embodiment of the present invention, $R_3$ and $R_4$ form pyrrolinyl, pyrrolidinyl, piperidyl or morpholinyl along with N atoms connected thereto.

In one embodiment of the present invention, $R_5$ and $R_6$ are each independently selected from hydrogen and $C_{1-6}$ alkyl. In one embodiment of the present invention, $R_5$ and $R_6$ are each independently selected from hydrogen and $C_{1-4}$ alkyl. In one embodiment of the present invention, $R_5$ and $R_6$ are each independently selected from hydrogen, methyl, ethyl, propyl, isopropyl, butyl, sec-butyl and tert-butyl. In one embodiment of the present invention, $R_5$ and $R_6$ are hydrogen.

In one embodiment of the present invention, $L_1$ is a bond or —CR'R"—, —NR'— or —S—, and R' and R" are each independently selected from hydrogen and $C_{1-6}$ alkyl. In one embodiment of the present invention, $L_1$ is a bond, —NR'— or —S—, and R' and R" are each independently selected from hydrogen and $C_{1-6}$ alkyl. In one embodiment of the present invention, $L_1$ is a bond or —NR'—, and R' is selected from hydrogen and $C_{1-6}$ alkyl. In one embodiment of the present invention, $L_1$ is a bond.

In one embodiment of the present invention, for formula (A), when $R^a$ is present, at least one $R^a$ is connected to any one of $Y_1$, $Y_2$, $Y_3$ and $Y_4$. In one embodiment of the present invention, for formula (a), when $R^a$ is present, at least one $R^a$ is connected to any one of $Y_1$, $Y_2$ and $Y_3$. In one embodiment of the present invention, for formula (c), at least one $R^a$ is present, and at least one $R^a$ is connected to any one of $X_5$, $X_6$, $X_7$ and $X_8$.

In one embodiment of the present invention, for formula (A), the Li group is connected to $X_1$, $X_2$ or $X_3$ in formula (A). In one embodiment of the present invention, for formula (a), the $L_1$ group is connected to $X_1$, $X_2$ or $X_3$ in formula (a). In one embodiment of the present invention, for formula (c), the $L_1$ group is connected to $X_1$, $X_2$, $X_3$ or $X_4$ in formula (c).

In one embodiment of the present invention, the $L_1$ group is connected to an N atom.

In one embodiment of the present invention, $Cy_1$ is a group shown as general formula (A-1), (A-2), (A-3), (a), (b) or (c) below that is unsubstituted or substituted by one or more $R^a$:

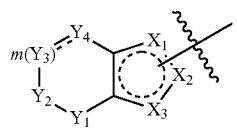

(A-1)

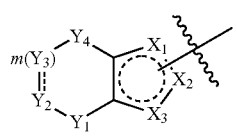

(A-2)

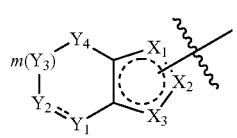

(A-3)

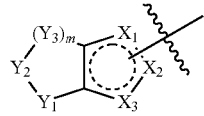

(a)

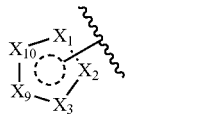

(b)

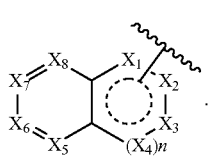

(c)

In one embodiment of the present invention, $Cy_1$ is a group shown as general formula (A-11), (a-1), (a-2), (b-1), (c-1) or (c-2) below that is unsubstituted or substituted by one or more $R^a$:

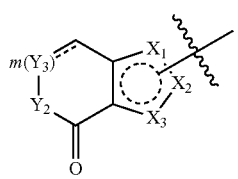

(A-11)

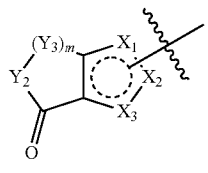

(a-1)

(a-2)

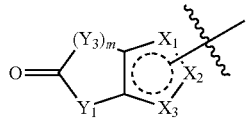

(b-1)

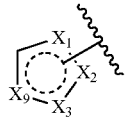

(c-1)

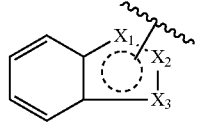

(c-2)

In one embodiment of the present invention, when $Cy_1$ is formula (c-1) or (c-2), formula (c-1) or (c-2) is substituted by one or more $R^a$.

In one embodiment of the present invention, when $Cy_1$ is formula (b-1), $X_1$, $X_2$, $X_3$ and $X_9$ are not C=O.

In one embodiment of the present invention, for formula (A-11), when $R^a$ is present, at least one Ra is connected to $Y_2$. In one embodiment of the present invention, for formula (a-1), when $R^a$ is present, at least one $R^a$ is connected to $Y_2$.

In one embodiment of the present invention, for formula (a-2), when $R^a$ is present, at least one $R^a$ is connected to $Y_1$. In one embodiment of the present invention, for formula (b-1), when $R^a$ is present, at least one $R^a$ is connected to a ring-forming carbon atom. In one embodiment of the present invention, for formulas (c-1) and (c-2), at least one $R^a$ is present, and at least one $R^a$ is connected to a benzene ring group.

In one embodiment of the present invention, m is an integer from 0 to 3. In one embodiment of the present invention, m is 1 or 2. In one embodiment of the present invention, n is an integer from 0 to 2. In one embodiment of the present invention, n is 1 or 2.

In one embodiment of the present invention, $R^c$ is absent, or is each independently selected from hydrogen atom when present; or two $R^c$ form an oxo group together.

In one embodiment of the present invention, $R^d$ is absent, or is each independently selected from hydrogen atom.

In one embodiment of the present invention, $Y_1$, $Y_2$, $Y_3$ and $Y_4$ are each independently selected from $CR^cR^c$ and $NR^d$. In one embodiment of the present invention, at least one of $Y_1$, $Y_2$, $Y_3$ and $Y_4$ is C=O. In one embodiment of the present invention, $Y_1$, $Y_2$ and $Y_3$ are each independently selected from $CH_2$, NH, CH and N.

In one embodiment of the present invention, $X_1$, $X_2$, $X_3$, $X_4$, $X_9$ and $X_{10}$ are each independently selected from $CR^cR^c$ and $NR^d$, and at least one of $X_1$, $X_2$ and $X_3$ is N or $NR^d$. In one embodiment of the present invention, $X_1$, $X_2$, $X_3$, $X_4$ and $X_9$ are each independently selected from $CH_2$, CH, N, NH and C=O, and at least one of $X_1$, $X_2$ and $X_3$ is N or NH.

In one embodiment of the present invention, $X_5$, $X_6$, $X_7$ and $X_8$ are each independently selected from $CR^cR^c$ and $NR^d$.

In one embodiment of the present invention, $Cy_1$ is a group shown as general formula (A-11) or (a-1) below that is unsubstituted or substituted by one or more $R^a$:

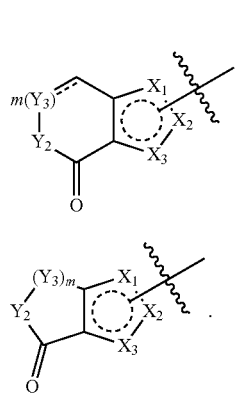

In one embodiment of the present invention, in formulas (A-11) and (a-1), $Y_2$ and $Y_3$ are each independently selected from $CH_2$, NH, CH and N. In one embodiment of the present invention, in formulas (A-11) and (a-1), $X_1$, $X_2$ and $X_3$ are each independently selected from $CH_2$, CH, N, NH and C=O, and at least one of $X_1$, $X_2$ and $X_3$ is N or NH.

In one embodiment of the present invention, in formula (A-11), $X_1$ and $X_2$ are each independently selected from $CH_2$, CH, N and NH. In one embodiment of the present invention, in formula (a-1), $X_1$ and $X_2$ are each independently selected from $CH_2$, CH, N and NH. In one embodiment of the present invention, in formulas (A-11) and (a-1), $Y_2$ is NH. In one embodiment of the present invention, in formulas (A-11) and (a-1), $Y_3$ is $CH_2$ or CH. In one embodiment of the present invention, in formulas (A-11) and (a-1), when $R^a$ is present, at least one $R^a$ is connected to the position $Y_2$. In one embodiment of the present invention, in formulas (A-11) and (a-1), the $L_1$ group is connected to $X_1$, $X_2$ or $X_3$. In one embodiment of the present invention, in formulas (A-11) and (a-1), the $L_1$ group is connected to an N atom.

In one embodiment of the present invention, $Cy_1$ is one of the following groups that is unsubstituted or substituted by one or more $R^a$:

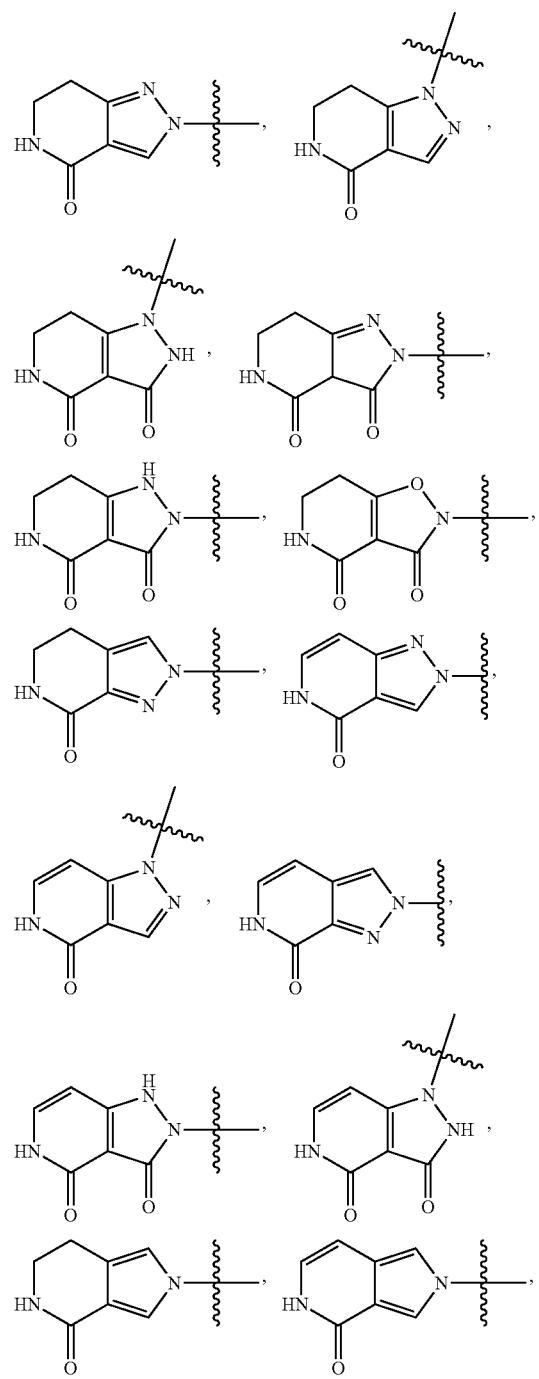

-continued

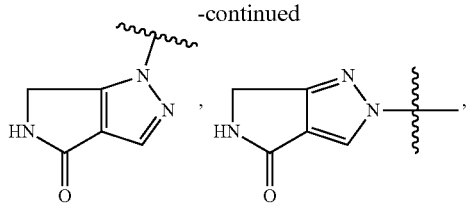

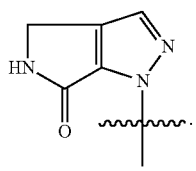

In one embodiment of the present invention, $Cy_1$ is a group shown as general formula (b-1) below that is unsubstituted or substituted by one or more $R^a$:

(b-1)

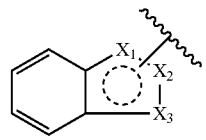

In one embodiment of the present invention, in formula (b-1), $X_1$, $X_2$, $X_3$ and $X_9$ are each independently selected from $CH_2$, CH, N and NH, and at least one of $X_1$, $X_2$ and $X_3$ is N or NH.

In one embodiment of the present invention, in formula (b-1), the Li group is connected to the N atom in formula (b-1). In one embodiment of the present invention, in formula (b-1), when $R^a$ is present, at least one $R^a$ is connected to the carbon atom of formula (b-1).

In one embodiment of the present invention, $Cy_1$ is one of the following groups that is unsubstituted or substituted by one or more $R^a$:

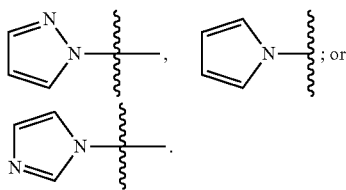

In one embodiment of the present invention, $Cy_1$ is a group shown as general formula (c-1) below that is substituted by one or more $R^a$:

(c-1)

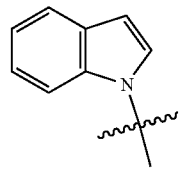

In one embodiment of the present invention, in formula (c-1), $X_1$, $X_2$ and $X_3$ are each independently selected from $CH_2$, CH, N, NH and C=O, and at least one of $X_1$, $X_2$ and $X_3$ is N or NH.

In one embodiment of the present invention, in formula (c-1), at least one $R^a$ is connected to the benzene ring moiety in formula (c-1). In one embodiment of the present invention, in formula (c-1), the $L_1$ group is connected to $X_1$, $X_2$ or $X_3$. In one embodiment of the present invention, in formula (c-1), the $L_1$ group is connected to the N atom in formula (c-1).

In one embodiment of the present invention, $Cy_1$ is the following group that is substituted by one or more substituent $R^a$:

In one embodiment of the present invention, each $R^a$ is independently selected from hydroxyl, amino, carboxyl, cyano, nitro, halogen, aminocarbonyl, $C_{1-6}$ alkyl optionally substituted by one or more $R^b$, $C_{1-6}$ alkoxy optionally substituted by one or more $R^b$, $C_{1-6}$ alkoxy $C_{1-6}$ alkyl optionally substituted by one or more $R^b$, $C_{1-6}$ alkoxy $C_{1-6}$ alkoxy optionally substituted by one or more $R^b$, $C_{1-6}$ alkylthio optionally substituted by one or more $R^b$, $C_{1-6}$ alkylthio $C_{1-6}$ alkyl optionally substituted by one or more $R^b$, $C_{1-6}$ alkylamino optionally substituted by one or more $R^b$, $(C_{1-6}$ alkyl$)_2$ amino optionally substituted by one or more $R^b$, $C_{1-6}$ alkylamino $C_{1-6}$ alkyl optionally substituted by one or more $R^b$, $(C_{1-6}$ alkyl$)_2$ amino $C_{1-6}$ alkyl optionally substituted by one or more $R^b$, $C_{1-6}$ alkylaminocarbonyl optionally substituted by one or more $R^b$, $(C_{1-6}$ alkyl$)_2$ aminocarbonyl optionally substituted by one or more $R^b$, $C_{1-6}$ alkylaminocarbonyl $C_{1-6}$ alkyl optionally substituted by one or more $R^b$, $(C_{1-6}$ alkyl$)_2$ aminocarbonyl $C_{1-6}$ alkyl optionally substituted by one or more $R^b$, $C_{1-6}$ alkylcarbonylamino optionally substituted by one or more $R^b$, $C_{1-6}$ alkylcarbonylamino $C_{1-6}$ alkyl optionally substituted by one or more $R^b$, $C_{1-6}$ alkylcarbonyl optionally substituted by one or more $R^b$, $C_{1-6}$ alkylcarbonyl $C_{1-6}$ alkyl optionally substituted by one or more $R^b$, $Cy_2$- optionally substituted by one or more $R^b$, $Cy_2$-$C_{1-6}$ alkyl optionally substituted by one or more $R^b$, $Cy_2$-$C_{1-6}$ alkoxy optionally substituted by one or more $R^b$, $Cy_2$-carbonyl optionally substituted by one or more $R^b$, $Cy_2$-aminocarbonyl optionally substituted by one or more $R^b$ and $Cy_2$-carbonylamino optionally substituted by one or more $R^b$.

In one embodiment of the present invention, each $R^a$ is independently selected from hydroxyl, amino, carboxyl, cyano, nitro, halogen, aminocarbonyl, $C_{1-6}$ alkyl optionally substituted by one or more $R^b$, $C_{1-6}$ alkoxy optionally substituted by one or more $R^b$, $C_{1-6}$ alkoxy $C_{1-6}$ alkyl optionally substituted by one or more $R^b$, $C_{1-6}$ alkoxy $C_{1-6}$ alkoxy optionally substituted by one or more $R^b$, $C_{1-6}$ alkylamino optionally substituted by one or more $R^b$, $(C_{1-6}$ alkyl$)_2$ amino optionally substituted by one or more $R^b$, $C_{1-6}$ alkylamino $C_{1-6}$ alkyl optionally substituted by one or more $R^b$, $(C_{1-6}$ alkyl$)_2$ amino $C_{1-6}$ alkyl optionally substituted by one or more $R^b$, $C_{1-6}$ alkylaminocarbonyl optionally substituted by one or more $R^b$, $(C_{1-6}$ alkyl$)_2$ aminocarbonyl optionally substituted by one or more $R^b$, $C_{1-6}$ alkylaminocarbonyl $C_{1-6}$ alkyl optionally substituted by one or more $R^b$, $(C_{1-6}$ alkyl$)_2$ aminocarbonyl $C_{1-6}$ alkyl optionally substituted by one or more $R^b$, $C_{1-6}$ alkylcarbonylamino optionally substituted by one or more $R^b$, $C_{1-6}$ alkylcarbonylamino $C_{1-6}$ alkyl optionally substituted by one or more $R^b$, $C_{1-6}$ alkylcarbonyl optionally substituted by one or more $R^b$, $C_{1-6}$ alkylcarbonyl $C_{1-6}$ alkyl optionally substituted by one or more $R^b$, $Cy_2$- optionally substituted by one or more $R^b$, $Cy_2$-$C_{1-6}$ alkyl optionally substituted by one or more $R^b$, $Cy_2$-$C_{1-6}$ alkoxy optionally substituted by one or more $R^b$, $Cy_2$-carbonyl optionally substituted by one or more $R^b$, $Cy_2$-aminocarbonyl optionally substituted by one or more $R^b$, and $Cy_2$-carbonylamino optionally substituted by one or more $R^b$.

In one embodiment of the present invention, each $R^a$ is independently selected from hydroxyl, amino, carboxyl, cyano, nitro, halogen, aminocarbonyl, $C_{1-6}$ alkyl optionally substituted by one or more $R^b$, $C_{1-6}$ alkoxy optionally substituted by one or more $R^b$, $C_{1-6}$ alkoxy $C_{1-6}$ alkyl optionally substituted by one or more $R^b$, $C_{1-6}$ alkoxy $C_{1-6}$ alkoxy optionally substituted by one or more $R^b$, $C_{1-6}$ alkylamino optionally substituted by one or more $R^b$, $(C_{1-6}$ alkyl$)_2$ amino optionally substituted by one or more $R^b$, $C_{1-6}$ alkylamino $C_{1-6}$ alkyl optionally substituted by one or more $R^b$, $(C_{1-6}$ alkyl$)_2$ amino $C_{1-6}$ alkyl optionally substituted by one or more $R^b$, $C_{1-6}$ alkylaminocarbonyl optionally substituted by one or more $R^b$, $(C_{1-6}$ alkyl$)_2$ aminocarbonyl optionally substituted by one or more $R^b$, $C_{1-6}$ alkylaminocarbonyl $C_{1-6}$ alkyl optionally substituted by one or more $R^b$, $(C_{1-6}$ alkyl$)_2$ aminocarbonyl $C_{1-6}$ alkyl optionally substituted by one or more $R^b$, $C_{1-6}$ alkylcarbonylamino optionally substituted by one or more $R^b$, $C_{1-6}$ alkylcarbonylamino $C_{1-6}$ alkyl optionally substituted by one or more $R^b$, $C_{1-6}$ alkylcarbonyl optionally substituted by one or more $R^b$, $C_{1-6}$ alkylcarbonyl $C_{1-6}$ alkyl optionally substituted by one or more $R^b$, $Cy_2$- optionally substituted by one or more $R^b$, $Cy_2$-$C_{1-6}$ alkyl optionally substituted by one or more $R^b$, $Cy_2$-$C_{1-6}$ alkoxy optionally substituted by one or more $R^b$, $Cy_2$-carbonyl optionally substituted by one or more $R^b$, and $Cy_2$-aminocarbonyl optionally substituted by one or more $R^b$.

In one embodiment of the present invention, each $R^a$ is independently selected from hydroxyl, amino, carboxyl, cyano, nitro, halogen, aminocarbonyl, $C_{1-6}$ alkyl optionally substituted by one or more $R^b$, $C_{1-6}$ alkoxy optionally substituted by one or more $R^b$, $C_{1-6}$ alkoxy $C_{1-6}$ alkyl optionally substituted by one or more $R^b$, $C_{1-6}$ alkoxy $C_{1-6}$ alkoxy optionally substituted by one or more $R^b$, $C_{1-6}$ alkylamino optionally substituted by one or more $R^b$, $C_{1-6}$ alkylamino $C_{1-6}$ alkyl optionally substituted by one or more $R^b$, $C_{1-6}$ alkylaminocarbonyl optionally substituted by one or more $R^b$, $C_{1-6}$ alkylaminocarbonyl $C_{1-6}$ alkyl optionally substituted by one or more $R^b$, $C_{1-6}$ alkylcarbonylamino optionally substituted by one or more $R^b$, $C_{1-6}$ alkylcarbonylamino $C_{1-6}$ alkyl optionally substituted by one or more $R^b$, $C_{1-6}$ alkylcarbonyl optionally substituted by one or more $R^b$, $C_{1-6}$ alkylcarbonyl $C_{1-6}$ alkyl optionally substituted by one or more $R^b$, $Cy_2$- optionally substituted by one or more $R^b$, $Cy_2$-$C_{1-6}$ alkyl optionally substituted by one or more $R^b$, $Cy_2$-$C_{1-6}$ alkoxy optionally substituted by one or more $R^b$, $Cy_2$-carbonyl optionally substituted by one or more $R^b$ and $Cy_2$-aminocarbonyl optionally substituted by one or more $R^b$.

In one embodiment of the present invention, each $R^a$ is independently selected from halogen, cyano, $C_{1-6}$ alkyl optionally substituted by at least one of halogen, $C_{1-6}$ alkyl, $C_{1-6}$ alkoxy and 3-6 membered cycloalkyl, 3-8 membered cycloalkyl optionally substituted by at least one of halogen, $C_{1-6}$ alkyl and $C_{1-6}$ alkoxy, phenyl optionally substituted by at least one of halogen, $C_{1-6}$ alkyl and $C_{1-6}$ alkoxy, and 5-6 membered heteroaryl optionally substituted by at least one of halogen, $C_{1-6}$ alkyl and $C_{1-6}$ alkoxy.

In one embodiment of the present invention, $R^a$ is each independently selected from $C_{1-6}$ alkyl optionally substituted by halogen; halogen; aminocarbonyl; $C_{1-6}$ alkylaminocarbonyl optionally substituted by halogen; $(C_{1-6}$ alkyl$)_2$ aminocarbonyl optionally substituted by halogen; 3-8 membered cycloalkylaminocarbonyl optionally substituted by at least one of halogen, $C_{1-6}$ alkyl and $C_{1-6}$ alkoxy; phenylaminocarbonyl optionally substituted by at least one of halogen, $C_{1-6}$ alkyl and $C_{1-6}$ alkoxy; 5-6 membered heteroarylaminocarbonyl optionally substituted by at least one of halogen, $C_{1-6}$ alkyl and $C_{1-6}$ alkoxy; and 5-10 membered heterocyclylcarbonyl optionally substituted by at least one of halogen, $C_{1-6}$ alkyl and $C_{1-6}$ alkoxy.

In one embodiment of the present invention, each $R^a$ is independently selected from hydroxyl, amino, cyano, halogen, aminocarbonyl, $C_{1-4}$ alkyl optionally substituted by one or more $R^b$, $C_{1-4}$ alkoxy optionally substituted by one or more $R^b$, $C_{1-4}$ alkoxy $C_{1-4}$ alkyl optionally substituted by one or more $R^b$, $C_{1-4}$ alkoxy $C_{1-4}$ alkoxy optionally substituted by one or more $R^b$, $C_{1-4}$ alkylthio optionally substituted by one or more $R^b$, $C_{1-4}$ alkylthio $C_{1-4}$ alkyl optionally substituted by one or more $R^b$, $C_{1-4}$ alkylamino optionally substituted by one or more $R^b$, $(C_{1-4}$ alkyl$)_2$ amino optionally substituted by one or more $R^b$, $C_{1-4}$ alkylamino $C_{1-4}$ alkyl optionally substituted by one or more $R^b$, $(C_{1-4}$ alkyl$)_2$ amino $C_{1-4}$ alkyl optionally substituted by one or more $R^b$, $C_{1-4}$ alkylaminocarbonyl optionally substituted by one or more $R^b$, $(C_{1-4}$ alkyl$)_2$ aminocarbonyl optionally substituted by one or more $R^b$, $C_{1-4}$ alkylaminocarbonyl $C_{1-4}$ alkyl optionally substituted by one or more $R^b$, $(C_{1-4}$ alkyl$)_2$ aminocarbonyl $C_{1-4}$ alkyl optionally substituted by one or more $R^b$, $C_{1-4}$ alkylcarbonylamino optionally substituted by one or more $R^b$, $C_{1-4}$ alkylcarbonylamino $C_{1-4}$ alkyl optionally substituted by one or more $R^b$, $C_{1-4}$ alkylcarbonyl optionally substituted by one or more $R^b$, $C_{1-4}$ alkylcarbonyl $C_{1-4}$ alkyl optionally substituted by one or more $R^b$, $Cy_2$- optionally substituted by one or more $R^b$, $Cy_2$-$C_{1-4}$ alkyl optionally substituted by one or more $R^b$, $Cy_2$-$C_{1-4}$ alkoxy optionally substituted by one or more $R^b$, $Cy_2$-carbonyl optionally substituted by one or more $R^b$, $Cy_2$-aminocarbonyl optionally substituted by one or more $R^b$ and $Cy_2$-carbonylamino optionally substituted by one or more $R^b$.

In one embodiment of the present invention, $R^a$ is each independently selected from halogen, cyano, $C_{1-4}$ alkyl optionally substituted by at least one of halogen, $C_{1-6}$ alkyl, $C_{1-6}$ alkoxy and 3-5 membered cycloalkyl, 3-5 membered cycloalkyl optionally substituted by at least one of halogen, $C_{1-6}$ alkyl and $C_{1-6}$ alkoxy, phenyl optionally substituted by at least one of halogen, $C_{1-6}$ alkyl and $C_{1-6}$ alkoxy, and 5-6 membered nitrogen heteroaryl optionally substituted by at least one of halogen, $C_{1-6}$ alkyl and $C_{1-6}$ alkoxy. In one embodiment of the present invention, $R^a$ is each independently selected from fluorine; chlorine; bromine; cyano; methyl, ethyl, propyl, isopropyl, butyl, isobutyl, sec-butyl and tert-butyl optionally substituted by at least one of halogen, $C_{1-6}$ alkyl, $C_{1-6}$ alkoxy and 3-5 membered cycloalkyl; cyclopropyl, cyclobutyl and cyclopentyl optionally substituted by at least one of halogen and $C_{1-6}$ alkyl; phenyl optionally substituted by at least one of halogen and $C_{1-6}$ alkyl; and pyrrolyl, imidazolyl, pyrazolyl, oxazolyl and thiazolyl optionally substituted by at least one of halogen and $C_{1-6}$ alkyl.

In one embodiment of the present invention, each $R^a$ is independently selected from aminocarbonyl, $C_{1-4}$ alkylaminocarbonyl optionally substituted by halogen, $(C_{1-4}$ alkyl$)_2$ aminocarbonyl optionally substituted by halogen, 3-5 membered cycloalkylaminocarbonyl optionally substituted by at least one of halogen, $C_{1-6}$ alkyl and $C_{1-6}$ alkoxy, phenylaminocarbonyl optionally substituted by at least one of halogen, $C_{1-6}$ alkyl and $C_{1-6}$ alkoxy and 5-6 membered nitrogen containing heterocyclylcarbonyl optionally substituted by at least one of halogen, $C_{1-6}$ alkyl and $C_{1-6}$ alkoxy.

In one embodiment of the present invention, $R^a$ is each independently selected from aminocarbonyl, methylaminocarbonyl optionally substituted by halogen, ethylaminocarbonyl optionally substituted by halogen, propylaminocarbonyl optionally substituted by halogen, isopropylaminocarbonyl optionally substituted by halogen, n-aminocarbonyl optionally substituted by halogen, isobutylaminocarbonyl optionally substituted by halogen, sec-butylaminocarbonyl optionally substituted by halogen, tert-butylaminocarbonyl optionally substituted by halogen, cyclopropylaminocarbonyl optionally substituted by at least one of halogen and $C_{1-6}$ alkyl, cyclobutylaminocarbonyl optionally substituted by at least one of halogen and $C_{1-6}$ alkyl, cyclopentylaminocarbonyl optionally substituted by at least one of halogen and $C_{1-6}$ alkyl, phenylaminocarbonyl optionally substituted by at least one of halogen and $C_{1-6}$ alkyl, pyrrolidinylcarbonyl optionally substituted by at least one of halogen and $C_{1-6}$ alkyl, piperidylcarbonyl optionally substituted by at least one of halogen and $C_{1-6}$ alkyl and piperazinylcarbonyl optionally substituted by at least one of halogen and $C_{1-6}$ alkyl.

In one embodiment of the present invention, $R^a$ is each independently selected from aminocarbonyl, methylaminocarbonyl optionally substituted by halogen, ethylaminocarbonyl optionally substituted by halogen, propylaminocarbonyl optionally substituted by halogen, isopropylaminocarbonyl optionally substituted by halogen, n-aminocarbonyl optionally substituted by halogen, isobutylaminocarbonyl optionally substituted by halogen, sec-butylaminocarbonyl optionally substituted by halogen, tert-buty 1 aminocarbonyl optionally substituted by halogen, cyclopropylaminocarbonyl optionally substituted by at least one of halogen, $C_{1-6}$ alkyl and $C_{1-6}$ alkoxy, cyclobutylaminocarbonyl optionally substituted by at least one of halogen, $C_{1-6}$ alkyl and $C_{1-6}$ alkoxy, cyclopentylaminocarbonyl optionally substituted by at least one of halogen, $C_{1-6}$ alkyl and $C_{1-6}$ alkoxy; phenylaminocarbonyl optionally substituted by at least one of halogen, $C_{1-6}$ alkyl and $C_{1-6}$ alkoxy; azetidinylcarbonyl optionally substituted by at least one of halogen, $C_{1-6}$ alkyl and $C_{1-6}$ alkoxy, pyrrolidinylcarbonyl optionally substituted by at least one of halogen, $C_{1-6}$ alkyl and $C_{1-6}$ alkoxy, piperidylcarbonyl optionally substituted by at least one of halogen, $C_{1-6}$ alkyl and $C_{1-6}$ alkoxy, piperazinylcarbonyl optionally substituted by at least one of halogen, $C_{1-6}$ alkyl and $C_{1-6}$ alkoxy and morpholinylcarbonyl optionally substituted by at least one of halogen, $C_{1-6}$ alkyl and $C_{1-6}$ alkoxy.

In one embodiment of the present invention, when $R^a$ is each independently selected from azetidinylcarbonyl optionally substituted by at least one of halogen, $C_{1-6}$ alkyl and $C_{1-6}$ alkoxy, pyrrolidinylcarbonyl optionally substituted by at least one of halogen, $C_{1-6}$ alkyl and $C_{1-6}$ alkoxy, piperidylcarbonyl optionally substituted by at least one of halogen, $C_{1-6}$ alkyl and $C_{1-6}$ alkoxy, piperazinylcarbonyl optionally substituted by at least one of halogen, $C_{1-6}$ alkyl and $C_{1-6}$ alkoxy and morpholinylcarbonyl optionally substituted by at least one of halogen, $C_{1-6}$ alkyl and $C_{1-6}$ alkoxy, the ring-forming nitrogen atom located on the ring is bonded with carbonyl (C=O).

In one embodiment of the present invention, $Cy_2$ is each independently selected from 3-8 membered cycloalkyl, 5-10 membered heterocyclyl, phenyl, naphthyl and 5-10 membered heteroaryl. In one embodiment of the present invention, $Cy_2$ is each independently selected from 3-6 membered cycloalkyl, 5-6 membered heterocyclyl, phenyl, naphthyl and 5-6 membered heteroaryl.

In one embodiment of the present invention, each $R^b$ is independently selected from hydroxyl, amino, carboxyl, cyano, nitro, halogen, aminocarbonyl, $C_{1-6}$ alkyl, $C_{1-6}$ alkoxy, amino $C_{1-6}$ alkyl, $C_{1-6}$ haloalkyl, $C_{1-6}$ alkoxy $C_{1-6}$ alkyl, $C_{1-6}$ alkoxy $C_{1-6}$ alkoxy, amino $C_{1-6}$ alkoxy, $C_{1-6}$ haloalkoxy, $C_{1-6}$ alkylthio, $C_{1-6}$ alkylamino, $(C_{1-6}$ alkyl$)_2$ amino, $C_{1-6}$ alkylaminocarbonyl, $(C_{1-6}$ alkyl$)_2$ aminocarbonyl, $C_{1-6}$ alkylcarbonylamino and $C_{1-6}$ alkylcarbonyl. In one embodiment of the present invention, each $R^b$ is independently selected from hydroxyl, amino, carboxyl, cyano, nitro, halogen, aminocarbonyl, $C_{1-6}$ alkyl, $C_{1-6}$ alkoxy, amino $C_{1-6}$ alkyl, $C_{1-6}$ haloalkyl, $C_{1-6}$ alkoxy $C_{1-6}$ alkyl, $C_{1-6}$ alkoxy $C_{1-6}$ alkoxy, amino $C_{1-6}$ alkoxy, $C_{1-6}$ haloalkoxy, $C_{1-6}$ alkylthio, $C_{1-6}$ alkylamino, $C_{1-6}$ alkylaminocarbonyl, $C_{1-6}$ alkylcarbonylamino and $C_{1-6}$ alkylcarbonyl.

In one embodiment of the present invention, each $R^b$ is independently selected from hydroxyl, amino, cyano, halogen, aminocarbonyl, $C_{1-4}$ alkyl, CM alkoxy, amino $C_{1-4}$ alkyl, $C_{1-4}$ haloalkyl, $C_{1-4}$ alkoxy $C_{1-4}$ alkyl, $C_{1-4}$ alkoxy $C_{1-4}$ alkoxy, amino $C_{1-4}$ alkoxy, $C_{1-4}$ haloalkoxy, $C_{1-4}$ alkylthio, $C_{1-4}$ alkylamino, $(C_{1-4}$ alkyl$)_2$ amino, $C_{1-4}$ alkylaminocarbonyl, $(C_{1-4}$ alkyl$)_2$ aminocarbonyl, $C_{1-4}$ alkylcarbonylamino and $C_{1-4}$ alkylcarbonyl.

In one embodiment of the present invention, the substituents A are each independently selected from hydroxyl, amino, carboxyl, cyano, nitro, halogen, $C_{1-6}$ alkyl, $C_{1-6}$ alkoxy, amino $C_{1-6}$ alkyl, $C_{1-6}$ alkoxy $C_{1-6}$ alkyl, $C_{1-6}$ alkoxy $C_{1-6}$ alkoxy, amino $C_{1-6}$ alkoxy, $C_{1-6}$ alkylamino, $(C_{1-6}$ alkyl$)_2$ amino, $C_{1-6}$ alkylaminocarbonyl, $(C_{1-6}$ alkyl$)_2$ aminocarbonyl, $C_{1-6}$ alkylcarbonylamino, $C_{1-6}$ alkylcarbonyl, $C_{1-6}$ haloalkyl, $C_{1-6}$ haloalkoxy, $C_{1-6}$ alkylthio, 3-8 membered cycloalkyl, 5-10 membered heterocyclyl, phenyl, naphthyl, 5-10 membered heteroaryl and oxo.

In one embodiment of the present invention, the substituents A are each independently selected from hydroxyl, amino, carboxyl, cyano, nitro, halogen, $C_{1-4}$ alkyl, $C_{1-4}$ alkoxy, amino $C_{1-4}$ alkyl, $C_{1-4}$ alkoxy $C_{1-4}$ alkyl, $C_{1-4}$ alkoxy $C_{1-4}$ alkoxy, amino $C_{1-4}$ alkoxy, $C_{1-4}$ alkylamino, $(C_{1-4}$ alkyl$)_2$ amino, $C_{1-4}$ alkylaminocarbonyl, $(C_{1-4}$ alkyl$)_2$ aminocarbonyl, $C_{1-4}$ alkylcarbonylamino, $C_{1-4}$ alkylcarbonyl, $C_{1-4}$ haloalkyl, $C_{1-4}$ haloalkoxy, $C_{1-4}$ alkylthio, 3-6 membered cycloalkyl, 5-10 membered heterocyclyl, phenyl, naphthyl, 5-10 membered heteroaryl and oxo.

In one embodiment of the present invention, in formulas (b) and (b-1), an aminocarbonyl group

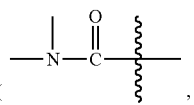

wherein the N atom is bonded with the aforementioned group recorded in the present invention, or the N atom is contained in a nitrogen containing heterocyclic ring) is bonded with the ring structure. In one embodiment of the present invention, in formulas (b) and (b-1), an aminocarbonyl group

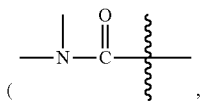 [SMILES: *C(=O)N(C)C]

wherein the N atom is bonded with the aforementioned group recorded in the present invention, or the N atom is contained in a nitrogen containing heterocyclic ring) is connected to the ring-forming carbon atom.

In one embodiment of the present invention, in formula (c), $X_5$, $X_6$, $X_7$ or $X_8$ is bonded with an aminocarbonyl group

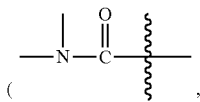 [SMILES: *C(=O)N(C)C]

wherein the N atom is bonded with the aforementioned group recorded in the present invention, or the N atom is contained in a nitrogen containing heterocyclic ring). In one embodiment of the present invention, in formulas (c-1) and (c-2), an aminocarbonyl group

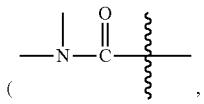 [SMILES: *C(=O)N(C)C]

wherein the N atom is bonded with the aforementioned group recorded in the present invention, or the N atom is contained in a nitrogen containing heterocyclic ring) is connected to a benzene ring structure. In one embodiment of the present invention, in formula (c), $X_5$, $X_6$, $X_7$ and $X_8$ each independently represent CH.

In one embodiment of the present invention, in formula (c), $X_5$, $X_6$, $X_7$ and $X_8$ are not C=O.

In one embodiment of the present invention, in formulas (A-1) and (A-2), $Y_1$ is C=O, and $Y_2$ represents $NR^d$.

In one embodiment of the present invention, the ring-forming nitrogen atom located on the ring is bonded with carbonyl (C=O) to form aminocarbonyl.

In one embodiment of the present invention, the compound of the present invention or the pharmaceutically acceptable salt, ester, stereoisomer or tautomer thereof is provided, and the compound is selected from:

| Serial number | Structural formula |
|---|---|
| A1 | |
| A2 | |
| A3 | |
| A4 | |
| A5 | |
| A6 | |
| A7 | |
| A8 | |
| A9 | |

| Serial number | Structural formula |
|---|---|
| A10 | 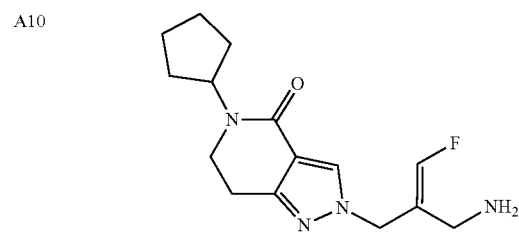 |
| A11 | 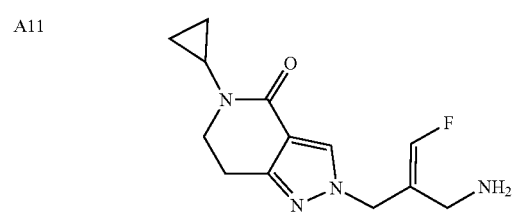 |
| A12 | 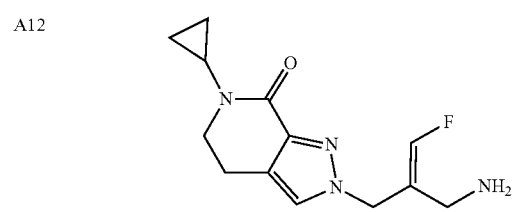 |
| A13 | 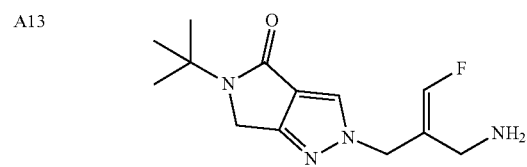 |
| A14 | 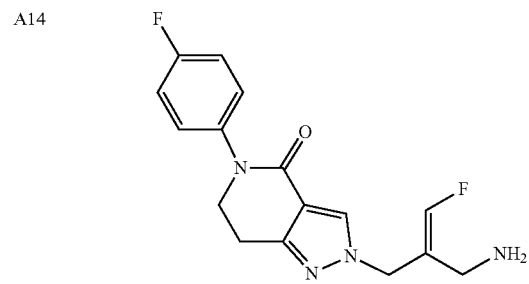 |
| A15 | 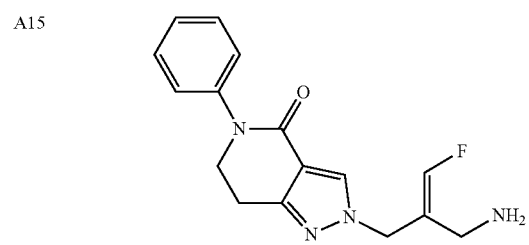 |
| A16 | 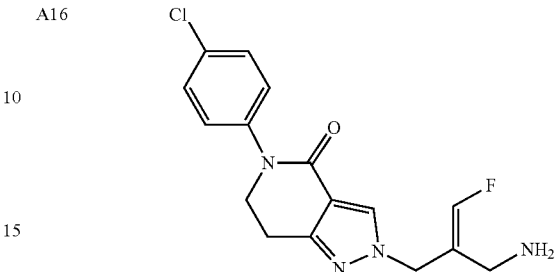 |
| A17 | 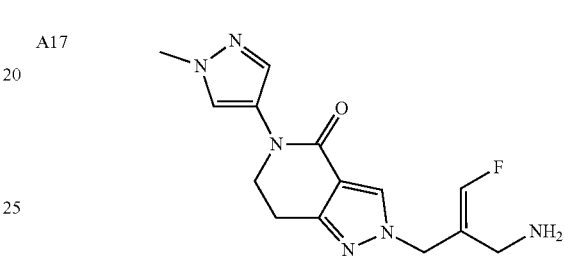 |
| A18 | 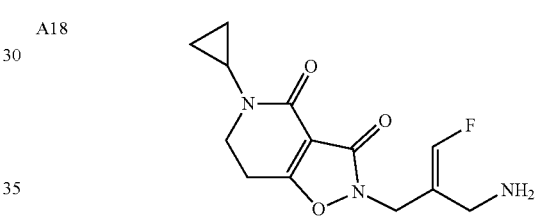 |
| A19 | 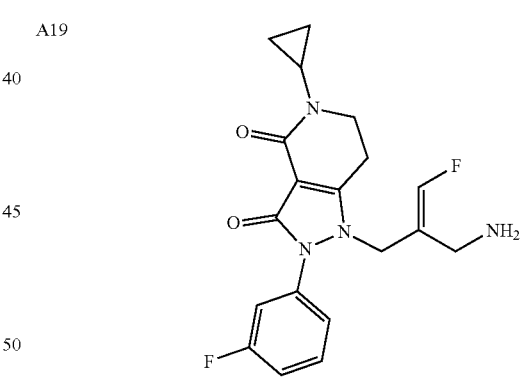 |
| A20 | 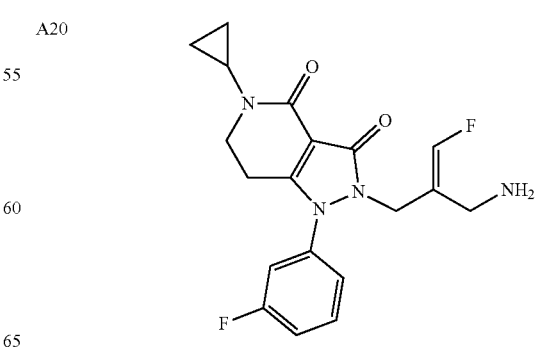 |

| Serial number | Structural formula |
|---|---|
| A21 | |
| A22 | |
| A23 | |
| A24 | |
| A25 | |
| A26 | |
| A27 | |
| A28 | |
| A29 | |
| A30 | |
| A31 | |
| A32 | |
| A33 | |
| A34 | |
| A35 | |

-continued

| Serial number | Structural formula |
|---|---|
| A36 | |
| A37 | |
| A38 | |
| A39 | |
| A40 | |
| A41 | |
| A42 | |

-continued

| Serial number | Structural formula |
|---|---|
| A44 | |
| A45 | |
| A46 | |
| A47 | |
| A48 | |
| A49 | |

| Serial number | Structural formula |
|---|---|
| A50 | |
| A51 | |
| A52 | |
| B1 | |
| B2 | |
| B3 | |
| B4 | |
| B5 | |
| B6 | |
| B7 | |
| B8 | |
| B9 | |
| B10 | |
| B11 | |

| Serial number | Structural formula |
| --- | --- |
| B12 |  |
| B13 | |
| B14 | |
| B15 | |
| B16 | |
| B17 | |
| Serial number | Structural formula |
| --- | --- |
| B18 |  |
| B19 | |
| B20 | |
| B21 | |
| B22 | |
| B23 | |
| B24 | |

-continued
| Serial number | Structural formula |
|---|---|
| B25 | 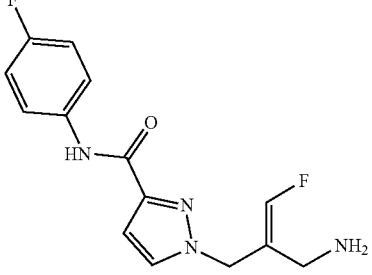 |
| B26 | 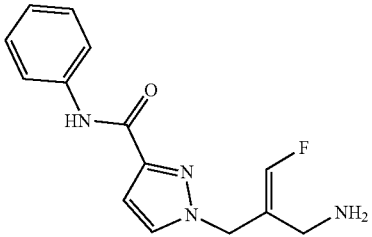 [SMILES: NC/C(=C\F)Cn1ccc(C(=O)Nc2ccccc2)c1] |
| B27 | 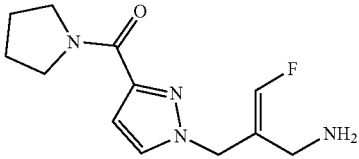 [SMILES: NC/C(=C\F)Cn1ccc(C(=O)N2CCCC2)n1] |
| B28 | 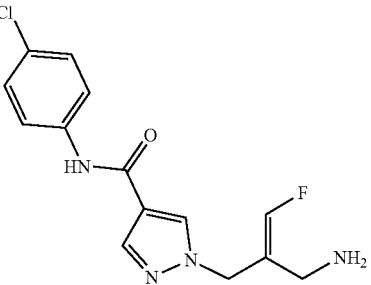 |
| B29 | 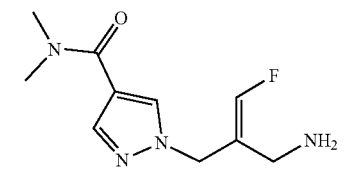 [SMILES: CN(C)C(=O)c1cnn(C/C(=C/F)CN)c1] |
| B30 | 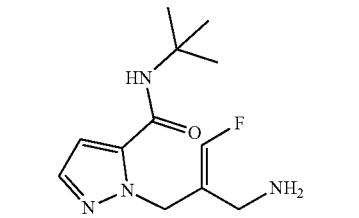 [SMILES: CC(C)(C)NC(=O)c1ccnn1C/C(=C/F)CN] |
| B31 | 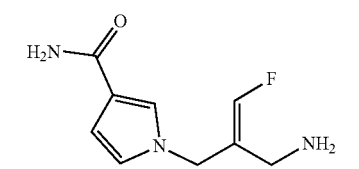 [SMILES: NC/C(=C\F)Cn1ccc(C(N)=O)c1] |
-continued
| Serial number | Structural formula |
|---|---|
| C1 | 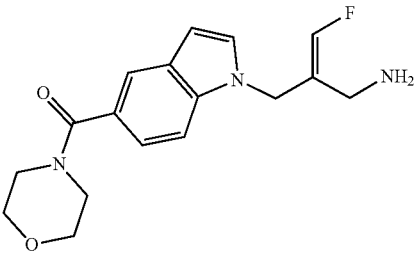 [SMILES: NC/C(=C\F)Cn1ccc2cc(C(=O)N3CCOCC3)ccc21] |
| C2 | 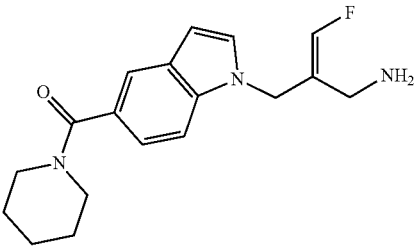 [SMILES: NC/C(=C\F)Cn1ccc2cc(C(=O)N3CCCCC3)ccc21] |
| C3 | 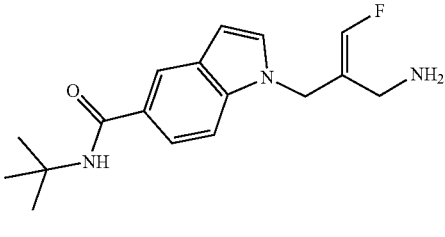 [SMILES: CC(C)(C)NC(=O)c1ccc2c(ccn2C/C(=C/F)CN)c1] |
| C4 | 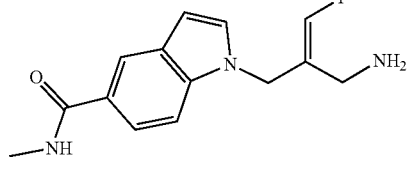 |
| C5 | 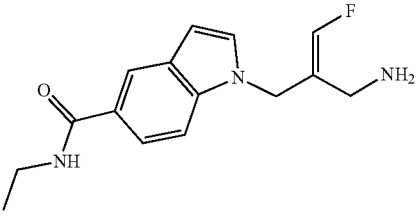 [SMILES: CCNC(=O)c1ccc2c(ccn2C/C(=C/F)CN)c1] |
| C6 | 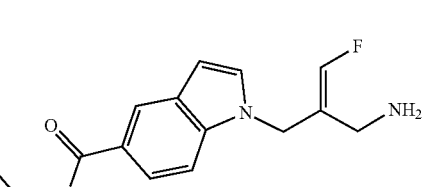 |

| Serial number | Structural formula |
|---|---|
| C7 |  |
| C8 | |
| C9 | |
| C10 | |
| C11 | |
| C12 | |
| C13 | |

| Serial number | Structural formula |
|---|---|
| C14 | 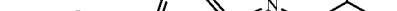 |
| C15 | |

In one embodiment of the present invention, provided is a pharmaceutical composition, which comprises the compound of the present invention or a pharmaceutically acceptable salt, ester, stereoisomer or tautomer thereof described above, and also optionally comprises one or more pharmaceutically acceptable carriers.

In one embodiment of the present invention, provided is a use of the compound of the present invention or a pharmaceutically acceptable salt, ester, stereoisomer or tautomer thereof described above or the pharmaceutical composition of the present invention described above in the manufacture of a medicament for preventing and/or treating diseases related to or mediated by the SSAO/VAP-1 protein.

In one embodiment of the present invention, provided is a method for preventing and/or treating diseases related to or mediated by the SSAO/VAP-1 protein, wherein the pharmaceutical composition of the compound of the present invention or a pharmaceutically acceptable salt, ester, stereoisomer or tautomer thereof described above or the pharmaceutical composition described above is administered to a subject in need of treatment at an effective dose.

In one embodiment of the present invention, a compound of formula I or a pharmaceutically acceptable salt, ester, stereoisomer or tautomer thereof is provided:

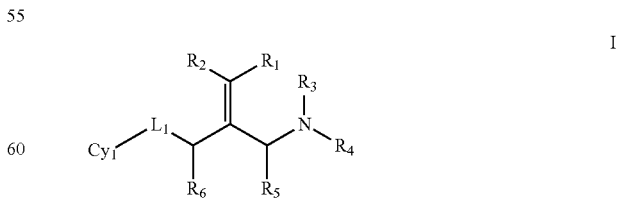

I wherein $R_1$ and $R_2$ are each independently selected from hydrogen and halogen, and $R_1$ and $R_2$ are not both hydrogen; $R_3$ and $R_4$ are each independently selected from hydrogen and $C_{1-6}$ alkyl, or form a 5-10 membered nitrogen containing heterocycle optionally substituted by a substituent along with a N atom connected thereto;

$R_5$ and $R_6$ are each independently selected from hydrogen and $C_{1-6}$ alkyl;

$L_1$ is absent, or is —Cr'R"—, —N—, —O—, —S—, —$SO_2$—, S(O), —SONR'—, —$SO_2$NR'— or —NR'CONR'—, and R' and R" are each independently selected from hydrogen and $C_{1-6}$ alkyl;

$Cy_1$ is a group that is unsubstituted or substituted by one or more $R^a$ shown in general formula (A), (a), (b) or (c) below:

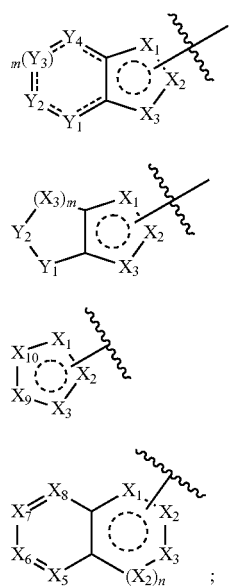

m is an integer from 0 to 3, and n is an integer from 0 to 2;

$Y_1$, $Y_2$, $Y_3$ and $Y_4$ are each independently selected from $CH_2$, CH, NH, N, O, S and C=O;

$X_1$, $X_2$, $X_3$, $X_4$, $X_9$ and $X_{10}$ are each independently selected from $CH_2$, CH, N, O, S, NH and C=O, $X_5$, $X_6$, $X_7$ and $X_8$ are each independently selected from CH and N, and at least one of $X_1$, $X_2$ and $X_3$ is N or NH;

each $R^a$ is independently selected from hydroxyl, amino, carboxyl, cyano, nitro, halogen, and $C_{1-6}$ alkyl, $C_{2-6}$ alkenyl, $C_{2-6}$ alkynyl, $C_{1-6}$ alkoxy, $C_{1-6}$ alkoxy $C_{1-6}$ alkyl, $C_{1-6}$ alkoxy $C_{1-6}$ alkoxy, $C_{1-6}$ alkylthio, $C_{1-6}$ alkylthio $C_{1-6}$ alkyl, $C_{1-6}$ alkylamino, ($C_{1-6}$ alkyl)$_2$ amino, $C_{1-6}$ alkylamino $C_{1-6}$ alkyl, $C_{1-6}$ alkylaminocarbonyl, $C_{1-6}$ alkylaminocarbonyl $C_{1-6}$ alkyl, $C_{1-6}$ alkylcarbonylamino, $C_{1-6}$ alkylcarbonylamino $C_{1-6}$ alkyl, ($C_{1-6}$ alkyl)$_2$ amino $C_{1-6}$ alkyl, $C_{1-6}$ alkylcarbonyl, $C_{1-6}$ alkylcarbonyl $C_{1-6}$ alkyl, $C_{1-6}$ alkylaminosulfonyl, alkylaminosulfonyl $C_{1-6}$ alkyl, $C_{1-6}$ alkylsulfonylamino, $C_{1-6}$ alkylsulfonylamino $C_{1-6}$ alkyl, $C_{1-6}$ alkylsulfonyl, $C_{1-6}$ alkylsulfonyl $C_{1-6}$ alkyl, $Cy_2$-, $Cy_2$-$C_{1-6}$ alkyl, $Cy_2$-$C_{1-6}$ alkoxy, $Cy_2$-carbonyl and $Cy_2$-aminocarbonyl unsubstituted or substituted by one or more $R^b$, $Cy_2$ is 3-12 membered cycloalkyl, 3-12 membered cycloalkenyl, 3-12 membered heterocyclyl, aryl or 5-14 membered heteroaryl;

each $R^b$ is independently selected from hydroxyl, amino, carboxyl, cyano, nitro, halogen, $C_{1-6}$ alkyl, $C_{2-6}$ alkenyl, $C_{2-6}$ alkynyl, $C_{1-6}$ alkoxy, $C_{1-6}$ alkoxy $C_{1-6}$ alkyl, $C_{1-6}$ alkoxy $C_{1-6}$ alkoxy, $C_{1-6}$ alkylthio, $C_{1-6}$ alkylamino, ($C_{1-6}$ alkyl)$_2$ amino, $C_{1-6}$ alkylaminocarbonyl, $C_{1-6}$ alkylcarbonylamino, $C_{1-6}$ alkylcarbonyl, $C_{1-6}$ alkylaminosulfonyl, $C_{1-6}$ alkylsulfonylamino and $C_{1-6}$ alkylsulfonyl; with the proviso that when $Cy_1$ is formula (c), formula (c) is substituted by one or more $R^a$;

with the proviso that when $Cy_1$ is formula (b), $X_1$, $X_2$, $X_3$, $X_9$ and $X_{10}$ are not C=O;

=== represents a single bond or a double bond; and

◌ represents a double bond optionally present in the ring structure.

In one embodiment of the present invention, a compound of formula I below or a pharmaceutically acceptable salt, ester, stereoisomer or tautomer thereof is provided:

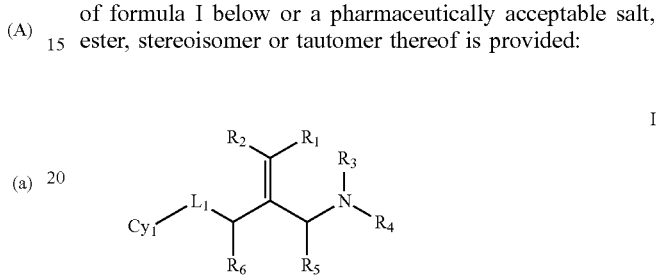

I wherein $R_1$ and $R_2$ are each independently selected from hydrogen and halogen, and $R_1$ and $R_2$ are not both hydrogen;

$R_3$ and $R_4$ are each independently selected from hydrogen and $C_{1-6}$ alkyl, or form a 5-10 membered nitrogen containing heterocycle optionally substituted by a substituent along with a N atom connected thereto;

$R_5$ and $R_6$ are each independently selected from hydrogen and $C_{1-6}$ alkyl;

$L_1$ is absent, or is —Cr'R"—, —N—, —O—, —S—, —$SO_2$—, S(O), —SONR'—, —$SO_2$NR'— or —NR'CONR'—, and R' and R" are each independently selected from hydrogen and $C_{1-6}$ alkyl;

$Cy_1$ is a group that is unsubstituted or substituted by one or more $R^a$ shown in general formula (A-1), (A-2), (A-3), (a), (b) or (c) below:

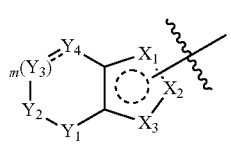

(A-1)

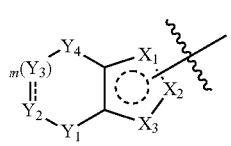

(A-2)

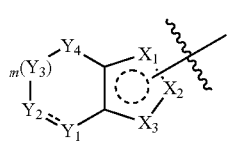

(A-3)

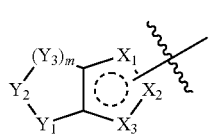

(a)

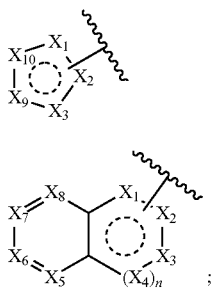
(b)

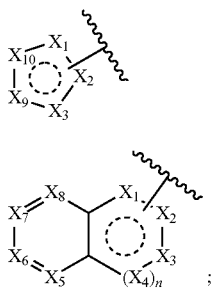
(c)

m is an integer from 0 to 3, and n is an integer from 0 to 2;

$Y_1$, $Y_2$, $Y_3$ and $Y_4$ are each independently selected from $CH_2$, CH, NH, N, O, S and C=O;

$X_1$, $X_2$, $X_3$, $X_4$, $X_9$ and $X_{10}$ are each independently selected from $CH_2$, CH, N, O, S, NH and C=O, $X_5$, $X_6$, $X_7$ and $X_8$ are each independently selected from CH and N, and at least one of $X_1$, $X_2$ and $X_3$ is N or NH;

each $R^a$ is independently selected from hydroxyl, amino, carboxyl, cyano, nitro, halogen, and $C_{1-6}$ alkyl, $C_{2-6}$ alkenyl, $C_{2-6}$ alkynyl, $C_{1-6}$ alkoxy, $C_{1-6}$ alkoxy $C_{1-6}$ alkyl, $C_{1-6}$ alkoxy $C_{1-6}$ alkoxy, $C_{1-6}$ alkylthio, $C_{1-6}$ alkylthio $C_{1-6}$ alkyl, $C_{1-6}$ alkylamino, $(C_{1-6}$ alkyl$)_2$ amino, $C_{1-6}$ alkylamino $C_{1-6}$ alkyl, $C_{1-6}$ alkylaminocarbonyl, $C_{1-6}$ alkylaminocarbonyl $C_{1-6}$ alkyl, $C_{1-6}$ alkylcarbonylamino, $C_{1-6}$ alkylcarbonylamino $C_{1-6}$ alkyl, $(C_{1-6}$ alkyl$)_2$ amino $C_{1-6}$ alkyl, $C_{1-6}$ alkylcarbonyl, $C_{1-6}$ alkylcarbonyl $C_{1-6}$ alkyl, $C_{1-6}$ alkylaminosulfonyl, $C_{1-6}$ alkylaminosulfonyl $C_{1-6}$ alkyl, $C_{1-6}$ alkylsulfonylamino, $C_{1-6}$ alkylsulfonylamino $C_{1-6}$ alkyl, $C_{1-6}$ alkylsulfonyl, $C_{1-6}$ alkylsulfonyl $C_{1-6}$ alkyl, $Cy_2$-, $Cy_2$-$C_{1-6}$ alkyl, $Cy_2$-$C_{1-6}$ alkoxy, $Cy_2$-carbonyl and $Cy_2$-aminocarbonyl unsubstituted or substituted by one or more $R^b$, and $Cy_2$ is 3-12 membered cycloalkyl, 3-12 membered cycloalkenyl, 3-12 membered heterocyclyl, aryl or 5-14 membered heteroaryl;

each $R^b$ is independently selected from hydroxyl, amino, carboxyl, cyano, nitro, halogen, $C_{1-6}$ alkyl, $C_{2-6}$ alkenyl, $C_{2-6}$ alkynyl, $C_{1-6}$ alkoxy, $C_{1-6}$ alkoxy $C_{1-6}$ alkyl, $C_{1-6}$ alkoxy $C_{1-6}$ alkoxy, $C_{1-6}$ alkylthio, $C_{1-6}$ alkylamino, $(C_{1-6}$ alkyl$)_2$ amino, $C_{1-6}$ alkylaminocarbonyl, $C_{1-6}$ alkylcarbonylamino, $C_{1-6}$ alkylcarbonyl, $C_{1-6}$ alkylaminosulfonyl, $C_{1-6}$ alkylsulfonylamino and $C_{1-6}$ alkylsulfonyl;

with the proviso that when $Cy_1$ is formula (c), formula (c) is substituted by one or more $R^a$;

with the proviso that when $Cy_1$ is formula (b), $X_1$, $X_2$, $X_3$, $X_9$ and $X_{10}$ are not C=O;

═══ represents a single bond or a double bond;

⌒ represents a double bond optionally present in the ring structure.

In one embodiment of the present invention, $R_1$ and $R_2$ are each independently selected from hydrogen and halogen, and $R_1$ and $R_2$ are not both hydrogen;

$R_3$ and $R_4$ are each independently selected from hydrogen and $C_{1-6}$ alkyl;

$R_5$ and $R_6$ are each independently selected from hydrogen and $C_{1-6}$ alkyl;

$L_1$ is absent, or is —CR'R"—, —N—, —O— or —S—, and R' and R" are each independently selected from hydrogen and $C_{1-6}$ alkyl;

$Cy_1$ is a group that is unsubstituted or substituted by one or more $R^a$ shown in general formula (A-1), (A-2), (A-3), (a), (b) or (c) below:

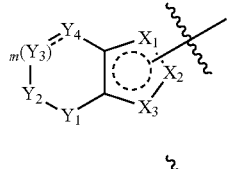
(A-1)

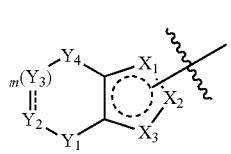
(A-2)

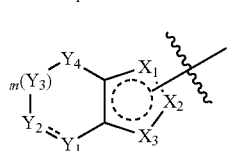
(A-3)

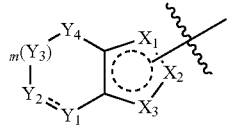
(a)

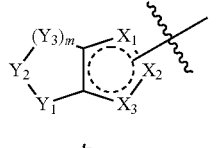
(b)

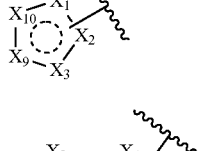
(c)

m is an integer from 0 to 3, and n is an integer from 0 to 2;

$Y_1$, $Y_2$, $Y_3$ and $Y_4$ are each independently selected from $CH_2$, CH, NH, N and C=O;

$X_1$, $X_2$, $X_3$, $X_4$, $X_9$ and $X_{10}$ are each independently selected from $CH_2$, CH, N, NH and C=O, $X_5$, $X_6$, $X_7$ and $X_8$ are each independently selected from CH and N, and at least one of $X_1$, $X_2$ and $X_3$ is N or NH;

each $R^a$ is independently selected from hydroxyl, amino, carboxyl, cyano, nitro, halogen, and $C_{1-6}$ alkyl, $C_{1-6}$ alkoxy, $C_{1-6}$ alkoxy $C_{1-6}$ alkyl, $C_{1-6}$ alkoxy $C_{1-6}$ alkoxy, $C_{1-6}$ alkylthio, $C_{1-6}$ alkylthio $C_{1-6}$ alkyl, $C_{1-6}$ alkylamino, $C_{1-6}$ alkylamino $C_{1-6}$ alkyl, $C_{1-6}$ alkylaminocarbonyl, $C_{1-6}$ alkylaminocarbonyl $C_{1-6}$ alkyl, $C_{1-6}$ alkylcarbonylamino, $C_{1-6}$ alkylcarbonylamino $C_{1-6}$ alkyl, $C_{1-6}$ alkylcarbonyl, $C_{1-6}$ alkylcarbonyl $C_{1-6}$ alkyl, $Cy_2$, $Cy_2$-$C_{1-6}$ alkyl, $Cy_2$-$C_{1-6}$ alkoxy, $Cy_2$-carbonyl and $Cy_2$-aminocarbonyl unsubstituted or substituted by one or more substituents $R^b$, and $Cy_2$ is 3-8 membered cycloalkyl, 5-10 membered heterocyclyl, phenyl or 5-10 membered heteroaryl;

each $R^b$ is independently selected from hydroxyl, amino, carboxyl, cyano, nitro, halogen, $C_{1-6}$ alkyl, $C_{1-6}$ alkoxy, $C_{1-6}$ alkoxy $C_{1-6}$ alkyl, $C_{1-6}$ alkoxy $C_{1-6}$ alkoxy, $C_{1-6}$ alkylthio, $C_{1-6}$ alkylamino, $C_{1-6}$ alkylaminocarbonyl, $C_{1-6}$ alkylcarbonylamino and $C_{1-6}$ alkylcarbonyl;

with the proviso that when $Cy_1$ is formula (c), formula (c) is substituted by one or more $R^a$;

with the proviso that when $Cy_1$ is formula (b), $X_1$, $X_2$, $X_3$, $X_9$ and $X_{10}$ are not C=O; and $\overset{\cdot\cdot}{\cdot\cdot}$ represents a double bond optionally present in the ring structure.

In one embodiment of the present invention, $Cy_1$ is a group that is unsubstituted or substituted by one or more $R^a$ shown in general formula (A-11), (a-1), (a-2), (b-1), (c-1) or (c-2) below:

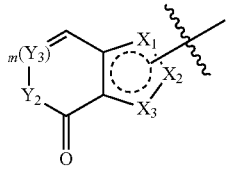 (A-11)

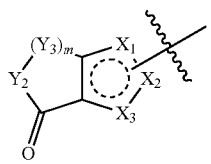 (a-1)

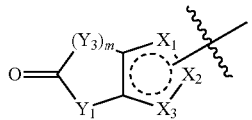 (a-2)

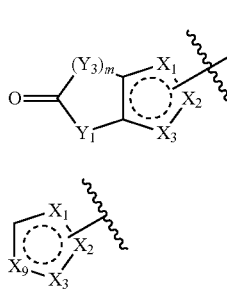 (b-1)

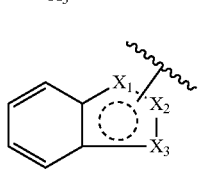 (c-1)

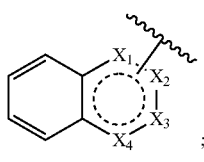 (c-2)

m is an integer that is 1 or 2;

$Y_1$, $Y_2$ and $Y_3$ are each independently selected from $CH_2$, CH, NH and N;

$X_1$, $X_2$, $X_3$, $X_4$ and $X_9$ are each independently selected from $CH_2$, CH, N, NH and C=O, and at least one of $X_1$, $X_2$ and $X_3$ is N or NH;

with the proviso that when $Cy_1$ is formula (c-1) or (c-2), formula (c-1) or (c-2) is substituted by one or more $R^a$;

with the proviso that when $Cy_1$ is formula (b-1), $X_1$, $X_2$, $X_3$ and $X_9$ are not C=O; and $\overset{\cdot\cdot}{\cdot\cdot}$ represents a double bond optionally present in the ring structure.

In one embodiment of the present invention, $Cy_1$ is a group that is unsubstituted or substituted by one or more $R^a$ shown in general formula (A-11) or (a-1) below:

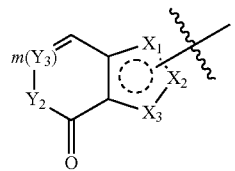 (A-11)

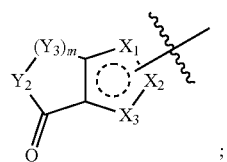 (a-1)

m is an integer that is 1 or 2;

$Y_2$ and $Y_3$ are each independently selected from $CH_2$, CH, NH and N;

$X_1$, $X_2$ and $X_3$ are each independently selected from $CH_2$, CH, N and NH, and at least one of $X_1$, $X_2$ and $X_3$ is N or NH;

$\overset{\cdot\cdot}{\cdot\cdot}$ represents a double bond optionally present in the ring structure.

In one embodiment of the present invention, $R_1$ and $R_2$ are each independently selected from hydrogen and halogen, and $R_1$ and $R_2$ are not both hydrogen;

$R_3$ and $R_4$ are each independently selected from hydrogen and $C_{1-6}$ alkyl;

$R_5$ and $R_0$ are each independently selected from hydrogen and $C_{1-6}$ alkyl;

$L_1$ is absent;

$Cy_1$ is one of the following groups unsubstituted or substituted by one or more $R^a$:

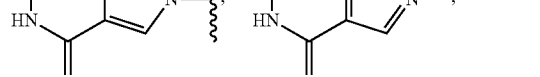
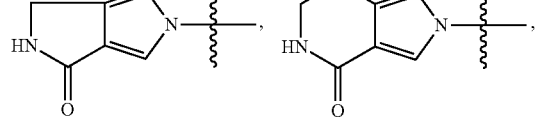
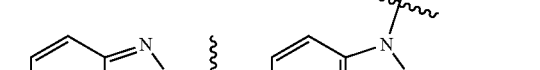
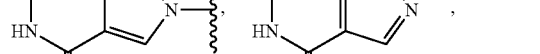
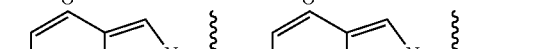
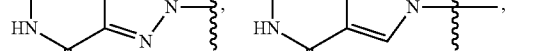

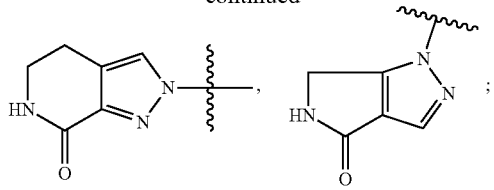

each $R^a$ is independently selected from hydroxyl, amino, carboxyl, cyano, nitro, halogen, and $C_{1-6}$ alkyl, $C_{1-6}$ alkoxy, $C_{1-6}$ alkoxy $C_{1-6}$ alkyl, $C_{1-6}$ alkoxy $C_{1-6}$ alkoxy, $C_{1-6}$ alkylamino, $C_{1-6}$ alkylamino $C_{1-6}$ alkyl, $C_{1-6}$ alkylaminocarbonyl, $C_{1-6}$ alkylaminocarbonyl $C_{1-6}$ alkyl, $C_{1-6}$ alkylcarbonylamino, $C_{1-6}$ alkylcarbonylamino $C_{1-6}$ alkyl, $C_{1-6}$ alkylcarbonyl, $C_{1-6}$ alkylcarbonyl $C_{1-6}$ alkyl, $Cy_2$, $Cy_2$-$C_{1-6}$ alkyl, $Cy_2$-$C_{1-6}$ alkoxy, $Cy_2$-carbonyl and $Cy_2$-aminocarbonyl unsubstituted or substituted by one or more substituents $R^b$, and $Cy_2$ is 3-8 membered cycloalkyl, 5-10 membered heterocyclyl, phenyl or 5-10 membered heteroaryl;

each $R^b$ is independently selected from hydroxyl, amino, carboxyl, cyano, nitro, halogen, $C_{1-6}$ alkyl, $C_{1-6}$ alkoxy, $C_{1-6}$ alkoxy $C_{1-6}$ alkyl, $C_{1-6}$ alkoxy $C_{1-6}$ alkoxy, $C_{1-6}$ alkylthio, $C_{1-6}$ alkylamino, $C_{1-6}$ alkylaminocarbonyl, $C_{1-6}$ alkylcarbonylamino and $C_{1-6}$ alkylcarbonyl;

⟨⋯⟩ represents a double bond optionally present in the ring structure; and preferably, $Cy_2$ is 3-6 membered cycloalkyl, 5-6 membered heterocyclyl, phenyl or 5-6 membered heteroaryl.

In one embodiment of the present invention, $Cy_1$ is a group that is unsubstituted or substituted by one or more $R^a$ shown in general formula (b-1) below:

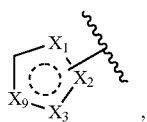
(b-1)

$X_1$, $X_2$, $X_3$ and $X_9$ are each independently selected from $CH_2$, CH, N and NH, and at least one of $X_1$, $X_2$ and $X_3$ is N or NH;

⟨⋯⟩ represents a double bond optionally present in the ring structure; with the proviso that in general formula (b-1), $X_1$, $X_2$, $X_3$ and $X_9$ are not C=O.

In one embodiment of the present invention, $R_1$ and $R_2$ are each independently selected from hydrogen and halogen, and $R_1$ and $R_2$ are not both hydrogen;

$R_3$ and $R_4$ are each independently selected from hydrogen and $C_{1-6}$ alkyl;

$R_5$ and $R_0$ are each independently selected from hydrogen and $C_{1-6}$ alkyl;

$L_1$ is absent;

$Cy_1$ is one of the following groups unsubstituted or substituted by one or more $R^a$:

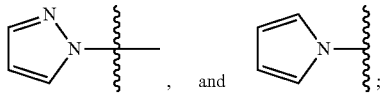

each $R^a$ is independently selected from hydroxyl, amino, carboxyl, cyano, nitro, halogen, and $C_{1-6}$ alkyl, $C_{1-6}$ alkoxy, $C_{1-6}$ alkoxy $C_{1-6}$ alkyl, $C_{1-6}$ alkoxy $C_{1-6}$ alkoxy, $C_{1-6}$ alkylamino, $C_{1-6}$ alkylamino $C_{1-6}$ alkyl, $C_{1-6}$ alkylaminocarbonyl, $C_{1-6}$ alkylaminocarbonyl $C_{1-6}$ alkyl, $C_{1-6}$ alkylcarbonylamino, $C_{1-6}$ alkylcarbonylamino $C_{1-6}$ alkyl, $C_{1-6}$ alkylcarbonyl, $C_{1-6}$ alkylcarbonyl $C_{1-6}$ alkyl, $Cy_2$, $Cy_2$-$C_{1-6}$ alkyl, $Cy_2$-$C_{1-6}$ alkoxy, $Cy_2$-carbonyl and $Cy_2$-aminocarbonyl unsubstituted or substituted by one or more substituents $R^b$, and $Cy_2$ is 3-8 membered cycloalkyl, 5-10 membered heterocyclyl, phenyl or 5-10 membered heteroaryl;

each $R^b$ is independently selected from hydroxyl, amino, carboxyl, cyano, nitro, halogen, $C_{1-6}$ alkyl, $C_{1-6}$ alkoxy, $C_{1-6}$ alkoxy $C_{1-6}$ alkyl, $C_{1-6}$ alkoxy $C_{1-6}$ alkoxy, $C_{1-6}$ alkylthio, $C_{1-6}$ alkylamino, $C_{1-6}$ alkylaminocarbonyl, $C_{1-6}$ alkylcarbonylamino and $C_{1-6}$ alkylcarbonyl.

In one embodiment of the present invention, $Cy_1$ is one of the following groups unsubstituted or substituted by one or more $R^a$:

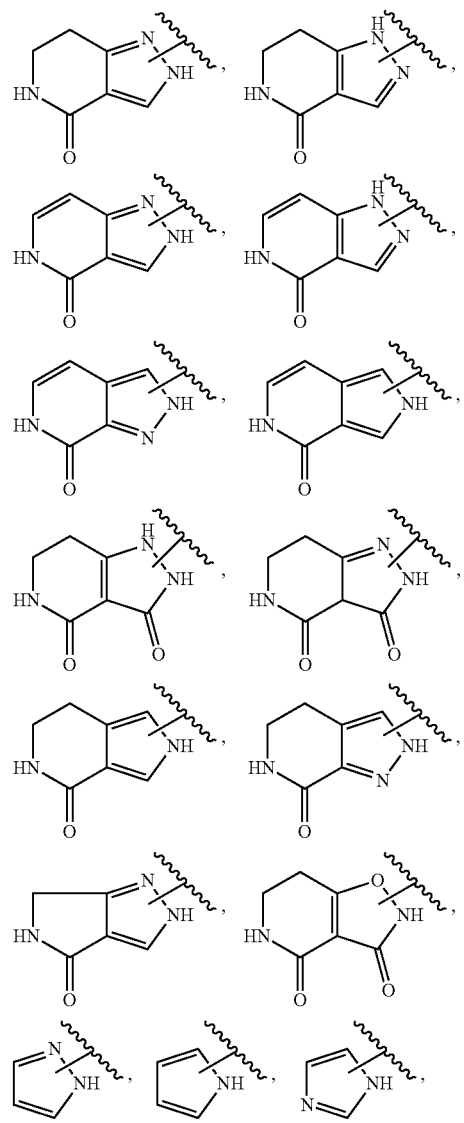

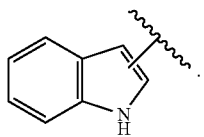

In one embodiment of the present invention, $R_1$ and $R_2$ are each independently selected from hydrogen and fluorine, and $R_1$ and $R_2$ are not both hydrogen.

In one embodiment of the present invention, $Cy_1$ is one of the following groups substituted by one or more $R^a$:

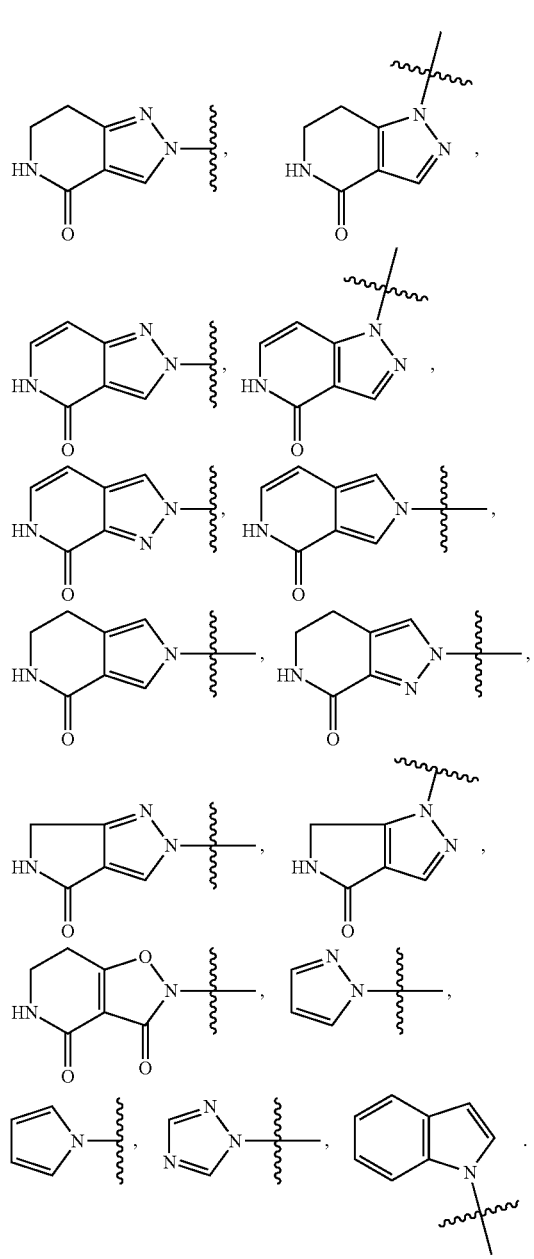

In one embodiment of the present invention, each $R^a$ is independently selected from hydroxyl, amino, carboxyl, cyano, nitro, halogen, and $C_{1-6}$ alkyl, $C_{1-6}$ alkoxy, $C_{1-6}$ alkylaminocarbonyl, $Cy_2$, $Cy_2$-carbonyl and $Cy_2$-aminocarbonyl unsubstituted or substituted by one or more substituents $R^b$, and $Cy_2$ is 3-6 membered cycloalkyl, 5-6 membered heterocyclyl, phenyl or 5-6 membered heteroaryl.

In one embodiment of the present invention, each $R^b$ is independently selected from hydroxyl, amino, carboxyl, cyano, nitro, halogen, $C_{1-6}$ alkyl and $C_{1-6}$ alkoxy.

In one embodiment of the present invention, $Cy_1$ is one of the following groups substituted by one or more $R^a$:

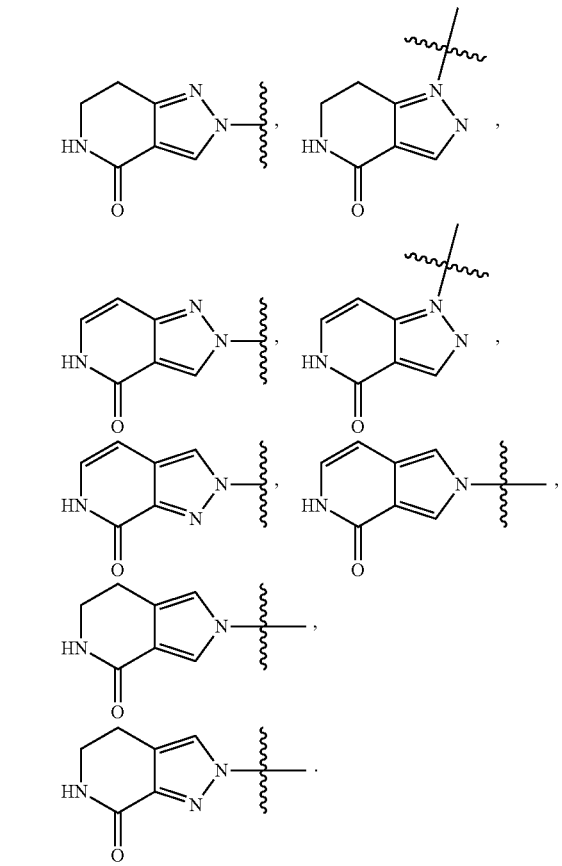

In one embodiment of the present invention, each $R^a$ is independently selected from hydroxyl, amino, carboxyl, cyano, nitro, halogen, and $C_{1-6}$ alkyl and 3-6 membered cycloalkyl unsubstituted or substituted by one or more substituents $R^a$.

In one embodiment of the present invention, each $R^b$ is independently selected from hydroxyl, amino, cyano, nitro and halogen.

The "pharmaceutically acceptable salt" described in the present invention refers to a pharmaceutically acceptable addition salt of acid or base of the compound of formula I or an addition salt of a solvate thereof. When an acidic functional group (such as —COOH, —OH, —SO$_3$H, etc.) is present in the compound, the acidic functional group may be a salt formed with an appropriate inorganic or organic cation (base), including a salt formed with alkali metal, alkaline earth metal or the like, an ammonium salt, and a salt formed with a nitrogenous organic base. When a basic functional group (such as —NH$_2$, etc.) is present in the compound, the basic functional group may be a salt formed with an appropriate inorganic or organic anion (acid), including a salt formed with an inorganic acid salt or organic acid. Such a "pharmaceutically acceptable salt" includes, but is not limited to, acid salts such as hydrochloride, hydrobromide, hydriodate, sulfate, phosphate, nitrate, benzene sulfonate, benzoate, p-toluene sulfonate, 2,3-dihydroxysuccinate, camphorsulfonate, citrate, methanesulfonate, ethanesulfonate, propanesulfonate, fumarate, gluconate, glutamate, hydroxyethylsulfonate, lactate, maleate, malate, mandelate, muconate, pamoate, pantothenate, succinate, tartrate and the like, preferably benzoate, benzenesulfonate, p-toluene sulfonate, methanesulfonate, citrate, maleate, fumarate, tartrate, alkanoic acid (HOOC—(CH$_2$)$_n$—COOH (wherein n is 0 to 4)) salts (such as formate, acetate and propionate). In addition, the "pharmaceutically acceptable salt" also includes, but is not limited to, salts formed by the following bases: arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, meglumine, glucosamine, histidine, hydrabamine, isopropylamine, lysine, methylglucamine, morpholine, piperazine, piperidine, procaine, purine, theobromine, triethylamine, trimethylamine, tripropylamine and tromethamine; and in addition, the "pharmaceutically acceptable salt" may also be lithium salt, sodium salt, potassium salt, calcium salt, magnesium salt, zinc salt, barium salt, aluminum salt, ferric salt, copper salt, ferrous salt, manganese salt, divalent manganese salt or the like.

The "pharmaceutically acceptable ester" of the compound of the present invention refers to an ester of the compound of the present invention that is hydrolyzed in vivo, and includes an ester that can be easily decomposed in the human body to leave the parent compound or the salt thereof. Suitable ester groups include, for example, ester groups derived from pharmaceutically acceptable aliphatic carboxylic acids (in particular alkanoic acid, alkenoic acid, cyclic alkanoic acid and alkanoic diacid), wherein each alkyl or alkenyl preferably has six or less carbon atoms. Representative examples of a specific ester include, but are not limited to, formate, acetate, propionate, butyrate, acrylate and ethylsuccinate.

In the present invention, during reaction, the N atom of an amino group can be optionally protected with an amino-protecting group. The "amino-protecting group" refers to a chemical group that is connected to the amino group and can be easily removed under a certain condition, and includes, but is not limited to, alkoxycarbonyl groups, acyl groups and alkyl groups, such as tert-butoxycarbonyl, benzyloxycarbonyl, fluorenylmethoxycarbonyl, allyloxycarbonyl, phthaloyl, benzyl, p-methoxybenzyl, triphenylmethyl, etc. Those skilled in the art can carry out appropriate selection and operation according to the common textbook *Greene's Protective Groups in Organic Synthesis* (4$^{th}$ edition) in the art.

The phrase "pharmaceutically acceptable" means that the substance or composition must be pharmaceutically and/or toxicologically compatible with other ingredients contained in the preparation and/or the pharmaceutical composition.

The "isomers" described in the present invention include a stereoisomer and a tautomer.

The stereoisomer means that an enantiomer will be produced when an asymmetric carbon atom is present in a compound, or that a cis-trans isomer will be produced when a carbon-carbon double bond or a ring structure is present in a compound.

The "tautomer" means a functional group isomer that is produced due to the rapid shifting of a certain atom between two positions in a molecule, and the tautomer is a special functional group isomer. For example, a tautomer of a carbonyl compound comprising α-H may be:

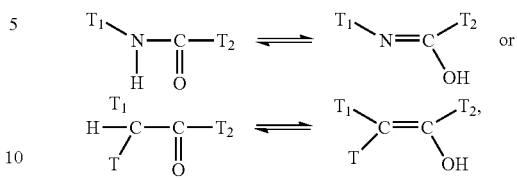

wherein T, T$_1$ and T$_2$ are each independently selected from any group that meets the bonding rule of the compound.

The "tautomer" may also be, for example, other prototropic tautomers, specifically such as a phenol-keto tautomer, a nitroso-oximino tautomer and an imine-enamine tautomer. However, it is not limited to this, and those skilled in the art can easily judge the existence of a tautomer and a specific form thereof in a compound.

Therefore, all enantiomers, diastereomers, racemates, cis-trans isomers, geometric isomers, epimers, tautomers and mixtures thereof of the compound of formula I are included in the scope of the present invention.

The pharmaceutical composition of the present invention comprises at least one of the compound of formula I and a pharmaceutically acceptable salt, ester, stereoisomer and tautomer thereof, and optionally one or more pharmaceutically acceptable carriers.

The pharmaceutical composition of the present invention can be administered to a patient or subject in need of prophylaxis and/or treatment in any suitable manner known in the art, for example, oral, parenteral (including subcutaneous, intramuscular, intravenous, intra-arterial, intradermal, intrathecal, and epidural), transdermal, rectal, nasal, transpulmonary, topical (including buccal and sublingual), vaginal, intraperitoneal, intrapulmonary, intranasal and other administrations.

The pharmaceutical composition of the present invention can be formulated into a conventional solid preparation, such as tablet, capsule, pill, granule, etc., and can also be formulated into an oral liquid preparation, such as oral solution, oral suspension, syrup, etc. In the preparation of an oral preparation, one or more of suitable excipient, diluent, sweetener, solubilizer, lubricant, binder, tablet disintegrant, stabilizer, preservative and encapsulating material may be added. For parenteral administration, the pharmaceutical composition can be formulated into an injection, including a solution injection, a sterile powder for injection and a concentrated solution for injection. The injection can be produced by a conventional method existing in the pharmaceutical field, and during the preparation process, no additive may be added, or an appropriate additive may be added according to the property of the medicament. For rectal administration, the pharmaceutical composition can be formulated into a suppository and the like. For transpulmonary administration, the pharmaceutical composition can be formulated into a inhalant, spray or the like. In the present invention, suitable solid carriers include, but are not limited to, cellulose, glucose, lactose, mannitol, magnesium stearate, magnesium carbonate, sodium carbonate, sodium saccharin, sucrose, dextrin, talc, starch, pectin, gelatin, tragacanth, arabic gum, sodium alginate, p-hydroxylbenzoate, methylcellulose, sodium carboxymethyl cellulose, low melting wax, cocoa butter, etc. Suitable liquid carriers include, but are not limited to, water, ethanol, polyol (such as glycerol, propylene glycol, liquid polyethylene glycol, etc.), vegetable oil, glyceride, and mixtures thereof.

Methods for preparing the pharmaceutical composition of the present invention are generally known. The pharmaceutical composition of the present invention is prepared by known methods, including conventional mixing, granulating, tableting, coating, dissolving or lyophilizing.

The pharmaceutical formulation is preferably in unit dosage form. In this form, the formulation is subdivided into unit dosages containing an appropriate quantity of active components. The unit dosage form can be packaged into packages containing a discrete quantity of formulation, such as packaged tablets, capsules, or powders in a vial or an ampoule.

Dosage of a medicament depends on various factors, including the age, weight and state of a patient, as well as the route of administration. The precise dosage administered is determined based on the judgment of a treating physician. The usual dosage for administration of the active compound may be, for example, about 0.01 to about 100 mg/day, about 0.05 to about 75 mg/day, about 0.1 to about 50 mg/day, or about 5 to about 10 mg/day. The desired dosage also depends on the specific compound employed, the severity of the disease, the route of administration, the weight and health status of a patient, and the judgment of a treating physician.

The compound of the present invention also includes a compound in which one or more hydrogen atoms, fluorine atoms, carbon atoms, nitrogen atoms, oxygen atoms and sulfur atoms are replaced with radioisotopes or stable isotopes. These labeled compounds can be used for metabolic or pharmacokinetic studies, biological analysis as ligands for receptors, etc.

The compound of the present invention can be used for treating and/or preventing diseases related to or mediated by the SSAO/VAP-1 protein, which comprises administering the compound of the present invention to a subject.

The pharmaceutical composition comprising the compound of the present invention can be used for treating and/or preventing diseases related to or mediated by the SSAO/VAP-1 protein, which comprises administering the compound of the present invention to a subject.

Preparation Method for Compound of Formula (I) of the Present Invention

The compound of the present invention can be prepared by a variety of methods including standard chemical methods. Unless otherwise stated, any variable defined above will continue to have the meaning defined above. Exemplary general synthesis methods are elaborated in the following schemes, and can be easily modified to prepare other compounds of the present invention. Those skilled in the art can perform the following reactions according to a conventional method (such as *Organic Synthesis* ($2^{nd}$ edition), Michael B. Smith etc.) taught in the art. The specific compounds of the present invention were specifically prepared in examples.

In one embodiment of the present invention, the compound of general formula (I) was obtained through a reaction between formula (SM1) and formula (SM2),

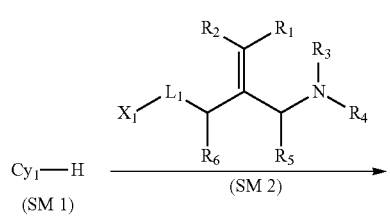

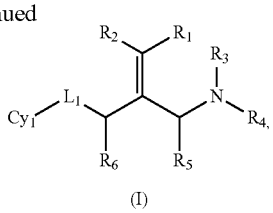

wherein $Cy_1$, $R_1$, $R_2$, $R_3$, $R_4$, $R_5$, $R_6$ and $L_1$ are described as above; and $X_1$ is a leaving group, including but not limited to halogen or sulfonate.

Further, when $R_3$ and $R_4$ are hydrogen, in the process of preparation, the hydrogen on N in

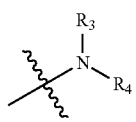

needed to be protected, thus forming

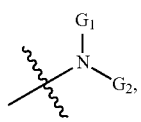

wherein $G_1$ and $G_2$ are amino-protecting groups.

The "amino-protecting groups" are protecting groups commonly used by those skilled in the art, such as tert-butoxycarbonyl, benzyloxycarbonyl, tert-butyl, 9-fluorenylmethoxycarbonyl, allyloxycarbonyl, trifluoroacetyl, chloroacetyl, triphenylmethyl, tetrahydropyranyl, 4-methoxybenzyl, 2,4-dimethoxybenzyl, o-nitrobenzenesulfonyl, and phthaloyl. Moreover, the method for protecting and deprotecting amino groups can also be performed through methods known to those skilled in the art. For example, reference can be made to the steps recorded in *Protective Groups in Organic Synthesis* ($3^{rd}$ edition).

In one embodiment of the present invention, the compound of general formula (I') was prepared through the following steps:

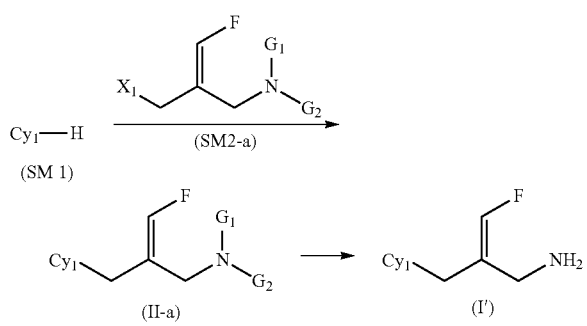

wherein the definitions of $Cy_1$, $G_1$, $G_2$ and $X_1$ are described as above.

(1) Formula (SM1) was dissolved in organic solvent[1], and the solution was added with a suitable base to react with formula (SM2-a) to give formula (II-a);

(2) Formula (II-a) was dissolved in organic solvent², and the solution was added with a suitable deprotecting reagent for deprotection, so that formula (I') was obtained.

In one embodiment of the present invention, the compound of general formula (I') was prepared through the following steps:

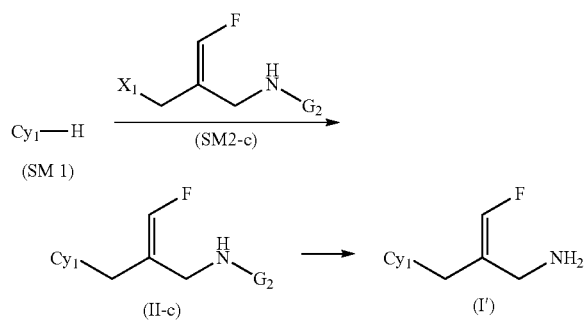

wherein the definitions of $Cy_1$ and $X_1$ are described as above; and $G_2$ is selected from tert-butoxycarbonyl, benzyloxycarbonyl, tert-butyl, 9-fluorenylmethoxycarbonyl, allyloxycarbonyl, trifluoroacetyl, chloroacetyl, triphenylmethyl, tetrahydropyranyl, 4-methoxybenzyl, 2,4-dimethoxybenzyl, and o-nitrobenzenesulfonyl.

(1) Formula (SM1) was dissolved in organic solvent¹, and the solution was added with formula (SM2-c) and a base to give formula (II-c);

(2) Formula (II-c) was dissolved in organic solvent², and the solution was added with a deprotecting agent for deprotection, so that formula (I') was obtained.

In one embodiment of the present invention, the compound of general formula (I') was prepared through the following steps:

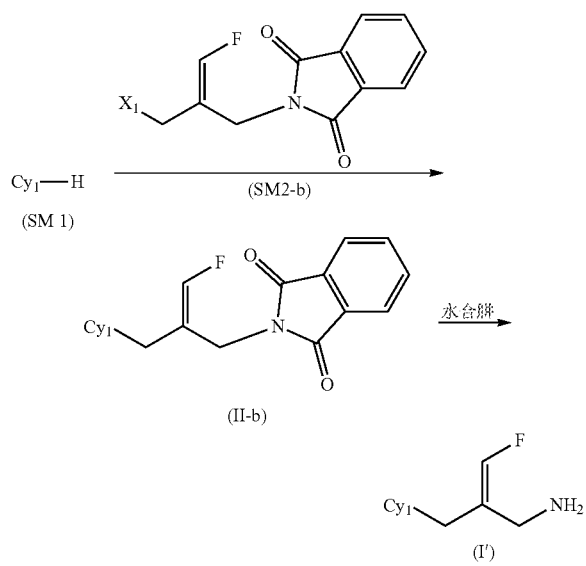

wherein the definitions of $Cy_1$ and $X_1$ are described as above.

(1) Formula (SM1) was dissolved in organic solvent¹, and the solution was added with a suitable base to react with formula (SM2-b) to give formula (II-b);

(2) Formula (II-b) was dissolved in organic solvent², and the solution was added with hydrazine hydrate for hydrazinolysis, so that formula (I') was obtained.

In one embodiment of the present invention, the organic solvent¹ was DMF, DMA, ACN, methanol, ethanol, isopropanol, or THF.

In one embodiment of the present invention, the organic solvent² was methanol, ethanol, or isopropanol.

In one embodiment of the present invention, the base was sodium hydride, cesium carbonate, or potassium carbonate.

In one embodiment of the present invention, the deprotecting agent was hydrochloric acid, trifluoroacetic acid, hydrobromic acid, trimethyliodosilane, or the like.

In one embodiment of the present invention, a phase-transfer catalyst may be added to give the target compound during the reaction, and the phase-transfer catalyst may be a catalyst commonly used in the art, including but not limited to, for example, copper acetate, copper chloride, palladium on carbon, ferric chloride, palladium acetate, [1,1'-bis(diphenylphosphino)ferrocene]palladium dichloride, tetrabutylammonium bromide, benzyltriethylammonium chloride, tetrabutylammonium chloride, etc.

The "suitable deprotecting agent" refers to a reagent which those skilled in the art use to perform a deprotection reaction by selecting a corresponding acid, base or oxidant according to different types of amino-protecting groups $G_1$ and $G_2$ in a chemical structure. Those recorded in *Protective Groups in Organic Synthesis* (3$^{rd}$ edition) may be adopted.

In the present invention, the "acid" may be acids commonly used in the art, including organic acids and inorganic acids. The organic acids may include, for example, formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid and ethylsulfonic acid; and the inorganic acids may include, for example, hydrochloric acid, sulfuric acid, nitric acid, carbonic acid, hydrobromic acid, phosphoric acid, hydroiodic acid, etc. Hydrochloric acid is preferred.

In the present invention, the "base" may be bases commonly used in the art, including organic bases and inorganic bases. The organic bases may include, for example, methylamine, ethylamine, propylamine, N,N-diisopropylethylamine, trimethylamine, triethylamine, N-methyl morpholine, dicyclohexylamine, ethanolamine, diethanolamine, triethanolamine, meglumine, diethanolamine, ethylenediamine, pyridine, methylpyridine, quinoline, etc.; and the inorganic bases may include, for example, hydroxides, carbonates and bicarbonates of alkali metals (such as lithium, sodium, potassium and cesium); hydroxides, carbonates and bicarbonates of alkaline earth metals (magnesium, calcium, strontium and barium); sodium tert-butoxide, potassium tert-butoxide, sodium ethoxide, etc.

In the present invention, the "oxidant" may be an oxidant commonly used in the art, including but not limited to ceric ammonium nitrate, 2,3-dichloro-5,6-dicyano-p-benzoquinone, copper chloride, manganese dioxide, permanganate, dichromate, peroxyacetic acid, peroxybenzoic acid, etc.

In the present invention, the "organic solvent¹" refers to a single or mixed organic solvent commonly used in the art, including but not limited to ethers, alkanes, haloalkanes, aromatic hydrocarbons, alcohols, etc. Specifically, the organic solvent may be N,N-dimethylformamide, N,N-dimethylacetamide, dimethylsulfoxide, aromatic hydrocarbons (such as toluene, benzene, dimethylbenzene, trimethylbenzene, etc.), saturated hydrocarbons (such as cyclohexane, hexane, etc.), halohydrocarbons (such as dichloromethane, chloroform, 1,2-dichloroethane, etc.), ethers (such as tetrahydrofuran, diethyl ether, dioxane, 1,2-dimethoxyethane, etc.), esters (such as methyl acetate, ethyl acetate, etc.), ketones (such as acetone, methyl ethyl ketone, etc.), nitriles (such as acetonitrile, etc.), alcohols (such as methanol, ethanol, isopropanol, tert-butanol, etc.), water, mixed solvents of water and these, or the like.

In the present invention, the "organic solvent[2]" refers to a single or mixed organic solvent commonly used in the art, including but not limited to ethers, alkanes, haloalkanes, aromatic hydrocarbons, alcohols, etc. Specifically, the organic solvent may be N,N-dimethylformamide, N,N-dimethylacetamide, dimethylsulfoxide, aromatic hydrocarbons (such as toluene, benzene, dimethylbenzene, trimethylbenzene, etc.), saturated hydrocarbons (such as cyclohexane, hexane, etc.), halohydrocarbons (such as dichloromethane, chloroform, 1,2-dichloroethane, etc.), ethers (such as tetrahydrofuran, diethyl ether, dioxane, 1,2-dimethoxyethane, etc.), esters (such as methyl acetate, ethyl acetate, etc.), ketones (such as acetone, methyl ethyl ketone, etc.), nitriles (such as acetonitrile, etc.), alcohols (such as methanol, ethanol, isopropanol, tert-butanol, etc.), water, mixed solvents of water and these, or the like.

In the present invention, in the aforementioned reaction process, the reaction temperature can be adjusted as required, such as high temperature, room temperature, low temperature, etc. High temperature usually refers to a temperature higher than 30° C., and heating can be performed when necessary. Room temperature usually refers to 15° C. to 30° C. Low temperature usually refers to a temperature lower than 15° C., and cooling can be performed when necessary.

EXAMPLES

If specific reaction conditions are not specified in the examples, conventional conditions or conditions recommended by the manufacturers shall be adopted. The adopted reagents or instruments, without manufacturers, are all commercially-available conventional products.

In the present invention, unless otherwise stated: (i) the temperature is expressed in Celsius (° C.), and operation is performed at room temperature; (ii) the reaction process is tracked by thin-layer chromatography (TLC) or LC-MS; (iii) the final product has clear proton nuclear magnetic resonance spectroscopy ($^1$H-NMR) data and mass spectrometry (MS) data.

The abbreviations and English expressions used in the present invention have the following meanings:
DCM: dichloromethane
DIPEA: N,N-diisopropylethylamine
-Boc: tert-butoxycarbonyl
(BOC)$_2$O: di-tert-butyl dicarbonate
TEA: triethylamine
DMSO: dimethyl sulfoxide
DMA or DMAc: dimethylacetamide
DMAP: 4-dimethylaminopyridine
DMF: N,N-dimethylformamide
EDCI: 1-(3-dimethylaminopropyl)-3-ethylcarbodiimide hydrochloride
EtOH: ethanol
EtONa: sodium ethoxide
aq. HCl: diluted hydrochloric acid
NaH: sodium hydride
N$_2$H$_4$: hydrazine
AcONa: sodium acetate
Ac$_2$O: acetic anhydride
ACN: acetonitrile
THF: tetrahydrofuran
CuI: cuprous iodide
Cs$_2$Co$_3$: cesium carbonate
K$_2$CO$_3$: potassium carbonate
EA: ethyl acetate
MeOH: methanol
MTBE: methyl tert-butyl ether
PE: petroleum ether
HATU: 2-(7-azabenzotriazol-1-yl)-N,N,N',N'-tetramethyluronium hexafluorophosphate
TBAB: tetrabutylammonium bromide (E)-2-(2-(bromomethyl)-3-fluoroallyl)isoindole-1,3-dione was prepared with reference to a synthesis method for the intermediate (Ian A. McDonald, Philipe Bey. *A general preparation of fluoroallylamine enzyme inhibitors incorporating a β-substituted heteroatom. Tetrahedron Letters*, Vol. 26, No. 32, pp 3807-3810, 1985) reported by Ian A. McDonald, et al.

Example 1: Synthesis of (E)-2-(2-(aminomethyl)-3-fluoroallyl)-5-cyclopropyl-2,5,6,7-tetrahydro-4H-pyrazolo[4,3-c]pyridin-4-one (Compound A1)

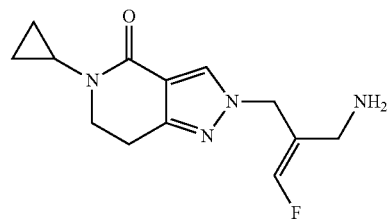 [SMILES: NC/C(=C\F)Cn1cc2c(n1)CCN(C1CC1)C2=O]

Step 1: Synthesis of (E)-1-cyclopropyl-3-((dimethylamino)methylene) piperidin-2,4-dione

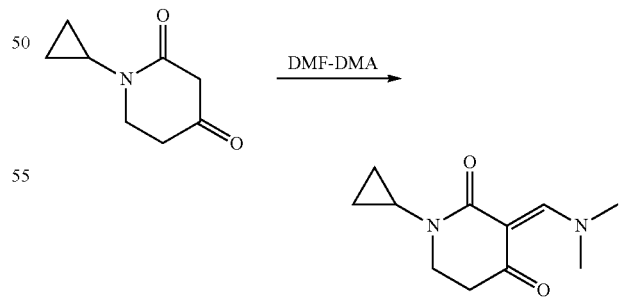

The material cyclopropylpiperidin-2,4-dione (5 g, 32.6 mmol, 1.0 eq.) was slowly added to DMF-DMA (5 g, 41.8 mmol, 1.28 eq.) to react at 25° C. for 2 h. After the reaction was completed, as detected by TLC, the reaction system was concentrated to give a crude product (theoretical yield: 6.789 g), which was directly used in the next step.

Step 2: Synthesis of 5-cyclopropyl-2,5,6,7-tetrahydro-4H-pyrazolo[4,3-c]pyridin-4-one

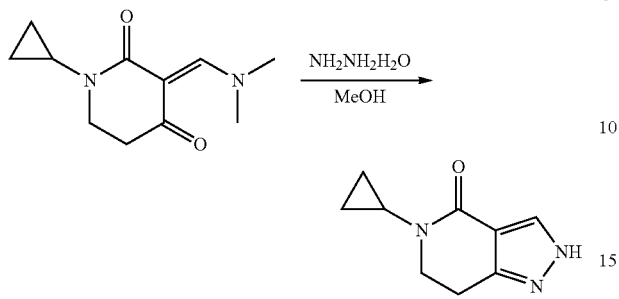

The crude product (E)-1-cyclopropyl-3-((dimethylamino)methylene) piperidin-2,4-dione (6.789 g, 32.6 mmol) obtained in the previous step was dissolved in MeOH (50 mL). Then the solution was added with 85% hydrazine hydrate (2.1 g, 35.9 mmol, 1.1 eq.), and reacted at reflux for 0.5 h. After the reaction was completed, as detected by TLC, the reaction solution was concentrated, and laid aside until a large amount of white solids were precipitated. Then the resulting mixture was added with a small amount of MTBE, and filtered under vacuum. The filter cake was recrystallized with 2-fold volume of 95% EtOH, filtered under vacuum, and dried at 50° C. to give a product (3.7 g, two-step yield: 64%).

Step 3: Synthesis of (E)-2-(2-((5-cyclopropyl-4-oxo-4,5,6,7-tetrahydro-2H-pyrazolo[4,3-c]pyridin-2-yl)methyl)-3-fluoroallyl)isoindole-1,3-dione

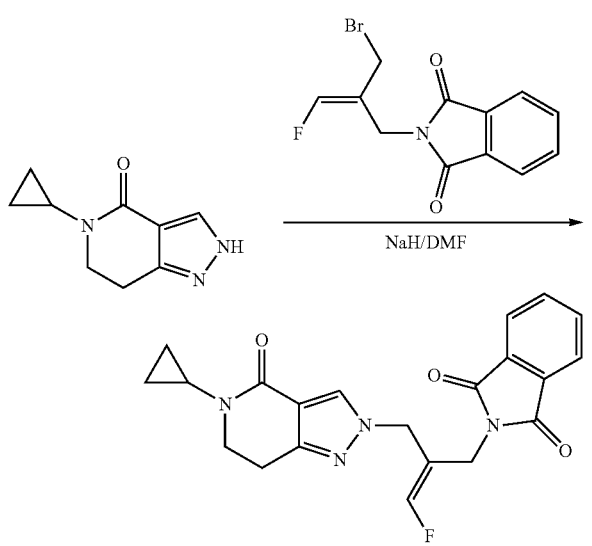

The intermediate 5-cyclopropyl-2,5,6,7-tetrahydro-4H-pyrazolo[4,3-c]pyridin-4-one (1.0 g, 5.643 mmol, 1 eq.) was dissolved in DMF (2.5 mL). After cooling to 0° C., the solution was added with 60% NaH (248 mg, 6.207 mmol, 1.1 eq.) in $N_2$ atmosphere, and stirred for 30 min in $N_2$ atmosphere. Then a solution of (E)-2-(2-(bromomethyl)-3-fluoroallyl)isoindole-1,3-dione (2.019 g, 6.722 mmol, 1.2 eq.) in DMF (2.5 mL) was added dropwise to react at the room temperature of 18° C. for 1 h After the reaction was completed, as detected by TLC, the reaction solution was added with water (10 mL) and extracted with DCM:MeOH=10:1 (15 mL×3). The organic phase was washed with water, dried over anhydrous sodium sulfate, and filtered, and the filtrate was concentrated under reduced pressure. The crude product was purified by silica gel column chromatography (eluent DCM:MeOH=200:1) to give a product (583 mg, yield: 26.2%).

Step 4: Synthesis of (E)-2-(2-(aminomethyl)-3-fluoroallyl)-5-cyclopropyl-2,5,6,7-tetrahydro-4H-pyrazolo[4,3-c]pyridin-4-one

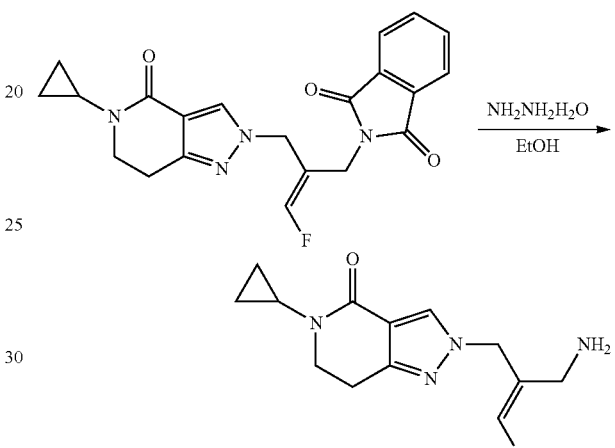

The intermediate (E)-2-(2-((5-cyclopropyl-4-oxo-4,5,6,7-tetrahydro-2H-pyrazolo[4,3-c]pyridin-2-yl)methyl)-3-fluoroallyl)isoindole-1,3-dione (583 mg, 1.478 mmol, 1 eq.) was dissolved in EtOH (15 mL). Then the solution was added with 85% hydrazine hydrate (305 mg, 5.174 mmol, 3.5 eq.), and reacted at reflux for 2 h. After the reaction was completed, as detected by TLC, the reaction solution was filtered under vacuum, and the filtrate was concentrated. The crude product was purified by preparative thin-layer chromatography (DCM:MeOH=10:1) to give a product (70 mg, yield: 17.9%).

$^1$HNMR (400 MHz, DMSO-$d_6$) δ(ppm): 8.12 (s, 1H), 6.79-7.00 (d, 1H), 4.70-4.71 (d, 2H), 3.48-3.51 (t, 2H), 3.04-3.05 (d, 2H), 2.75-2.78 (t, 2H), 2.59-2.65 (m, 1H), 0.71-0.76 (m, 2H), 0.59-0.61 (m, 2H).

Molecular formula: $C_{13}H_{17}FN_4O$, molecular weight: 264.30, LC-MS (Pos, m/z)=265.25 [M+H]$^+$.

Example 2: Synthesis of (E)-1-(2-(aminomethyl)-3-fluoroallyl)-5-cyclopropyl-1,5,6,7-tetrahydro-4H-pyrazolo[4,3-c]pyridin-4-one (Compound A2) Hydrochloride

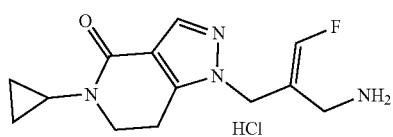 [SMILES: NC/C(=C\F)Cn1ncc2c1CCN(C1CC1)C2=O ; Cl]

Step 1: Synthesis of (E)-1-cyclopropyl-3-((dimethylamino)methylene) piperidin-2,4-dione

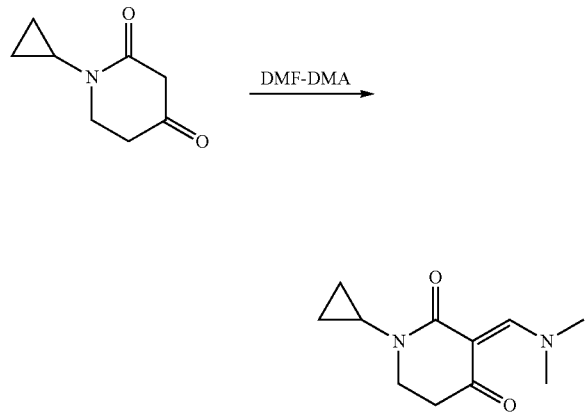

The material cyclopropylpiperidin-2,4-dione (20 g, 0.130 mol, 1.0 eq.) was slowly added to DMF-DMA (19.9 g, 0.167 mol, 1.28 eq.), and the mixture was stirred at 25° C. for 2 h. After the reaction was completed, as detected by TLC, the reaction system was concentrated at 50° C. to give a crude product, which was directly used in the next step.

Step 2: Synthesis of 5-cyclopropyl-1,5,6,7-tetrahydro-4H-pyrazolo[4,3-c]pyridin-4-one

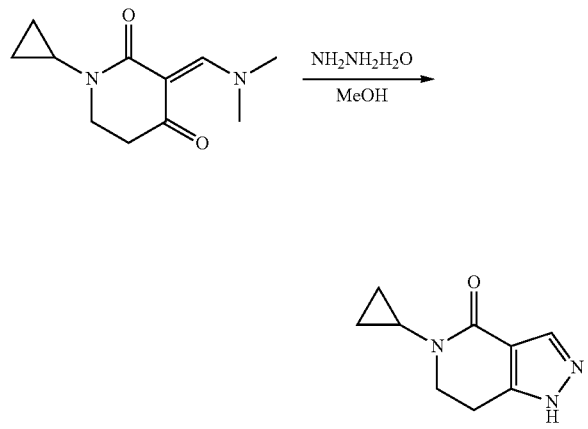

The intermediate (E)-1-cyclopropyl-3-((dimethylamino)methylene) piperidin-2,4-dione (27.073 g, 0.130 mol) was dissolved in MeOH (100 mL). Then the solution was added with 85% hydrazine hydrate (8.4 g, 0.143 mol, 1.1 eq.), and reacted at reflux for 1 h. After the reaction was completed, as detected by TLC, the reaction solution was concentrated to give a crude product. The crude product was recrystallized with 95% EtOH, and filtered under vacuum, and the filter cake was dried at 50° C. to give a product (16 g, yield: 69.6%).

Step 3: Synthesis of (E)-2-(2-((5-cyclopropyl-4-oxo-4,5,6,7-tetrahydro-1H-pyrazolo[4,3-c]pyridin-1-yl)methyl)-3-fluoroallyl)isoindole-1,3-dione

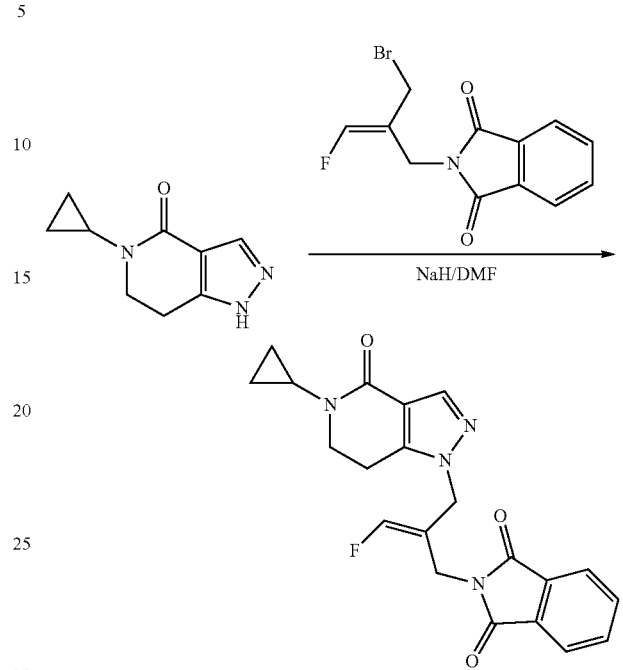

The intermediate 5-cyclopropyl-1,5,6,7-tetrahydro-4H-pyrazolo[4,3-H]pyridin-4-one (2000 mg, 11.286 mmol, 1 eq.) was dissolved in DMF (5 mL). After cooling to 0° C., the solution was added with 60% NaH (496 mg, 12.414 mmol, 1.1 eq.) in $N_2$ atmosphere, and stirred for 30 min in $N_2$ atmosphere. Then a solution of (E)-2-(2-(bromomethyl)-3-fluoroallyl)isoindole-1,3-dione (4037 mg, 13.543 mmol, 1.2 eq.) in DMF (5 mL) was added dropwise to react at the room temperature of 19° C. overnight. After the reaction was completed, as detected by TLC, the reaction solution was added with water (20 mL) and extracted with DCM: MeOH=10:1 (30 mL×3). The organic phase was washed with water, dried over anhydrous sodium sulfate, and filtered, and the filtrate was concentrated under reduced pressure. The crude product was purified by silica gel column chromatography (eluent DCM:MeOH=200:1) to give a product (100 mg, yield: 2.2%).

Step 4: Synthesis of (E)-1-(2-(aminomethyl)-3-fluoroallyl)-5-cyclopropyl-1,5,6,7-tetrahydro-4H-pyrazolo[4,3-c]pyridin-4-one hydrochloride

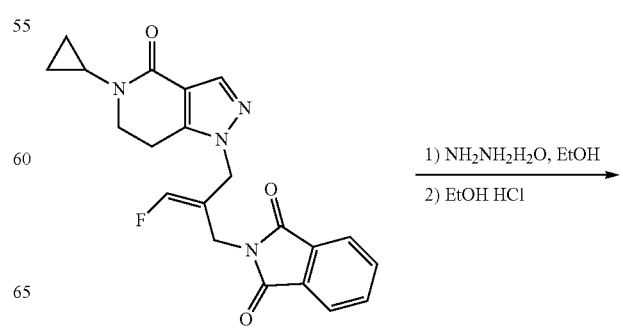

-continued

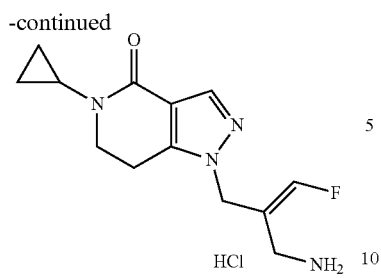

The intermediate (E)-2-(2-((5-cyclopropyl-4-oxo-4,5,6,7-tetrahydro-1H-pyrazolo[4,3-c]pyridin-1-yl)methyl)-3-fluoroallyl)isoindole-1,3-dione (70 mg, 0.177 mmol, 1 eq.) was dissolved in EtOH (1.75 mL). Then the solution was added with 85% hydrazine hydrate (36 mg, 0.621 mmol, 3.5 eq.), and reacted at reflux for 2 h. After the reaction was completed, as detected by TLC, the reaction solution was filtered under vacuum, and the filtrate was concentrated. The crude product was purified by preparative thin-layer chromatography (DCM:MeOH=10:1) to give a crude product. The crude product was dissolved in a small amount of ethanol. The solution was added with hydrogen chloride ethanol (0.1 mL) and stirred for 1 h, so that solids were precipitated. Then MTBE and PE were added, so that white solids were precipitated. The resulting mixture was filtered under vacuum, and the filter cake was dried to give a product (40 mg, yield: 74.9%).

$^{1}$HNMR (400 MHz, DMSO-$d_6$) δ(ppm): 8.46 (s, 3H), 7.72 (s, 1H), 7.06-7.26 (d, 1H), 4.89 (d, 2H), 3.54-3.57 (t, 2H), 3.43-3.44 (d, 2H), 2.98-3.02 (t, 2H), 2.57-2.62 (m, 1H), 0.71-0.76 (t, 2H), 0.56-0.60 (m, 2H).

Molecular formula: $C_{13}H_{18}ClFN_4O$, molecular weight: 300.76, LC-MS (Pos, m/z)=264.8 $[M+H]^+$.

Example 3: Synthesis of (E)-2-(2-(aminomethyl)-3-fluoroallyl)-5-ethyl-2,5,6,7-tetrahydro-4H-pyrazolo[4,3-c]pyridin-4-one (Compound A6) Hydrochloride

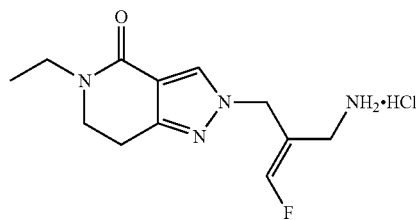

Step 1: Synthesis of Intermediate (E)-(3-fluoro-2-((5-ethyl-4-oxo-4,5,6,7-tetrahydro-2H-pyrazolo[4,3-c]pyridin-2-yl)methyl)allyl)tert-butyl carbamate

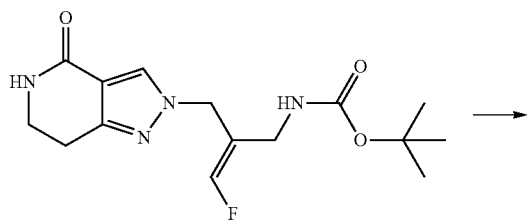

The intermediate (E)-(3-fluoro-2-((4-oxo-4,5,6,7-tetrahydro-2H-pyrazolo [4,3-c]pyridin-2-yl)methyl)allyl)tert-butyl carbamate (1.0 g, 3.08 mmol, 1.0 eq.) was dissolved in tetrahydrofuran (10 mL). Then the solution was added with sodium hydride (160 mg, 4.0 mmol, 1.3 eq., 60%) to react at room temperature for 30 min. The reaction solution was added with iodoethane (576 mg, 3.7 mmol, 1.2 eq.), and heated to 60° C. to react for 4 h. After the reaction was completed, as detected by LC-MS, water (10 mL) was added to the reaction flask, and ethyl acetate (20 mL×3) was added for extraction. The organic phase was dried and concentrated. The crude product was purified by preparative thin-layer chromatography (MeOH:DCM=1:20) to give a product (180 mg, yield: 16%).

Step 2: Synthesis of Compound (E)-2-(2-(aminomethyl)-3-fluoroallyl)-5-ethyl-2,5,6,7-tetrahydro-4H-pyrazolo[4,3-c]pyridin-4-one hydrochloride

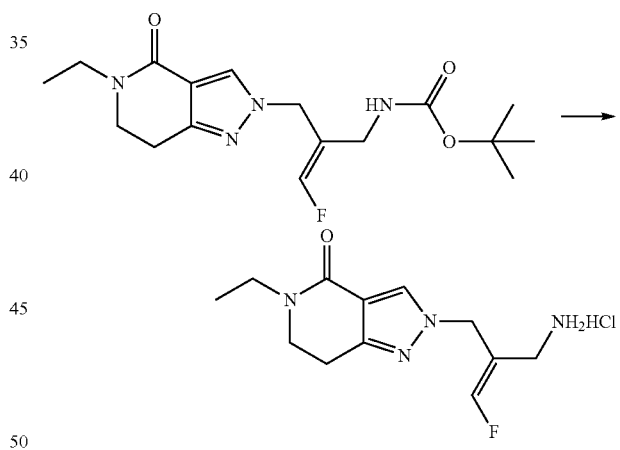

The intermediate (E)-(3-fluoro-2-((5-ethyl-4-oxo-4,5,6,7-tetrahydro-2H-pyrazolo[4,3-c]pyridin-2-yl)methyl)allyl) tert-butyl carbamate (180 mg, 0.51 mmol, 1.0 eq.) was dissolved in ethanol (2 mL). Then the solution was added with hydrogen chloride ethanol solution (2 mL) to react for 12 h. After the reaction was completed, as detected by LC-MS, the reaction solution was concentrated under reduced pressure, dissolved with water, and lyophilized to give a product (120 mg, yield: 83%).

$^{1}$HNMR (400 MHz, DMSO-$d_6$) δ(ppm): 8.47 (s, 3H), 8.27 (s, 1H), 7.37 (s, 0.5H), 7.16 (s, 0.5H), 4.93 (s, 2H), 3.52-3.56 (m, 2H), 3.39-3.42 (m, 2H), 3.32-3.33 (d, 2H), 2.81-2.84 (m, 2H), 1.04-1.07 (m, 3H).

Molecular formula: $C_{12}H_{17}FN_4O$, molecular weight: 252.29, LC-MS (Pos, m/z)=253.22$[M+H]^+$.

Example 4: Synthesis of (E)-2-(2-(aminomethyl)-3-fluoroallyl)-5-tert-butyl-2,5,6,7-tetrahydro-4H-pyrazolo[4,3-c]pyridin-4-one (Compound A7) Hydrochloride

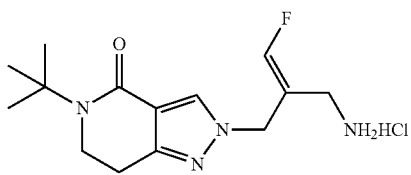

Step 1: Synthesis of ethyl 3-(tert-butylamino)propionate

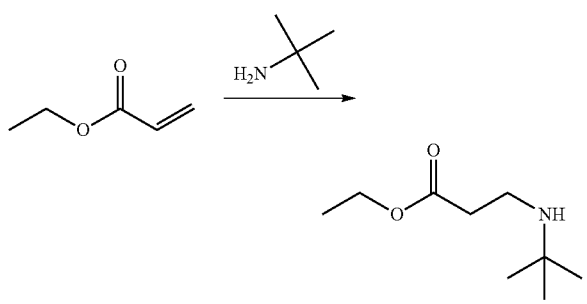

Tert-butylamine (87.66 g, 1.20 mol, 1.2 eq.) was dissolved in ethanol (400 mL). Then the solution was slowly added with ethyl acrylate (100.00 g, 1.00 mol, 1.0 eq.) dropwise under an ice bath to react at room temperature overnight. After no materials were left, as detected by GC, the reaction solution was concentrated under reduced pressure to give a product (173 g, yield: 99%).

Step 2: Synthesis of ethyl 3-(tert-butyl(3-ethoxy-3-oxopropyl)amino)-3-oxopropionate

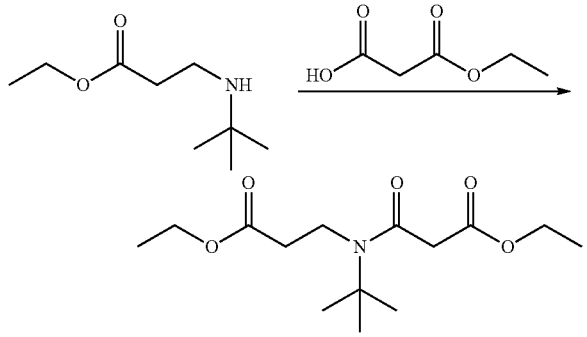

The intermediate ethyl 3-(tert-butylamino)propionate (70.00 g, 0.404 mol, 1.0 eq.), monoethyl malonate (53.37 g, 0.404 mol, 1.0 eq.), 4-dimethylaminopyridine (9.88 g, 0.0808 mmol, 0.2 eq.) and triethylamine (102.30 g, 1.010 mol, 2.5 eq.) were dissolved in dichloromethane (490 mL), and the solution was stirred under an ice bath for 15 min. Then 1-(3-dimethylaminopropyl)-3-ethylcarbodiimide hydrochloride (93.02 g, 0.485 mol, 1.2 eq.) was added in batches, and the solution reacted at room temperature overnight. After the reaction was completed, as detected by TLC, under an ice bath, water and concentrated hydrochloric acid (3:1, 360 mL) were added to the reaction flask, and the mixture was stirred for 15 min, followed by liquid separation. The aqueous phase was extracted with dichloromethane (300 mL). The organic phases were combined, washed successively with saturated aqueous sodium bicarbonate solution (800 mL) and saturated aqueous sodium chloride solution (800 mL×2), dried over anhydrous sodium sulfate, and filtered, and the filtrate was concentrated under reduced pressure to give a product (114 g, yield: 98.2%).

Step 3: Synthesis of 1-tert-butylpiperidin-2,4-dione

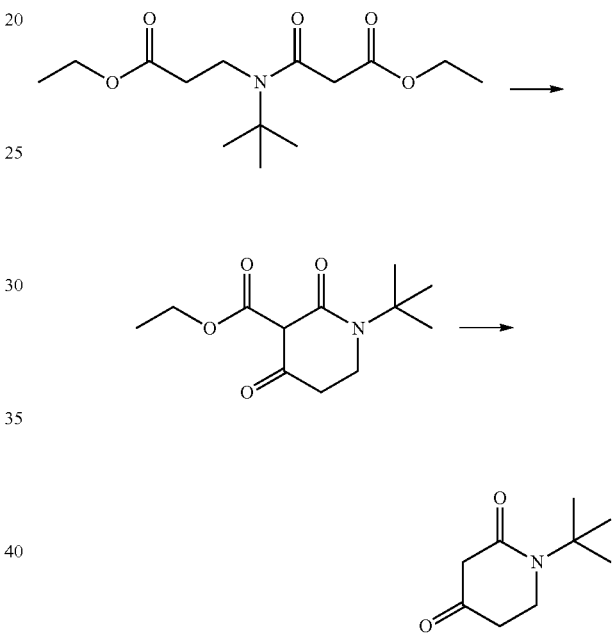

Ethyl 3-(tert-butyl(3-ethoxy-3-oxopropyl)amino)-3-oxopropionate (114.00 g, 0.397 mol, 1.0 eq.) and sodium ethoxide (53.99 g, 0.793 mol, 2.0 eq.) were dissolved in ethanol (456 mL) to react at 80° C. for 4 h. After the reaction was completed, as detected by TLC, the reaction solution was concentrated under reduced pressure to give a sodium salt of the intermediate ethyl 1-tert-butyl-2,4-dioxopiperidin-3-carboxylate. Then water was added, and the pH of the mixture was adjusted to 2 with concentrated hydrochloric acid. The reaction was performed at 85° C. for 5 h, and then at 95° C. for 1.5 h. After the reaction was completed, as detected by LC-MS, the reaction solution was cooled to room temperature, and sodium chloride was added until the reaction solution was saturated. Dichloromethane (400 mL×3) was added for extraction. The organic phase was dried and concentrated to give an oily crude product. After cooling, solids were precipitated. Then MTBE was added, and the mixture was stirred, so that a large amount of solids were precipitated. The resulting mixture was filtered under vacuum, and the filter cake was rinsed with a small amount of MTBE and dried to give a product (45.3 g, yield: 67.48%).

Step 4: Synthesis of 5-tert-butyl-2,5,6,7-tetrahydro-4H-pyrazolo[4,3-c]pyridin-4-one

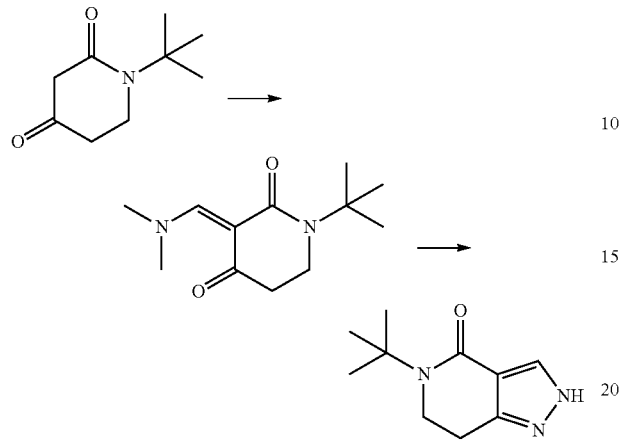

The intermediate 1-tert-butylpiperidin-2,4-dione (40 g, 0.207 mol, 1.0 eq.) was dissolved in N,N-dimethylformamide dimethyl acetal (35.04 g, 0.265 mol, 1.28 eq.) to react at room temperature for 3 h. After the reaction was completed, as detected by TLC, the reaction solution was concentrated under reduced pressure to give the intermediate (E)-1-tert-butyl-3-((dimethylamino) methylene)piperidin-2,4-dione. The intermediate was added with methanol (200 mL) and hydrazine hydrate (15.3 g, 0.228 mol, 1.1 eq.), and reacted at reflux for 1 h. After the reaction was completed, as detected by LC-MS, the reaction solution was concentrated under reduced pressure, added with MTBE (300 mL), and stirred overnight, and a large amount of solids were precipitated. The resulting mixture was filtered under vacuum, and the filter cake was rinsed with MTBE and dried to give a product (40.00 g, yield: 87.7%).

Step 5: Synthesis of (E)-2-(2-((5-tert-butyl-4-oxo-4,5,6,7-tetrahydro-2H-pyrazolo[4,3-c]pyridin-2-yl)methyl)-3-fluoroallyl)isoindolin-1,3-dione

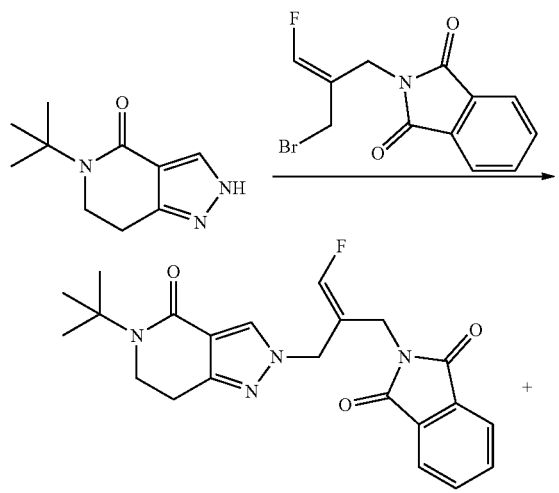

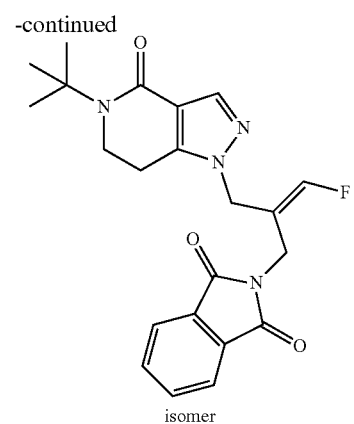

isomer 5-tert-butyl-2,5,6,7-tetrahydro-4H-pyrazolo[4,3-c]pyridin-4-one (1.08 g, 5.59 mmol, 1.0 eq.) was dissolved in DMF (10 mL). After cooling to 0° C., the solution was added with NaH (mass fraction: 60%, 246 mg, 6.147 mmol, 1.1 eq.), stirred for 30 min, and added with a solution of (E)-2-(2-(bromomethyl)-3-fluoroallyl)isoindolin-1,3-dione (2.00 g, 6.706 mmol, 1.2 eq.) in DMF (5 mL) dropwise to react at room temperature for 1 h. After the reaction was completed, as detected by LC-MS, the reaction solution was added with water (12 mL) and extracted with a mixture of dichloromethane and methanol (10:1, 25 mL×3), followed by liquid separation. The organic phases were combined, backwashed with water, dried over anhydrous sodium sulfate and filtered, and the filtrate was concentrated under reduced pressure. The crude product was purified by silica gel column chromatography (PE:EA=3:1-2:1, added with 0.5% triethylamine) to give the product (E)-2-(2-((5-tert-butyl-4-oxo-4,5,6,7-tetrahydro-2H-pyrazolo[4,3-c]pyridin-2-yl)methyl)-3-fluoroallyl)isoindolin-1,3-dione (1.3 g, yield: 56.7%) and the positional isomer (E)-2-(2-((5-(tert-butyl)-4-oxo-4,5,6,7-tetrahydro-1H-pyrazolo[4,3-c]pyridin-1-yl)methyl)-3-fluoroallyl)isoindolin-1,3-dione (350 mg, yield: 15.3%).

Step 6: Synthesis of (E)-2-(2-(aminomethyl)-3-fluoroallyl)-5-tert-butyl-2,5,6,7-tetrahydro-4H-pyrazolo[4,3-c]pyridin-4-one hydrochloride

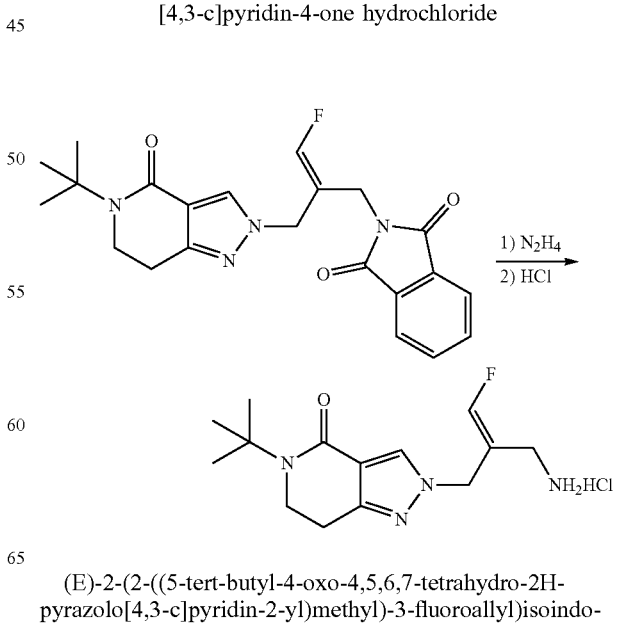

(E)-2-(2-((5-tert-butyl-4-oxo-4,5,6,7-tetrahydro-2H-pyrazolo[4,3-c]pyridin-2-yl)methyl)-3-fluoroallyl)isoindolin-1,3-dione (1000 mg, 2.438 mmol, 1.0 eq.) was dissolved in EtOH (30 mL). Then the solution was added with hydrazine hydrate (502.4 mg, 8.531 mmol, 3.5 eq., 85%), and refluxed for 2 h. After the reaction was completed, as detected by LC-MS, the reaction solution was filtered under vacuum, and the filtrate was concentrated under reduced pressure. The resulting solution was added with EA (30 mL), refluxed, and filtered while hot. The filtrate was concentrated under reduced pressure, diluted with a small amount of ethanol, added with hydrogen chloride ethanol solution, and stirred at room temperature for 30 min. The resulting mixture was added with acetonitrile and concentrated under reduced pressure to give the product (E)-2-(2-(aminomethyl)-3-fluoroallyl)-5-tert-butyl-2,5,6,7-tetrahydro-4H-pyrazolo[4,3-c]pyridin-4-one hydrochloride (747.9 mg, yield: 98%).

$^1$HNMR (400 MHz, DMSO-d$_6$) δ(ppm): 8.51 (brs, 3H), 8.22 (s, 1H), 7.16-7.36 (d, J=82 Hz, 1H), 4.93 (s, 2H), 3.52-3.56 (t, 2H), 3.31-3.32 (d, 2H), 2.73-2.76 (t, 2H), 2.08 (s, 1H), 1.42 (s, 9H).

Molecular formula: $C_{14}H_{21}FN_4O$, molecular weight: 280.35, LC-MS (Pos, m/z)=281.23[M+H]$^+$.

Example 5: Synthesis of (E)-2-(2-(aminomethyl)-3-fluoroallyl)-5-cyclobutyl-2,5,6,7-tetrahydro-4H-pyrazolo[4,3-c]pyridin-4-one (Compound A9) Hydrochloride

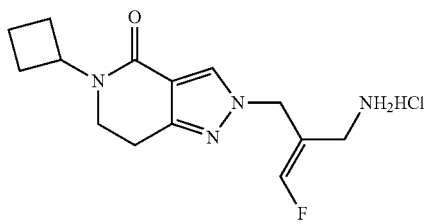

Step 1: Synthesis of ethyl 3-(cyclobutylamino)propionate

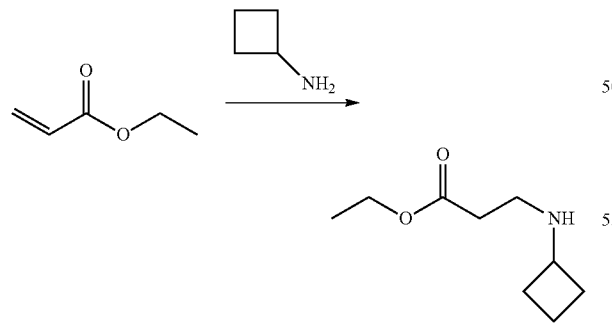

The material cyclobutylamine (4.26 g, 59.93 mmol, 1.2 eq.) was dissolved in ethanol (50 mL). Then the solution was slowly added with ethyl acrylate (5.0 g, 49.94 mmol, 1.0 eq.) dropwise under an ice bath to react for 12 h. After no materials were left, as detected by TLC, the reaction solution was concentrated under reduced pressure at 80° C. to give a product (8.55 g, yield: 100%).

Step 2: Synthesis of ethyl 3-(cyclobutyl(3-ethoxy-3-oxopropyl)amino)-3-oxopropionate

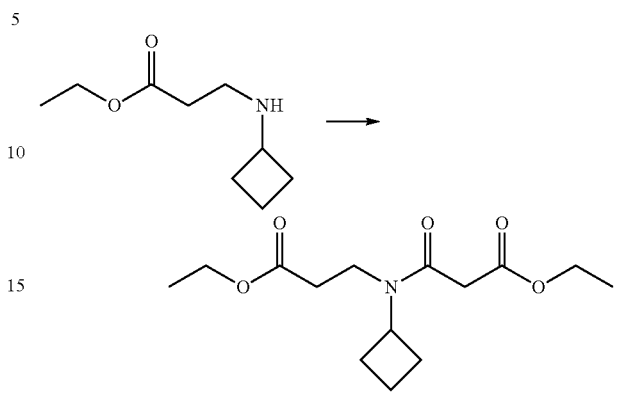

The intermediate ethyl 3-(cyclobutylamino)propionate (8.55 g, 49.94 mmol, 1.0 eq.) was dissolved in dichloromethane (100 mL). Then the solution was cooled to 0° C. in an ice-water bath, added with monoethyl malonate (6.6 g, 49.94 mmol, 1.0 eq.) dropwise, and after addition, stirred for 10 min. Then the mixture was successively added with triethylamine (12.6 g, 124.85 mmol, 2.5 eq.), 4-dimethylaminopyridine (609.6 mg, 4.99 mmol, 0.1 eq.) and 1-(3-dimethylaminopropyl)-3-ethylcarbodiimide hydrochloride (11.5 g, 59.93 mmol, 1.2 eq.) to react for 12 h. After the reaction was completed, as detected by TLC, the reaction solution was added with 2.5 mol/L hydrochloric acid (100 mL) and stirred for 10 min, followed by liquid separation. The aqueous phase was extracted with dichloromethane (50 mL). The organic phases were combined, washed successively with saturated aqueous sodium carbonate solution (50 mL) and water (50 mL), followed by liquid separation. The organic phase was dried over anhydrous magnesium sulfate and filtered, and the filtrate was concentrated under reduced pressure to give a product (10.1 g, yield: 71.1%).

Step 3: Synthesis of ethyl 1-cyclobutyl-2,4-dioxopiperidin-3-carboxylate

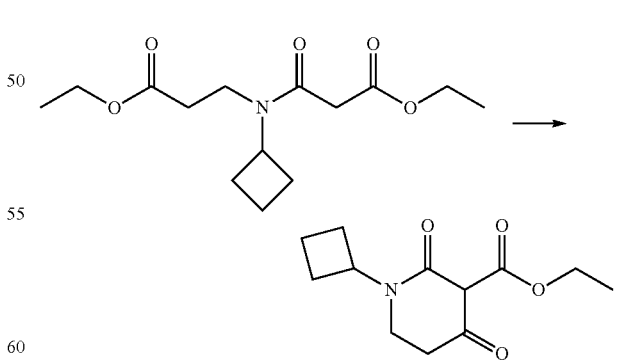

The intermediate ethyl 3-(cyclobutyl(3-ethoxy-3-oxopropyl)amino)-3-oxopropionate (10.1 g, 35.40 mmol, 1.0 eq.) was dissolved in ethanol (50 mL). The solution was added with sodium ethoxide (6.0 g, 88.49 mmol, 2.5 eq.) to react at 80° C. for 1 h. After the reaction was completed, as detected by TLC, the reaction solution was concentrated under reduced pressure to give a product (8.47 g, yield: 100%).

Step 4: Synthesis of 1-cyclobutylpiperidin-2,4-dione

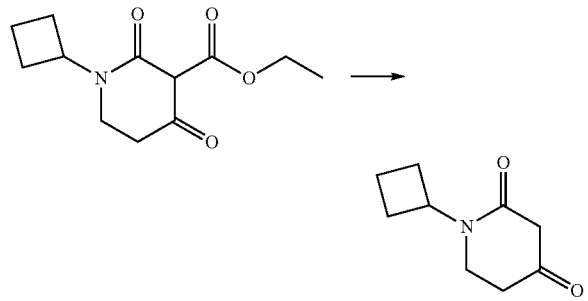

The intermediate ethyl 1-cyclobutyl-2,4-dioxopiperidin-3-carboxylate (8.47 g, 35.40 mmol, 1.0 eq.) was dissolved in water (20 mL) and concentrated hydrochloric acid (30 mL) to react at 120° C. for 2 h. After the reaction was completed, as detected by TLC, the reaction solution was cooled to room temperature, and extracted with dichloromethane (50 mL×3). The organic phases were combined, dried over anhydrous magnesium sulfate, and filtered, and the filtrate was concentrated to give a product (3 g, yield: 50.8%).

Step 5: Synthesis of 1-cyclobutyl-3-((dimethylamino)methylene)piperidin-2,4-dione

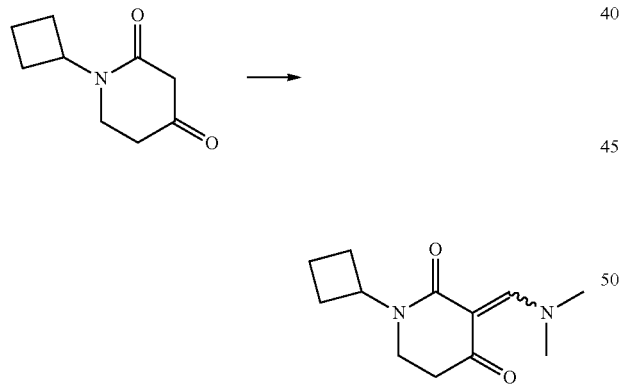

The intermediate 1-cyclobutylpiperidin-2,4-dione (3 g, 17.94 mmol, 1.0 eq.) was dissolved in dichloromethane (2 mL). The solution was added with N,N-dimethylformamide dimethyl acetal (2.35 g, 19.74 mmol, 1.1 eq.) to react at room temperature for 1 h. After the reaction was completed, as detected by TLC, the reaction solution was concentrated under reduced pressure to give a product (3.98 g, yield: 100%).

Step 6: Synthesis of 5-cyclobutyl-2,5,6,7-tetrahydro-4H-pyrazolo[4,3-c]pyridin-4-one

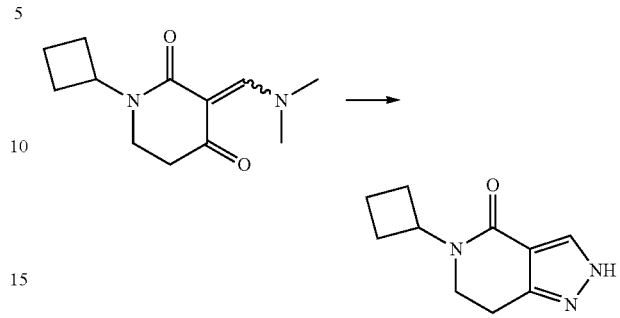

The intermediate (E)-1-cyclobutyl-3-((dimethylamino)methylene) piperidin-2,4-dione (3.98 g, 17.94 mmol, 1.0 eq.) and hydrazine hydrate (1.16 g, 19.73 mmol, 1.1 eq.) were dissolved in methanol (4 mL). Then the solution was heated to reflux for 1 h. After the reaction was completed, as detected by TLC, the reaction solution was concentrated under reduced pressure. The crude product was purified by column chromatography (DCM:MeOH=100:1-50:1) to give a product (2.1 g, yield: 61.2%).

Step 7: Synthesis of (E)-2-(2-((5-cyclobutyl-4-oxo-4,5,6,7-tetrahydro-2H-pyrazolo[4,3-c]pyridin-2-yl)methyl)-3-fluoroallyl)isoindolin-1,3-dione

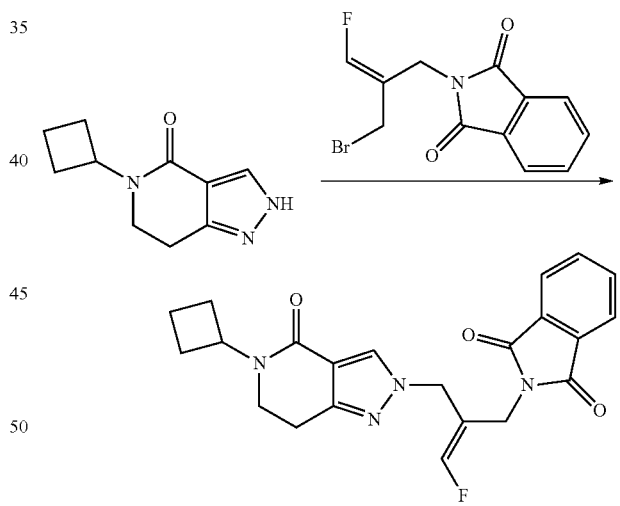

The intermediate 5-cyclobutyl-2,5,6,7-tetrahydro-4H-pyrazolo[4,3-c]pyridine-4-one (1.0 g, 5.23 mmol, 1.0 eq.) was dissolved in DMF (5 mL). The solution was cooled in an ice-water bath, added with NaH (mass fraction: 60%, 230 mg, 5.75 mmol, 1.1 eq.), stirred at room temperature for 30 min, and then added with a solution of (E)-2-(2-(bromomethyl)-3-fluoroallyl)isoindolin-1,3-dione (2.0 g, 6.29 mmol, 1.2 eq.) in DMF (5 mL) dropwise. After addition, the reaction was performed for 1 h. After the reaction was completed, as detected by TLC, the reaction solution was added with water (50 mL) and extracted with ethyl acetate (50 mL×3). The organic phase was washed with water (50 mL×2), dried over anhydrous magnesium sulfate and filtered, and the filtrate was concentrated under reduced pressure. The crude product was purified by preparative thin-layer chromatography (PE:EA=1:2) to give a product (572 mg, yield: 27.2%).

Step 8: Synthesis of (E)-2-(2-(aminomethyl)-3-fluoroallyl)-5-cyclobutyl-2,5,6,7-tetrahydro-4H-pyrazolo[4,3-c]pyridin-4-one hydrochloride

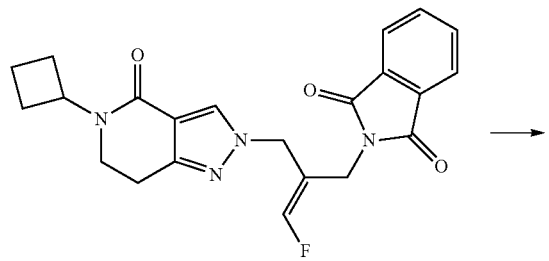

The intermediate (E)-2-(2-((5-cyclobutyl-4-oxo-4,5,6,7-tetrahydro-2H-pyrazolo[4,3-c]pyridin-2-yl)methyl)-3-fluoroallyl)isoindolin-1,3-dione (572 mg, 1.40 mmol, 1.0 eq.) was dissolved in EtOH (10 mL). Then the solution was added with hydrazine hydrate (245 mg, 4.90 mmol, 3.5 eq.) to react at 80° C. for 3 h. After the reaction was completed, as detected by LC-MS, the reaction solution was cooled to room temperature and filtered under vacuum, and the filtrate was concentrated. The crude product was slurried with dichloromethane (10 mL) and filtered, and the filtrate was concentrated under reduced pressure. The crude product was purified by preparative thin-layer chromatography (DCM:MeOH=10:1) to give an oily liquid (296 mg). The resulting product was dissolved in dichloromethane (2 mL), added with hydrogen chloride ethanol solution (129 mg) dropwise, stirred for 10 min, and concentrated under reduced pressure to give a product (256 mg, yield: 58%).

$^1$HNMR (400 MHz, DMSO-$d_6$) δ(ppm): 8.43 (s, 3H), 8.26 (s, 1H), 7.36 (s, 0.5H), 7.15 (s, 0.5H), 4.93-4.92 (m, 3H), 3.57-3.54 (m, 2H), 3.34-3.33 (m, 2H), 2.83-2.80 (m, 2H), 2.20-2.13 (m, 2H), 2.06-1.99 (m, 2H), 1.67-1.66 (m, 2H).

Molecular formula: $C_{14}H_{19}FN_4O$, molecular weight: 278.33, LC-MS (Pos, m/z)=279.19[M+H]$^+$.

Example 6: Synthesis of (E)-2-(2-(aminomethyl)-3-fluoroallyl)-5-cyclopentyl-2,5,6,7-tetrahydro-4H-pyrazolo[4,3-c]pyridin-4-one (Compound A10) Hydrochloride

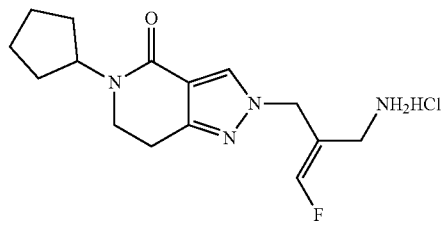

Step 1: Synthesis of Intermediate ethyl 3-(cyclopentylamino)propionate

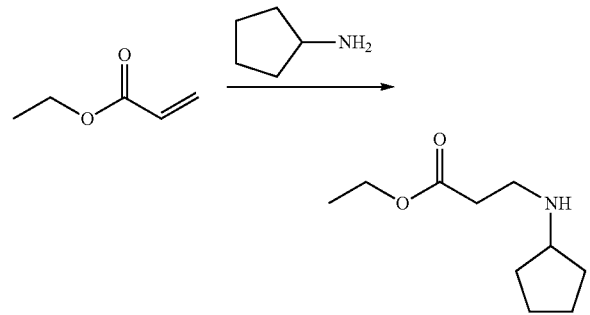

The material cyclopentylamine (5.1 g, 60 mmol, 1.0 eq.) was dissolved in ethanol (10 mL). Then the solution was slowly added with ethyl acrylate (5.0 g, 50 mmol, 1.0 eq.) dropwise under an ice bath to react for 12 h. After no materials were left, as detected by TLC, the reaction solution was concentrated under reduced pressure to give a product (9.2 g, yield: 99%).

Step 2: Synthesis of Intermediate ethyl 3-(cyclopentyl(3-ethoxy-3-oxopropyl)amino)-3-oxopropionate

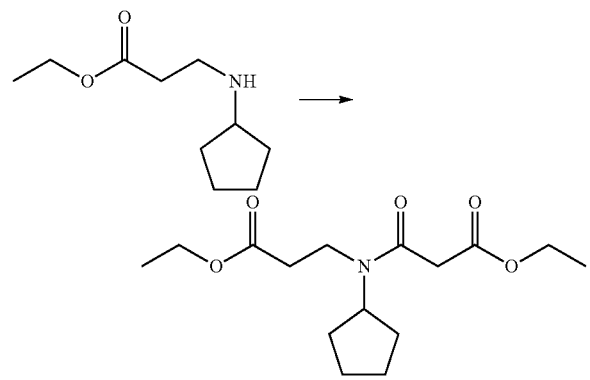

The intermediate ethyl 3-(cyclopentylamino)propionate (8.2 g, 44.26 mmol, 1.0 eq.), monoethyl malonate (5.85 g, 44.26 mmol, 1.0 eq.), 4-dimethylaminopyridine (1.08 g, 8.85 mmol, 0.2 eq.) and triethylamine (10.3 g, 101.8 mmol, 2.3 eq.) were dissolved in dichloromethane (100 mL). After being stirred for 5 min, the solution was added with 1-(3-dimethylaminopropyl)-3-ethylcarbodiimide hydrochloride (8.49 g, 53.11 mmol, 1.2 eq.) in batches to react for 12 h. After the reaction was completed, as detected by TLC, water and concentrated hydrochloric acid (3:1, 100 mL) were added to a reaction flask, and the mixture was stirred for 10 min, followed by liquid separation. The aqueous phase was extracted with dichloromethane (100 mL). The organic phases were combined, washed successively with saturated aqueous sodium carbonate (100 mL) and water (100 mL×2), dried over anhydrous sodium sulfate, and filtered, and the filtrate was concentrated under reduced pressure to give a product (11.5 g, yield: 87%).

Step 3: Synthesis of Intermediate ethyl 1-cyclopentyl-2,4-dioxopiperidin-3-carboxylate

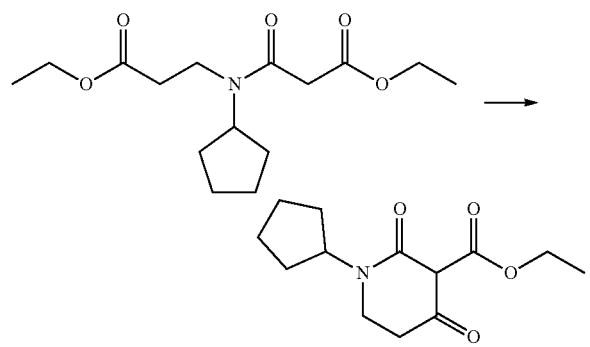

The intermediate ethyl 3-(cyclopentyl(3-ethoxy-3-oxo-propyl)amino)-3-oxopropionate (11.5 g, 38.4 mmol, 1.0 eq.) and sodium ethoxide (5.23 g, 76.8 mmol, 2.0 eq.) were dissolved in ethanol (100 mL) to react at 80° C. for 2 h. After the reaction was completed, as detected by LC-MS, the reaction solution was concentrated under reduced pressure to give a product (9.73 g, yield: 100%).

Step 4: Synthesis of Intermediate 1-cyclopentylpiperidin-2,4-dione

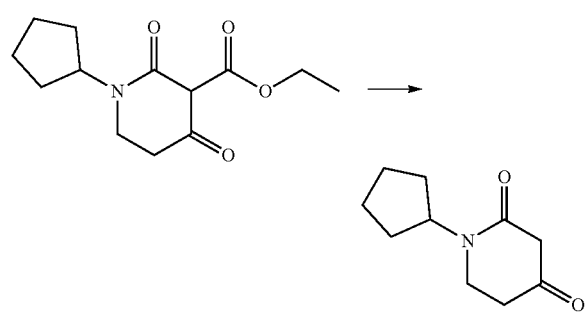

The intermediate ethyl 1-cyclopentyl-2,4-dioxopiperidin-3-carboxylate (9.72 g, 38.4 mmol, 1.0 eq.) was dissolved in water (50 mL) and concentrated hydrochloric acid (20 mL) to react at 120° C. for 1.5 h. After the reaction was completed, as detected by LC-MS, the solution was cooled to room temperature and added with sodium chloride solid until saturated. Dichloromethane (100 mL×3) was added for extraction. The organic phase was dried and concentrated to give a product (6.95 g, yield: 100%).

Step 5: Synthesis of Intermediate 1-cyclopentyl-3-((dimethylamino)methylene)piperidin-2,4-dione

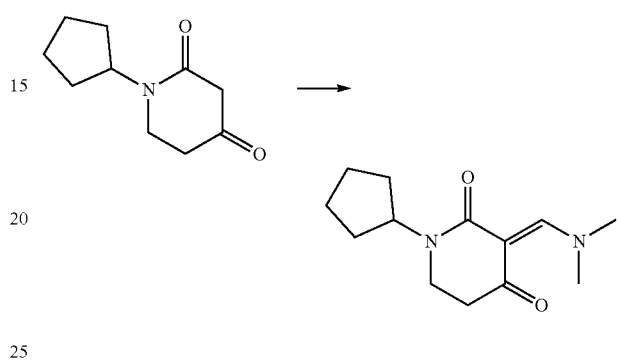

The intermediate 1-cyclopentylpiperidin-2,4-dione (6.95 g, 38.4 mmol, 1.0 eq.) was dissolved N,N-dimethylformamide dimethyl acetal (5.04 g, 42.24 mmol, 1.1 eq.) to react for 1 h. After the reaction was completed, as detected by LC-MS, the reaction solution was concentrated under reduced pressure to give a product (9.07 g, yield: 100%).

Step 6: Synthesis of Intermediate 5-cyclopentyl-2,5,6,7-tetrahydro-4H-pyrazolo[4,3-c]pyridin-4-one

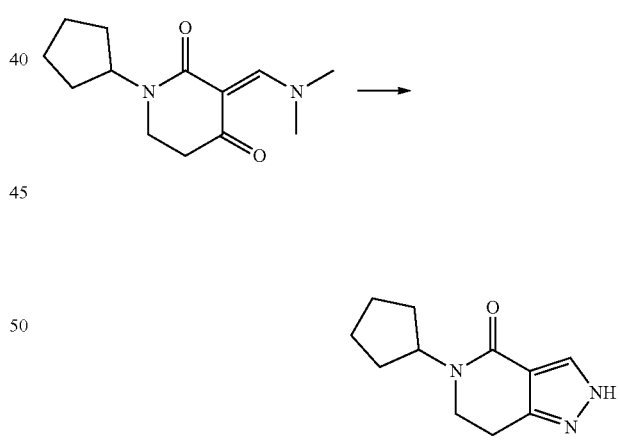

The intermediate 1-cyclopentyl-3-((dimethylamino)methylene)piperidin-2,4-dione (9.07 g, 38.4 mmol, 1.0 eq.) and hydrazine hydrate (2.114 g, 42.24 mmol, 1.1 eq.) were dissolved in methanol (50 mL) to react at 60° C. for 40 min. After the reaction was completed, as detected by LC-MS, the reaction solution was cooled to room temperature and concentrated under reduced pressure. The crude product was first purified by silica gel column chromatography (DCM: MeOH=50:1), and then slurried with methyl tert-butyl ether (50 mL), and filtered under vacuum to give a product (3.1 g, yield: 39%).

Step 7: Synthesis of Intermediate (E)-2-(2-((5-cyclopentyl-4-oxo-4,5,6,7-tetrahydro-2H-pyrazolo[4,3-c]pyridin-2-yl)methyl)-3-fluoroallyl)isoindolin-1,3-dione

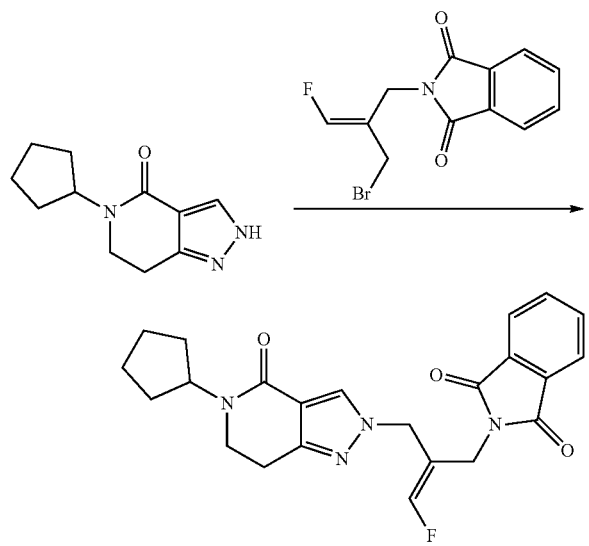

The intermediate 5-cyclopentyl-2,5,6,7-tetrahydro-4H-pyrazolo[4,3-c]pyridin-4-one (1.0 g, 4.87 mmol, 1.0 eq.) was dissolved in DMF (5 mL). Then the solution was added with sodium hydride (214 mg, 5.36 mmol, 1.12 eq., 60%), stirred for 30 min, and then added with a solution of (E)-2-(2-(bromomethyl)-3-fluoroallyl)isoindolin-1,3-dione (1.74 g, 5.84 mmol, 1.2 eq.) in DMF (5 mL) dropwise to react for 1 h. After the reaction was completed, as detected by LC-MS, the reaction solution was added with water (10 mL) and extracted with ethyl acetate (50 mL×2), followed by liquid separation. The organic phase was washed with water (50 mL×2), dried over anhydrous sodium sulfate, filtered and concentrated under reduced pressure. The crude product was purified by silica gel column chromatography (PE:EA=1:1) to give a product (700 mg, yield: 34%).

Step 8: Synthesis of Compound (E)-2-(2-(aminomethyl)-3-fluoroallyl)-5-cyclopentyl-2,5,6,7-tetrahydro-4H-pyrazolo[4,3-c]pyridin-4-one hydrochloride

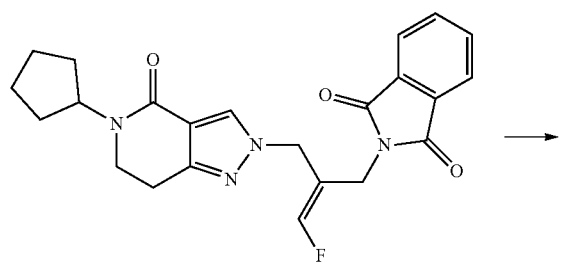

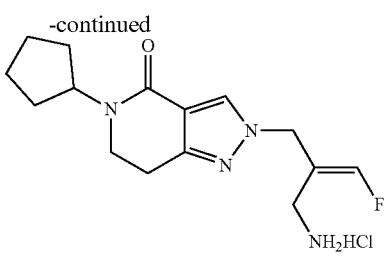

The intermediate (E)-2-(2-((5-cyclopentyl-4-oxo-4,5,6,7-tetrahydro-2H-pyrazolo[4,3-c]pyridin-2-yl)methyl)-3-fluoroallyl)isoindolin-1,3-dione (700 mg, 1.65 mmol, 1.0 eq.) was dissolved in EtOH (10 mL). Then the solution was added with hydrazine hydrate (290 mg, 5.77 mmol, 3.5 eq.) to react at 80° C. for 30 min. After the reaction was completed, as detected by LC-MS, the reaction solution was filtered under vacuum, and the filtrate was concentrated. The crude product was purified by preparative thin-layer chromatography (DCM:MeOH=10:1). The obtained oil was dissolved in methanol (2 mL). The resulting solution was added with hydrogen chloride ethanol solution (0.25 mL) dropwise, stirred for 30 min, and concentrated under reduced pressure to give a product (230 mg, yield: 42%).

$^1$HNMR (400 MHz, DMSO-$d_6$) δ(ppm): 8.37 (s, 3H), 8.24 (s, 1H), 7.36 (s, 0.5H), 7.16 (s, 0.5H), 4.91 (s, 3H), 3.42-3.45 (m, 2H), 3.34-3.35 (d, 2H), 2.78-2.81 (m, 2H), 1.69 (s, 4H), 1.54 (s, 4H).

Molecular formula: $C_{15}H_{21}FN_4O$, molecular weight: 292.36, LC-MS (Pos, m/z)=293.20[M+H]$^+$.

Example 7: Synthesis of (E)-2-(2-(aminomethyl)-3-fluoroallyl)-5-(tert-butyl)-5,6-dihydropyrrolo[3,4-c]pyrazol-4(2H)-one (Compound A13)

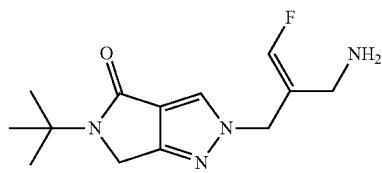 [SMILES: CC(C)(C)N1Cc2nn(C/C(=C/F)CN)cc2C1=O]

Step 1: Synthesis of Intermediate ethyl tert-butyl glycinate

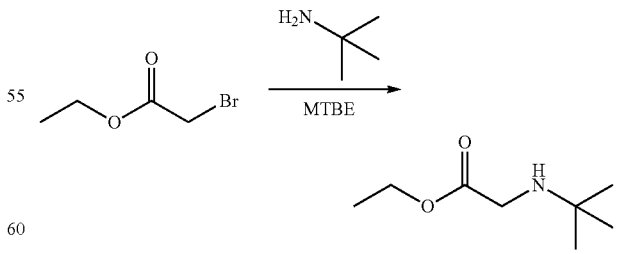

Ethyl bromoacetate (10.0 g, 59.88 mmol, 1.0 eq.) was added dropwise to a solution of tert-butyl amine (21.9 g, 299.40 mmol, 5.0 eq.) in methyl tert-butyl ether (200 mL). After addition, the mixture was stirred at room temperature for 40 h. The reaction solution was filtered, and the filtrate was concentrated. The concentrated solution was added with methyl tert-butyl ether (100 mL), washed successively with water (30 mL) and saturated brine (50 mL), and filtered, and the filtrate was concentrated to give a product (8.5 g, yield: 89.2%).

Step 2: Synthesis of Intermediate ethyl 3-(tert-butyl (2-ethoxy-2-oxoethyl) amino)-3-oxopropionate

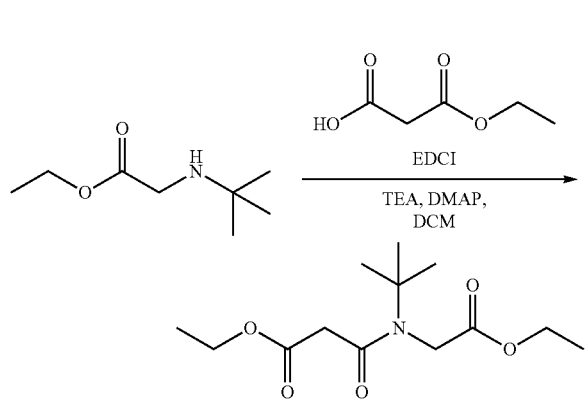

Ethyl tert-butyl glycinate (6.0 g, 37.68 mmol, 1.0 eq.), monoethyl malonate (5.48 g, 41.15 mmol, 1.1 eq.), triethylamine (8.77 g, 86.67 mmol, 2.3 eq.) and DMAP (921 mg, 7.54 mmol, 0.2 eq.) were successively added to DCM (150 mL), then EDCI (8.62 g, 45.22 mmol, 1.2 eq.) was added to DCM in batches. The mixture was stirred at room temperature overnight. After the reaction was completed, as detected by TLC, the reaction solution was poured into 1 mol/L hydrochloric acid (300 mL), followed by liquid separation. The organic phase was washed successively with water (50 mL) and saturated brine (100 mL), dried over anhydrous sodium sulfate, and filtered, and the filtrate was concentrated to give a product (10.0 g, yield: 97.1%).

Step 3: Synthesis of Intermediate ethyl 1-(tert-butyl)-2,4-dioxopyrrolidin-3-carboxylate

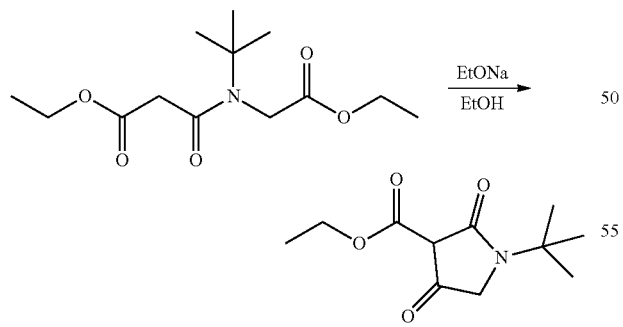

Sodium ethoxide (4.98 g, 73.17 mmol, 2.0 eq.) was added to ethanol (100 mL), then ethyl 3-(tert-butyl(2-ethoxy-2-oxoethyl)amino)-3-oxopropionate (10.0 g, 36.59 mmol, 1.0 eq.) was added to the solution of sodium ethoxide in ethanol with stirring at room temperature. The resulting mixture was stirred at room temperature for 5 h. After the reaction was completed, as detected by TLC, the reaction solution was concentrated to give a crude product (calculated according to theoretical yield), which was directly used in the next step.

Step 4: Synthesis of Intermediate 1-(tert-butyl)pyrrolidin-2,4-dione

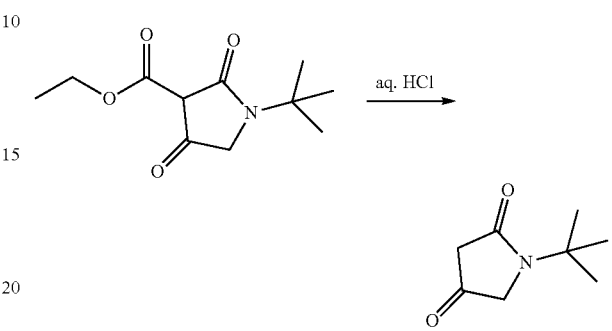

Ethyl 1-(tert-butyl)-2,4-dioxopyrrolidin-3-carboxylate (8.31 g, 36.57 mmol, 1.0 eq.) was added to 1 mol/L hydrochloric acid (150 mL) in batches. After addition, the mixture was stirred at 85° C. for 4 h. After the reaction was completed, as detected by TLC, the reaction solution was cooled to room temperature, and added with DCM (200 mL), followed by liquid separation.

The organic phase was washed with water (50 mL) and saturated brine (50 mL), dried over anhydrous sodium sulfate, and filtered, and the filtrate was concentrated to give a product (4.2 g, two-step yield: 74.0%).

Step 5: Synthesis of Intermediate 1-(tert-butyl)-3-((dimethylamino) methylene)pyrrolidin-2,4-dione

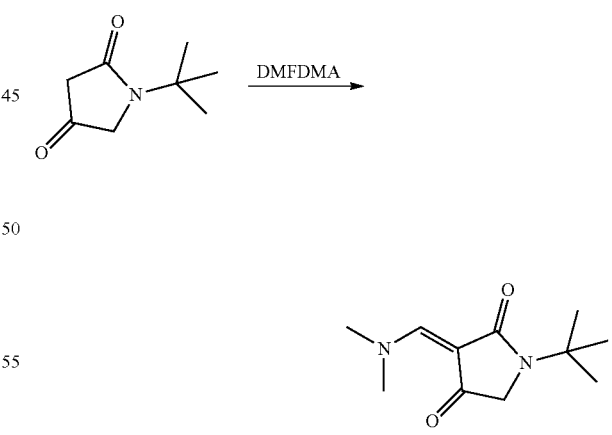

1-(tert-butyl)pyrrolidin-2,4-dione (2.20 g, 14.18 mmol, 1.0 eq.) was added to 1,1-dimethoxy-N,N-dimethylmethylamine (1.69 g, 14.18 mmol, 1.0 eq.). Then the mixture was stirred at room temperature for 0.5 h. After the reaction was completed, as detected by TLC, methanol was evaporated off under reduced pressure to give a product (crude product, calculated according to theoretical yield), which was directly used in the next step.

Step 6: Synthesis of Intermediate 1-benzyl-5-(tert-butyl)-5,6-dihydropyrrolo [3,4-c]pyrazol-4(1H)-one

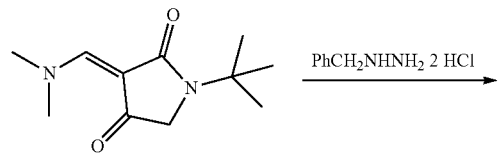

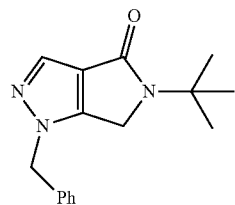

Benzylhydrazine dihydrochloride (2.76 g, 14.17 mmol, 1.0 eq.) and 1-(tert-butyl)-3-((dimethylamino)methylene)pyrrolidin-2,4-dione (2.98 g, 14.17 mmol, 1.0 eq.) were successively added to ethanol (30 mL), and the mixture was stirred at 20° C. for 1 h. Then the mixture was heated to 90° C. to react for 3 h. After the reaction was completed, as detected by TLC, the reaction solution was cooled to room temperature, poured into saturated aqueous sodium bicarbonate solution (50 mL) and extracted with DCM (25 mL×3). The organic phase was washed with water (20 mL) and saturated brine (20 mL), dried over anhydrous sodium sulfate, and filtered, and the filtrate was concentrated. The crude product was purified by silica gel column chromatography (petroleum ether:ethyl acetate=1:1) to give a product (3.0 g, two-step yield: 78.6%).

Step 7: Synthesis of Intermediate 5-(tert-butyl)-5,6-dihydropyrrolo[3,4-c]pyrazol-4(2H)-one

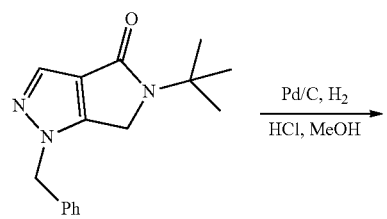

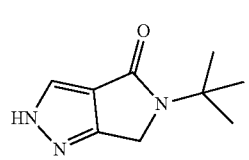

The intermediate 1-benzyl-5-(tert-butyl)-5,6-dihydropyrrolo[3,4-c]pyrazol-4(1H)-one (3.0 g, 11.14 mmol, 1.0 eq.) was dissolved in methanol (45 mL). Then the solution was added with concentrated hydrochloric acid (1.0 mL) and wet palladium on carbon (1.0 g) to react in hydrogen atmosphere for 40 h. After the reaction was completed, as detected by TLC, the reaction solution was filtered through celite, and the filtrate was concentrated to give a product (1.8 g, yield: 90.2%).

Step 8: Synthesis of Intermediate (E)-2-(2-((5-(tert-butyl)-4-oxo-5,6-dihydropyrrolo[3,4-c]pyrazol-2(4H)-yl)methyl)-3-fluoroallyl)isoindolin-1,3-dione

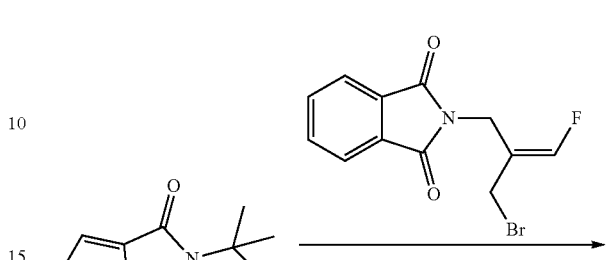

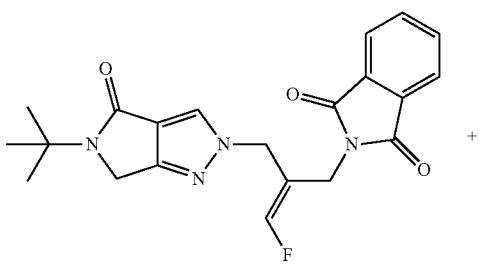

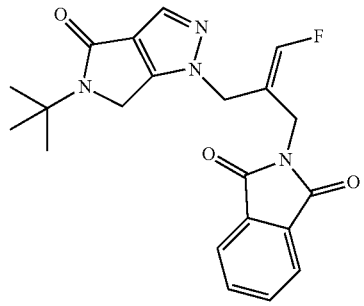

isomer 5-(tert-butyl)-5,6-dihydropyrrolo[3,4-c]pyrazol-4(2H)-one (359 mg, 2.01 mmol, 1.2 eq.), cesium carbonate (1.20 g, 3.69 mmol, 2.2 eq.) and (E)-2-(2-(bromomethyl)-3-fluoroallyl)isoindolin-1,3-dione (500 mg, 1.68 mmol, 1.0 eq.) were added to DMAc (10 mL). Then the mixture was stirred at 55° C. for 16 h. After the reaction was completed, as detected by TLC, the reaction solution was filtered, and the filter cake was rinsed with ethyl acetate (30 mL). The organic phase was washed with water (20 mL) and saturated brine (20 mL), dried over anhydrous sodium sulfate, and filtered, and the filtrate was concentrated. The crude product was purified by preparative thin-layer chromatography (ethyl acetate) to give a product (320 mg, 0.81 mmol, yield: 48.0%) and a positional isomer (E)-2-(2-((5-(tert-butyl)-4-oxo-5,6-dihydropyrrolo[3,4-c]pyrazol-1(4H)-yl)methyl)-3-fluoroallyl)isoindole-1,3-dione (100 mg, yield: 15.0%).

Step 9: Synthesis of Compound (E)-2-(2-(aminomethyl)-3-fluoroallyl)-5-(tert-butyl)-5,6-dihydropyrrolo[3,4-c]pyrazol-4(2H)-one

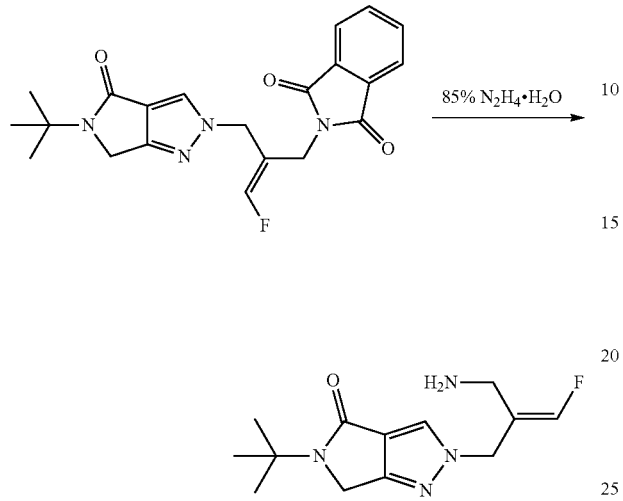

The intermediate (E)-2-(2-((5-(tert-butyl)-4-oxo-5,6-dihydropyrrolo [3,4-c]pyrazol-2(4H)-yl)methyl)-3-fluoroallyl)isoindolin-1,3-dione (320 mg, 0.81 mmol, 1.0 eq.) and 85% hydrazine hydrate (190 mg, 3.23 mmol, 4.0 eq.) were successively added to ethanol (8.0 mL). Then the mixture was stirred at 40° C. for 15 h. After the reaction was completed, as detected by TLC, the reaction solution was cooled to room temperature and filtered, and the filter cake was rinsed with a small amount of ethanol. The filtrate was concentrated, added with absolute ethanol (4 mL), and filtered, and the resulting filtrate was concentrated. The crude product was purified by preparative thin-layer chromatography (dichloromethane:methanol, 5:1, v/v) to give a product (85 mg, yield: 39.54%).

$^1$HNMR (400 MHz, DMSO-d$_6$) δ(ppm): 8.05 (s, 1H), 6.87-7.08 (d, 1H), 4.83 (d, 2H), 4.43 (s, 2H), 3.16 (s, 2H), 3.10 (d, 2H), 1.43 (s, 9H).

Molecular formula: $C_{13}H_{19}FN_4O$, molecular weight: 266.32, LC-MS (m/z)=267.24 [M+H]$^+$.

Example 8: Synthesis of (E)-2-(2-(aminomethyl)-3-fluoroallyl)-5-(4-fluorophenyl)-2,5,6,7-tetrahydro-4H-pyrazolo[4,3-c]pyridine (Compound A14) Hydrochloride

Step 1: Synthesis of Intermediate (E)-(3-fluoro-2-((5-(4-fluorophenyl)-4-oxo-4,5,6,7-tetrahydro-2H-pyrazolo[4,3-c]pyridin-2-yl)methyl)allyl)tert-butyl carbamate

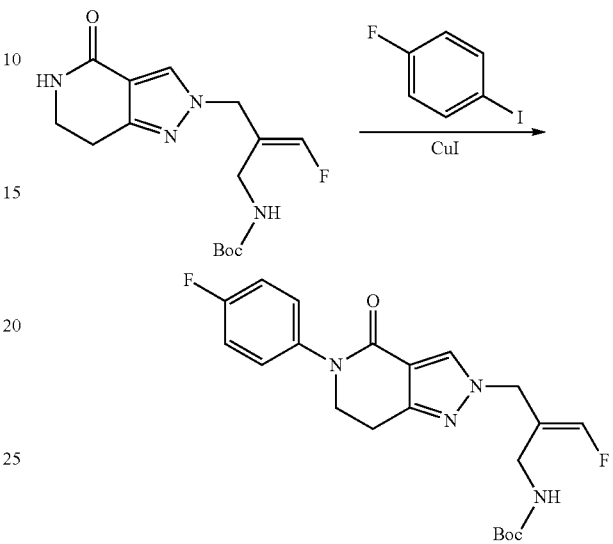

The intermediate (E)-(3-fluoro-2-((4-oxo-4,5,6,7-tetrahydro-2H-pyrazolo [4,3-c]pyridin-2-yl)methyl)allyl)tert-butyl carbamate (200 mg, 0.62 mol, 1.0 eq.) was dissolved in N,N-dimethylacetamide (2 mL). Then the solution was added with 1-fluoro-4-iodobenzene (412.9 mg, 1.86 mmol, 3.0 eq.), anhydrous potassium carbonate (171.1 mg, 1.24 mmol, 2.0 eq.) and cuprous iodide (11.8 mg, 0.06 mmol, 0.1 eq.), and heated to 130° C. in nitrogen atmosphere to react for 16 h. After the reaction was completed, as detected by TLC, the reaction solution was cooled to room temperature, added with water (20 mL) and extracted with ethyl acetate (20 mL×3), followed by liquid separation. The organic phases were combined, dried over anhydrous magnesium sulfate, and filtered, and the filtrate was concentrated under reduced pressure. The crude product was purified by preparative thin-layer chromatography (MeOH:DCM=1:20) to give a product (97 mg, yield: 40.5%).

Step 2: Synthesis of Compound (E)-2-(2-(aminomethyl)-3-fluoroallyl)-5-(4-fluorophenyl)-2,5,6,7-tetrahydro-4H-pyrazolo[4,3-c]pyridine hydrochloride

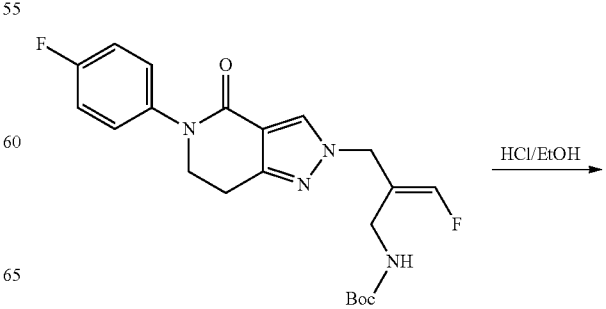

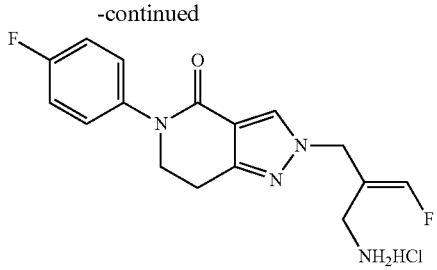

The intermediate (E)-(3-fluoro-2-((5-(4-fluorophenyl)-4-oxo-4,5,6,7-tetrahydro-2H-pyrazolo[4,3-c]pyridin-2-yl) methyl)allyl)tert-butyl carbamate (97 mg, 0.23 mmol, 1.0 eq.) was dissolved in 30% hydrogen chloride ethanol solution (2 mL). Then the solution was stirred at room temperature for 3 h. After the reaction was completed, as detected by LC-MS, the reaction solution was concentrated under reduced pressure. The crude product was purified by reversed phase column chromatography (eluted with 0.5% aqueous trifluoroacetic acid solution) and lyophilized to give a product (25 mg, yield: 30.6%).

$^1$HNMR (400 MHz, DMSO-$d_6$) δ(ppm): 8.37-8.35 (s, 4H), 7.39-7.34 (m, 2.5H), 7.25-7.19 (m, 2.5H), 4.94 (m, 2H), 3.96-3.93 (m, 2H), 3.39-3.38 (m, 2H), 3.00-2.97 (m, 2H).

Molecular formula: $C_{16}H_{16}F_2N_4O$, molecular weight: 318.33, LC-MS (Pos, m/z)=319.13 [M+H]$^+$.

Example 9: Synthesis of (E)-1-(2-(aminomethyl)-3-fluoroallyl)-5-cyclopropyl-2-(3-fluorophenyl)-1,2,6,7-tetrahydro-3H-pyrazolo[4,3-c]pyridin-3,4(5H)-dione (Compound A19)

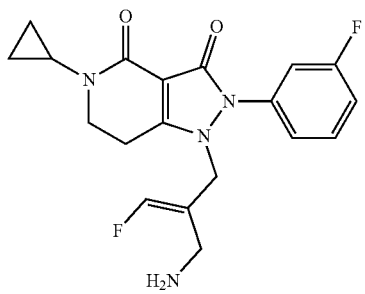 [SMILES: NC/C(=C\F)Cn1c2c(c(=O)n1-c1cccc(F)c1)C(=O)N(C1CC1)CC2]

Step 1: Synthesis of 5-cyclopropyl-2-(3-fluorophenyl)-1,2,6,7-tetrahydro-3H-pyrazolo[4,3-c]pyridin-3,4(5H)-dione

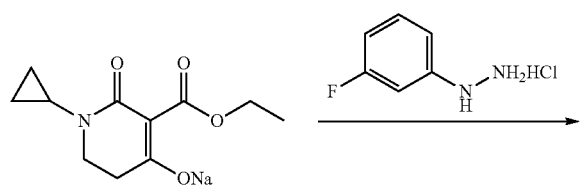

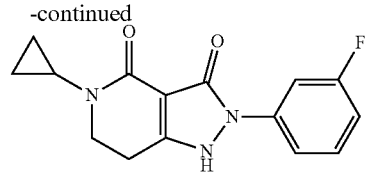

1-cyclopropyl-5-(ethoxycarbonyl)-6-oxo-1,2,3,6-tetrahydropyridin-4-sodium alkoxide (1.0 g, 4.05 mmol) and m-fluorophenylhydrazine hydrochloride (656.3 mg, 4.05 mmol) were added to ethanol (10 mL). Then the mixture was heated to 80° C. to react overnight. After the reaction was completed, as detected by TLC, aqueous citric acid solution was added to the reaction solution to adjust the pH to 6-7. The aqueous phase was extracted with ethyl acetate. The organic phases were combined, dried over anhydrous sodium sulfate, and filtered, and the filtrate was concentrated under reduced pressure. The crude product was purified by silica gel column chromatography (DCM:MeOH=40:1-20:1) to give a product (440.0 mg, yield: 37.8%).

Step 2: Synthesis of (E)-5-cyclopropyl-1-(2-((1,3-dioxoisoindolin-2-yl) methyl)-3-fluoroallyl)-2-(3-fluorophenyl)-1,2,6,7-tetrahydro-3H-pyrazolo[4,3-c]pyridin-3,4(5H)-dione

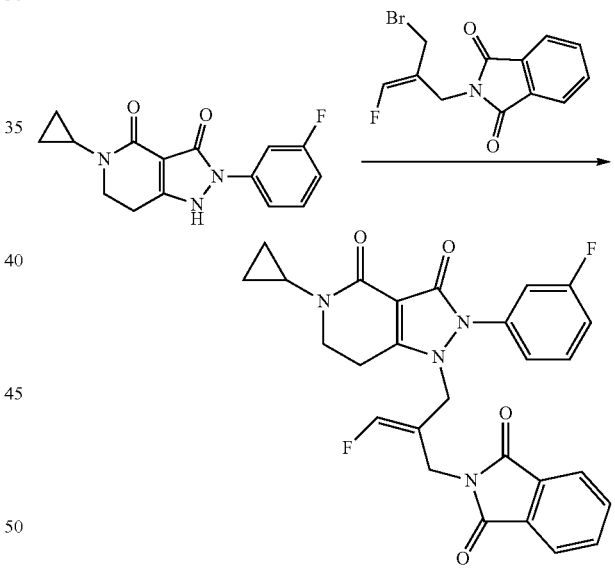

5-cyclopropyl-2-(3-fluorophenyl)-1,2,6,7-tetrahydro-3H-pyrazolo[4,3-c]pyridin-3,4(5H)-dione (440.0 mg, 1.54 mmol), (E)-2-(2-(bromomethyl)-3-fluoroallyl)isoindolin-1,3-dione (551.0 mg, 1.85 mmol) and potassium carbonate (425.6 mg, 3.08 mmol) were added to DMA (8 mL). Then the mixture was stirred at room temperature for 12 h and filtered under vacuum, and the filtrate was concentrated under reduced pressure, added with ethyl acetate (50 mL), washed with water (10 mL×4) and saturated brine (10 mL), dried over anhydrous sodium sulfate, and filtered. The filtrate was concentrated reduced pressure, and the crude product was purified by silica gel column chromatography (DCM:MeOH=200:1-40:1) to give a product (450.0 mg, yield: 58.0%).

Step 3: Synthesis of (E)-1-(2-(aminomethyl)-3-fluoroallyl)-5-cyclopropyl-2-(3-fluorophenyl)-1,2,6,7-tetrahydro-3H-pyrazolo[4,3-c]pyridin-3,4(5H)-dione

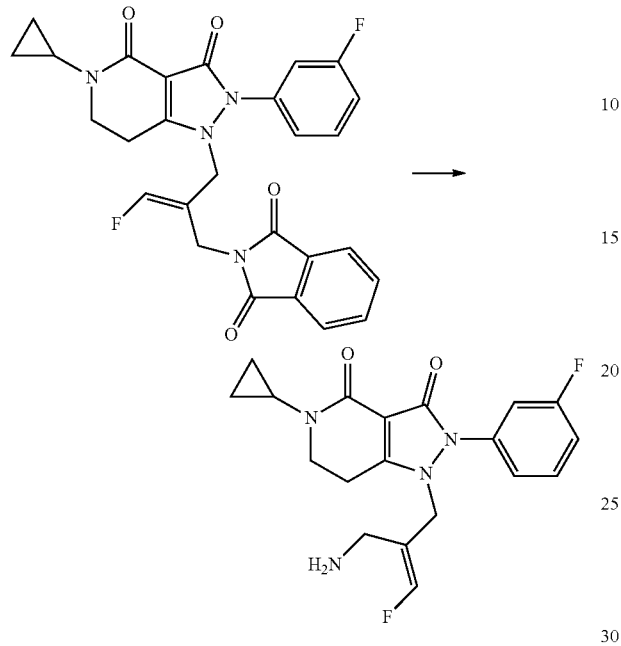

(E)-5-cyclopropyl-1-(2-((1,3-dioxoisoindolin-2-yl)methyl)-3-fluoroallyl)-2-(3-fluorophenyl)-1,2,6,7-tetrahydro-3H-pyrazolo[4,3-c]pyridin-3,4(5H)-dione (450.0 mg, 0.893 mmol) was added to ethanol (5 mL) and hydrazine hydrate (49% wt, 446.8 mg, 8.93 mmol). Then the mixture was stirred overnight at room temperature. After the reaction was completed, as detected by TLC, the reaction solution was filtered, and the filtrate was concentrated under reduced pressure. The crude product was purified by preparative thin-layer chromatography (DCM:MeOH=10:1) to give a product (100.0 mg, yield: 29.9%).

$^1$HNMR (400 MHz, DMSO-$d_6$) δ(ppm): 7.95 (s, 2H), 7.57-7.47 (m, 3H), 7.38 (s, 0.5H), 7.29-7.24 (m, 1H), 7.18 (s, 0.5H), 5.19-5.18 (d, 2H), 3.61-3.58 (t, 2H), 3.57-3.51 (d, 2H), 2.85-2.81 (t, 2H), 2.73-2.69 (m, 1H), 0.79-0.76 (m, 2H), 0.69-0.66 (m, 2H).

Molecular formula: $C_{19}H_{20}F_2N_4O_2$, molecular weight: 375.24, LC-MS (Pos, m/z)=375.22[M+H]$^+$.

Example 10: Synthesis of (E)-1-(2-(aminomethyl)-3-fluoroallyl)-5-(tert-butyl)-1,5,6,7-tetrahydro-4H-pyrazolo[4,3-c]pyridin-4-one (Compound A21)

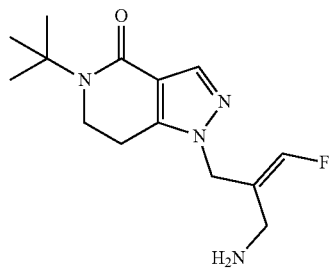 [SMILES: CC(C)(C)N1CCc2c(cnn2C/C(=C/F)CN)C1=O]

Step 1: Synthesis of (E)-1-(2-(aminomethyl)-3-fluoroallyl)-5-(tert-butyl)-1,5,6,7-tetrahydro-4H-pyrazolo[4,3-c]pyridin-4-one

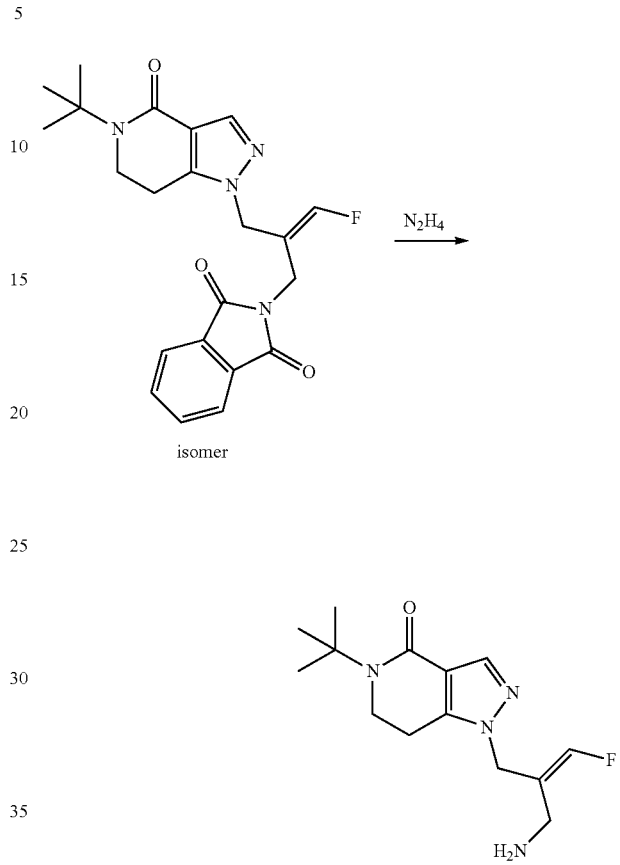

(E)-2-(2-((5-(tert-butyl)-4-oxo-4,5,6,7-tetrahydro-1H-pyrazolo[4,3-c]pyridin-1-yl)methyl)-3-fluoroallyl)isoindolin-1,3-dione (350 mg, 0.853 mmol, 1.0 eq.) prepared in Example 4 was dissolved in EtOH (15 mL). Then hydrazine hydrate (175.8 mg, 2.984 mmol, 3.5 eq.) was added, and the reaction was refluxed for 2 h. After the reaction was completed, as detected by LC-MS, the reaction solution was filtered under vacuum, and the filtrate was concentrated under reduced pressure. The resulting solution was added with EA (20 mL), refluxed, and filtered while hot. After cooling, the filtrate was filtered under vacuum, and the resulting filtrate was concentrated under reduced pressure to give the product (E)-1-(2-(aminomethyl)-3-fluoroallyl)-5-(tert-butyl)-1,5,6,7-tetrahydro-4H-pyrazolo[4,3-c]pyridin-4-one (192.2 mg, yield: 80.0%).

$^1$HNMR (400 MHz, DMSO-$d_6$) δ(ppm): 7.63 (s, 1H), 6.78-6.99 (d, J=84 Hz, 1H), 4.70 (d, 2H), 3.56-3.59 (t, 2H), 3.04-3.05 (d, 2H), 2.90-2.94 (t, 2H), 1.43 (s, 9H).

Molecular formula: $C_{14}H_{21}FN_4O$, molecular weight: 280.35, LC-MS (Pos, m/z)=281.22[M+H]$^+$.

Example 11: Synthesis of (E)-2-(2-(aminomethyl)-3-fluoroallyl)-5-cyclopropyl-2,5,6,7-tetrahydro-4H-pyrrolo[3,4-c]pyridin-4-one (Compound A22)

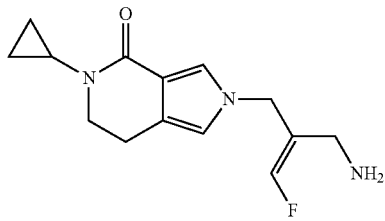 [SMILES: NC/C(=C\F)Cn1cc2c(c1)C(=O)N(C1CC1)CC2]

Step 1: Synthesis of Intermediate 1-cyclopropyl-3-((dimethylamino)methylene)piperidin-2,4-dione

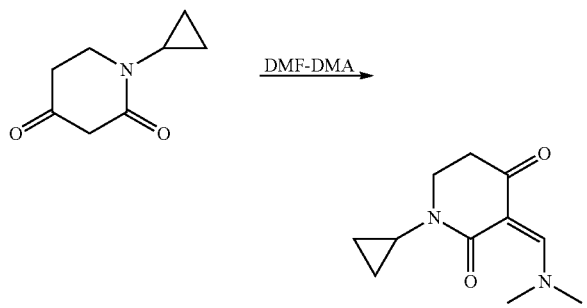

1-cyclopropylpiperidin-2,4-dione (2.50 g, 1633 mmol, 1.0 eq.) was added to 1,1-dimethoxy-N,N-dimethylmethylamine (2.14 g, 17.95 mmol, 1.1 eq.). Then the mixture was stirred at room temperature for 0.5 h. After the reaction was completed, as detected by TLC, excessive 1,1-dimethoxy-N,N-dimethylmethylamine was evaporated off under reduced pressure to give a crude product (calculated according to theoretical yield), which was directly used in the next step.

Step 2: Synthesis of Intermediate ((1-cyclopropyl-2,4-dioxopiperidin-3-ylidene)methyl)glycine

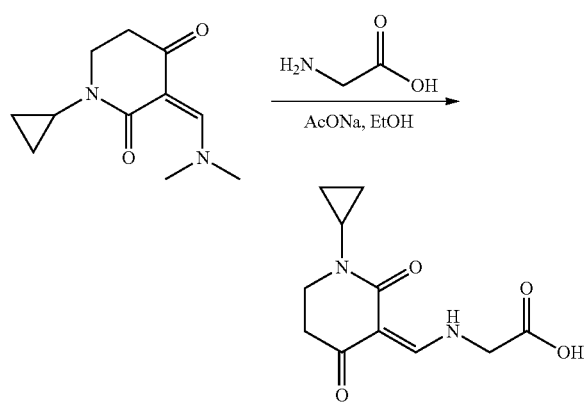

The crude product 1-cyclopropyl-3-((dimethylamino)methylene)piperidin-2,4-dione (3.40 g, 16.33 mmol, 1.0 eq.) obtained in the previous step, glycine (1.23 g, 16.33 mmol, 1.0 eq.) and sodium acetate (1.61 g, 19.59 mmol, 1.2 eq.) were added to ethanol (50 mL). Then the mixture was stirred at 50° C. until the reaction was completed. The reaction solution was concentrated to give a crude product (calculated according to theoretical yield), which was directly used in the next step.

Step 3: Synthesis of Intermediate 2-acetyl-5-cyclopropyl-2,5,6,7-tetrahydro-4H-pyrrolo[3,4-c]pyridin-4-one

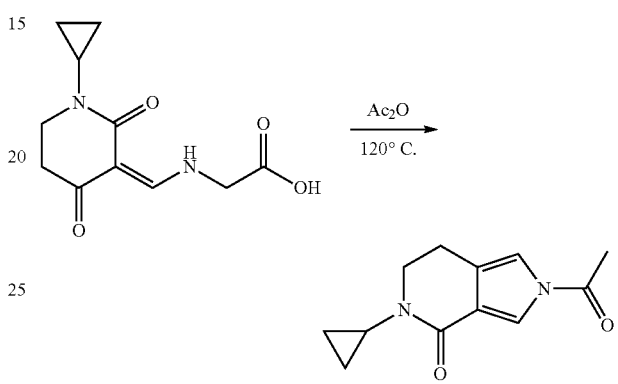

((1-cyclopropyl-2,4-dioxopiperidin-3-ylidene)methyl)glycine (3.89 g, 16.33 mmol, 1.0 eq.) was added to acetic anhydride (40 mL). Then the mixture was stirred at 120° C. for 5 h. After the reaction was completed, as detected by LC-MS, the reaction solution was concentrated and poured into saturated aqueous sodium bicarbonate solution (100 mL). Ethyl acetate (30 mL×2) was added for extraction. The organic phase was washed with saturated brine (40 mL), dried over anhydrous sodium sulfate, and filtered, and the filtrate was concentrated to give a crude product (calculated according to theoretical yield), which was directly used in the next step.

Step 4: Synthesis of Intermediate 5-cyclopropyl-2,5,6,7-tetrahydro-4H-pyrrolo[3,4-c]pyridin-4-one

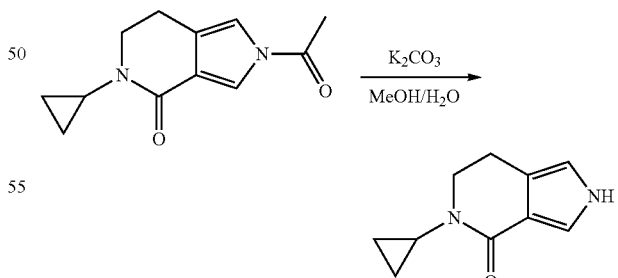

2-acetyl-5-cyclopropyl-2,5,6,7-tetrahydro-4H-pyrrolo[3,4-c]pyridin-4-one (3.55 g, 16.33 mmol, 1.0 eq.) and potassium carbonate (4.51 g, 32.66 mmol, 2.0 eq.) were successively added to a mixed solvent of methanol (30 mL) and water (30 mL). Then the mixture was stirred at room temperature for 3 h. After the reaction was completed, as detected by TLC, the reaction solution was concentrated, added with ethyl acetate (100 mL), washed successively with water (30 mL) and saturated brine (30 mL), dried over anhydrous sodium sulfate, and filtered, and the filtrate was concentrated. The —5 crude product was purified by silica gel column chromatography (petroleum ether:ethyl acetate=1:1-0:1, v/v) to give a product (950 mg, four-step yield: 33.1%).

Step 5: Synthesis of Intermediate (Z)-2-(2-((5-cyclopropyl-4-oxo-4,5,6,7-tetrahydro-2H-pyrrolo[3,4-c]pyridin-2-yl)methyl)-3-fluoroallyl)isoindolin-1,3-dione

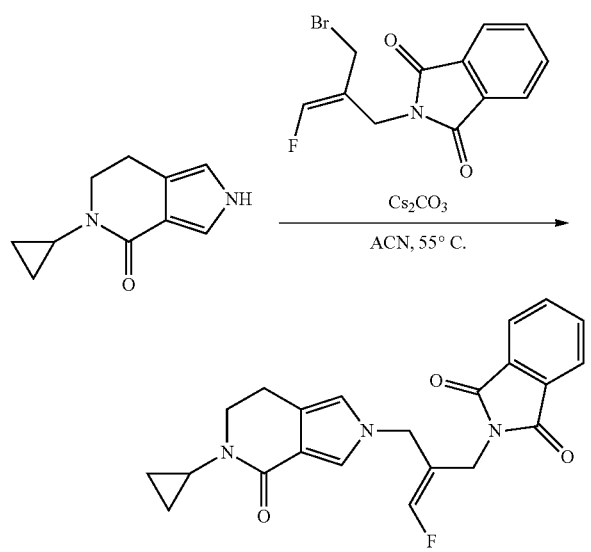

5-cyclopropyl-2,5,6,7-tetrahydro-4H-pyrrolo[3,4-c]pyridin-4-one (900 mg, 5.11 mmol, 1.0 eq.), cesium carbonate (2.50 g, 7.66 mmol, 1.5 eq.) and (E)-2-(2-(bromomethyl)-3-fluoroallyl)isoindolin-1,3-dione (1.67 g, 5.62 mmol, 1.1 eq.) were added to acetonitrile (30 mL). Then the mixture was stirred at 55° C. for 16 h. When there were a small amount of materials left, as detected by TLC, the reaction solution was cooled to room temperature and filtered, and the filter cake was washed once with ethyl acetate (15 mL) and concentrated. The crude product was purified by silica gel column chromatography (petroleum ether:ethyl acetate=1:1-0:1, v/v) to give a product (1.05 g, 2.67 mmol, yield: 52.3%).

Step 6: Synthesis of Compound (E)-2-(2-(aminomethyl)-3-fluoroallyl)-5-cyclopropyl-2,5,6,7-tetrahydro-4H-pyrrolo[3,4-c]pyridin-4-one

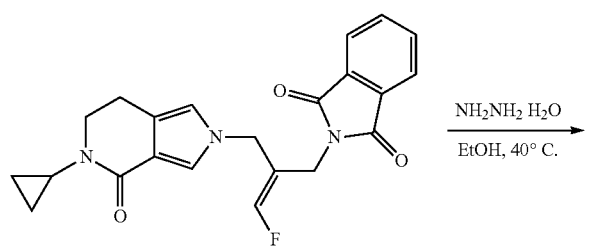

-continued

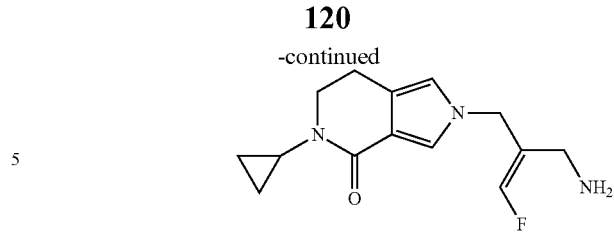

(Z)-2-(2-((5-cyclopropyl-4-oxo-4,5,6,7-tetrahydro-2H-pyrrolo[3,4-c]pyridin-2-yl)methyl)-3-fluoroallyl)isoindolin-1,3-dione (600 mg, 1.53 mmol, 1.0 eq.) and 85% hydrazine hydrate (898 mg, 15.25 mmol, 10 eq.) were successively added to ethanol (15 mL). Then the mixture was stirred at 40° C. for 5 h. After the reaction was completed, as detected by TLC, the reaction solution was cooled to room temperature and filtered, and the filter cake was washed with a small amount of ethanol. The filtrate was concentrated, added with absolute ethanol (10 mL), and filtered, and the resulting filtrate was concentrated. The crude product was purified by preparative thin-layer chromatography (dichloromethane: methanol, 5:1, v/v) to give a product (105 mg, yield: 26.2%).

$^1$HNMR (400 MHz, DMSO-$d_6$) δ(ppm): 8.09 (brs, 2H), 7.30 (s, 1H), 7.31-7.10 (d, 1H), 6.66 (s, 1H), 4.70 (s, 2H), 3.37-3.41 (m, 2H), 3.20 (s, 2H), 2.60-2.63 (m, 3H), 0.69-0.74 (m, 2H), 0.55-0.56 (m, 2H).

Molecular formula: $C_{14}H_{18}FN_3O$, molecular weight: 263.32, LC-MS (m/z)=264.20 [M+H]$^+$.

Example 12: Synthesis of (E)-2-(2-(aminomethyl)-3-fluoroallyl)-2,5,6,7-tetrahydro-4H-pyrazolo[4,3-c]pyridin-4-one (Compound A23) Hydrochloride

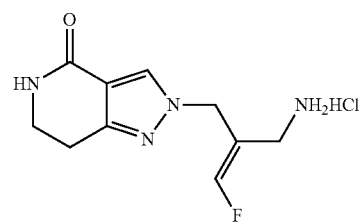

Step 1: Synthesis of Intermediate (E)-2-(2-((5-(tert-butyl)-4-oxo-4,5,6,7-tetrahydro-2H-pyrazolo[4,3-c]pyridin-2-yl)methyl)-3-fluoroallyl)isoindolin-1,3-dione

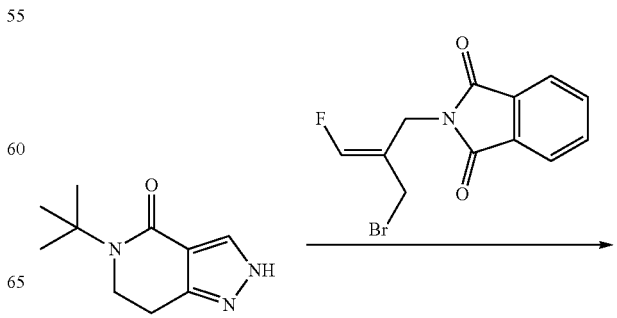

-continued

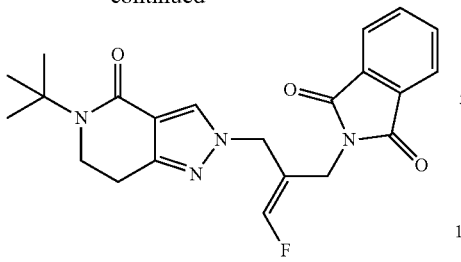

The intermediate 5-(tert-butyl)-2,5,6,7-tetrahydro-4H-pyrazolo[4,3-c]pyridin-4-one (5.0 g, 25.87 mmol, 1.0 eq.) was dissolved in DMF (20 mL). In nitrogen atmosphere, the solution was cooled to −10° C., and added with sodium hydride (1.14 g, 28.46 mmol, 1.1 eq., 60%) to react for 30 min. Then a solution of (E)-2-(2-(bromomethyl)-3-fluoroallyl)isoindolin-1,3-dione (9.3 g, 31.04 mmol, 1.2 eq.) in DMF (10 mL) was slowly added dropwise to the reaction solution to react for 2 h. After the reaction was completed, as detected by LC-MS, the reaction solution was added with saturated aqueous ammonium chloride solution (100 mL) and extracted with ethyl acetate (100 mL×3). The organic phase was washed with water (100 mL×3), dried over anhydrous sodium sulfate, filtered, and concentrated under reduced pressure. The crude product was purified by silica gel column chromatography (PE:EA=1:1) to give a product (5.9 g, yield: 59%).

Step 2: Synthesis of Intermediate (E)-2-(3-fluoro-2-((4-oxo-4,5,6,7-tetrahydro-2H-pyrazolo[4,3-c]pyridin-2-yl)methyl)allyl)isoindolin-1,3-dione

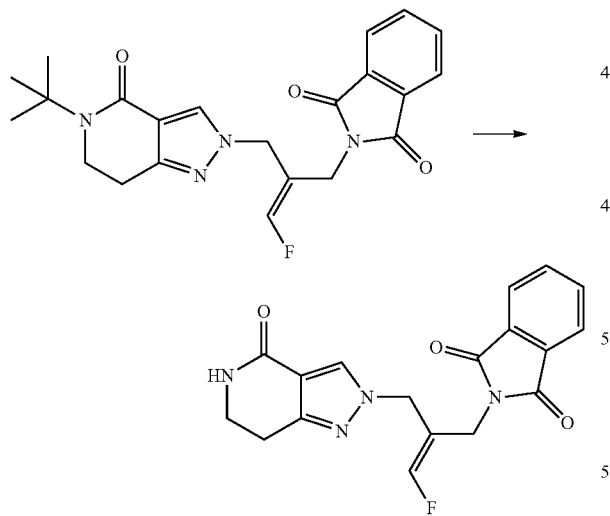

The intermediate (E)-2-(2-((5-(tert-butyl)-4-oxo-4,5,6,7-tetrahydro-2H-pyrazolo[4,3-c]pyridin-2-yl)methyl)-3-fluoroallyl)isoindolin-1,3-dione (6.3 g, 15.34 mmol, 1.0 eq.) was dissolved in concentrated hydrochloric acid (30 mL) and ethanol (30 mL) to react at 60° C. for 12 h. After the reaction was completed, as detected by LC-MS, the reaction solution was concentrated under reduced pressure. The crude product was slurried with ethyl acetate (50 mL), and filtered under vacuum to give a product (5.4 g, yield: 99%).

Step 3: Synthesis of Intermediate (E)-2-(2-(aminomethyl)-3-fluoroallyl)-2,5,6,7-tetrahydro-4H-pyrazolo[4,3-c]pyridin-4-one

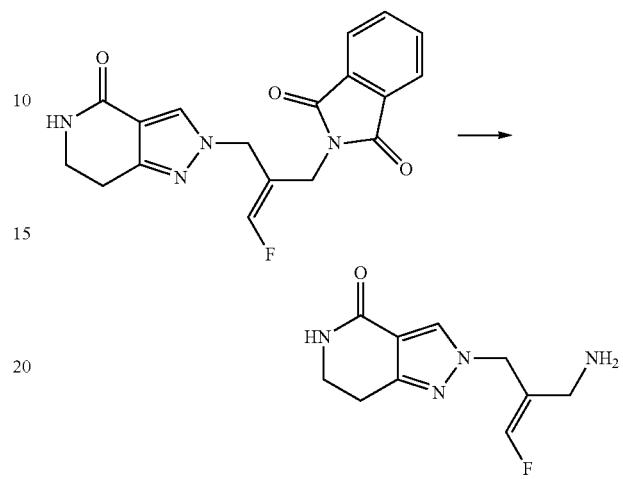

The intermediate (E)-2-(3-fluoro-2-((4-oxo-4,5,6,7-tetrahydro-2H-pyrazolo[4,3-c]pyridin-2-yl)methyl)allyl)isoindolin-1,3-dione (5.4 g, 15.24 mmol, 1.0 eq.) and hydrazine hydrate (3.05 g, 60.96 mmol, 4.0 eq.) were dissolved in ethanol (100 mL) to react at 80° C. for 1.5 h. After the reaction was completed, as detected by LC-MS, the reaction solution was cooled to room temperature and filtered. The mother liquor was concentrated under reduced pressure to give a product (3.4 g, yield: 100%).

Step 4: Synthesis of Intermediate (E)-(3-fluoro-2-((4-oxo-4,5,6,7-tetrahydro-2H-pyrazolo[4,3-c]pyridin-2-yl)methyl)allyl)tert-butyl carbamate

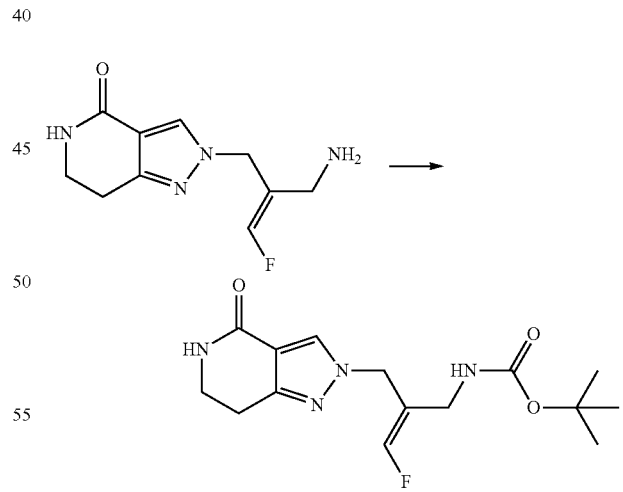

The intermediate (E)-2-(2-(aminomethyl)-3-fluoroallyl)-2,5,6,7-tetrahydro-4H-pyrazolo[4,3-c]pyridin-4-one (3.4 g, 15.24 mmol, 1.0 eq.), di-tert-butyl dicarbonate (6.65 g, 30.48 mmol, 2.0 eq.), 4-dimethylaminopyridine (171 mg, 1.52 mmol, 0.1 eq.) and triethylamine (2.31 g, 22.86 mmol, 1.5 eq.) were dissolved in dichloromethane (50 mL) to react for 2.5 h. After the reaction was completed, as detected by LC-MS, the reaction solution was added with saturated aqueous sodium carbonate solution (50 mL) and extracted with dichloromethane (50 mL×3). The organic phase was dried and concentrated. The crude product was purified by silica gel column chromatography (MeOH:DCM=1:60) to give a product (2.57 g, yield: 51%).

Step 5: Synthesis of Compound (E)-2-(2-(aminomethyl)-3-fluoroallyl)-2,5,6,7-tetrahydro-4H-pyrazolo[4,3-c]pyridin-4-one hydrochloride

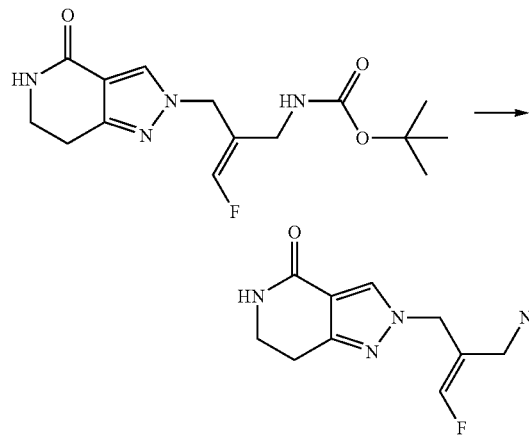

The intermediate (E)-(3-fluoro-2-((4-oxo-4,5,6,7-tetrahydro-2H-pyrazolo [4,3-c]pyridin-2-yl)methyl)allyl)tert-butyl carbamate (200 mg, 0.61 mmol, 1.0 eq.) was dissolved in ethanol (2 mL). Then the solution was added with hydrogen chloride ethanol solution (2 mL) to react for 2.5 h. After the reaction was completed, as detected by LC-MS, the reaction solution was concentrated under reduced pressure. The crude product was slurried with ethyl acetate (5 mL) and filtered under vacuum, and the filter cake was dried to give a product (150 mg, yield: 93%).

$^1$H NMR (400 MHz, DMSO-$d_6$) δ(ppm): 8.55 (s, 3H), 8.30 (s, 1H), 7.44 (s, 1H), 7.37 (s, 0.5H), 7.17 (s, 0.5H), 4.97 (s, 2H), 3.35-3.38 (m, 2H), 3.31-3.33 (d, 2H), 2.72-2.76 (m, 2H).

Molecular formula: $C_{10}H_{13}FN_4O$, molecular weight: 224.24, LC-MS (Pos, m/z)=225.16[M+H]$^+$.

Example 13: Synthesis of (E)-2-(2-(aminomethyl)-3-fluoroallyl)-5-methyl-2,5,6,7-tetrahydro-4H-pyrazolo[4,3-c]pyridin-4-one (Compound A24) Hydrochloride

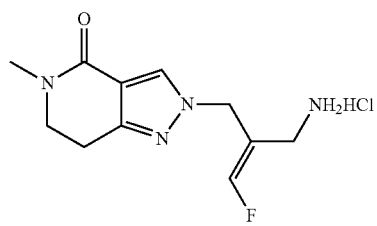

Step 1: Synthesis of Intermediate (E)-(3-fluoro-2-((5-methyl-4-oxo-4,5,6,7-tetrahydro-2H-pyrazolo[4,3-c]pyridin-2-yl)methyl)allyl)tert-butyl carbamate

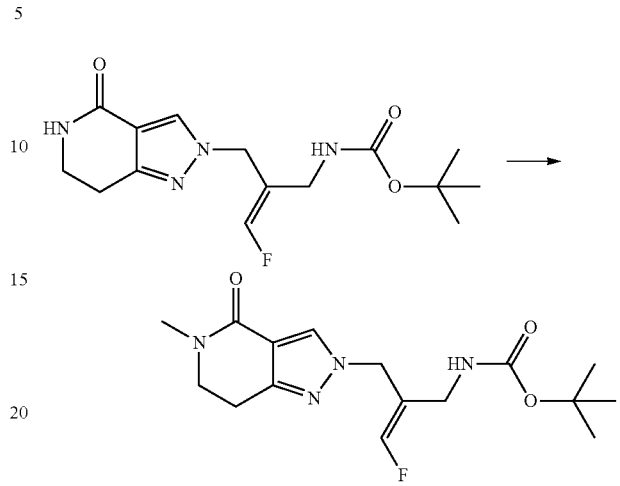

The intermediate (E)-(3-fluoro-2-((4-oxo-4,5,6,7-tetrahydro-2H-pyrazolo [4,3-c]pyridin-2-yl)methyl)allyl)tert-butyl carbamate (500 mg, 1.54 mmol, 1.0 eq.) was dissolved in tetrahydrofuran (5 mL). Then the solution was added with sodium hydride (80 mg, 2.0 mmol, 1.3 eq., 60%) to react at room temperature for 30 min. The reaction solution was added with iodomethane (263 mg, 1.85 mmol, 1.2 eq.) to react for 2 h. After the reaction was completed, as detected by LC-MS, water (5 mL) was added to the reaction flask, and ethyl acetate (10 mL×3) was added for extraction. The organic phase was dried and concentrated. The crude product was purified by silica gel column chromatography (MeOH:DCM=1:80) to give a product (100 mg, yield: 19%).

Step 2: Synthesis of (E)-2-(2-(aminomethyl)-3-fluoroallyl)-5-methyl-2,5,6,7-tetrahydro-4H-pyrazolo[4,3-c]pyridin-4-one hydrochloride

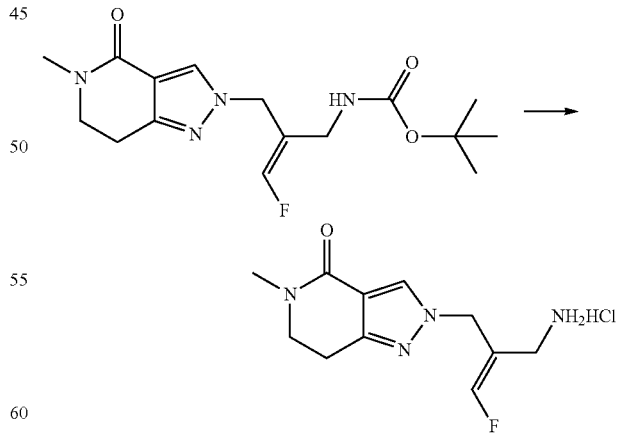

The intermediate (E)-(3-fluoro-2-((5-methyl-4-oxo-4,5,6,7-tetrahydro-2H-pyrazolo[4,3-c]pyridin-2-yl)methyl)allyl) tert-butyl carbamate (100 mg, 0.29 mmol, 1.0 eq.) was dissolved in ethanol (1 mL). Then the solution was added with hydrogen chloride ethanol solution (1 mL) to react for 12 h. After the reaction was completed, as detected by LC-MS, the reaction solution was concentrated under reduced pressure to give a product (55 mg, yield: 69%).

$^1$HNMR (400 MHz, DMSO-d$_6$) δ(ppm): 8.41 (s, 3H), 8.25 (s, 1H), 7.37 (s, 0.5H), 7.16 (s, 0.5H), 4.91-4.92 (d, 2H), 3.52-3.56 (m, 2H), 3.33-3.35 (d, 2H), 2.92 (s, 3H), 2.83-2.85 (m, 2H).

Molecular formula: C$_{11}$H$_{15}$FN$_4$O, molecular weight: 238.27, LC-MS (Pos, m/z)=239.19[M+H]$^+$.

Example 14: Synthesis of (E)-2-(2-(aminomethyl)-3-fluoroallyl)-5-ethyl-2,5,6,7-tetrahydro-4H-pyrrolo[3,4-c]pyridin-4-one (Compound A25)

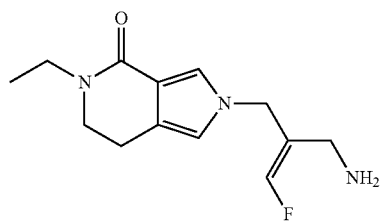 [SMILES: CCN1CCc2cn(C/C(=C/F)CN)cc2C1=O]

Step 1: Synthesis of Intermediate ethyl 3-(ethylamino)propionate

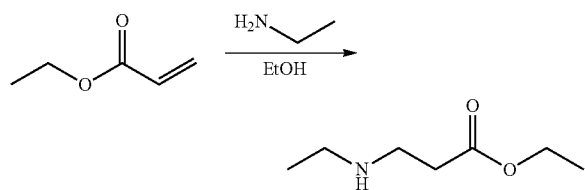

65% aqueous ethylamine solution (29.1 g, 419.51 mmol, 1.4 eq., 65%) was dissolved in ethanol (100 mL). Then the solution was added with a solution of ethyl acrylate (30.00 g, 299.65 mmol, 1.0 eq.) in ethanol (20 mL) dropwise (1.5 h). After addition, the mixture was stirred at room temperature for 1 h. The reaction solution was concentrated to give a product (42.0 g, yield: 96.5%).

Step 2: Synthesis of Intermediate ethyl 3-((3-ethoxy-3-oxopropyl)(ethyl) amino)-3-oxopropionate

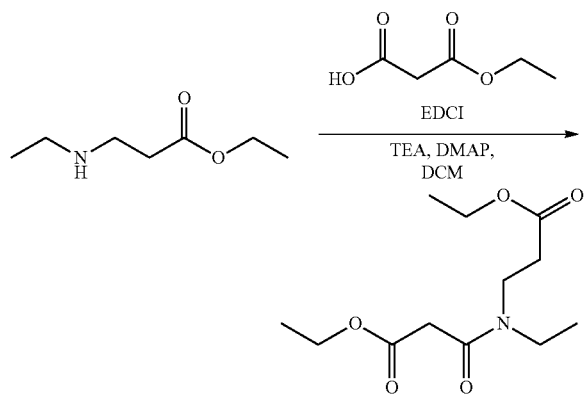

The intermediate ethyl 3-(ethylamino)propionate (20.0 g, 137.74 mmol, 1.0 eq.), monoethyl malonate (18.20 g, 137.74 mmol, 1.0 eq.), triethylamine (32.06 g, 316.80 mmol, 2.3 eq.) and DMAP (3.37 g, 27.55 mmol, 0.2 eq.) were successively added to DCM (500 mL), then EDCI (31.69 g, 165.29 mmol, 1.2 eq.) was added in batches. The mixture was stirred at room temperature overnight. After the reaction was completed, as detected by TLC, the reaction solution was poured into water (300 mL), and the pH was adjusted to 3-4 with 3 mol/L hydrochloric acid, followed by liquid separation. The organic phase was washed successively with water (150 mL×2) and saturated brine (300 mL), dried over anhydrous sodium sulfate, and filtered, and the filtrate was concentrated to give a product (29.0 g, yield: 81.2%).

Step 3: Synthesis of Intermediate ethyl 1-ethyl-2,4-dioxopiperidin-3-carboxylate

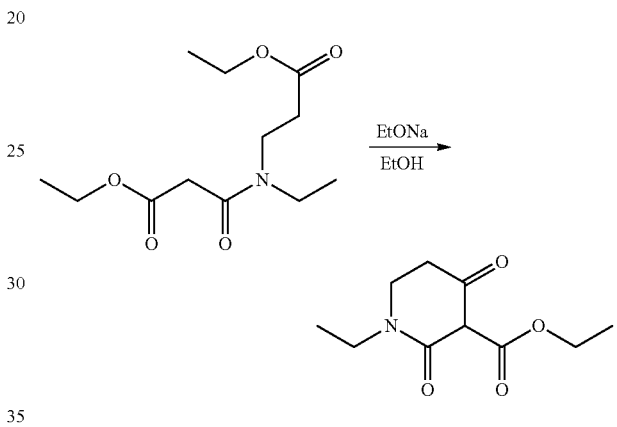

Sodium (5.14 g, 223.68 mmol, 2.0 eq.) was added to ethanol (150 mL) and the mixture was stirred until the reaction was completed. Then ethyl 3-((3-ethoxy-3-oxopropyl)(ethyl)amino)-3-oxopropionate (29.0 g, 118.84 mmol, 1.0 eq.) was added to the solution of sodium ethoxide in ethanol. After addition, the mixture was stirred at room temperature for 2 h. After the reaction was completed, as detected by TLC, the reaction solution was concentrated to give a crude product (calculated according to theoretical yield), which was directly used in the next step.

Step 4: Synthesis of Intermediate 1-ethylpiperidin-2,4-dione

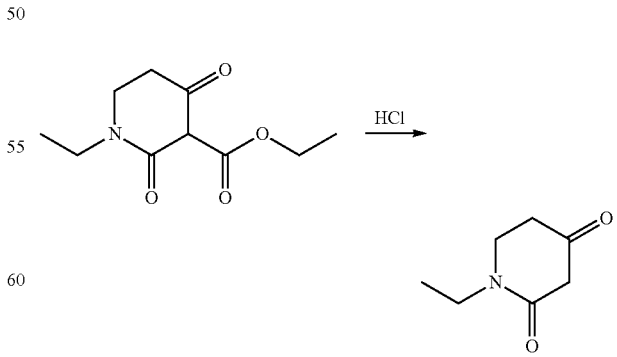

Ethyl 1-ethyl-2,4-dioxopiperidin-3-carboxylate (23.85 g, 111.84 mmol, 1.0 eq.) was added to 2 mol/L hydrochloric acid (300 mL) in batches. Then the mixture was heated to 100° C. to react for 3 h. After the reaction was completed, as detected by TLC, the reaction solution was cooled to room temperature and extracted with DCM (150 mL×3). The organic phase was washed successively with water (100 mL) and saturated brine (100 mL), dried over anhydrous sodium sulfate, and filtered, and the filtrate was concentrated to give a product (12.0 g, two-step yield: 76.0%).

Step 5: Synthesis of Intermediate 1-ethyl-3-((dimethylamino)methylene)piperidin-2,4-dione

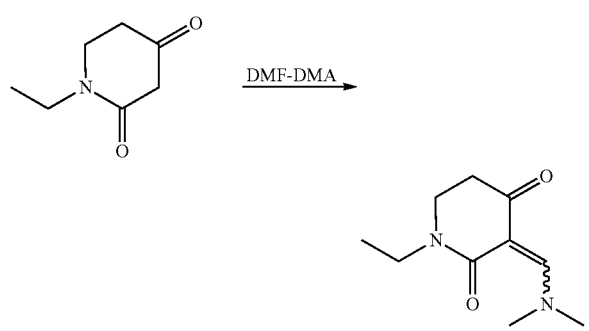

The intermediate 1-ethylpiperidin-2,4-dione (6.00 g, 42.50 mmol, 1.0 eq.) was added to 1,1-dimethoxy-N,N-dimethylmethylamine (5.32 g, 44.63 mmol, 1.05 eq.). Then the mixture was stirred at room temperature for 0.5 h. After the reaction was completed, as detected by TLC, the reaction solution was concentrated to give a crude product (calculated according to theoretical yield), which was directly used in the next step.

Step 6: Synthesis of Intermediate ((1-ethyl-2,4-dioxopiperidin-3-ylidene)methyl)glycine

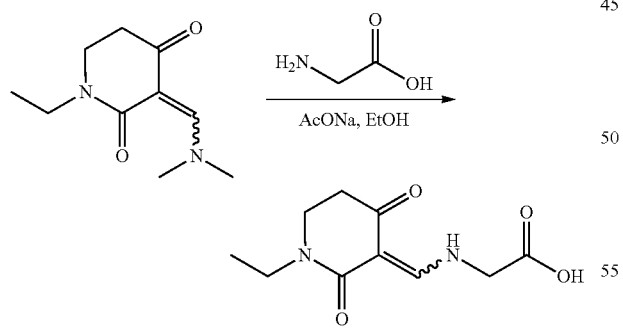

The intermediate 1-ethyl-3-((dimethylamino)methylene)piperidin-2,4-dione (8.85 g, 42.49 mmol, 1.0 eq.), glycine (3.19 g, 42.49 mmol, 1.0 eq.) and sodium acetate (4.18 g, 50.99 mmol, 1.2 eq.) were added to ethanol (100 mL). Then the mixture was stirred at 50° C. until the reaction was completed. The reaction solution was concentrated to give a crude product (calculated according to theoretical yield), which was directly used in the next step.

Step 7: Synthesis of Intermediate 2-acetyl-5-ethyl-2,5,6,7-tetrahydro-4H-pyrrolo[3,4-c]pyridin-4-one

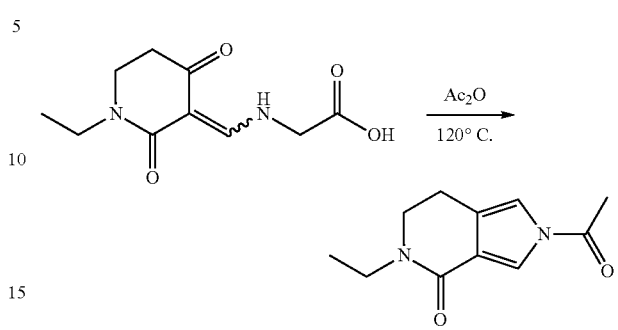

The intermediate ((1-ethyl-2,4-dioxopiperidin-3-ylidene)methyl)glycine (10.12 g, 42.49 mmol, 1.0 eq.) was added to acetic anhydride (80 mL). Then the mixture was stirred at 120° C. for 5 h. After the reaction was completed, as detected by LC-MS, the reaction solution was concentrated, and the residue was poured into saturated aqueous sodium bicarbonate solution (200 mL). Ethyl acetate (50 mL×3) was added for extraction. The organic phase was washed with saturated brine (100 mL), dried over anhydrous sodium sulfate and filtered, and the filtrate was concentrated to give a crude product (calculated according to theoretical yield), which was directly used in the next step.

Step 8: Synthesis of Intermediate 5-ethyl-2,5,6,7-tetrahydro-4H-pyrrolo[3,4-c]pyridin-4-one

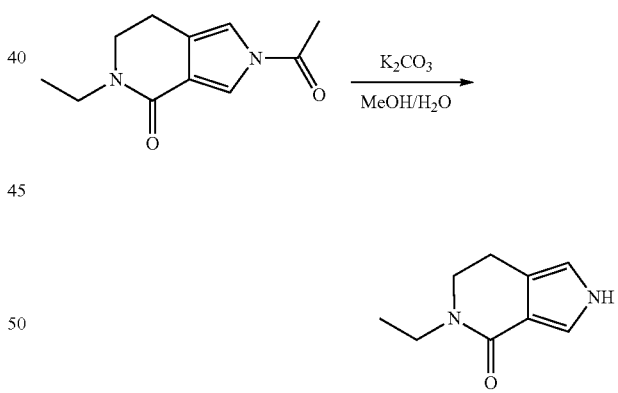

The intermediate 2-acetyl-5-ethyl-2,5,6,7-tetrahydro-4H-pyrrolo[3,4-c]pyridin-4-one (8.76 g, 42.49 mmol, 1.0 eq.) and potassium carbonate (11.74 g, 84.98 mmol, 2.0 eq.) were successively added to a mixed solvent of methanol (50 mL) and water (50 mL). Then the mixture was stirred at room temperature for 3 h. After the reaction was completed, as detected by TLC, the reaction solution was concentrated, added with ethyl acetate (200 mL), washed successively with water (50 mL) and saturated brine (50 mL), dried over anhydrous sodium sulfate, and filtered, and the filtrate was concentrated. The crude product was purified by silica gel column chromatography (ethyl acetate:petroleum ether, 1:1-1:0, v/v) to give a product (2.2 g, four-step yield: 31.53%).

Step 9: Synthesis of Intermediate (Z)-2-(2-((5-ethyl-4-oxo-4,5,6,7-tetrahydro-2H-pyrrolo[3,4-c]pyridin-2-yl)methyl)-3-fluoroallyl)isoindolin-1,3-dione

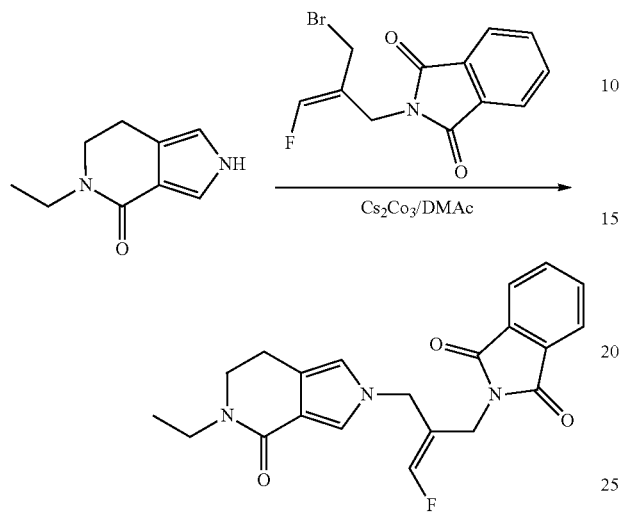

5-ethyl-2,5,6,7-tetrahydro-4H-pyrrolo[3,4-c]pyridin-4-one (1.5 g, 9.13 mmol, 1.0 eq.), cesium carbonate (4.46 g, 13.70 mmol, 1.5 eq.) and (E)-2-(2-(bromomethyl)-3-fluoroallyl)isoindolin-1,3-dione (3.00 g, 10.05 mmol, 1.1 eq.) were added to DMA (20 mL). Then the mixture was stirred at 55° C. for 16 h. When there were a small amount of materials left, as detected by TLC, the reaction solution was cooled to room temperature and filtered, and the filter cake was rinsed with ethyl acetate (40 mL). The organic phase was washed successively with water (20 mL×2) and saturated brine (20 mL), dried over anhydrous sodium sulfate, and filtered, and the filtrate was concentrated. The crude product was purified by silica gel column chromatography (ethyl acetate) to give a product (1.45 g, yield: 41.6%).

Step 10: Synthesis of Compound (E)-2-(2-(aminomethyl)-3-fluoroallyl)-5-ethyl-2,5,6,7-tetrahydro-4H-pyrrolo[3,4-c]pyridin-4-one

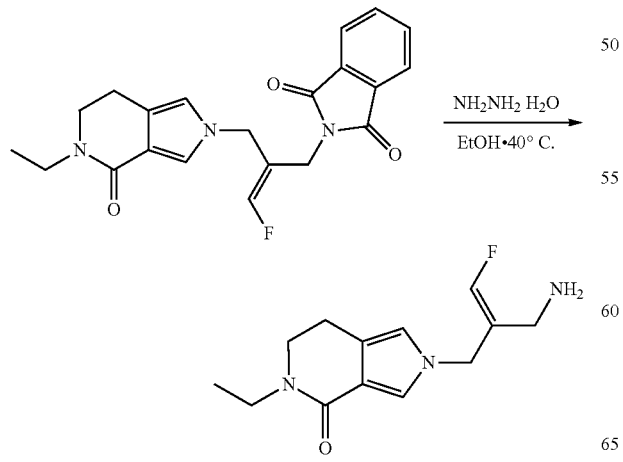

(Z)-2-(2-((5-ethyl-4-oxo-4,5,6,7-tetrahydro-2H-pyrrolo[3,4-c]pyridin-2-yl)methyl)-3-fluoroallyl)isoindolin-1,3-dione (1.45 g, 3.80 mmol, 1.0 eq.) and 85% hydrazine hydrate (1.12 g, 19.01 mmol, 5 eq.) were successively added to ethanol (20 mL). Then the mixture was stirred at 40° C. for 15 h. After the reaction was completed, as detected by TLC, the reaction solution was cooled to room temperature and filtered, and the filter cake was rinsed with a small amount of ethanol. The filtrate was concentrated, added with absolute ethanol (10 mL), and filtered, and the resulting filtrate was concentrated to give a crude product (750 mg), and 375 mg of the crude product was purified by preparative thin-layer chromatography (dichloromethane:methanol, 5:1, v/v) to give a product (85 mg, yield: 17.8%).

$^1$HNMR (400 MHz, DMSO-d$_6$) δ(ppm): 7.22 (s, 1H), 6.96-7.17 (d, 1H), 6.61 (s, 1H), 4.58 (d, 2H), 3.37-3.44 (m, 4H), 3.13 (d, 2H), 2.65-2.68 (t, 2H), 1.02-1.06 (t, 3H).

Molecular formula: C$_{13}$H$_{18}$FN$_3$O, molecular weight: 251.31, LC-MS (n/z)=252.28 [M+H]$^+$.

Example 15: Synthesis of (E)-1-(2-(aminomethyl)-3-fluoroallyl)-5-(tert-butyl)-5,6-dihydropyrrolo[3,4-c]pyrazol-4(1H)-one (Compound A26)

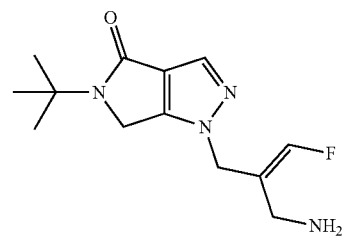 [SMILES: CC(C)(C)N1Cc2c(cnn2C/C(=C/F)CN)C1=O]

Step 1: Synthesis of Compound (E)-1-(2-(aminomethyl)-3-fluoroallyl)-5-(tert-butyl)-5,6-dihydropyrrolo[3,4-c]pyrazol-4(11H)-one

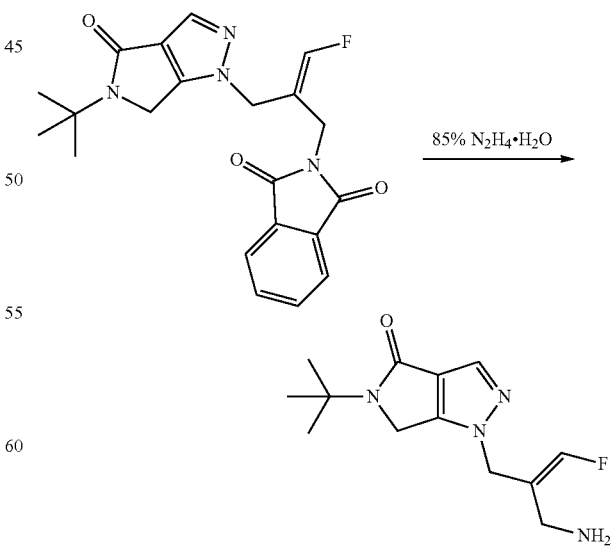

(E)-2-(2-((5-(tert-butyl)-4-oxo-5,6-dihydropyrrolo[3,4-c]pyrazol-1(4H)-yl)methyl)-3-fluoroallyl)isoindole-1,3-dione (100 mg, 0.25 mmol, 1.0 eq.) prepared in Example 7 and 85% hydrazine hydrate (59 mg, 1.01 mmol, 4.0 eq.) were successively added to ethanol (5.0 mL). Then the mixture was stirred at 40° C. for 5 h. After the reaction was completed, as detected by TLC, the reaction solution was cooled to room temperature and filtered, and the filter cake was rinsed with a small amount of ethanol. The filtrate was concentrated, added with absolute ethanol (3.0 mL), and filtered, and the resulting filtrate was concentrated. The crude product was purified by preparative thin-layer chromatography (dichloromethane:methanol, 5:1, v/v) to give a product (35 mg, yield: 52.1%).

$^1$HNMR (400 MHz, DMSO-d$_6$) δ(ppm): 7.58 (s, 1H), 7.02-7.23 (d, 1H), 4.85 (d, 2H), 4.54 (s, 2H), 3.26 (d, 2H), 1.43 (m, 9H).

Molecular formula: $C_{13}H_{19}FN_4O$, molecular weight: 266.32, LC-MS (m/z)=267.22 [M+H$^+$].

Example 16: Synthesis of (E)-2-(2-(aminomethyl)-3-fluoroallyl)-5-isopropyl-2,5,6,7-tetrahydro-4H-pyrazolo[4,3-c]pyridin-4-one (Compound A27) Hydrochloride

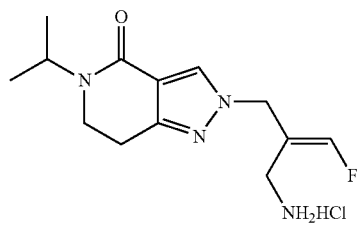

Step 1: Synthesis of ethyl 3-(isopropylamino)propionate

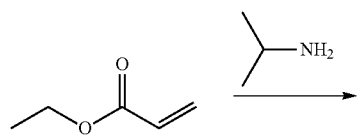

The material isopropylamine (7.09 g, 0.12 mol, 1.2 eq.) was dissolved in ethanol (20 mL). Then the solution was slowly added with ethyl acrylate (10 g, 0.1 mol, 1.0 eq.) dropwise under an ice bath to react for 12 h. After no materials were left, as detected by TLC, the reaction solution was concentrated under reduced pressure to give a product (15 g, yield: 94%).

Step 2: Synthesis of ethyl 3-(isopropyl(3-ethoxy-3-oxopropyl)amino)-3-oxopropionate

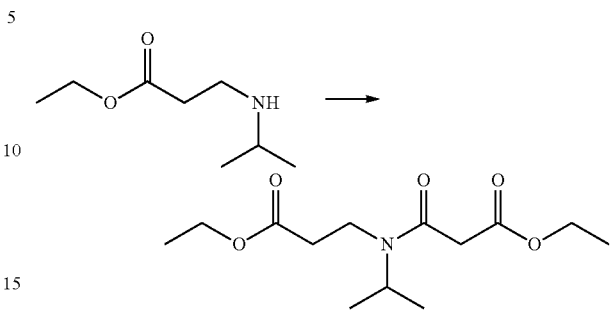

The intermediate ethyl 3-(isopropylamino)propionate (15 g, 94.2 mmol, 1.0 eq.), monoethyl malonate (12.44 g, 94.2 mmol, 1.0 eq.), 4-dimethylaminopyridine (2.3 g, 18.84 mmol, 0.2 eq.) and triethylamine (21.9 g, 220 mmol, 2.3 eq.) were dissolved in dichloromethane (150 mL), and the solution was stirred for 10 min. Then 1-(3-dimethylaminopropyl)-3-ethylcarbodiimide hydrochloride (21.66 g, 113 mmol, 1.2 eq.) was added in batches under an ice bath. After addition, the solution was reacted at room temperature for 2 h. After the reaction was completed, as detected by TLC, the reaction solution was added with water and concentrated hydrochloric acid (4:1, 150 mL), and the mixture was stirred for 10 min, followed by liquid separation. The aqueous phase was extracted with dichloromethane (100 mL×2). The organic phases were combined, washed successively with saturated aqueous sodium carbonate solution (150 mL) and water (150 mL×2), dried over anhydrous sodium sulfate, and filtered, and the filtrate was concentrated under reduced pressure to give a product (17.25 g, yield: 67%).

Step 3: Synthesis of ethyl 1-isopropyl-2,4-dioxopiperidin-3-carboxylate

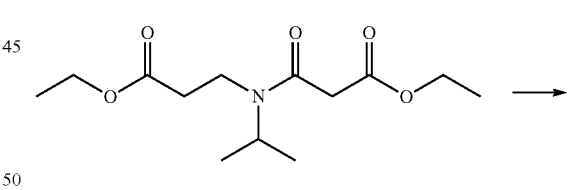

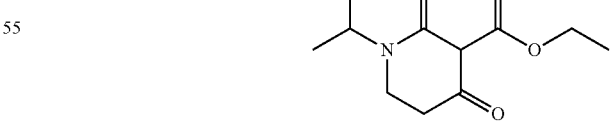

The intermediate ethyl 3-(isopropyl(3-ethoxy-3-oxopropyl)amino)-3-oxopropionate (17.25 g, 63.11 mmol, 1.0 eq.) and sodium ethoxide (8.59 g, 126 mmol, 2.0 eq.) were dissolved in ethanol (100 mL) to react at 80° C. for 1 h. After the reaction was completed, as detected by TLC, the reaction solution was concentrated under reduced pressure to give a product (14.34 g, yield: 100%).

Step 4: Synthesis of 1-isopropylpiperidin-2,4-dione

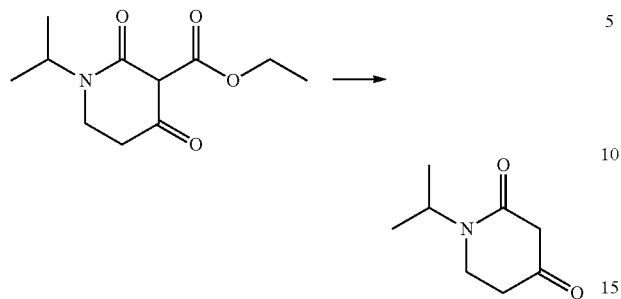

The intermediate ethyl 1-isopropyl-2,4-dioxopiperidin-3-carboxylate (14.23 g, 63.11 mmol, 1.0 eq.) was dissolved in water (80 mL) and concentrated hydrochloric acid (20 mL) to react at 110° C. for 1 h. After the reaction was completed, as detected by LC-MS, the reaction solution was cooled to room temperature and extracted with dichloromethane (100 mL×3). The organic phase was dried and concentrated to give a product (7.14 g, yield: 72%).

Step 5: Synthesis of 1-isopropyl-3-((dimethyl-amino)methylene)piperidin-2,4-dione

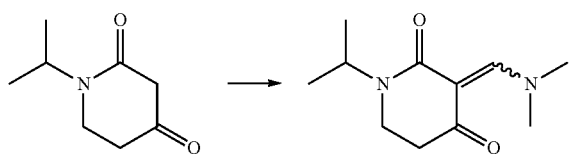

The intermediate 1-isopropylpiperidin-2,4-dione (7.14 g, 46 mmol, 1.0 eq.) was dissolved in N,N-dimethylformamide dimethyl acetal (6.03 g, 50.6 mmol, 1.1 eq.) to react for 0.5 h. After the reaction was completed, as detected by LC-MS, the reaction solution was concentrated under reduced pressure to give a product (9.67 g, yield: 100%).

Step 6: Synthesis of 5-isopropyl-2,5,6,7-tetrahydro-4H-pyrazolo[4,3-c]pyridin-4-one

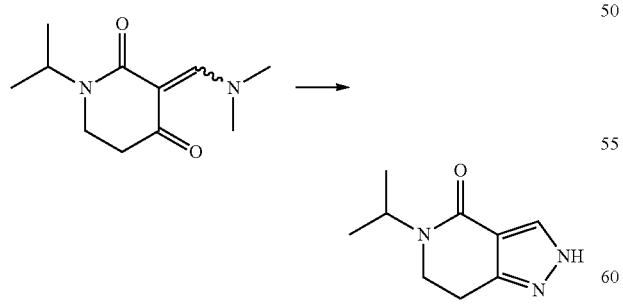

The intermediate 1-isopropyl-3-((dimethylamino)methylene)piperidin-2,4-dione (9.67 g, 46 mmol, 1.0 eq.) and hydrazine hydrate (2.506 g, 50.06 mmol, 1.1 eq.) were dissolved in methanol (50 mL) to react at 60° C. for 30 min. After the reaction was completed, as detected by LC-MS, the reaction solution was cooled to room temperature and concentrated under reduced pressure. The crude product was recrystallized with ethyl acetate (80 mL) and filtered under vacuum, and the filter cake was dried to give a product (4.5 g, yield: 54%).

Step 7: Synthesis of (E)-2-(2-((5-isopropyl-4-oxo-4,5,6,7-tetrahydro-2H-pyrazolo[4,3-c]pyridin-2-yl)methyl)-3-fluoroallyl)isoindolin-1,3-dione

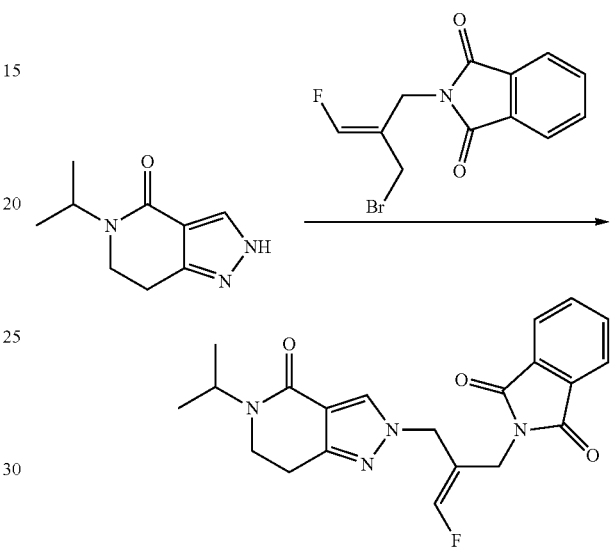

The intermediate 5-isopropyl-2,5,6,7-tetrahydro-4H-pyrazolo[4,3-c]pyridin-4-one (300 mg, 1.67 mmol, 1.0 eq.) was dissolved in DMF (1.5 mL). Then the solution was added with NaH (87 mg, 2.21 mmol, 1.3 eq.), stirred for 30 min, and then added with a solution of (E)-2-(2-(bromomethyl)-3-fluoroallyl)isoindolin-1,3-dione (599 mg, 2.0 mmol, 1.2 eq.) in DMF (1.5 mL) dropwise to react for 30 min. After the reaction was completed, as detected by LC-MS, the reaction solution was added with water (10 mL) and extracted with ethyl acetate (20 mL×2). The organic phase was washed with water (20 mL×2), dried over anhydrous sodium sulfate, and filtered, and the filtrate was concentrated under reduced pressure. The crude product was purified by silica gel column chromatography (PE:EA=1:2) to give a product (200 mg, yield: 30%).

Step 8: Synthesis of (E)-2-(2-(aminomethyl)-3-fluoroallyl)-5-isopropyl-2,5,6,7-tetrahydro-4H-pyrazolo[4,3-c]pyridin-4-one hydrochloride

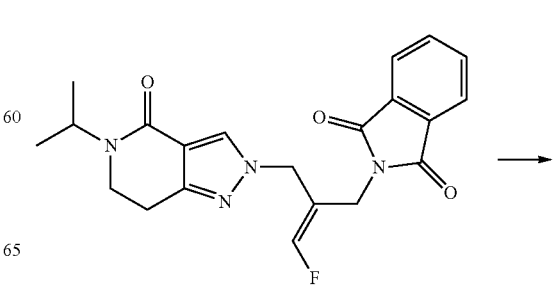

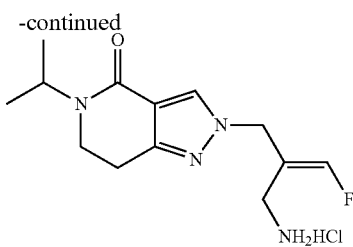

The intermediate (E)-2-(2-((5-isopropyl-4-oxo-4,5,6,7-tetrahydro-2H-pyrazolo[4,3-c]pyridin-2-yl)methyl)-3-fluoroallyl)isoindolin-1,3-dione (200 mg, 0.5 mmol, 1.0 eq.) was dissolved in EtOH (2 mL). Then the solution was added with hydrazine hydrate (88 mg, 1.75 mmol, 3.5 eq.) to react at 80° C. for 30 min. After the reaction was completed, as detected by TLC, the reaction solution was filtered, and the filtrate was concentrated. The crude product was purified by preparative thin-layer chromatography (DCM:MeOH=10:1) to give an oily liquid. The oily liquid was added with methanol (2 mL), followed by hydrogen chloride ethanol solution (0.15 mL), stirred for 5 min, and concentrated under reduced pressure to give a product (60 mg, yield: 39%).

$^1$HNMR (400 MHz, DMSO-$d_6$) δ(ppm): 8.24 (s, 3H), 8.20 (s, 1H), 7.36 (s, 0.5H), 7.16 (s, 0.5H), 4.86-4.87 (d, 2H), 4.73-4.80 (m, 1H), 3.40-3.44 (m, 2H), 3.34 (s, 2H), 2.77-2.79 (m, 2H), 1.11 (s, 3H), 1.09 (s, 3H).

Molecular formula: $C_{13}H_{20}ClFN_4O$, molecular weight: 302.78, LC-MS (Pos, m/z)=267.28[M+H]$^+$.

Example 17: Synthesis of (E)-1-(2-(aminomethyl)-3-fluoroallyl)-N-ethyl-1H-pyrazole-4-carboxamide (Compound B1)

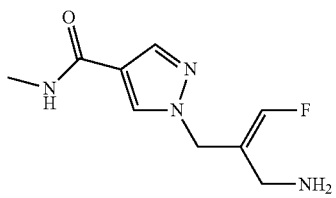

Step 1: Synthesis of methyl 1H-pyrazole-4-carboxylate

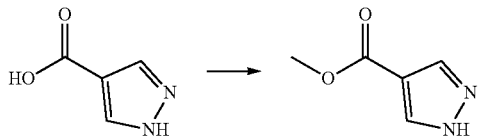

1H-pyrazole-4-carboxylic acid (10.0 g, 0.0892 mol, 1.0 eq.) was dissolved in methanol (36.0 mL). Then the solution was added with sulfuric acid (10.0 mL) dropwise at 0° C., and heated to 75° C. to react overnight. After the reaction was completed, as detected by LC-MS, the reaction solution was poured into cold water (50.0 mL). Saturated aqueous sodium carbonate solution was added dropwise to adjust the pH to 8-9, and ethyl acetate (20.0 mL×4) was added for extraction. The organic phase was dried over anhydrous sodium sulfate and concentrated under reduced pressure to give a product (10.37 g, yield: 92.2%).

Step 2: Synthesis of methyl (E)-1-(2-((1,3-dioxoisoindolin-2-yl)methyl)-3-fluoroallyl)-1H-pyrazole-4-carboxylate

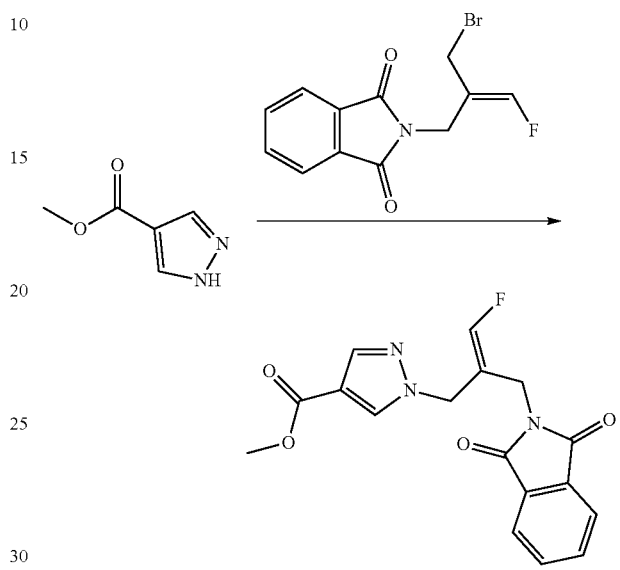

Methyl 1H-pyrazole-4-carboxylate (2.0 g, 15.86 mmol, 1.0 eq.), (E)-2-(2-(bromomethyl)-3-fluoroallyl)isoindolin-1,3-dione (5.2 g, 17.44 mmol, 1.1 eq.) and potassium carbonate (3.29 g, 23.79 mmol, 1.5 eq.) were dissolved in acetonitrile (20.0 mL) to react at room temperature overnight. After the reaction was completed, as detected by TLC, the reaction solution was added with water (30.0 mL) and extracted with ethyl acetate (20.0 mL×2). The organic phase was dried over anhydrous sodium sulfate and concentrated under reduced pressure to give a product (6.0 g, crude product).

Step 3: Synthesis of methyl (E)-1-(2-(aminomethyl)-3-fluoroallyl)-1H-pyrazole-4-carboxylate

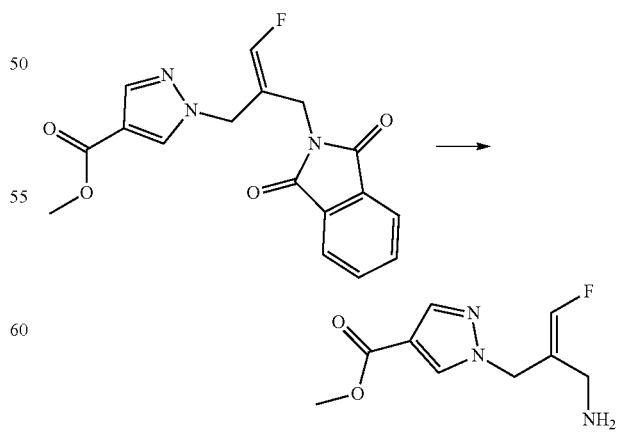

Methyl (E)-1-(2-((1,3-dioxoisoindolin-2-yl)methyl)-3-fluoroallyl)-1H-pyrazole-4-carboxylate (6.0 g, crude product) was dissolved in ethanol (60.0 mL). Then the solution was added with hydrazine hydrate (10.27 g, 174.44 mmol, 85%) to react overnight at room temperature. After the reaction was completed, as detected by LC-MS, The reaction solution was filtered, and the filtrate was concentrated under reduced pressure, and then added with toluene. The resulting mixture was concentrated under reduced pressure to obtain the product (5.0 g, crude product).

Step 4: Synthesis of methyl (E)-1-(2-(((tert-butoxycarbonyl)amino) methyl)-3-fluoroallyl)-1H-pyrazole-4-carboxylate

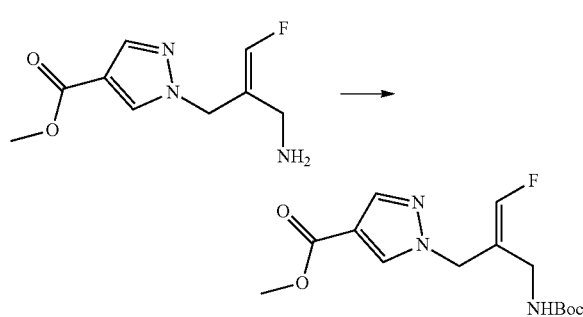

Methyl (E)-1-(2-(aminomethyl)-3-fluoroallyl)-1H-pyrazole-4-carboxylate (5.0 g, crude product) and sodium carbonate (1.85 g, 17.44 mmol, 1.0 eq.) were dissolved in tetrahydrofuran (20.0 mL) and water (10.0 mL) to react at 40° C. for 2.5 h. After the materials reacted completely, as detected by TLC, the reaction solution was concentrated under reduced pressure, extracted with ethyl acetate (40.0 mL×2), dried over anhydrous sodium sulfate, and filtered, and the filtrate was concentrated under reduced pressure to give a product (3.2 g, three-step yield: 64.4%).

Step 5: Synthesis of (E)-1-(2-(((tert-butoxycarbonyl)amino)methyl)-3-fluoroallyl)-1H-pyrazole-4-carboxylic acid

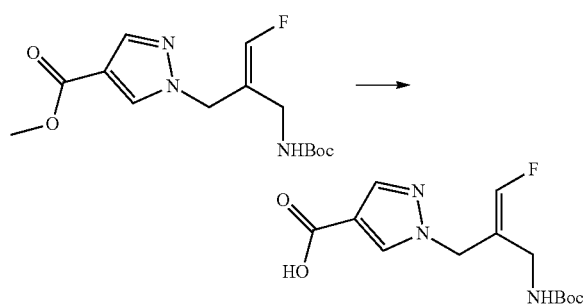

Methyl (E)-1-(2-(((tert-butoxycarbonyl)amino)methyl)-3-fluoroallyl)-1H-pyrazole-4-carboxylate (1.98 g, 6.32 mmol, 1.0 eq.) and NaOH (1.517 g, 37.915 mmol) were dissolved in methanol (9.0 mL) and water (9.0 mL) to react at 60° C. for 4 h. After the materials reacted completely, as detected by TLC, the reaction solution was concentrated under reduced pressure and added with water (20.0 mL). Citric acid was added to adjust the pH to 5-6, and dichloromethane (20.0 mL×4) was added for extraction. The organic phase was dried over anhydrous sodium sulfate and concentrated under reduced pressure. The crude product was slurried with a small amount of ethyl acetate (2.5 mL), and filtered under vacuum, and the filter cake was the product (690.0 mg, yield: 36.5%).

Step 6: Synthesis of (E)-(3-fluoro-2-((4-(methylcarbamoyl)-1H-pyrazol-1-yl)methyl)allyl)tert-butyl carbamate

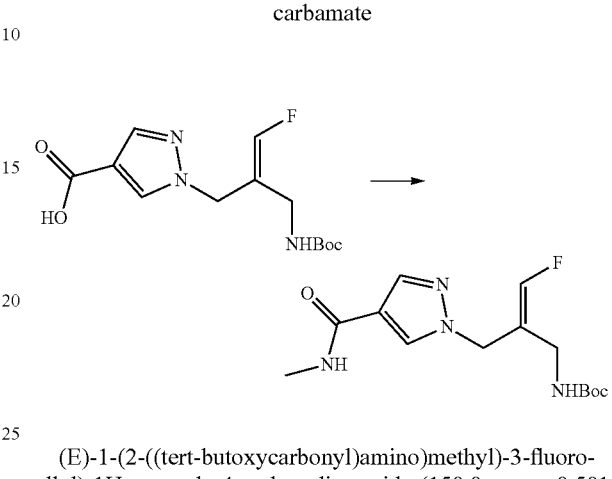

(E)-1-(2-((tert-butoxycarbonyl)amino)methyl)-3-fluoroallyl)-1H-pyrazole-4-carboxylic acid (150.0 mg, 0.501 mmol, 1.0 eq.) and DIPEA (272.0 mg, 2.11 mmol, 4.2 eq.) were dissolved in DMF (2.0 mL). In nitrogen atmosphere, the solution was added with HATU (286.0 mg, 0.752 mmol, 1.5 eq.) at 0° C., stirred for 0.5 h, and then added with methylamine hydrochloride (41.0 mg, 0.601 mmol, 1.2 eq.). The mixture was slowly warmed to room temperature overnight. After the reaction was completed, as detected by TLC, ethyl acetate (40.0 mL) was added to the reaction solution, and the mixture was washed successively with saturated aqueous sodium carbonate solution (4.0 mL), saturated aqueous ammonium chloride solution (4.0 mL) and saturated aqueous sodium chloride solution (4.0 mL). The organic phase was dried over anhydrous sodium sulfate and concentrated under reduced pressure. The crude product was purified by silica gel column chromatography (DCM:MeOH=150:1-30:1) to give a product (133.0 mg, yield: 85%).

Step 7: Synthesis of (E)-1-(2-(aminomethyl)-3-fluoroallyl)-N-methyl-1H-pyrazole-4-carboxamide

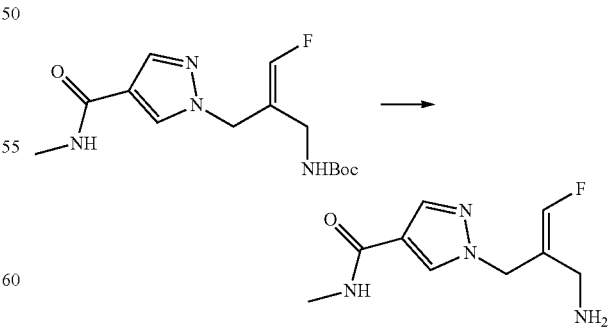

(E)-(3-fluoro-2-((4-(methylcarbamoyl)-1H-pyrazol-1-yl)methyl)allyl)tert-butyl carbamate (133.0 mg, 0.426 mmol, 1.0 eq.) was dissolved in ethanol (1.0 mL). Then the solution was added with hydrogen chloride ethanol solution (1.0 mL)

dropwise to react at room temperature for 2 h. After the reaction was completed, as detected by TLC, the reaction solution was concentrated under reduced pressure. The crude product was purified by preparative thin-layer chromatography (DCM:MeOH=8:1) to give a product (80.0 mg, yield: 88.9%).

¹HNMR (400 MHz, DMSO-d₆) δ(ppm): 8.16 (s, 1H), 8.03-8.01 (d, 1H), 7.82 (s, 1H), 7.03-6.82 (d, 1H), 4.76-4.75 (d, 2H), 3.06-3.05 (d, 2H), 2.71-2.69 (d, 3H), 1.71 (s, 2H).

Molecular formula: $C_9H_{13}FN_4O$, molecular weight: 212.23, LC-MS (Pos, m/z)=213.19[M+H]⁺

Example 18: Synthesis of (E)-1-(2-(aminomethyl)-3-fluoroallyl)-N-ethyl-1H-pyrazole-4-carboxamide (Compound B2)

Step 1: Synthesis of tert-butyl (E)-(2-((4-(ethylcarbamoyl)-1H-pyrazol-1-yl)methyl)-3-fluoroallyl)carbamate (E)-1-(2-(((tert-butoxycarbonyl)amino)methyl)-3-fluoroallyl)-1H-pyrazole-4-carboxylic acid (500.0 mg, 1.67 mmol, 1.0 eq.) was added to DMF (4.0 mL), and DIPEA (1.29 g, 10.02 mmol, 6.0 eq.) and HATU (952.5 g, 2.50 mmol, 1.5 eq.) were added under an ice bath. The mixture was stirred for 2 h, and then added with ethylamine hydrochloride (340.4 mg, 4.17 mmol, 2.5 eq.). The resulting mixture was gradually warmed to room temperature and stirred for 12 h. After the reaction was completed, as detected by TLC, the reaction solution was added with EA (70 mL) and aqueous sodium carbonate solution (40 mL), followed by liquid separation. The organic phase was dried over anhydrous sodium sulfate and filtered, and the filtrate was concentrated under reduced pressure. The crude product was purified by preparative thin-layer chromatography (DCM:MeOH=20:1) to give a product (426.0 mg, yield: 78.1%).

Step 2: Synthesis of (E)-1-(2-(aminomethyl)-3-fluoroallyl)-N-ethyl-1H-pyrazole-4-carboxamide

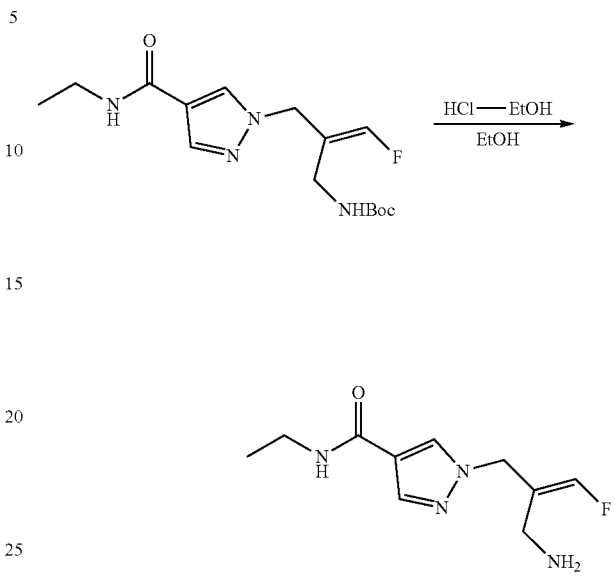

(E)-(2-((4-(ethylcarbamoyl)-1H-pyrazol-1-yl)methyl)-3-fluoroallyl)tert-butyl carbamate (426.0 mg, 1.30 mmol, 1.0 eq.) was added to EtOH (4 mL), and hydrogen chloride ethanol solution (4 mL) was added dropwise under an ice bath. The mixture was gradually warmed to room temperature and stirred for 3 h. After the reaction was completed, as detected by TLC, the reaction solution was concentrated under reduced pressure, and the pH was adjusted to 7-8 with saturated aqueous sodium carbonate solution. DCM (50 mL) was added, followed by liquid separation. The organic phase was dried over anhydrous sodium sulfate and filtered, and the filtrate was concentrated under reduced pressure. The crude product was purified by preparative thin-layer chromatography (DCM:MeOH=10:1) to give a product (157.0 mg, yield: 53.4%).

¹HNMR (400 MHz, DMSO-d₆) δ(ppm): 8.16 (s, 1H), 8.04-8.06 (m, 1H), 7.83 (s, 1H), 7.03 (s, 0.5H), 6.82 (s, 0.5H), 4.75 (m, 2H), 3.18-3.22 (m, 2H), 3.04-3.05 (m, 2H), 1.55 (s, 2H), 1.06-1.10 (m, 3H).

Molecular formula: $C_{10}H_{15}FN_4O$, molecular weight: 226.26, LC-MS (Pos, m/z)=227.21[M+H]⁺.

Example 19: Synthesis of (E)-1-(2-(aminomethyl)-3-fluoroallyl)-N-(tert-butyl)-1H-pyrazole-4-carboxamide (Compound B3)

Step 1: Synthesis of tert-butyl (E)-(2-((4-(tert-butyl-carbamoyl)-1H-pyrazol-1-yl)methyl)-3-fluoroallyl)carbamate

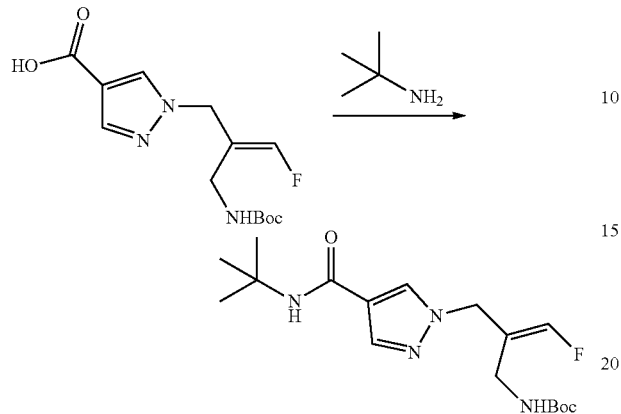

(E)-1-(2-((tert-butoxycarbonyl)amino)methyl)-3-fluoro-allyl)-1H-pyrazole-4-carboxylic acid (440.0 mg, 1.47 mmol, 1.0 eq.) was added to DMF (4.5 mL), and DIPEA (285.0 mg, 2.20 mmol, 1.5 eq.) and HATU (1.67 g, 4.41 mmol, 3.0 eq.) were added under an ice bath. The mixture was stirred under an ice bath for 2 h, and added with tert-butylamine (150.5 mg, 2.05 mmol, 1.4 eq.). The resulting mixture was gradually warmed room temperature and stirred for 12 h. After the reaction was completed, as detected by TLC, the reaction solution was concentrated under reduced pressure, and added with EA (100 mL) and aqueous sodium carbonate solution (60 mL), followed by liquid separation. The organic phase was dried over anhydrous sodium sulfate, and filtered, and the filtrate was concentrated under reduced pressure. The crude product was purified by preparative thin-layer chromatography (DCM:MeOH=20:1) to give a product (400.0 mg, yield: 76.7%).

Step 2: Synthesis of (E)-1-(2-(aminomethyl)-3-fluoroallyl)-N-(tert-butyl)-1H-pyrazole-4-carboxamide

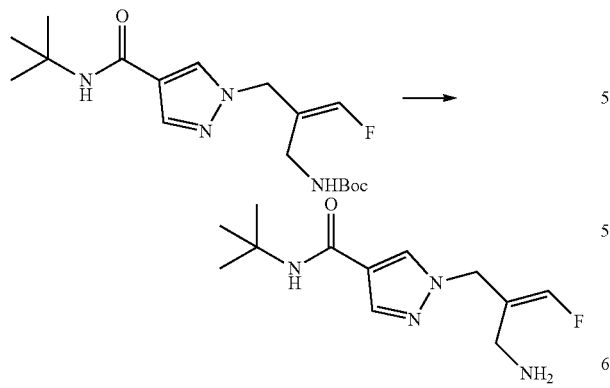

Tert-butyl (E)-(2-((4-(tert-butylcarbamoyl)-1H-pyrazol-1-yl)methyl)-3-fluoroallyl)carbamate (300.0 mg, 0.84 mmol, 1.0 eq.) was added to EtOH (4 mL), and hydrogen chloride ethanol solution (4 mL) was added dropwise under an ice bath. The mixture was gradually warmed to room temperature and stirred for 3 h. After the reaction was completed, as detected by TLC, the reaction solution was concentrated under reduced pressure, and the pH was adjusted to 7-8 with saturated aqueous sodium carbonate solution. DCM (30 mL) was added, followed by liquid separation. The aqueous phase was extracted with n-butanol (10 mL). The organic phases were combined, dried over anhydrous sodium sulfate, and filtered, and the filtrate was concentrated under reduced pressure. The crude product was purified by preparative thin-layer chromatography (DCM:MeOH=10:1) to give a product (92.0 mg, yield: 43%).

$^1$HNMR (400 MHz, DMSO-$d_6$) δ(ppm): 8.19 (s, 1H), 7.83 (s, 1H), 7.36 (s, 1H), 7.03 (s, 0.5H), 6.82 (s, 0.5H), 4.73-4.74 (d, 2H), 3.05 (d, 2H), 1.53-1.70 (s, 2H), 1.34 (s, 9H).

Molecular formula: $C_{12}H_{19}FN_4O$, molecular weight: 254.31, LC-MS (Pos, m/z)=255.24[M+H]$^+$.

Example 20: Synthesis of (E)-1-(2-(aminomethyl)-3-fluoroallyl)-N-cyclopropyl-1H-pyrazole-4-carbox-amide (Compound B4) Hydrochloride

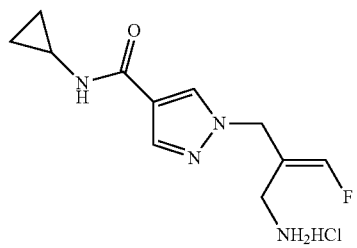

Step 1: Synthesis of tert-butyl (E)-(2-((4-(cyclopropylcarbamoyl)-1H-pyrazol-1-yl)methyl)-3-fluoroallyl)carbamate

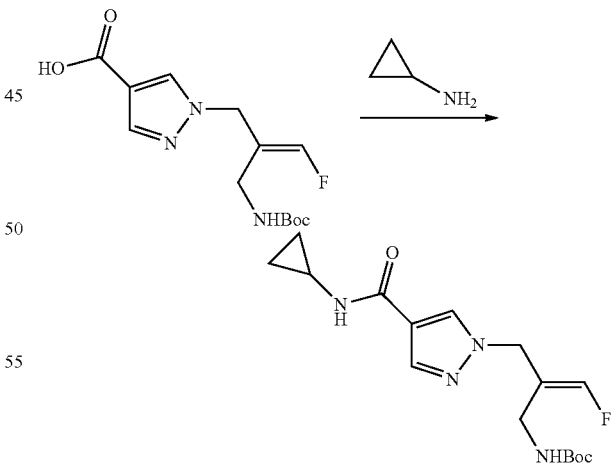

(E)-1-(2-((tert-butoxycarbonyl)amino)methyl)-3-fluoroallyl)-1H-pyrazole-4-carboxylic acid (133.0 mg, 0.44 mmol, 1.0 eq.) was added into DMF (3.0 mL), DIPEA (170.4 mg, 1.32 mmol, 3.0 eq.) and HATU (253.4 mg, 0.667 mmol, 1.5 eq.) were added under an ice bath, stirring was performed for 2 h, and cyclopropylamine (32.6 mg, 0.57 mmol, 1.3 eq.) was then added. The mixture was incubated at room temperature and stirred for 12 h. After the reaction was completed, as detected by TLC, the reaction solution was concentrated under reduced pressure and added with EA (50 mL), saturated aqueous ammonium chloride solution (30 mL) and saturated aqueous sodium chloride solution (30 mL), and liquid separation was performed. The organic phase was dried over anhydrous sodium sulfate and filtered, and the filtrate was concentrated under reduced pressure. The crude product was purified by silica gel column chromatography to give the product (97.6 mg, yield: 65.5%).

Step 2: Synthesis of (E)-1-(2-(aminomethyl)-3-fluoroallyl)-N-cyclopropyl-1H-pyrazole-4-carboxamide hydrochloride

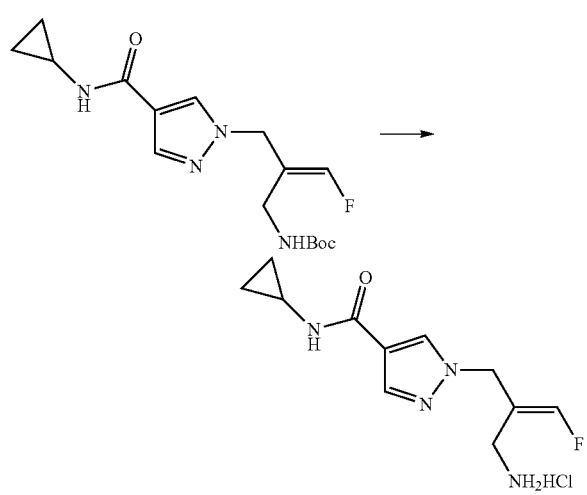

Tert-butyl (E)-2-((4-(cyclopropylcarbamoyl)-1H-pyrazol-1-yl)methyl)-3-fluoroallyl)carbamate (97.6 mg, 0.28 mmol, 1.0 eq.) was added into EtOH (3 mL), hydrogen chloride ethanol solution (3 mL) was added dropwise under an ice bath, and the mixture was incubated at room temperature and stirred for 2 h. After the reaction was completed, as detected by TLC, the reaction solution was concentrated under reduced pressure to give the product (35.7 mg, yield: 46.3%).

$^1$HNMR (400 MHz, DMSO-$d_6$) δ(ppm): 8.27 (s, 2H), 8.24 (s, 1H), 8.13-8.14 (d, 1H), 7.89 (s, 1H), 7.35 (s, 0.5H), 7.15 (s, 0.5H), 4.89-4.90 (d, 2H), 2.71-2.75 (m, 1H), 0.64-0.67 (m, 2H), 0.49-0.51 (m, 2H).

Molecular formula: $C_{11}H_{15}FN_4O$, molecular weight: 238.27, LC-MS (Pos, m/z)=239.21[M+H]$^+$.

Example 21: Synthesis of (E)-1-(2-aminomethyl-3-fluoroallyl)-N-ethyl-1H-pyrrole-3-carboxamide (Compound B11) Hydrochloride

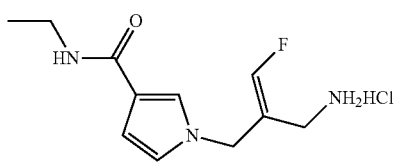

Step 1: Synthesis of methyl (Z)-1-(2-((1,3-dioxoisoindolin-2-yl)methyl)-3-fluoroallyl)-1H-pyrrole-3-carboxylate

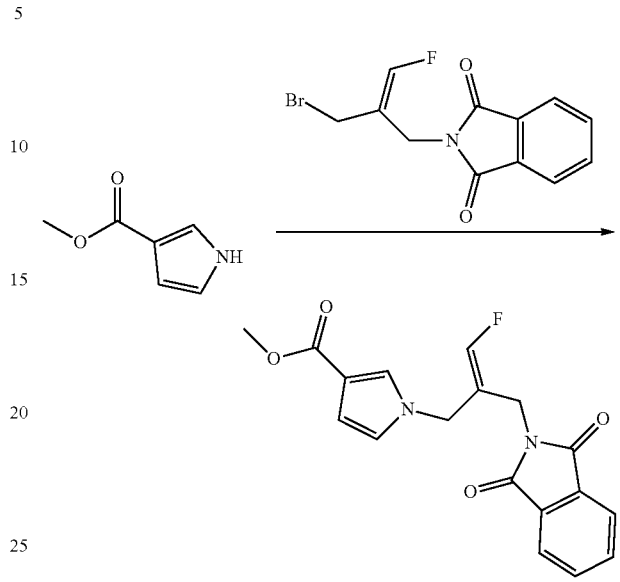

Methyl 1H-pyrrole-3-carboxylate (1.77 g, 14.19 mmol, 1.0 eq.), (E)-2-(2-bromomethyl-3-fluoroallyl)isoindoline-1,3-dione (5.50 g, 18.45 mmol, 1.3 eq.) and potassium carbonate (5.88 g, 42.57 mmol, 3.0 eq.) were added into DMF (100 mL), and the mixture was stirred at room temperature for 2 h. After the reaction was completed, as detected by TLC, the reaction solution was concentrated under reduced pressure, added with ethyl acetate (100 mL) and washed with water (50 mL×4). The organic phases were combined, dried over anhydrous sodium sulfate and filtered under vacuum, and the filtrate was concentrated under reduced pressure to give the product (5.89 g of crude product).

Step 2: Synthesis of methyl (E)-1-(2-aminomethyl-3-fluoroallyl)-1H-pyrrole-3-carboxylate

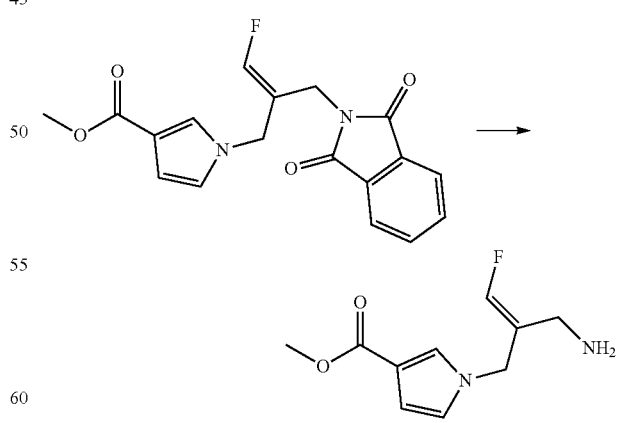

Methyl (Z)-1-(2-((1,3-dioxoisoindolin-2-yl)methyl)-3-fluoroallyl)-1H-pyrrole-3-carboxylate (5.89 g of crude product) and hydrazine hydrate (85%, 10.16 g, 172.6 mmol, 10.0 eq.) were added into ethanol (60 mL), and the mixture was stirred at room temperature overnight. After the reaction was completed, as detected by TLC, the reaction solution was added with ethyl acetate (60 mL) and washed with saturated aqueous NH₄Cl solution (30 mL×4). The organic phase was dried over anhydrous sodium sulfate and filtered under vacuum, and the filtrate was concentrated under reduced pressure to give the product (1.96 g of crude product).

Step 3: Synthesis of methyl (E)-1-(2-(((tert-butoxy-carbonyl)amino) methyl-3-fluoroallyl)-1H-pyrrole-3-carboxylate

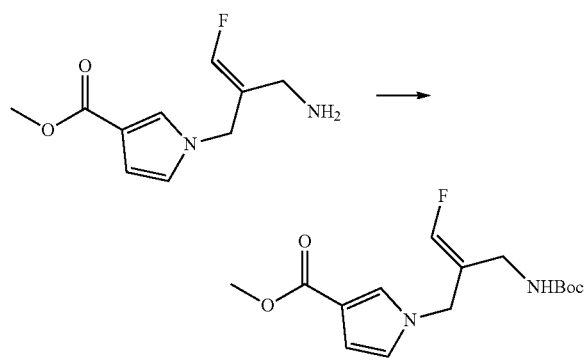

Methyl (E)-1-(2-aminomethyl-3-fluoroallyl)-1H-pyrrole-3-carboxylate (1.96 g of crude product) and triethylamine (1.40 g, 13.85 mmol, 1.5 eq.) were added into tetrahydrofuran (20 mL), (Boc)₂O (2.22 g, 10.16 mmol, 1.1 eq.) was added dropwise, and the mixture was stirred at room temperature for 2 h. After the reaction was completed, as detected by TLC, the reaction solution was added with ethyl acetate (80 mL), and saturated aqueous NH₄Cl solution (40 mL×2) was added for washing. The organic phase was dried over anhydrous sodium sulfate, filtered under vacuum and concentrated under reduced pressure. The crude product was purified by silica gel column chromatography to give the product (2.87 g, three-step yield: 65.0%).

Step 4: Synthesis of (E)-1-(2-(((tert-butoxycarbonyl)amino)methyl)-3-fluoroallyl)-1H-pyrrole-3-carboxylic acid

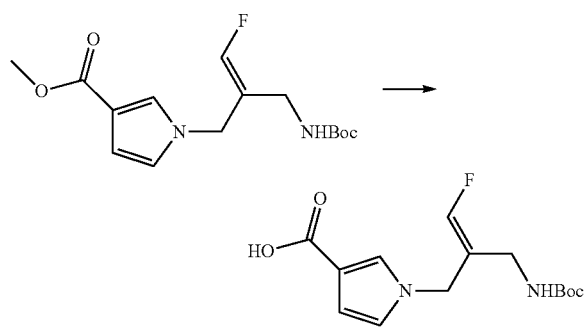

Methyl (E)-1-(2-(((tert-butoxycarbonyl)amino)methyl-3-fluoroallyl)-1H-pyrrole-3-carboxylate (2.87 g, 9.19 mmol, 1.0 eq.) was dissolved in methanol (15 mL). The solution was added with aqueous NaOH (2.21 g, 55.13 mmol, 6.0 eq.) solution (15 mL) and stirred at 60° C. for 4 h. After the reaction was completed, as detected by TLC, the reaction solution was concentrated under reduced pressure, 5% aqueous citric acid solution was added to adjust the pH to 4, and extraction was performed with DCM (50 mL). The organic phase was dried over anhydrous sodium sulfate and filtered, and the filtrate was concentrated under reduced pressure to give the product (2.00 g, yield: 73.0%).

Step 5: Synthesis of tert-butyl (E)-(2-((3-(ethylcarbamoyl)-1H-pyrrol-1-yl)methyl)-3-fluoroallyl)carbamate

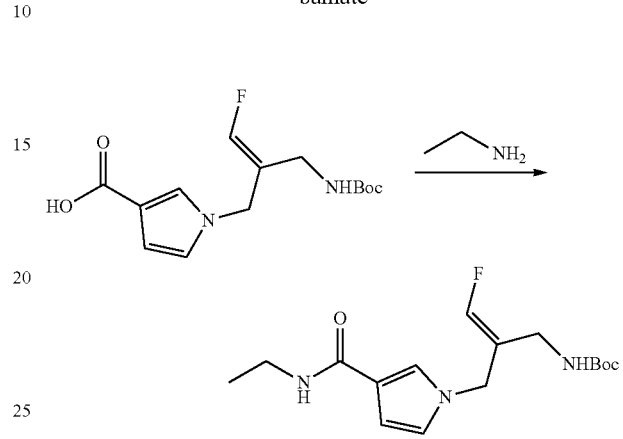

(E)-1-(2-(((tert-butoxycarbonyl)amino)methyl-3-fluoro-allyl)-1H-pyrrole-3-carboxylic acid (200.0 mg, 0.67 mmol, 1.0 eq.) was added into DMF (2 mL), DIPEA (519.8 mg, 4.02 mmol, 6.0 eq.) and HATU (382.4 mg, 1.01 mmol, 1.5 eq.) were added under an ice bath, and the mixture was stirred for 1 h. The mixture was added with ethylamine hydrochloride (164.0 mg, 2.01 mmol, 3.0 eq.), and incubated at room temperature overnight. After the reaction was completed, as detected by TLC, the reaction solution was concentrated under reduced pressure. The concentrate was dissolved in EA (60 mL), and saturated aqueous NaHCO₃ solution (50 mL), saturated aqueous NH₄Cl solution (50 mL) and saturated brine (50 mL×4) were sequentially used for washing. The organic phase was dried over anhydrous sodium sulfate and filtered, and the filtrate was concentrated under reduced pressure. The crude product was purified by preparative thin-layer chromatography (DCM:MeOH=40:1) to give the product (133.0 mg, yield: 61.0%).

Step 6: Synthesis of (E)-1-(2-aminomethyl-3-fluoroallyl)-N-ethyl-1H-pyrrole-3-carboxamide hydrochloride

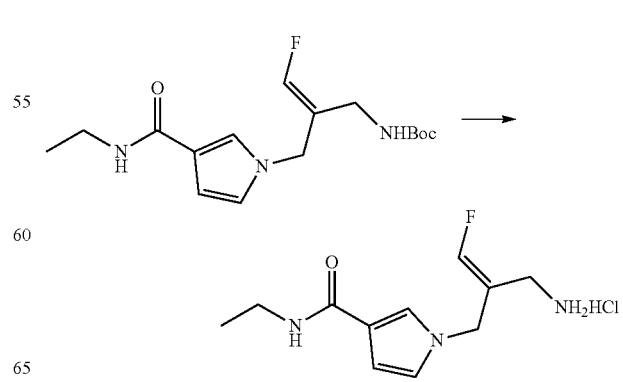

Tert-butyl (E)-(2-((3-(ethylcarbamoyl)-1H-pyrrol-1-yl)methyl)-3-fluoroallyl)carbamate (133.0 mg, 0.41 mmol) was added into EtOH (5.0 mL), hydrogen chloride ethanol solution (5.0 mL) was added dropwise under an ice bath, and the mixture was incubated at room temperature and stirred for 3 h. After the reaction was completed, as detected by TLC, the reaction solution was concentrated under reduced pressure, the crude product was slurried with methyl tert-butyl ether for 2 h, and filtration was performed to give the product (93.0 mg, yield: 86.9%).

$^1$HNMR (400 MHz, DMSO-$d_6$) δ(ppm): 8.55 (s, 3H), 7.84 (s, 1H), 7.37-7.36 (t, 1H), 7.32 (s, 0.5H), 7.11 (s, 0.5H), 6.88-6.87 (t, 1H), 6.49-6.47 (q, 1H), 4.74-4.73 (d, 2H), 3.24-3.16 (m, 4H), 1.06 (t, 3H).

Molecular formula: $C_{11}H_{17}ClN_3FO$, molecular weight: 261.73, LC-MS (Pos, m/z)=226.18[M+H]$^+$.

Example 22: Synthesis of (E)-1-(2-aminomethyl-3-fluoroallyl)-N-tert-butyl-1H-pyrrole-3-carboxamide (Compound B12)

Step 1: Synthesis of tert-butyl (E)-(2-((3-(tert-butylcarbamoyl)-1H-pyrrol-1-yl)methyl)-3-fluoroallyl) carbamate

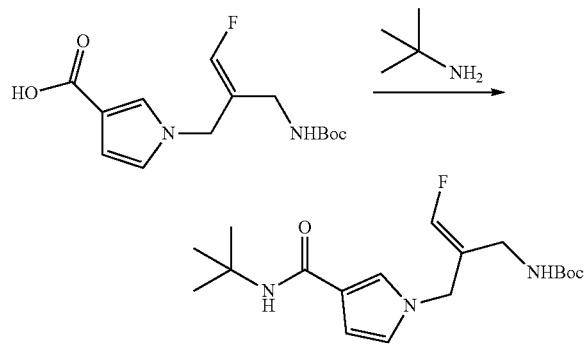

(E)-1-(2-(((tert-butoxycarbonyl)amino)methyl-3-fluoroallyl)-1H-pyrrole-3-carboxylic acid (200.0 mg, 0.67 mmol, 1.05 eq.) was added into DMF (2 mL), DIPEA (248.3 mg, 1.92 mmol, 3.0 eq.) and HATU (365.2 mg, 0.96 mmol, 1.5 eq.) were added under an ice bath, and the mixture was stirred under an ice bath for 1 h. The mixture was added with tert-butylamine (51.5 mg, 0.70 mmol, 1.1 eq.), and incubated at room temperature overnight. After the reaction was completed, as detected by TLC, the reaction solution was concentrated under reduced pressure. The concentrate was dissolved in EA (60 mL), and saturated aqueous NaHCO$_3$ solution (50 mL), saturated aqueous NH$_4$Cl solution (50 mL) and saturated brine (50 mL×4) were sequentially used for washing. The organic phase was dried over anhydrous sodium sulfate and filtered, and the filtrate was concentrated under reduced pressure. The crude product was purified by preparative thin-layer chromatography (DCM:MeOH=10:1) to give the product (165.0 mg, yield: 69.6%).

Step 2: Synthesis of (E)-1-(2-aminomethyl-3-fluoroallyl)-N-tert-butyl-1H-pyrrole-3-carboxamide

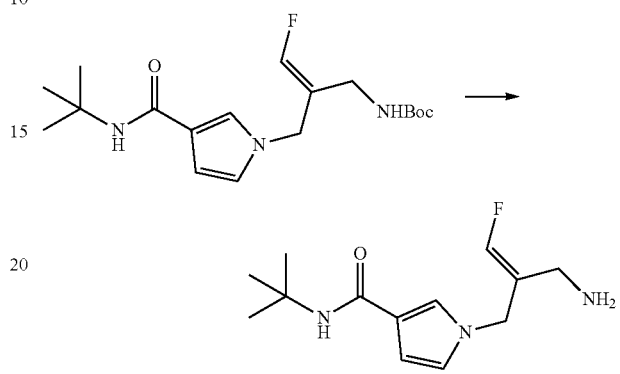

Tert-butyl (E)-(2-((3-(tert-butylcarbamoyl)-1H-pyrrol-1-yl)methyl)-3-fluoroallyl)carbamate (165.0 mg, 0.47 mmol) was added to EtOH (5.0 mL), hydrochloric acid ethanol solution (5.0 mL) was added dropwise under an ice bath, and the mixture was incubated at room temperature and stirred for 3 h. After the reaction was completed, as detected by TLC, the reaction solution was concentrated under reduced pressure and added with DCM (40 mL) and 15% aqueous NaOH solution (40 mL), followed by liquid separation. The organic phase was dried over anhydrous sodium sulfate and then filtered, and the filtrate was concentrated under reduced pressure. After separation and purification by preparative thin-layer chromatography (DCM:MeOH=10:1), (E)-1-(2-aminomethyl-3-fluoroallyl)-N-tert-butyl-1H-pyrrole-3-carboxamide was obtained (77.0 mg, yield: 65.1%).

$^1$HNMR (400 MHz, DMSO-$d_6$) δ(ppm): 7.31 (s, 1H), 7.01 (s, 0.5H), 6.96 (s, 1H), 6.79 (s, 0.5H), 6.72-6.71 (t, 1H), 6.44-6.43 (d, 1H), 4.50-4.49 (d, 2H), 3.03-3.02 (d, 2H), 1.71 (s, 2H), 1.33 (s, 9H).

Molecular formula: $C_{13}H_{20}FN_3O$, molecular weight: 253.32, LC-MS (Pos, m/z)=254.24[M+H]$^+$.

Example 23: Synthesis of (E)-1-(2-(aminomethyl)-3-fluoroallyl)-N-ethyl-1H-pyrazole-3-carboxamide (Compound B20)

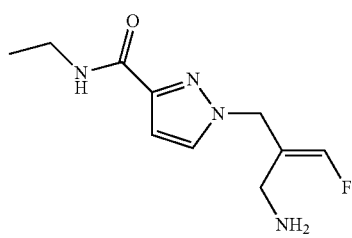 [SMILES: CCNC(=O)c1ccn(C/C(=C/F)CN)n1]

Step 1: Synthesis of tert-butyl (E)-(2-((3-(ethylcarbamoyl)-1H-pyrazol-1-yl)methyl)-3-fluoroallyl)carbamate

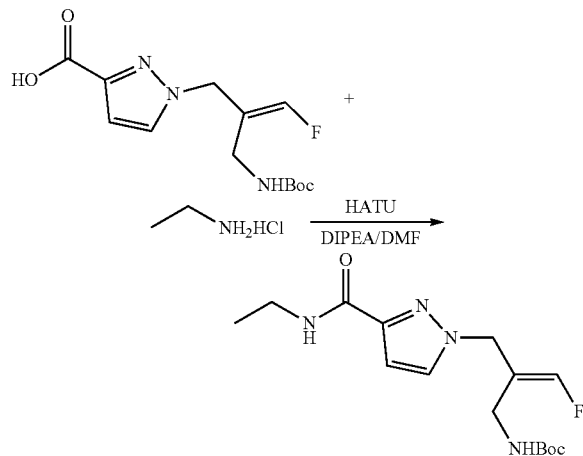

(E)-1-(2-(((tert-butoxycarbonyl)amino)methyl)-3-fluoroallyl)-1H-pyrazole-3-carboxylic acid (233.5 mg, 0.78 mmol, 1.0 eq.) was added into DMF (3 mL), DIPEA (604.5 mg, 4.68 mmol, 6.0 eq.) and HATU (444.8 mg, 1.17 mmol, 1.5 eq.) were added under an ice bath, stirring was performed for 2 h, and ethylamine hydrochloride (159.0 mg, 1.95 mmol, 2.5 eq.) was then added. The mixture was incubated at room temperature and stirred for 3 h. After the reaction was completed, as detected by TLC, the reaction solution was added with EA (40 mL) and saturated aqueous sodium carbonate solution (50 mL), followed by liquid separation. The organic phase was washed with saturated brine (50 mL), dried over anhydrous sodium sulfate and filtered, and the filtrate was concentrated under reduced pressure. The crude product was purified by preparative thin-layer chromatography (DCM:MeOH=20:1) to give the product (153.0 mg, yield: 60.2%).

Step 2: Synthesis of (E)-1-(2-(aminomethyl)-3-fluoroallyl)-N-ethyl-1H-pyrazole-3-carboxamide

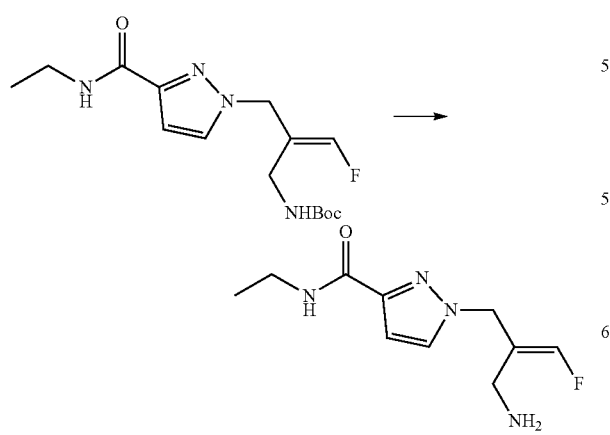

Tert-butyl (E)-(2-((3-(ethylcarbamoyl)-1H-pyrazol-1-yl)methyl)-3-fluoroallyl) carbamate (153.0 mg, 0.46 mmol, 1.0 eq.) was added into EtOH (3.0 mL), hydrogen chloride ethanol solution (3.0 mL) was added dropwise under an ice bath, and the mixture was incubated at room temperature and stirred for 3 h. After the reaction was completed, as detected by TLC, the reaction solution was concentrated under reduced pressure and added with DCM (25 mL) and saturated aqueous sodium carbonate solution (25 mL), followed by liquid separation. The organic phase was dried over anhydrous sodium sulfate and filtered. The filtrate was concentrated under reduced pressure, and the crude product was purified by preparative thin-layer chromatography (DCM:MeOH=10:1) to give the product (30.1 mg, yield: 28.6%).

$^1$HNMR (400 MHz, DMSO-d$_6$) δ(ppm): 8.01-8.03 (m, 1H), 7.81 (m, 1H), 7.00 (s, 0.5H), 6.79 (s, 0.5H), 6.61-6.62 (m, 1H), 4.79 (m, 2H), 3.20-3.26 (m, 2H), 3.06-3.07 (m, 2H), 1.69 (s, 2H), 1.06-1.10 (m, 3H).

Molecular formula: $C_{10}H_{15}FN_4O$, molecular weight: 226.26, LC-MS (Pos, m/z)=227.21[M+H]$^+$.

Example 24: Synthesis of (E)-1-(2-(aminomethyl)-3-fluoroallyl)-N-(tert-butyl)-1H-pyrazole-3-carboxamide (Compound B21)

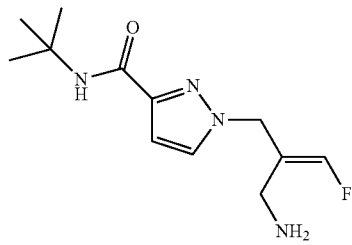 [SMILES: CC(C)(C)NC(=O)c1ccn(C/C(=C/F)CN)n1]

Step 1: Synthesis of methyl (E)-1-(2-((1,3-dioxoisoindolin-2-yl)methyl)-3-fluoroallyl)-1H-pyrazole-3-carboxylate

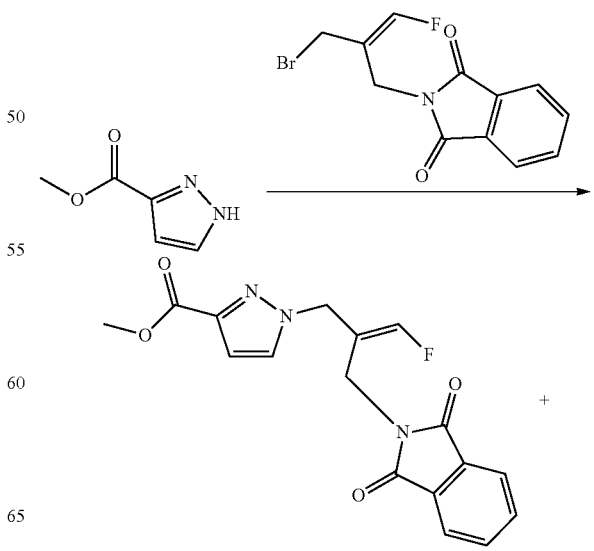

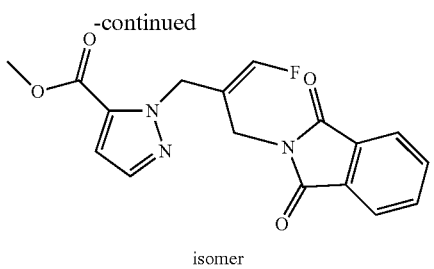

isomer (E)-2-(2-(bromomethyl)-3-fluoroallyl)isoindoline-1,3-dione (3.0 g, 10.0 mmol, 1.0 eq.), potassium carbonate (2.0 g, 15.0 mmol, 1.5 eq.) and methyl 1H-pyrazol-3-carboxylate (1.5 g) were added into DMF (10 mL), and the mixture was stirred at room temperature for 2 h. After the reaction was completed, as detected by TLC, DMF was removed by concentration under reduced pressure, EA (100 mL) and water (200 mL) were added, and liquid separation was performed. The organic phase was dried over anhydrous sodium sulfate and filtered, the filtrate was concentrated under reduced pressure, and the crude product was purified by silica gel column chromatography (PE:EA=6:1-1:1) to give the product methyl (E)-1-(2-((1,3-dioxoisoindolin-2-yl) methyl)-3-fluoroallyl)-1H-pyrazole-3-carboxylate (2.25 g, yield: 66.1%) and a positional isomer methyl (E)-1-(2-((1, 3-dioxoisoindolin-2-yl)methyl)-3-fluoroallyl)-1H-pyrazole-5-carboxylate (772.5 mg, yield: 22.7%).

Step 2: Synthesis of methyl (E)-1-(2-(aminomethyl)-3-fluoroallyl)-1H-pyrazole-3-carboxylate

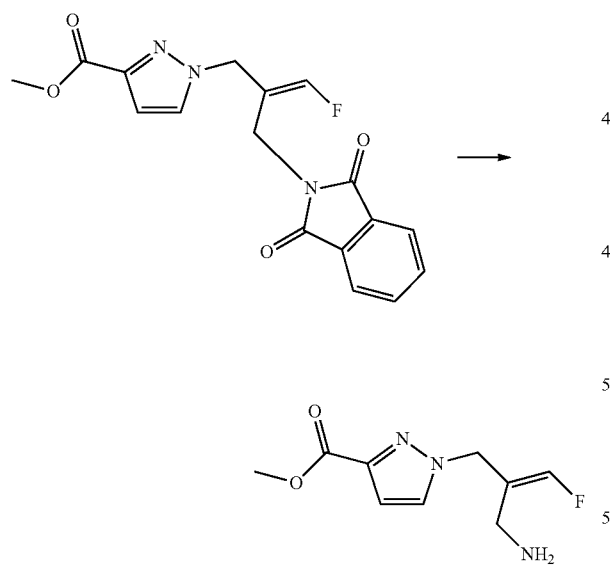

Methyl (E)-1-(2-((1,3-dioxoisoindolin-2-yl)methyl)-3-fluoroallyl)-1H-pyrazole-3-carboxylate (2.25 g, 6.55 mmol, 1.0 eq.) and hydrazine hydrate (984.2 mg, 19.6 mmol, 3.0 eq.) were added to ethanol (20 mL). The resulting solution was stirred at room temperature for 12 h and filtered under vacuum. The filtrate was concentrated, slurried with ethanol (20 mL) and filtered, and the filtrate obtained therefrom was concentrated under reduced pressure to give the product (1.79 g of crude product).

Step 3: Synthesis of methyl (E)-1-(2-(((tert-butoxycarbony)amino) methyl)-3-fluoroallyl)-1H-pyrazole-3-carboxylate

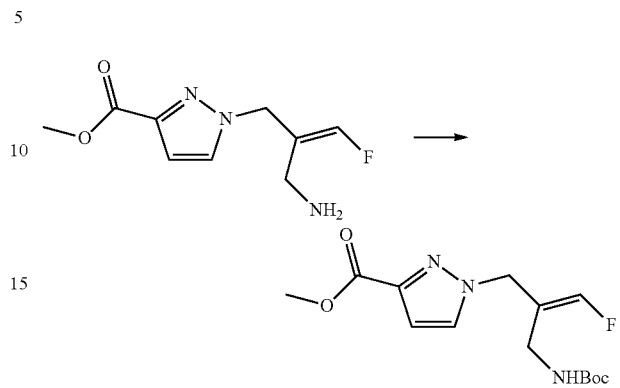

Methyl (E)-1-(2-(aminomethyl)-3-chloroallyl)-1H-pyrazole-3-carboxylate (1.79 g of crude product), triethylamine (993.6 mg, 9.82 mmol, 1.5 eq.) and di-tert-butyl dicarbonate (1.85 g, 8.51 mmol, 1.3 eq.) were added into THF (40 mL), and the resulting solution was stirred at room temperature for 2 h. After the reaction was completed, as detected by TLC, the reaction solution was added with EA (100 mL) and saturated aqueous ammonium chloride solution (150 mL), followed by liquid separation. The organic phase was dried over anhydrous sodium sulfate and filtered, and the filtrate was concentrated under reduced pressure. The crude product was purified by silica gel column chromatography (PE:EA=8:1-5:1) to give the product (545.1 mg, two-step yield: 27.2%).

Step 4: Synthesis of (E)-1-(2-(((tert-butoxycarbony) amino)methyl)-3-fluoroallyl)-1H-pyrazole-3-carboxylic acid

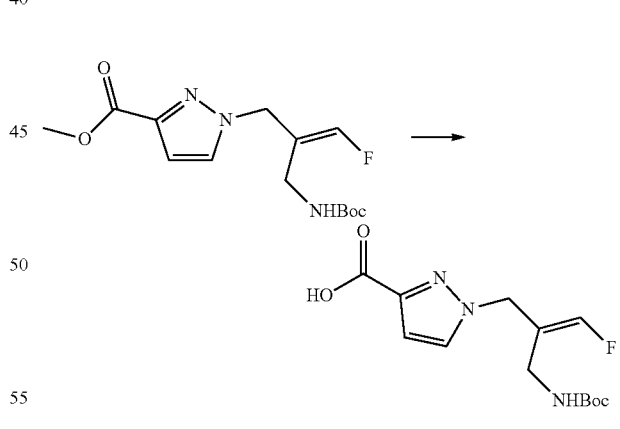

Methyl (E)-1-(2-(((tert-butoxycarbonyl)amino)methyl)-3-fluoroallyl)-1H-pyrazole-3-carboxylate (545.0 mg, 1.73 mmol, 1.0 eq.) was dissolved in methanol (5 mL). The solution was added with aqueous NaOH solution (6 mol/L, 2.5 mL) and stirred at 40° C. for 1 h. After the reaction was completed, as detected by TLC, the reaction solution was concentrated under reduced pressure and added with 5% aqueous citric acid solution to adjust the pH of the system to 4, and extraction was performed with DCM (50 mL). The organic phase was dried over anhydrous sodium sulfate and filtered, and the filtrate was concentrated under reduced pressure to give the product (490.7 mg of crude product).

Step 5: Synthesis of tert-butyl (E)-(2-((3-(tert-butyl-carbamoyl)-1H-pyrazol-1-yl)methyl)-3-fluoroallyl)carbamate

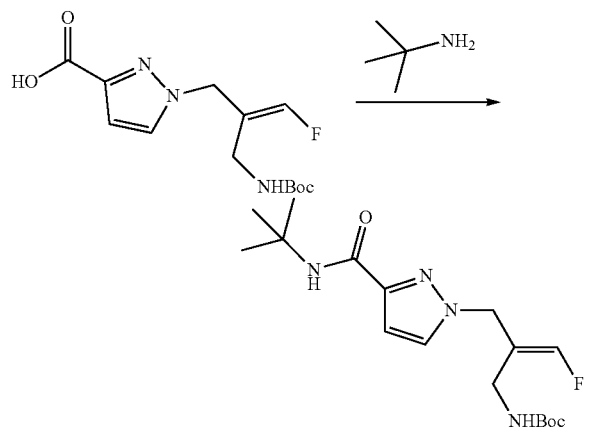

(E)-1-(2-(((tert-butoxycarbonyl)amino)methyl)-3-fluoroallyl)-1H-pyrazole-3-carboxylic acid (296.0 mg, 0.98 mmol, 1.0 eq.) was added into DMF (5 mL), DIPEA (382.8 mg, 2.96 mmol, 3.0 eq.) and HATU (563.5 mg, 1.48 mmol, 1.5 eq.) were added under an ice bath, stirring was performed for 2 h, and tert-butylamine (86.8 mg, 1.18 mmol, 1.2 eq.) was added. The mixture was incubated at room temperature and stirred for 12 h. After the reaction was completed, as detected by TLC, the reaction solution was concentrated under reduced pressure and added with EA (60 mL) and saturated aqueous sodium carbonate solution (50 mL), followed by liquid separation. The organic phase was washed with saturated brine (50 mL), dried over anhydrous sodium sulfate and filtered, and the filtrate was concentrated under reduced pressure. The crude product was purified by preparative thin-layer chromatography (DCM:MeOH=20:1) to give the product (200.0 mg, two-step yield: 32.6%).

Step 6: Synthesis of (E)-1-(2-(aminomethyl)-3-fluoroallyl)-N-(tert-butyl)-1H-pyrazole-3-carboxamide

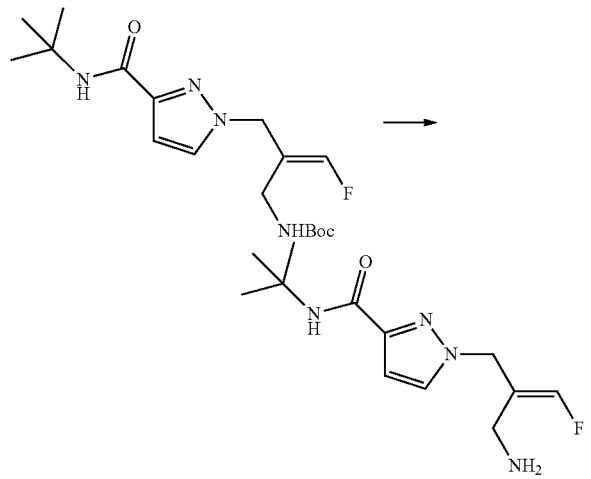

Tert-butyl (E)-(2-((3-(tert-butylcarbamoyl)-1H-pyrazol-1-yl)methyl)-3-fluoroallyl)carbamate (200.0 mg, 0.56 mmol, 1.0 eq.) was added into EtOH (3.0 mL), hydrogen chloride ethanol solution (3.0 mL) was added dropwise under an ice bath, and the mixture was incubated at room temperature and stirred for 3 h. After the reaction was completed, as detected by TLC, the reaction solution was concentrated under reduced pressure and added with DCM (40 mL) and saturated aqueous sodium carbonate solution (40 mL), followed by liquid separation. The organic phase was dried over anhydrous sodium sulfate and filtered. The filtrate was concentrated under reduced pressure, and the crude product was purified by preparative thin-layer chromatography (DCM:MeOH=10:1) to give the product (118.0 mg, yield: 82.5%).

$^1$HNMR (400 MHz, DMSO-$d_6$) δ(ppm): 7.81-7.82 (d, 1H), 7.04 (s, 1H), 7.02 (s, 0.5H), 6.81 (s, 0.5H), 6.60-6.61 (d, 1H), 4.78-4.79 (d, 2H), 3.06-3.07 (d, 2H), 1.36 (s, 9H).

Molecular formula: $C_{12}H_{19}FN_4O$, molecular weight: 254.31, LC-MS (Pos, m/z)=255.25[M+H]$^+$.

Example 25: Synthesis of (E)-1-(2-aminomethyl-3-fluoroallyl)-N-4-chlorophenyl-1H-pyrazole-4-carboxamide (Compound B28)

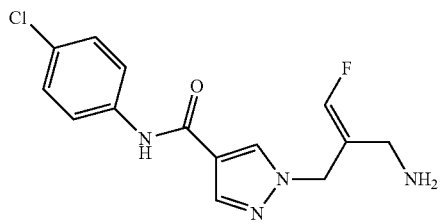 [SMILES: NC/C(=C\F)Cn1cc(C(=O)Nc2ccc(Cl)cc2)cn1]

Step 1: Synthesis of tert-butyl (E)-(2-((4-((4-chlorophenyl)carbamoyl)-1H-pyrazol-1-yl)methyl)-3-fluoroallyl)carbamate

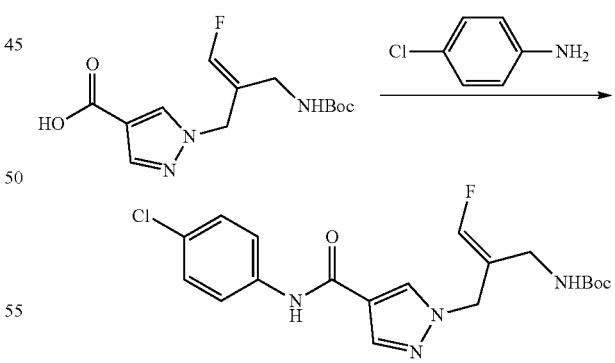

(E)-1-(2-(((tert-butoxycarbonyl)amino)methyl-3-fluoroallyl)-1H-pyrazole-4-carboxylic acid (190.0 mg, 0.64 mmol, 1.0 eq.) was added into DMF (2 mL), DIPEA (246.1 mg, 1.90 mmol, 3.0 eq.) and HATU (362.1 mg, 0.95 mmol, 1.5 eq.) were added under an ice bath, and the mixture was stirred under an ice bath for 1 h. The mixture was added with 4-chloroaniline (89.1 mg, 0.70 mmol, 1.1 eq.), and incubated at room temperature overnight. After the reaction was completed, as detected by TLC, the reaction solution was concentrated under reduced pressure. The concentrate was dissolved in EA (60 mL), and saturated aqueous NaHCO₃ solution (50 mL), saturated aqueous NH₄Cl solution (50 mL) and saturated brine (50 mL×4) were sequentially used for washing. The organic phase was dried over anhydrous sodium sulfate and filtered, and the filtrate was concentrated under reduced pressure. The crude product was purified by preparative thin-layer chromatography (DCM:MeOH=10:1) to give the product (90.0 mg, yield: 34.7%).

Step 2: Synthesis of (E)-1-(2-aminomethyl-3-fluoroallyl)-N-4-chlorophenyl-1H-pyrazole-4-carboxamide

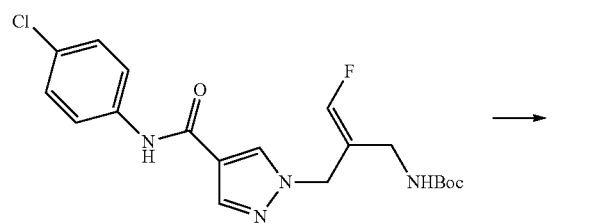

Tert-butyl (E)-(2-((4-((4-chlorophenyl)carbamoyl)-1H-pyrazol-1-yl)methyl)-3-fluoroallyl)carbamate (90.0 mg, 0.22 mmol) was added into EtOH (5.0 mL), hydrogen chloride ethanol solution (5.0 mL) was added dropwise under an ice bath, and the mixture was incubated at room temperature and stirred for 3 h. After the reaction was completed, as detected by TLC, the reaction solution was concentrated under reduced pressure and added with DCM (40 mL) and 15% aqueous NaOH solution (40 mL), followed by liquid separation. The organic phase was dried over anhydrous sodium sulfate and filtered, the filtrate was concentrated under reduced pressure, and the crude product was purified by preparative thin-layer chromatography (DCM:MeOH=10:1) to give the product (48.0 mg, yield: 70.6%).

¹H NMR (400 MHz, DMSO-d₆) δ(ppm): 9.96 (s, 1H), 8.40 (s, 1H), 8.04 (s, 1H), 7.75-7.73 (d, 2H), 7.41-7.38 (d, 2H), 7.09 (s, 0.5H), 6.87 (s, 0.5H), 4.82 (s, 2H), 3.09 (s, 2H), 1.81 (s, 2H).

Molecular formula: $C_{14}H_{14}N_4ClFO$, molecular weight: 308.74, LC-MS (Pos, m/z)=309.09[M+H]⁺.

Example 26: (E)-1-(2-(aminomethyl)-3-fluoroallyl)-N,N-dimethyl-1H-pyrazole-4-carboxamide (Compound B29)

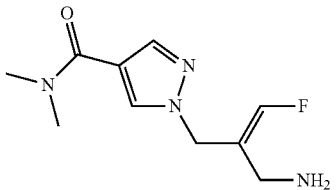 [SMILES: CN(C)C(=O)c1cnn(C/C(=C/F)CN)c1]

Step 1: Synthesis of tert-butyl (E)-(2-((4-(dimethylcarbamoyl)-1H-pyrazol-1-yl)methyl)-3-fluoroallyl) carbamate (E)-1-(2-(((tert-butoxycarbonyl)amino)methyl)-3-fluoroallyl)-1H-pyrazole-4-carboxylic acid (150.0 mg, 0.501 mmol, 1.0 eq.) and DIPEA (272.0 mg, 2.105 mmol, 4.2 eq.) were dissolved in DMF (2.0 mL). In nitrogen atmosphere, the solution was added with HATU (286.0 mg, 0.752 mmol, 1.5 eq.) at 0° C., stirred for 0.5 h, added with a solution of diethylamine in methanol (90.4 mg, 0.601 mmol, 1.2 eq., 30%) and incubated at room temperature overnight. After the reaction was completed, as detected by TLC, ethyl acetate (40.0 mL) was added into the reaction solution, and the mixture was washed successively with saturated aqueous sodium carbonate solution (4.0 mL), saturated aqueous ammonium chloride solution (4.0 mL) and saturated aqueous sodium chloride solution (4.0 mL). The organic phase was dried over anhydrous sodium sulfate and concentrated. The crude product was purified by silica gel column chromatography (DCM:MeOH=120:1-30:1) to give the product (132.0 mg, yield: 80.7%).

Step 2: Synthesis of (E)-1-(2-(aminomethyl)-3-fluoroallyl)-N,N-dimethyl-1H-pyrazole-4-carboxamide

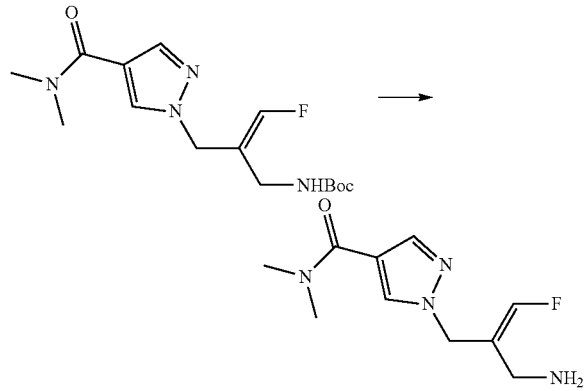

Tert-butyl(E)-(2-((4-(dimethylcarbamoyl)-1H-pyrazol-1-yl)methyl)-3-fluoroallyl)carbamate (132.0 mg, 0.404 mmol, 1.0 eq.) was dissolved in ethanol (1.0 mL). The solution was added with hydrogen chloride ethanol solution (1.5 mL) dropwise to react at room temperature for 2 h. After the reaction was completed, as detected by TLC, the reaction solution was concentrated under reduced pressure, and the crude product was purified by preparative thin-layer chromatography (DCM:MeOH=10:1) to give the product (37.0 mg, yield: 40.4%).

$^1$H NMR (400 MHz, DMSO-d$_6$) δ(ppm): 8.16 (s, 1H), 7.74 (s, 1H), 7.03-6.81 (d, 1H), 4.77 (s, 2H), 3.35-2.95 (m, 8H), 1.75 (s, 2H).

Molecular formula: C$_{10}$H$_{15}$FN$_4$O, molecular weight: 226.26, LC-MS (Pos, m/z)=227.19[M+H]$^+$ Example 27: Synthesis of (E)-1-(2-(aminomethyl)-3-fluoroallyl)-N-(tert-butyl)-1H-pyrazole-5-carboxamide (Compound B30)

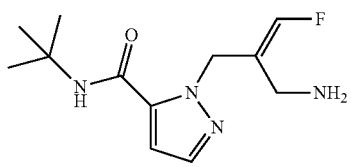 [SMILES: CC(C)(C)NC(=O)c1ccnn1C/C(=C/F)CN]

Step 1: Synthesis of methyl (E)-1-(2-(aminomethyl)-3-fluoroallyl)-1H-pyrazole-5-carboxylate

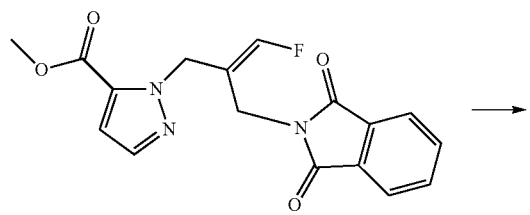

-continued

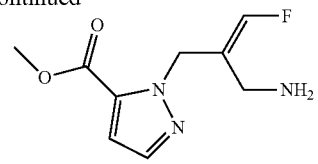

Methyl (E)-1-(2-((1,3-dioxoisoindolin-2-yl)methyl)-3-fluoroallyl)-1H-pyrazole-5-carboxylate (772.5 mg, 2.25 mmol, 1.0 eq.) was added to ethanol (20 mL), hydrazine hydrate (337.5 mg, 6.75 mmol, 3.0 eq.) was added, and the mixture was stirred at room temperature for 5 h. After the reaction was completed, as detected by TLC, DCM (150 mL) and water (80 mL) were added, and liquid separation was performed. The organic phase was dried over anhydrous sodium sulfate and filtered, and the filtrate was concentrated under reduced pressure to give the product (441.6 mg of crude product).

Step 2: Synthesis of methyl (E)-1-(2-(((tert-butoxycarbony)amino) methyl)-3-fluoroallyl)-1H-pyrazole-5-carboxylate

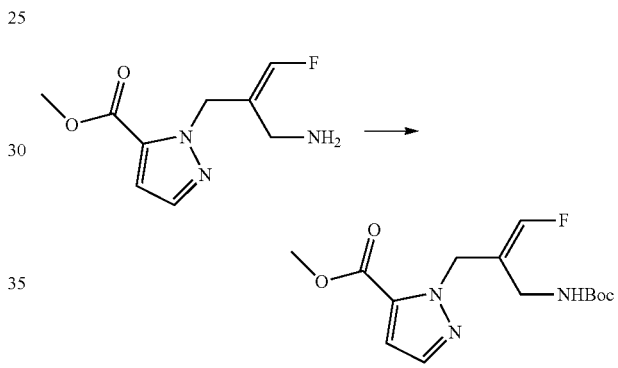

Methyl (E)-1-(2-(aminomethyl)-3-chloroallyl)-1H-pyrazole-5-carboxylate (441.6 mg of crude product) was dissolved in THF (7 mL). The solution was added with triethylamine (290.0 mg, 2.86 mmol) and di-tert-butyl dicarbonate (541.9 mg, 2.48 mmol) and stirred at room temperature for 2 h. After the reaction was completed, as detected by TLC, the reaction solution was added with EA (50 mL) and saturated aqueous ammonium chloride solution (60 mL), followed by liquid separation. The organic phase was dried over anhydrous sodium sulfate and filtered, and the filtrate was concentrated under reduced pressure. The crude product was purified by silica gel column chromatography (PE:EA=6:1-1:1) to give the product (176.6 mg, two-step yield: 27.2%).

Step 3: Synthesis of (E)-1-(2-(((tert-butoxycarbony)amino)methyl)-3-fluoroallyl)-1H-pyrazole-5-carboxylic acid

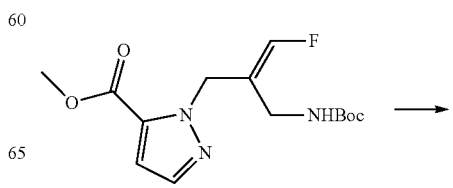

-continued

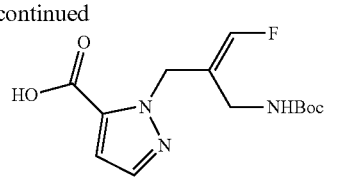

Methyl (E)-1-(2-(((tert-butoxycarbonyl)amino)methyl)-3-fluoroallyl)-1H-pyrazole-5-carboxylate (176.6 mg, 0.56 mmol, 1.0 eq.) was dissolved in methanol (2 mL). The solution was added with aqueous NaOH solution (6 mol/L, 1 mL) and stirred at 40° C. for 2 h. After the reaction was completed, as detected by TLC, the reaction solution was concentrated under reduced pressure and added with 5% aqueous citric acid solution to adjust the pH of the system to 4, and extraction was performed with DCM (20 mL). The organic phase was dried over anhydrous sodium sulfate and filtered, and the filtrate was concentrated to give the product (124.3 mg, yield: 74.1%).

Step 4: Synthesis of tert-butyl (E)-(2-((5-(tert-butylcarbamoyl)-1H-pyrazol-1-yl)methyl)-3-fluoroallyl) carbamate

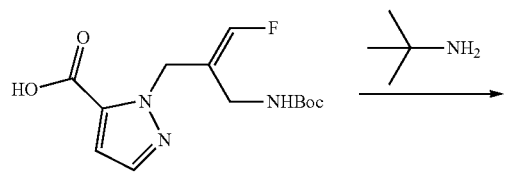

(E)-1-(2-(((tert-butoxycarbonyl)amino)methyl)-3-fluoroallyl)-1H-pyrazole-5-carboxylic acid (124.3 mg, 0.41 mmol, 1.0 eq.) was added into DMF (3 mL), DIPEA (160.7 mg, 1.24 mmol, 3.0 eq.) and HATU (236.6 mg, 0.62 mmol, 1.5 eq.) were added under an ice bath, stirring was performed for 2 h, and tert-butylamine (36.4 mg, 0.49 mmol, 1.2 eq.) was then added. The mixture was incubate at room temperature and stirred for 3 h. After the reaction was completed, as detected by TLC, the reaction solution was concentrated under reduced pressure and added with EA (50 mL) and saturated aqueous sodium carbonate solution (50 mL), followed by liquid separation. The organic phase was dried over anhydrous sodium sulfate and filtered, and the filtrate was concentrated under reduced pressure. The crude product was purified by preparative thin-layer chromatography (DCM:MeOH=20:1) to give the product (100.0 mg, yield: 68.0%).

Step 5: Synthesis of (E)-1-(2-(aminomethyl)-3-fluoroallyl)-N-(tert-butyl)-1H-pyrazole-5-carboxamide

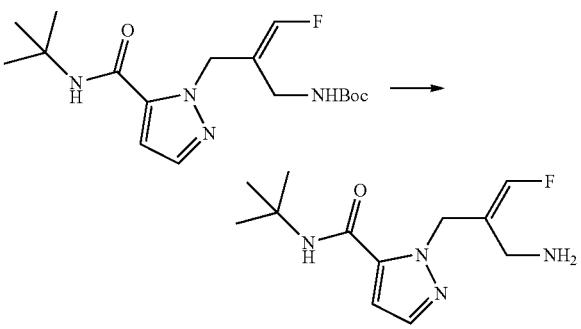

Tert-butyl (E)-(2-((5-(tert-butylcarbamoyl)-1H-pyrazol-1-yl)methyl)-3-fluoroallyl)carbamate (100.0 mg, 0.28 mmol, 1.0 eq.) was added into EtOH (2.5 mL), hydrogen chloride ethanol solution (2.5 mL) was added dropwise under an ice bath, and the mixture was incubate at room temperature and stirred for 2 h. After the reaction was completed, as detected by TLC, the reaction solution was concentrated under reduced pressure and added with DCM (30 mL) and saturated aqueous sodium carbonate solution (40 mL), followed by liquid separation. The organic phase was dried over anhydrous sodium sulfate and filtered. The filtrate was concentrated under reduced pressure, and the crude product was purified by preparative thin-layer chromatography (DCM:MeOH=10:1) to give the product (23.0 mg, yield: 32.3%).

$^1$HNMR (400 MHz, DMSO-d$_6$) δ(ppm): 8.0 (s, 1H), 7.48 (d, 1H), 6.92 (s, 0.5H), 6.80-6.81 (d, 1H), 6.70 (s, 0.5H), 5.07 (d, 2H), 3.05-3.06 (d, 2H), 1.36 (s, 9H).

Molecular formula: $C_{12}H_{19}FN_4O$, molecular weight: 254.31, LC-MS (Pos, m/z)=255.22[M+H]$^+$.

Example 28: Synthesis of (E)-1-(2-aminomethyl-3-fluoroallyl)-1H-pyrrole-3-carboxamide (Compound B31) Hydrochloride

Step 1: Synthesis of tert-butyl (E)-(2-((3-carbamoyl-1H-pyrrol-1-yl) methyl)-3-fluoroallyl)carbamate

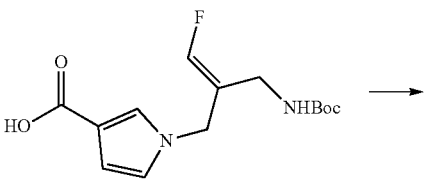

161

-continued

(E)-1-(2-(((tert-butoxycarbonyl)amino)methyl-3-fluoroallyl)-1H-pyrrole-3-carboxylic acid (200.0 mg, 0.67 mmol, 1.0 eq.) was added into DMF (2 mL), DIPEA (259.9 mg, 2.01 mmol, 3.0 eq.) and HATU (382.4 mg, 1.01 mmol, 1.5 eq.) were added under an ice bath, and the mixture was stirred for 1 h. The mixture was added with a solution of ammonia in methanol (5%, 685.1 mg, 2.01 mmol, 3.0 eq.), incubate at room temperature and stirred for 2 h. After the reaction was completed, as detected by TLC, the reaction solution was concentrated under reduced pressure. The concentrate was dissolved in EA (60 mL), and saturated aqueous NaHCO$_3$ solution (50 mL), saturated aqueous NH$_4$Cl solution (50 mL) and saturated brine (50 mL×4) were sequentially used for washing. The organic phase was dried over anhydrous sodium sulfate and filtered, and the filtrate was concentrated under reduced pressure. The crude product was purified by preparative thin-layer chromatography (DCM:MeOH=20:1) to give the product (155.0 mg, yield: 77.8%).

Step 2: Synthesis of (E)-1-(2-aminomethyl-3-fluoroallyl)-1H-pyrrole-3-carboxamide hydrochloride

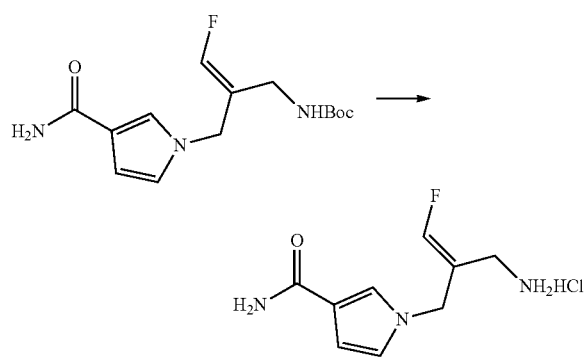

Tert-butyl (E)-(2-((3-carbamoyl-1H-pyrrol-1-yl)methyl)-3-fluoroallyl) carbamate (155.0 mg, 0.52 mmol) was added into EtOH (5.0 mL), hydrogen chloride ethanol solution (5.0 mL) was added dropwise under an ice bath, and the mixture was incubate at room temperature and stirred for 3 h. After the reaction was completed, as detected by TLC, the reaction solution was concentrated under reduced pressure, slurried with methyl tert-butyl ether for 2 h and filtered. The filter cake was collected to give the product (94.0 mg, yield: 77.2%).

$^1$HNMR (400 MHz, DMSO-d$_6$) δ(ppm): 8.54 (s, 3H), 7.64 (s, 2H), 7.41-7.40 (t, 1H), 7.31 (s, 0.5H), 7.11 (s, 0.5H), 6.88-6.87 (t, 1H), 6.50-6.49 (q, 1H), 4.74-4.73 (d, 2H), 3.25-3.23 (d, 2H).

Molecular formula: C$_9$H$_{12}$N$_3$FO, molecular weight: 197.21, LC-MS (Pos, m/z)=198.21[M+H]$^+$.

162

Example 29: Preparation of (E)-2-(2-(aminomethyl)-3-fluoroallyl)-5-ethyl-2,5-dihydro-4H-pyrazolo[4,3-c]pyridin-4-one (Compound A28) Hydrochloride and (E)-1-(2-(aminomethyl)-3-fluoroallyl)-5-ethyl-1,5-dihydro-4H-pyrazolo[4,3-c]pyridin-4-one (Compound A29) Hydrochloride

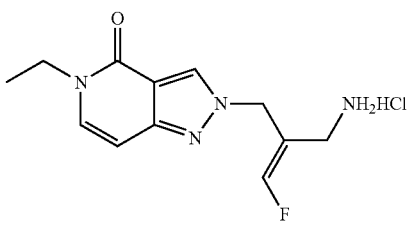

A28

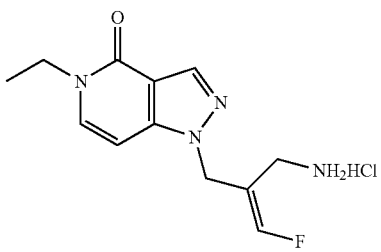

A29

Step 1: Synthesis of 4-chloro-2-(4-methoxybenzyl)-2H-pyrazolo[4,3-c]pyridine

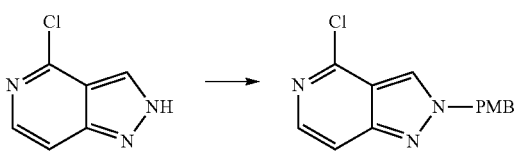

Materials 4-chloro-2H-pyrazolo[4,3-c]pyridine (5.0 g, 32.55 mmol, 1.0 eq.), 4-methoxybenzylchloride (5.58 g, 35.81 mmol, 1.1 eq.) and potassium carbonate (8.98 g, 65.1 mmol, 2.0 eq.) were dissolved in DMF (30 mL) to react at room temperature for 1.5 h. After no materials were left, as detected by LC-MS, the reaction solution was poured into water (50 mL) and ethyl acetate (80 mL×2) was added for extraction, and the organic phase was washed with water (100 mL×2), dried and concentrated to give the product (8.9 g, yield: 100%).

Step 2: Synthesis of Intermediate 2-(4-methoxybenzyl)-2,5-dihydro-4H-pyrazolo[4,3-c]pyridin-4-one

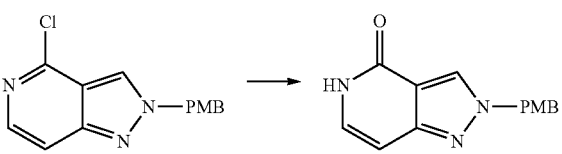

The intermediate 4-chloro-2-(4-methoxybenzyl)-2H-pyrazolo[4,3-c]pyridine (8.9 g, 32.51 mmol, 1.0 eq.) was dissolved in acetic acid (80 mL) and water (20 mL) to react at 100° C. for 12 h. After the reaction was completed, as detected by LC-MS, the reaction solution was concentrated under reduced pressure, the crude product was slurried with methyl tert-butyl ether (100 mL), and filtered under vacuum to give the product (8.3 g, yield: 100%).

Step 3: Synthesis of 5-ethyl-2-(4-methoxybenzyl)-2,5-dihydro-4H-pyrazolo[4,3-c]pyridin-4-one

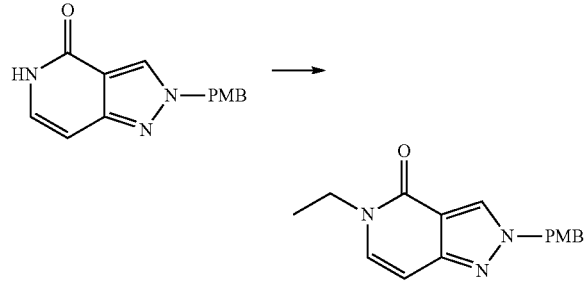

The intermediate 2-(4-methoxybenzyl)-2,5-dihydro-4H-pyrazolo[4,3-c]pyridin-4-one (8.3 g, 32.51 mmol, 1.0 eq.) and sodium hydride (1.95 g, 48.76 mmol, 1.5 eq.) were dissolved in DMF (80 mL). The mixture was stirred for min and added with iodoethane (7.6 g, 48.76 mmol, 1.5 eq.) dropwise to react at 60° C. for 30 min. After the reaction was completed, as detected by LC-MS, water (80 mL) was slowly added into the bottle, and extraction was performed with ethyl acetate (100 mL×4). The organic phase was washed with water (200 mL×4), dried and concentrated under reduced pressure, and the crude product was purified by silica gel column chromatography (PE:EA=1:1) to give the product (5.0 g, yield: 54%).

Step 4: Synthesis of Intermediate 5-ethyl-2,5-dihydro-4H-pyrazolo[4,3-c]pyridin-4-one

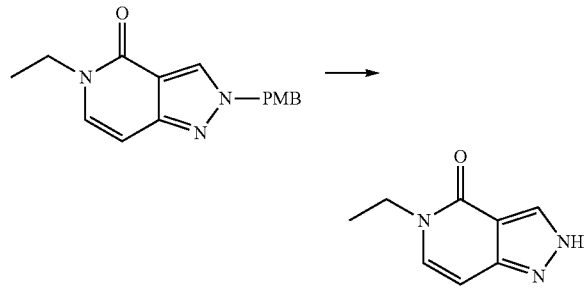

The intermediate 5-ethyl-2-(4-methoxybenzyl)-2,5-dihydro-4H-pyrazolo [4,3-c]pyridin-4-one (5.0 g, 17.64 mmol, 1.0 eq.) was dissolved in trifluoroacetic acid (50 mL) to react at 75° C. for 12 h. After the reaction was completed, as detected by LC-MS, the reaction solution was concentrated under reduced pressure. The crude product was first purified by silica gel column chromatography (PE:EA=1:1), then slurried with methyl tert-butyl ether (10 mL) and filtered under vacuum to give the product (1.1 g, yield: 38%).

Step 5: Synthesis of (E)-2-(2-((5-ethyl-4-oxo-4,5-dihydro-2H-pyrazolo [4,3-c]pyridin-2-yl)methyl)-3-fluoroallyl)isoindoline-1,3-dione and (E)-2-(2-((5-ethyl-4-oxo-4,5-dihydro-1H-pyrazolo[4,3-c]pyridin-1-yl)methyl)-3-fluoroallyl)isoindoline-1,3-dione The intermediate 5-ethyl-2,5-dihydro-4H-pyrazolo[4,3-c]pyridin-4-one (500 mg, 3.06 mmol, 1.0 eq.) was dissolved in DMF (3 mL). The solution was added with NaH (159 mg, 3.98 mmol, 1.3 eq.), stirred for 30 min and then added dropwise with a solution of (E)-2-(2-(bromomethyl)-3-fluoroallyl) isoindoline-1,3-dione (1.004 g, 3.37 mmol, 1.1 eq.) in DMF (2 mL) to react for 30 min. After the reaction was completed, as detected by LC-MS, the reaction solution was added with water (10 mL) and extracted with ethyl acetate (20 mL×2), followed by liquid separation. The organic phase was washed with water (20 mL×2), dried over anhydrous sodium sulfate, filtered and concentrated under reduced pressure. The crude product was slurried with methyl tert-butyl ether (10 mL) and filtered under vacuum to give a mixture of (E)-2-(2-((5-ethyl-4-oxo-4,5-dihydro-2H-pyrazolo[4,3-c]pyridin-2-yl)methyl)-3-fluoroallyl)isoindoline-1,3-dione and (E)-2-(2-((5-ethyl-4-oxo-4,5-dihydro-1H-pyrazolo[4,3-c]pyridin-1-yl)methyl)-3-fluoroallyl)isoindoline-1,3-dione (390 mg).

Step 6: (E)-2-(2-(aminomethyl)-3-fluoroallyl)-5-ethyl-2,5-dihydro-4H-pyrazolo[4,3-c]pyridin-4-one hydrochloride and (E)-1-(2-(aminomethyl)-3-fluoroallyl)-5-ethyl-1,5-dihydro-4H-pyrazolo[4,3-c]pyridin-4-one hydrochloride

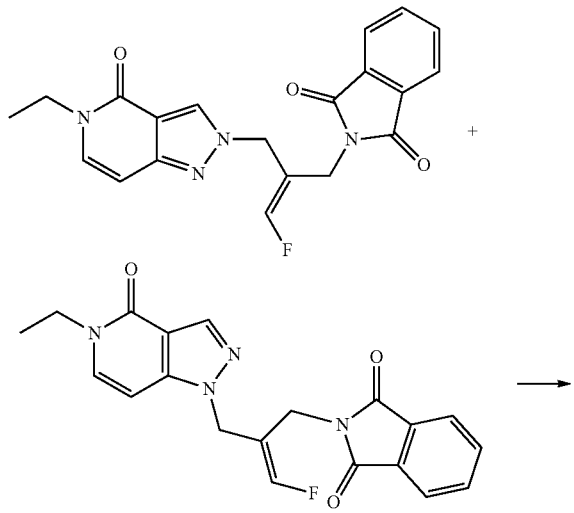

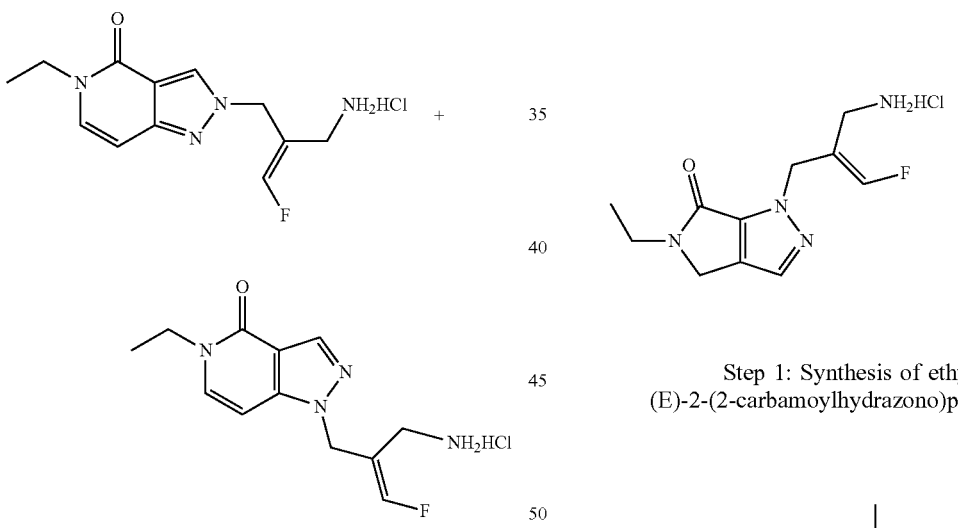

(E)-2-(2-((5-ethyl-4-oxo-4,5-dihydro-2H-pyrazolo[4,3-c]pyridin-2-yl)methyl)-3-fluoroallyl)isoindoline-1,3-dione and E)-2-(2-((5-ethyl-4-oxo-4,5-dihydro-1H-pyrazolo[4,3-c]pyridin-1-yl)methyl)-3-fluoroallyl)isoindoline-1,3-dione (390 mg, 1.02 mmol, 1.0 eq.) were dissolved in EtOH (8 mL). The solution was added with hydrazine hydrate (178 mg, 3.57 mmol, 3.5 eq.) to react at 80° C. for 30 min. After the reaction was completed, as detected by LC-MS, the reaction solution was cooled to room temperature and filtered under vacuum, and the filtrate was concentrated under reduced pressure. The crude product was first purified by preparative thin-layer chromatography (DCM:MeOH=10:1), and the obtained product was added with methanol (1 mL) for dissolution. The solution was then added with hydrogen chloride ethanol solution (0.015 mL) dropwise, stirred for 5 min and concentrated under reduced pressure. The crude product was purified by preparative thin-layer chromatography (dichloromethane:isopropanol:ammonia=10:1:0.5) to give (E)-2-(2-(aminomethyl)-3-fluoroallyl)-5-ethyl-2,5-dihydro-4H-pyrazolo[4,3-c]pyridin-4-one hydrochloride (18 mg, yield: 6.1%) with a low Rf value, which is a hydrochloride of compound A28, $^1$H NMR (400 MHz, DMSO-d$_6$) δ(ppm): 8.65 (s, 1H), 8.27 (s, 3H), 7.44 (s, 0.5H), 7.35-7.37 (d, 1H), 7.24 (s, 0.5H), 6.48-6.50 (m, 1H), 5.07-5.08 (d, 2H), 3.88-3.90 (m, 2H), 3.38-3.39 (m, 2H), 1.17-1.21 (m, 3H).

Molecular formula: $C_{12}H_{16}ClFN_4O$, molecular weight: 286.74, LC-MS (Pos, m/z)=251.21[M+H]$^+$.

and (E)-1-(2-(aminomethyl)-3-fluoroallyl)-5-ethyl-1,5-dihydro-4H-pyrazolo [4,3-c]pyridin-4-one hydrochloride (13 mg, yield: 4.4%) with a high Rf value, which is a hydrochloride of compound A29.

$^1$H NMR (400 MHz, DMSO-d$_6$) δ(ppm): 8.38 (s, 3H), 8.10 (s, 1H), 7.62-7.64 (d, 1H), 7.36 (s, 0.5H), 7.16 (s, 0.5H), 6.90-6.91 (d, 1H), 5.06-5.10 (d, 2H), 3.95-3.97 (m, 2H), 3.38-3.39 (m, 2H), 1.19-1.23 (m, 3H).

Molecular formula: $C_{12}H_{16}ClFN_4O$, molecular weight: 286.74, LC-MS (Pos, m/z)=251.19[M+H]$^+$.

Example 30: Synthesis of (E)-1-(2-(aminomethyl)-3-fluoroallyl)-5-ethyl-4,5-dihydropyrrolo[3,4-c]pyrazol-6(1H)-one (Compound A31) Hydrochloride

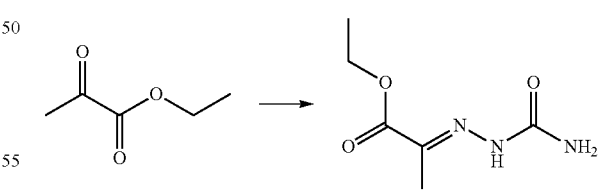

Step 1: Synthesis of ethyl (E)-2-(2-carbamoylhydrazono)propionate

Materials ethyl 2-oxopropionate (21 g, 0.18 mol, 1.0 eq.) and semicarbazide hydrochloride (20 g, 0.18 mol, 1.0 eq.) were dissolved in water (150 mL). The solution was added with sodium acetate (29 g, 0.35 mol, 1.9 eq.) and stirred at room temperature for 12 h. After the reaction was completed, as detected by TLC, the reaction solution was filtered under vacuum, and the filter cake was washed with a small amount of water and dried to give the product (29 g, yield: 94%), which was directly used in the next step.

Step 2: Synthesis of ethyl 4-formyl-1H-pyrazole-5-carboxylate

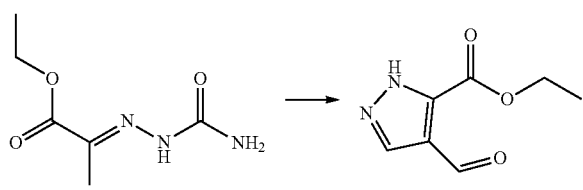

Under an ice bath, phosphorus oxychloride (32.8 mL) was added dropwise into DMF (71.3 mL). After addition, the ice bath was removed, and the mixture was incubate at room temperature and stirred for 30 min. The reaction solution was heated to 40° C. and added with ethyl (E)-2-(2-carbamoylhydrazono)propionate (26.6 g, 0.154 mol, 1.0 eq.). After addition, the mixture was heated to 80° C. to react for 3 h. After the reaction was completed, as detected by TLC, the reaction solution was poured into ice water, and the pH of the solution was adjusted to 10 with aqueous sodium hydroxide solution (mass fraction: 50%) under stirring. The aqueous solution was heated to 50° C. until a complete dissolution occurred, the pH of the solution was adjusted to 7 with concentrated hydrochloric acid under an ice bath, and extraction was performed with ethyl acetate (2×200 mL). The organic phases were combined, dried over anhydrous magnesium sulfate, filtered and concentrated, and the crude product was slurried with DCM to give the product (14 g, yield: 66%).

Step 3: Synthesis of ethyl 4-formyl-1-(4-methoxybenzyl)-1H-pyrazole-5-carboxylate

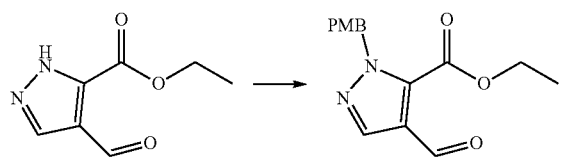

The intermediate ethyl 4-formyl-1H-pyrazole-5-carboxylate (10.5 g, 0.06 mol, 1.0 eq.) was dissolved in DMF (60 mL). The solution was added with potassium carbonate (25.9 g, 0.18 mol, 3.0 eq.) and p-methoxybenzyl chloride (12.2 g, 0.078 mol, 1.3 eq.) and stirred at room temperature for 3 h. After the reaction was completed, as detected by TLC, the reaction solution was added with water (200 mL) and extracted with ethyl acetate (2×200 mL). The organic phase was washed with saturated brine (2×200 mL), dried over anhydrous sodium sulfate, filtered under vacuum and concentrated, and the crude product was purified by silica gel column chromatography (EA:PE=0-1:2) to give the product (12.5 g, yield: 69%).

Step 4: Synthesis of ethyl 4-((ethylamino)methyl)-1-(4-methoxybenzyl)-1H-pyrazole-5-carboxylate

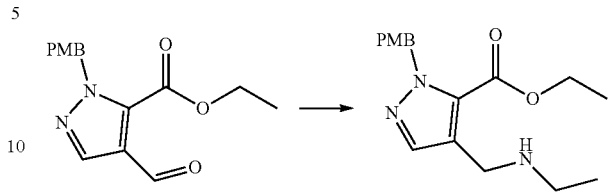

Ethylamine hydrochloride (4.0 g, 48.4 mmol, 4.0 eq.) was dissolved in MeOH (20 mL). The solution was added with triethylamine (4.9 g, 48.4 mmol, 4.0 eq.) and stirred for 10 min. The reaction solution was added with ethyl 4-formyl-1-(4-methoxybenzyl)-1H-pyrazole-5-carboxylate (3.5 g, 12.1 mmol, 1.0 eq.) and acetic acid (0.5 mL) and stirred at room temperature for 30 min.

The reaction solution was added with sodium cyanoborohydride (2.3 g, 36.3 mmol, 3.0 eq.) to react at room temperature for 12 h. After the reaction was completed, as detected by LC-MS, the pH of the solution was adjusted to 10 with saturated aqueous sodium bicarbonate solution, and extraction was performed with DCM (2×30 mL). The organic phase was washed with saturated brine (2×20 mL), dried over anhydrous sodium sulfate, filtered under vacuum and concentrated to give the product (4.3 g, yield: 100%).

Step 5: Synthesis of 4-((ethylamino)methyl)-1-(4-methoxybenzyl)-1H-pyrazole-5-carboxylic acid

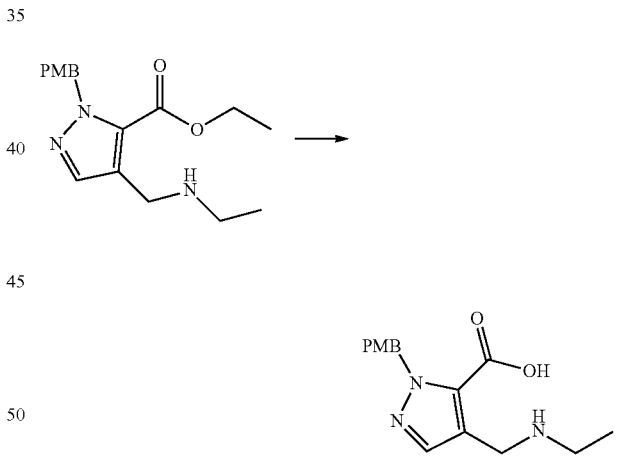

The intermediate ethyl 4-((ethylamino)methyl)-1-(4-methoxybenzyl)-1H-pyrazole-5-carboxylate (4.3 g of crude product, 13.5 mmol, 1.0 eq.) was dissolved in MeOH (20 mL) and water (20 mL). The solution was added with lithium hydroxide monohydrate (1.7 g, 40.6 mmol, 3.0 eq.) and stirred at 50° C. for 3 h. After the reaction was completed, as detected by LC-MS, the pH of the solution was adjusted to 2 with 2 mol/L of aqueous hydrochloric acid solution, and lyophilization was performed to give the product (5 g of crude product, yield: 100%).

Step 6: Synthesis of 5-ethyl-1-(4-methoxybenzyl)-4,5-dihydropyrrolo[3,4-c]pyrazol-6(1H)-one

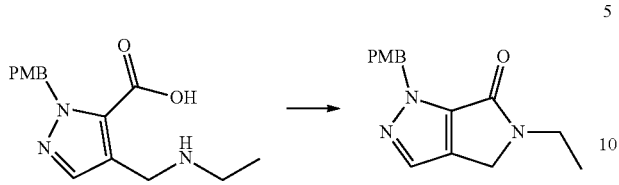

The intermediate 4-((ethylamino)methyl)-1-(4-methoxybenzyl)-1H-pyrazole-5-carboxylic acid (5.0 g of crude product, 17.28 mmol, 1.0 eq.) was dissolved in DMF (30 mL). The solution was added with HATU (8.5 g, 22.46 mmol, 1.9 eq.) and DIPEA (6.7 g, 51.84 mmol, 3.0 eq.) and stirred for 1.5 h. After the reaction was completed, as detected by LC-MS, the reaction solution was added with water (50 mL), extracted with ethyl acetate (2×50 mL) and concentrated, and the crude product was purified by preparative thin-layer chromatography (DCM:MeOH=20:1) to give the product (1.4 g, three-step yield: 30%).

Step 7: Synthesis of 5-ethyl-4,5-dihydropyrrolo[3,4-c]pyrazol-6(1H)-one

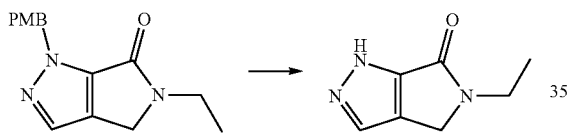

The intermediate 5-ethyl-1-(4-methoxybenzyl)-4,5-dihydropyrrolo[3,4-c]pyrazol-6(1H)-one (1.4 g, 5.16 mmol, 1.0 eq.) was dissolved in TFA (8 mL). The solution was added with anisole (0.15 mL) and stirred at 80° C. for 3 h. After the reaction was completed, as detected by TLC, the reaction solution was concentrated, and the crude product was purified by preparative thin-layer chromatography (DCM:MeOH=20:1) to give the product (560 mg, yield: 72%).

Step 8: Synthesis of (E)-2-(2-((5-ethyl-6-oxo-5,6-dihydropyrrolo[3,4-c]pyrazol-1(4H)-yl)methyl)-3-fluoroallyl)isoindoline-1,3-dione

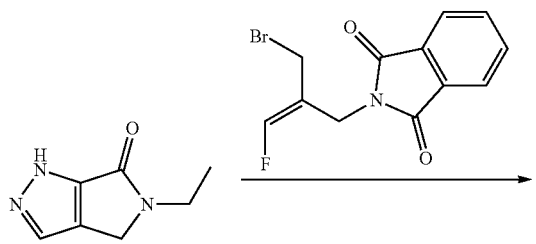

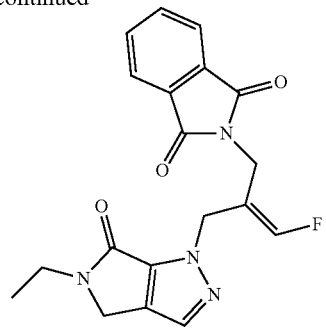

The intermediate 5-ethyl-4,5-dihydropyrrolo[3,4-c]pyrazol-6(1H)-one (560 mg, 3.7 mmol, 1.0 eq.) was dissolved in DMF (10 mL). The solution was added with potassium carbonate (1.5 g, 11.1 mmol, 3.0 eq.) and (E)-2-(2-(bromomethyl)-3-fluoroallyl)isoindoline-1,3-dione (1.3 g, 4.4 mmol, 1.2 eq.) and stirred at room temperature for 12 h. After the reaction was completed, as detected by TLC, the reaction solution was added with water (30 mL) and extracted with ethyl acetate (2×30 mL). The organic phase was dried over anhydrous sodium sulfate, filtered under vacuum and concentrated, and the crude product was purified by preparative thin-layer chromatography (DCM:MeOH=20:1) to give the product (300 mg, yield: 22%).

Step 9: Synthesis of (E)-1-(2-(aminomethyl)-3-fluoroallyl)-5-ethyl-4,5-dihydropyrrolo[3,4-c]pyrazol-6(1H)-one hydrochloride

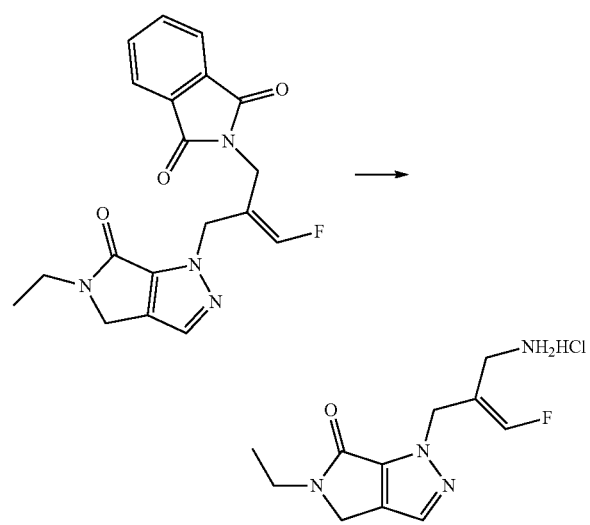

The intermediate (E)-2-(2-((5-ethyl-6-oxo-5,6-dihydropyrrolo[3,4-c]pyrazol-1(4H)-yl)methyl)-3-fluoroallyl)isoindoline-1,3-dione (300 mg, 0.814 mmol, 1.0 eq.) was dissolved in EtOH (5 mL). The solution was added with hydrazine hydrate (203.8 mg, 4.072 mmol, 5.0 eq.) and stirred at 45° C. for 3 h. After the reaction was completed, as detected by TLC, the reaction solution was cooled to room temperature. Solid was filtered off, and the filtrate was concentrated. Solid was filtered off again, and the filtrate was concentrated. The crude product was purified by preparative thin-layer chromatography (DCM:MeOH=5:1). The obtained oil was dissolved in DCM (3 mL), and the solution was added with hydrogen chloride ethanol solution (1 mL) dropwise.

After the reaction was completed, as detected by TLC, the solution was concentrated to give the product (90 mg, yield: 40%).

$^1$H-NMR (400 MHz, DMSO-d$_6$) δ(ppm): 8.35 (s, 3H), 7.54 (s, 1H), 7.31 (s, 0.5H), 7.11 (s, 0.5H), 4.99 (d, 2H), 4.23-4.29 (d, 2H), 3.46-3.47 (d, 4H), 1.16 (m, 3H).

Molecular formula: $C_{11}H_{16}ClFN_4O$, molecular weight: 238.27, LC-MS (m/z)=239.21 [M+H]$^+$.

Example 31: Synthesis of (E)-2-(2-(aminomethyl)-3-fluoroallyl)-1-bromo-5-cyclopropyl-2,5,6,7-tetrahydro-4H-pyrrolo[3,4-c]pyridin-4-one (Compound A32) Hydrochloride

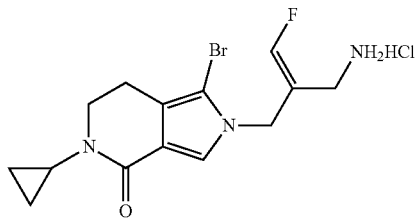

Step 1: Synthesis of Intermediate 1-cyclopropyl-3-((dimethylamino)methylene)piperidine-2,4-dione

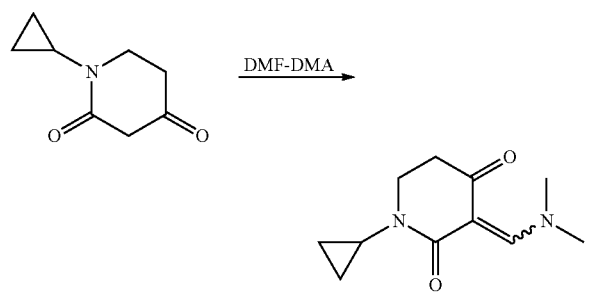

1-cyclopropylpiperazine-2,4-dione (50 g, 326.6 mmol, 1 eq.) was added into 1,1-dimethoxy-N,N-dimethylmethylamine (42.8 g, 359 mmol, 1.1 eq.) and the mixture was stirred at room temperature for 0.5 h. After the reaction was completed, as detected by TLC, the reaction solution was directly used in the next step.

Step 2: Synthesis of Intermediate ((1-cyclopropyl-2,4-dioxopiperidin-3-ylidene)methyl)glycine

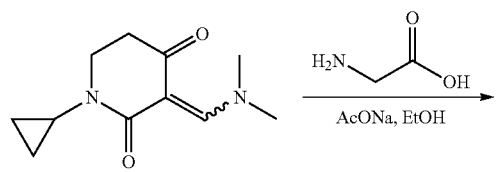

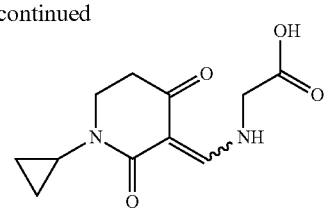

The 1-cyclopropyl-3-((dimethylamino)methylene)piperidine-2,4-dione solution obtained in the previous step was dissolved in ethanol (1000 mL). The solution was added with glycine (24.5 g, 326.6 mmol, 1 eq.) and sodium acetate (32.2 g, 391.8 mmol, 1.2 eq.), and heated to 50° C. to react for 6 h. When the reaction was completed, concentration was performed to give the product, which was directly used in the next step.

Step 3: Synthesis of Intermediate 2-acetyl-5-cyclopropyl-2,5,6,7-tetrahydro-4H-pyrrolo[3,4-c]pyridin-4-one

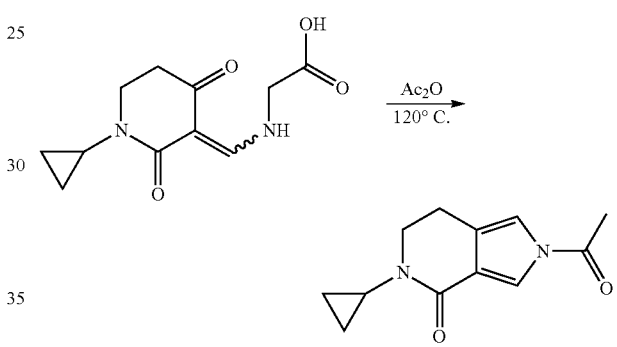

The crude product ((1-cyclopropyl-2,4-dioxopiperidin-3-ylidene)methyl) glycine obtained in the previous step was added to acetic anhydride (1000 mL) and the mixture was heated to 120° C. to react for 5 h. After the reaction was completed, acetic anhydride was removed by concentration, the concentrate was poured into saturated aqueous sodium bicarbonate solution, and the pH was adjusted to be neutral. Extraction was performed with ethyl acetate (300 mL×4). The organic phases were combined, dried and concentrated to give the product (calculated according to theoretical yield), which was directly used in the next step.

Step 4: Synthesis of Intermediate 5-cyclopropyl-2,5,6,7-tetrahydro-4H-pyrrolo[3,4-c]pyridin-4-one

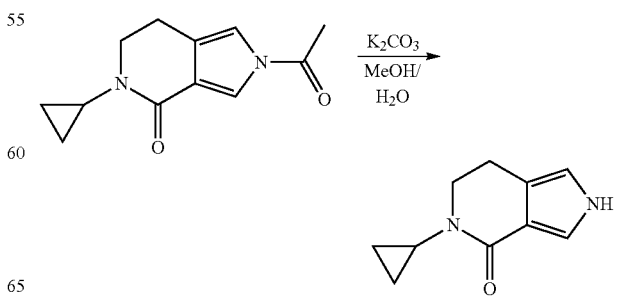

The crude product 2-acetyl-5-cyclopropyl-2,5,6,7-tetrahydro-4H-pyrrolo [3,4-c]pyridin-4-one was dissolved in methanol (300 mL). The solution was added with a solution of potassium carbonate (33.9 g, 464.3 mmol, 1.5 eq.) in water (300 mL) and stirred at room temperature for 20 min. After the reaction was completed, as detected by TLC, concentration was performed to remove methanol, the pH was adjusted to weak acidity, and extraction was performed with ethyl acetate. The organic phases were combined, dried and concentrated to give a crude product (37.8 g). The crude product underwent silica gel column chromatography (ethyl acetate:petroleum ether, 1:1-1:0, v/v) to give the product (13.05 g, four-step yield: 21.4%).

Step 5: Synthesis of Intermediate 1-bromo-5-cyclopropyl-2,5,6,7-tetrahydro-4H-pyrrolo[3,4-c]pyridin-4-one

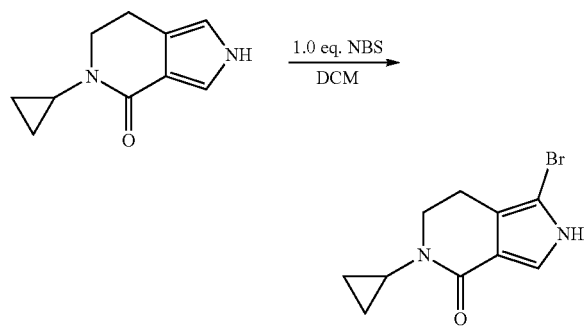

5-cyclopropyl-2,5,6,7-tetrahydro-4H-pyrrolo[3,4-c]pyridin-4-one (3 g, 17 mmol, 1 eq.) was dissolved in DCM (50 mL). The solution was added with NBS (3 g, 17 mmol, 1 eq.) batch by batch under an ice-water bath to react at 0° C. for 30 min. After the reaction was completed, as detected by TLC, the reaction solution was washed with water (50 mL) and saturated brine (50 mL) in sequence. The organic phase was dried and concentrated to give a crude product (4.47 g), which underwent silica gel column chromatography (petroleum ether:ethyl acetate=3:1, v/v) to give the product (2.82 g, yield: 65.6%).

Step 6: Synthesis of Intermediate tert-butyl (E)-(2-((1-bromo-5-cyclopropyl-4-oxo-4,5,6,7-tetrahydro-2H-pyrrolo[3,4-c]pyridin-2-yl)methyl)-3-fluoroallyl) carbamate

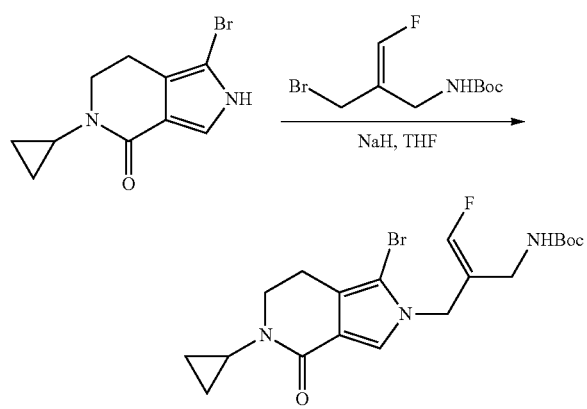

1-bromo-5-cyclopropyl-2,5,6,7-tetrahydro-4H-pyrrolo[3,4-c]pyridin-4-one (2.14 g, 8.37 mmol, 1 eq.) was dissolved in anhydrous THF (40 mL). NaH (670 mg, 16.74 mmol) was slowly added batch by batch under an ice-water bath. After addition, the mixture was stirred at 0° C. for 30 min, and added with tert-butyl (E)-(2-(bromomethyl)-3-fluoroallyl) carbamate (2.34 g, 8.74 mmol, 1.05 eq.) to react at room temperature for 40 h. After the reaction was completed, as detected by TLC, saturated aqueous ammonium chloride solution was added to quench the reaction. The organic phase was washed with water and saturated brine in sequence, dried and concentrated to give a crude product (3.89 g). The crude product underwent silica gel column chromatography (petroleum ether:ethyl acetate=4:1-3:1, v/v) to give the product (1.77 g, yield: 47.8%).

Step 7: Synthesis of Compound (E)-2-(2-(aminomethyl)-3-fluoroallyl)-1-bromo-5-cyclopropyl-2,5,6,7-tetrahydro-4H-pyrrolo[3,4-c]pyridin-4-one hydrochloride

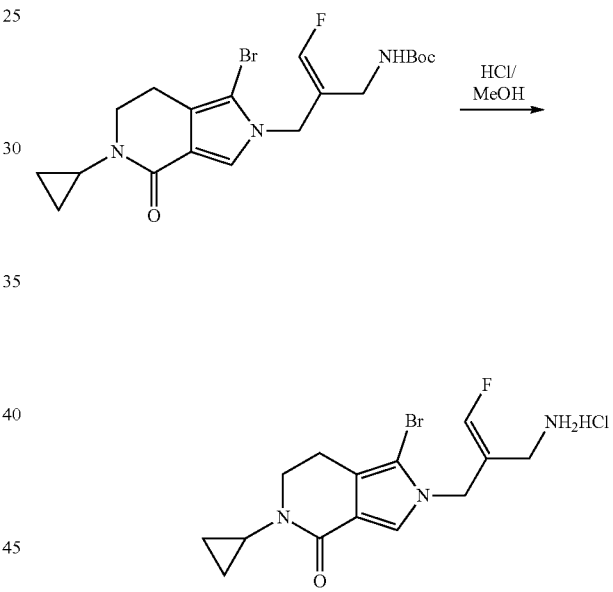

Tert-butyl (E)-(2-((1-bromo-5-cyclopropyl-4-oxo-4,5,6,7-tetrahydro-2H-pyrrolo[3,4-c]pyridin-2-yl)methyl)-3-fluoroallyl)carbamate (350 mg, 0.791 mmol, 1 eq.) was dissolved in hydrogen chloride ethanol solution (12 mL) and the mixture was stirred until the reaction was completed. The reaction solution was concentrated and lyophilization was performed to give the product (134 mg, yield: 49.6%).

$^1$H-NMR (400 MHz, DMSO-$d_6$) δ(ppm): 8.41 (brs, 3H), 7.55 (s, 1H), 7.30-7.02 (d, 1H), 4.76 (d, 2H), 3.42-3.47 (m, 2H), 3.29-3.30 (m, 2H), 2.56-2.65 (m, 3H), 0.71-0.77 (m, 2H), 0.56-0.60 (m, 2H).

Molecular formula: $C_{14}H_{17}BrFN_3O$, molecular weight: 342.21, LC-MS (m/z)=343.92[M+H]$^+$.

Example 32: Synthesis of (E)-2-(2-(aminomethyl)-3-fluoroallyl)-1,3-dibromo-5-cyclopropyl-2,5,6,7-tetrahydro-4H-pyrrolo[3,4-c]pyridin-4-one (Compound A33) Hydrochloride

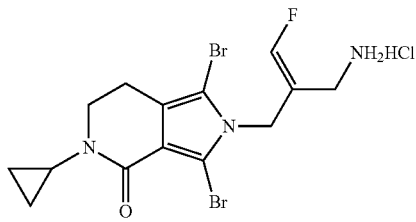

Step 1: Synthesis of 1,3-dibromo-5-cyclopropyl-2,5,6,7-tetrahydro-4H-pyrrolo[3,4-c]pyridin-4-one

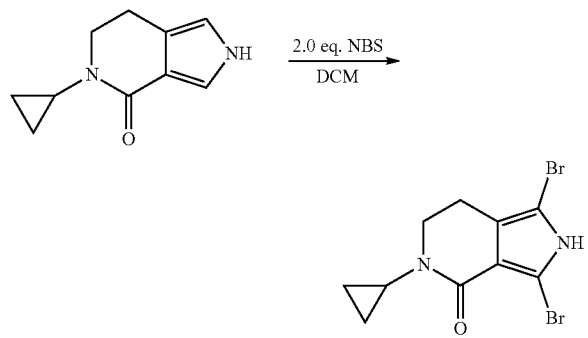

5-cyclopropyl-2,5,6,7-tetrahydro-4H-pyrrolo[3,4-c]pyridin-4-one (3 g, 17 mmol, 1 eq.) was dissolved in DCM (50 mL). The solution was added with NBS (6 g, 34 mmol, 2 eq.) batch by batch under an ice-water bath to react at room temperature for 20 min. After the reaction was completed, as detected by TLC, the reaction solution was washed with water (50 mL) and saturated brine (50 mL) in sequence. The organic phase was dried and concentrated to give a crude product (6.03 g), which underwent silica gel column chromatography (petroleum ether:ethyl acetate=5:1-4:1, v/v) to give the product (3.33 g, yield: 58.4%).

Step 2: Synthesis of tert-butyl (E)-(2-((1,3-dibromo-5-cyclopropyl-4-oxo-4,5,6,7-tetrahydro-2H-pyrrolo[3,4-c]pyridin-2-yl)methyl)-3-fluoroallyl)carbamate

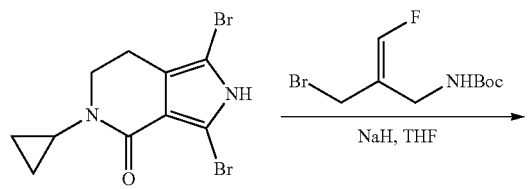

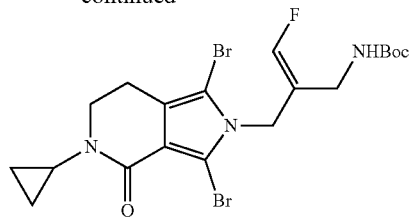

1,3-dibromo-5-cyclopropyl-2,5,6,7-tetrahydro-4H-pyrrolo[3,4-c]pyridin-4-one (3.83 g, 11.4 mmol, 1.0 eq.) was dissolved in anhydrous THF (60 mL). NaH (912 mg, 22.8 mmol, 2.0 eq.) was slowly added under an ice-water bath. After addition, the mixture was stirred at 0° C. for 30 min, and added with tert-butyl (E)-(2-(bromomethyl)-3-fluoroallyl)carbamate (3.06 g, 11.4 mmol, 1.0 eq.) to react at room temperature for 40 h. After the reaction was completed, as detected by TLC, saturated aqueous ammonium chloride solution was added to quench the reaction. The organic phase was washed with water and saturated brine in sequence, dried and concentrated to give a crude product (6.17 g). The crude product underwent silica gel column chromatography (petroleum ether: ethyl acetate=4:1-2:1, v/v) to give the product (3.98 g, yield: 67.5%).

Step 3: Synthesis of (E)-2-(2-(aminomethyl)-3-fluoroallyl)-1,3-dibromo-5-cyclopropyl-2,5,6,7-tetrahydro-4H-pyrrolo[3,4-c]pyridin-4-one hydrochloride

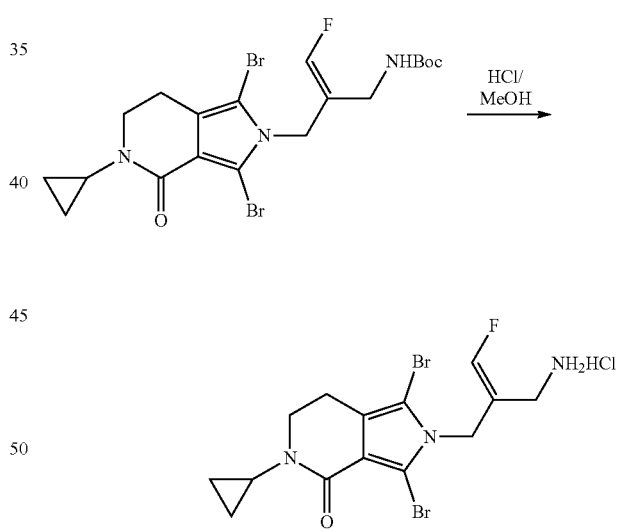

Tert-butyl (E)-(2-((1,3-dibromo-5-cyclopropyl-4-oxo-4,5,6,7-tetrahydro-2H-pyrrolo[3,4-c]pyridin-2-yl)methyl)-3-fluoroallyl)carbamate (400 mg, 0.767 mmol, 1 eq.) was dissolved in hydrogen chloride ethanol solution (12 mL) and the mixture was stirred until the reaction was completed. The reaction solution was concentrated and lyophilization was performed to give the product (103 mg, yield: 31.9%).

$^1$H-NMR (300 MHz, DMSO-$d_6$) δ(ppm): 8.53 (brs, 3H), 6.58-6.85 (d, 1H), 4.81-4.82 (d, 2H), 3.43-3.45 (m, 4H), 2.60-2.62 (m, 3H), 0.71-0.78 (m, 2H), 0.56-0.61 (m, 2H).

Molecular formula: $C_{14}H_{16}Br_2FN_3O$, molecular weight: 421.11, LC-MS (m/z)=421.94[M+H]$^+$.

Example 33: Synthesis of Compound (E)-2-(2-(aminomethyl)-3-fluoroallyl)-5-cyclopropyl-1-methyl-2,5,6,7-tetrahydro-4H-pyrrolo[3,4-c]pyridin-4-one (Compound A35) Hydrochloride

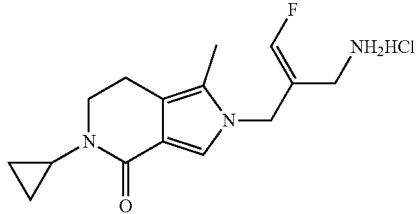

Step 1: Synthesis of Intermediate tert-butyl (E)-(2-((5-cyclopropyl-1-methyl-4-oxo-4,5,6,7-tetrahydro-2H-pyrrolo[3,4-c]pyridin-2-yl)methyl)-3-fluoroallyl)carbamate

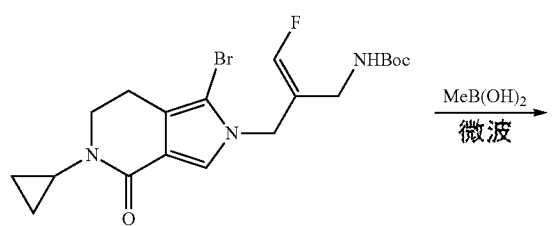

微波

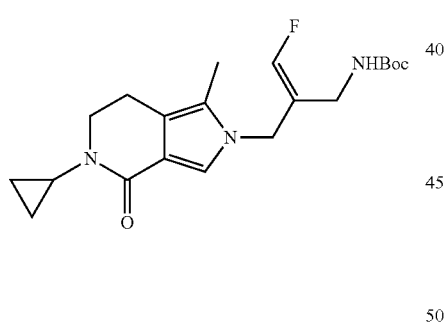

Tert-butyl (E)-(2-((1-bromo-5-cyclopropyl-4-oxo-4,5,6,7-tetrahydro-2H-pyrrolo[3,4-c]pyridin-2-yl)methyl)-3-fluoroallyl)carbamate (500 mg, 1.13 mmol, 1 eq.), potassium phosphate (720 mg, 3.39 mmol, 3 eq.), methylboronic acid (271 mg, 4.52 mmol, 4 eq.) and tricyclohexylphosphine (31.7 mg, 0.113 mmol, 0.1 eq.) were put into a microwave tube, and toluene (30 mL) was added. After bubbling was performed with $N_2$ for 5 min, $Pd_2(dba)_3$ (52 mg, 0.0565 mmol, 0.05 eq.) was added. Reaction was carried out under microwave at 120° C. for 1 h. After the reaction was completed, the reaction solution was concentrated, the crude product was purified by reversed phase column chromatography ($CH_3CN:H_2O=1:4$) and lyophilization was performed to give the product (230 mg, yield: 53.9%).

Step 2: Synthesis of Compound (E)-2-(2-(aminomethyl)-3-fluoroallyl)-5-cyclopropyl-1-methyl-2,5,6,7-tetrahydro-4H-pyrrolo[3,4-c]pyridin-4-one hydrochloride

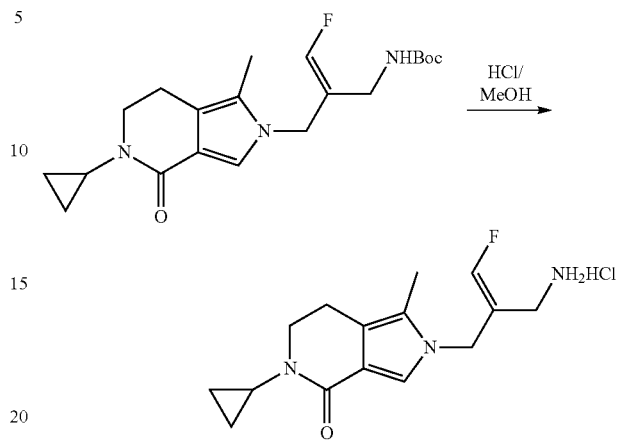

Tert-butyl (E)-(2-((5-cyclopropyl-1-methyl-4-oxo-4,5,6,7-tetrahydro-2H-pyrrolo[3,4-c]pyridin-2-yl)methyl)-3-fluoroallyl)carbamate (230 mg, 0.609 mmol, 1 eq.) was dissolved in hydrogen chloride ethanol solution (10 mL) and the mixture was stirred until the reaction was completed. The reaction solution was concentrated and lyophilization was performed to give the product (134.7 mg, yield: 79.7%).

$^1$H-NMR (300 MHz, DMSO-$d_6$) δ(ppm): 8.62 (brs, 3H), 7.33 (s, 1H), 6.87-7.14 (d, 1H), 4.74 (s, 2H), 3.37-3.41 (m, 2H), 3.24 (m, 2H), 2.52-2.63 (m, 3H), 2.07 (s, 3H), 0.68-0.72 (m, 2H), 0.55-0.58 (m, 2H).

Molecular formula: $C_{15}H_{21}ClFN_3O$, molecular weight: 277.34, LC-MS (n/z)=278.09[M+H]+.

Example 34: Synthesis of Compound (E)-2-(2-(aminomethyl)-3-fluoroallyl)-5-cyclopropyl-1,3-dimethyl-2,5,6,7-tetrahydro-4H-pyrrolo[3,4-c]pyridin-4-one (Compound A36) Hydrochloride

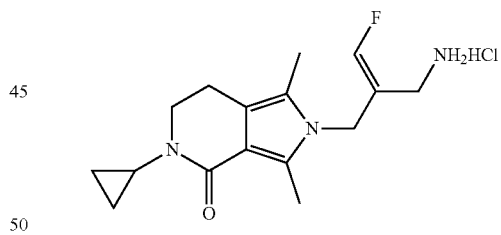

Step 1: Synthesis of tert-butyl (E)-(2-((5-cyclopropyl-1-methyl-4-oxo-4,5,6,7-tetrahydro-2H-pyrrolo[3,4-c]pyridin-2-yl)methyl)-3-fluoroallyl)carbamate

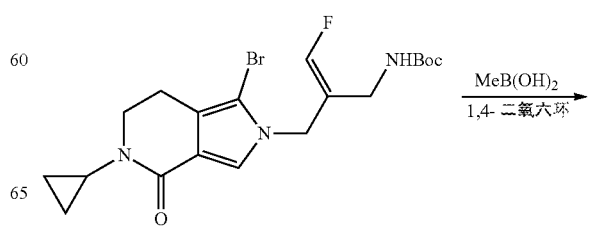

1,4-二氧六环

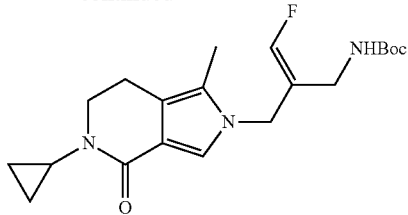

Tert-butyl (E)-(2-((1-bromo-5-cyclopropyl-4-oxo-4,5,6,7-tetrahydro-2H-pyrrolo[3,4-c]pyridin-2-yl)methyl)-3-fluoroallyl)carbamate (500 mg, 0.96 mmol, 1 eq.), methylboronic acid (230 mg, 3.84 mmol, 4 eq.) and potassium phosphate (1.63 g, 7.68 mmol, 8 eq.) were put into a flask, 1,4-dioxane (12 mL) was added, nitrogen was charged to replace by evacuation, and Pd(PPh$_3$)$_4$ (60 mg, 0.05 mmol, 0.05 eq.) was added. The mixture was stirred in nitrogen atmosphere for 5 h. After the reaction was completed, as detected by TLC, the reaction solution was concentrated and added with ethyl acetate. Water and saturated brine were sequentially used to perform washing, and after drying and concentration, a crude product (570 mg) was obtained. The crude product was purified by reversed phase column chromatography (CH$_3$CN:H$_2$O=1:3) to give the product (170 mg, yield: 45.2%).

Step 2: Synthesis of (E)-2-(2-(aminomethyl)-3-fluoroallyl)-5-cyclopropyl-1,3-dimethyl-2,5,6,7-tetrahydro-4H-pyrrolo[3,4-c]pyridin-4-one hydrochloride

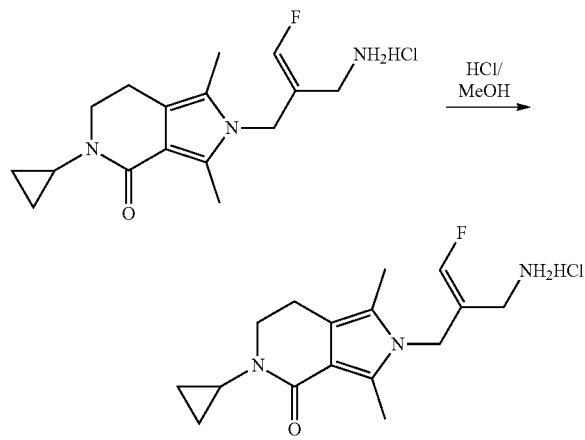

(E)-2-(2-(aminomethyl)-3-fluoroallyl)-5-cyclopropyl-1,3-dimethyl-2,5,6,7-tetrahydro-4H-pyrrolo[3,4-c]pyridin-4-one hydrochloride (170 mg, 0.434 mmol, 1 eq.) was dissolved in hydrogen chloride ethanol solution (10 mL) and the solution was stirred until the reaction was completed. The reaction solution was concentrated, and lyophilization was performed to give the product (102.8 mg, yield: 81.6%).

$^1$H-NMR (300 MHz, DMSO-d$_6$) δ(ppm): 8.62 (brs, 3H), 5.85-6.12 (d, 1H), 4.66 (s, 2H), 3.46 (s, 2H), 3.33-3.46 (m, 2H), 2.51-2.58 (m, 3H), 2.42 (s, 3H), 2.05 (s, 3H), 0.69-0.71 (m, 2H), 0.54 (m, 2H).

Molecular formula: C$_{16}$H$_{23}$ClFN$_3$O, molecular weight: 291.37, LC-MS (m/z)=292.20[M+H]$^+$ Example 35: Synthesis of (E)-2-(2-(aminomethyl)-3-fluoroallyl)-1-chloro-5-cyclopropyl-2,5,6,7-tetrahydro-4H-pyrrolo[3,4-c]pyridin-4-one (Compound A42)hydrochloride

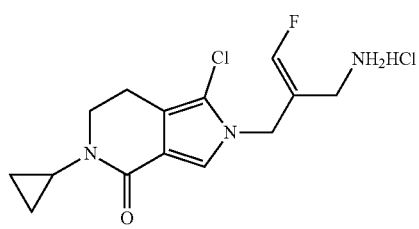

Step 1: Synthesis of 1-chloro-5-cyclopropyl-2,5,6,7-tetrahydro-4H-pyrrolo[3,4-c]pyridin-4-one

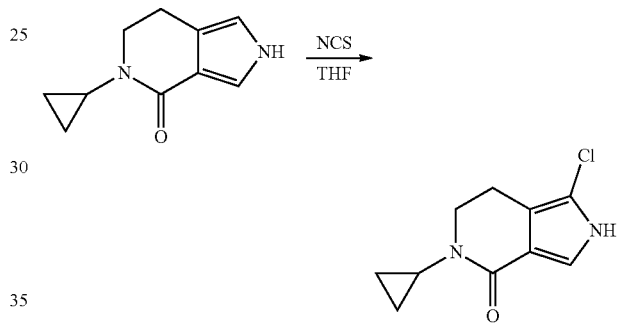

5-cyclopropyl-2,5,6,7-tetrahydro-4H-pyrrolo[3,4-c]pyridin-4-one (600 g, 3.4 mmol, 1 eq.) was dissolved in THF (20 mL). The solution was added with NCS (455 mg, 3.4 mmol, 1 eq.) batch by batch under an ice-water bath to react at room temperature for 30 min. After the reaction was completed, as detected by TLC, THF was evaporated off under reduced pressure, DCM (30 mL) was added, and water (30 mL) and saturated brine (30 mL) were sequentially used to perform washing. The organic phase was dried and concentrated to give a crude product (820 mg). The crude product was purified by silica gel column chromatography (petroleum ether:ethyl acetate=3:1, 1:1, v/v) to give the product (540 mg, yield: 75.4%).

Step 2: Synthesis of tert-butyl (E)-(2-((1-chloro-5-cyclopropyl-4-oxo-4,5,6,7-tetrahydro-2H-pyrrolo[3,4-c]pyridin-2-yl)methyl)-3-fluoroallyl)carbamate

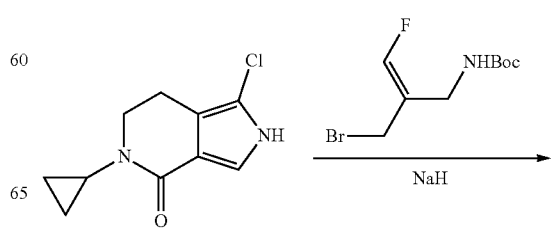

-continued

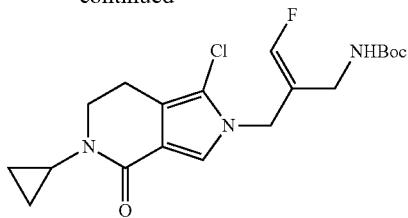

1-chloro-5-cyclopropyl-2,5,6,7-tetrahydro-4H-pyrrolo[3,4-c]pyridin-4-one (500 mg, 2.37 mmol, 1 eq.) was dissolved in anhydrous THF (20 mL). NaH (190 mg, 4.74 mmol) was slowly added batch by batch under an ice-water bath. After addition, the mixture was stirred at 0° C. for 30 min, and added with tert-butyl (E)-(2-(bromomethyl)-3-fluoroallyl) carbamate (668 mg, 2.49 mmol, 1.05 eq.) to react at room temperature for 23 h. After the reaction was completed, as detected by TLC, saturated aqueous ammonium chloride solution was added to quench the reaction. The organic phase was washed with water and saturated brine in sequence, dried and concentrated to give a crude product (1.03 g), and the crude product was purified by silica gel column chromatography (petroleum ether:ethyl acetate=2.5:1-2:1, v/v) to give the product (320 mg, yield: 34%).

Step 3: Synthesis of (E)-2-(2-(aminomethyl)-3-fluoroallyl)-1-chloro-5-cyclopropyl-2,5,6,7-tetrahydro-4H-pyrrolo[3,4-c]pyridin-4-one hydrochloride

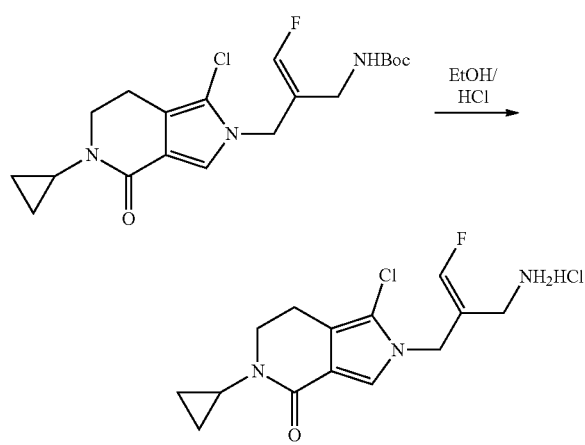

Tert-butyl (E)-(2-((1-chloro-5-cyclopropyl-4-oxo-4,5,6,7-tetrahydro-2H-pyrrolo[3,4-c]pyridin-2-yl)methyl)-3-fluoroallyl)carbamate (320 mg, 0.804 mmol, 1 eq.) was dissolved in hydrogen chloride ethanol solution (10 mL) and the mixture was stirred at room temperature for 4 h. After the reaction was completed, as detected by LC-MS, the reaction solution was concentrated to give a crude product (200 mg). The crude product was purified by C-18 column chromatography (CH$_3$CN:H$_2$O=1:4), and lyophilization was performed to give the product (34 mg, yield: 14.2%).

$^1$H-NMR (300 MHz, DMSO-d$_6$) δ(ppm): 8.41 (brs, 3H), 7.55 (s, 1H), 7.02-7.30 (d, 1H), 4.76 (s, 2H), 3.42-3.47 (m, 2H), 3.29-3.30 (m, 2H), 2.61-2.66 (m, 1H), 2.55-2.59 (m, 2H), 0.70-0.77 (m, 2H), 0.52-0.59 (m, 2H).

Molecular formula: C$_{14}$H$_{17}$ClFN$_3$O, molecular weight: 297.10, LC-MS (n/z)=297.74[M+H]$^+$.

Example 36: Synthesis of (E)-2-(2-(aminomethyl)-3-fluoroallyl)-5-cyclopropyl-2,5-dihydro-4H-pyrazolo[4,3-c]pyridin-4-one (Compound A41) and (E)-1-(2-(aminomethyl)-3-fluoroallyl)-5-cyclopropyl-1,5-dihydro-4H-pyrazolo[4,3-c]pyridin-4-one (Compound A44) Hydrochloride Step 1: Synthesis of 5-cyclopropyl-2-(4-methoxybenzyl)-2,5-dihydro-4H-pyrazolo[4,3-c]pyridin-4-one

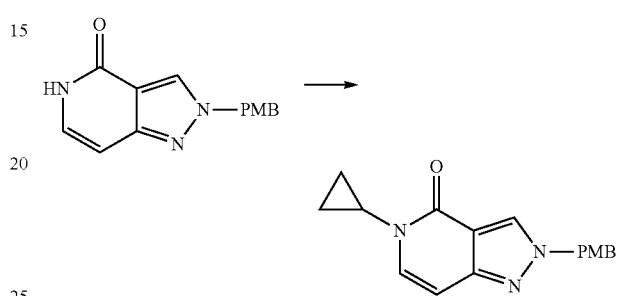

2-(4-methoxybenzyl)-2,5-dihydro-4H-pyrazolo[4,3-c]pyridin-4-one (6.4 g, 32.51 mmol, 1.0 eq.), cyclopropylboronic acid (10.77 g, 125.35 mmol, 5.0 eq.), copper acetate (13.66 g, 75.21 mmol, 3.0 eq.) and pyridine (9.92 g, 125.35 mmol, 5.0 eq.) were dissolved in toluene (150 mL) to react at 100° C. under air conditions for 47 h. The reaction solution was concentrated under reduced pressure, and the crude product was purified by silica gel column chromatography (PE:EA=1:1) to give the product (2.0 g, yield: 27%).

Step 2: Synthesis of 5-cyclopropyl-2,5-dihydro-4H-pyrazolo[4,3-c]pyridin-4-one

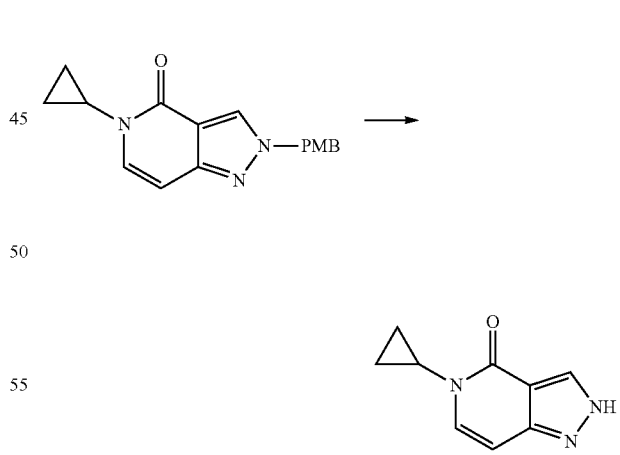

5-cyclopropyl-2-(4-methoxybenzyl)-2,5-dihydro-4H-pyrazolo[4,3-c]pyridin-4-one (2.0 g, 6.77 mmol, 1.0 eq.) was dissolved in trifluoroacetic acid (20 mL) to react at 75° C. for 14 h. After the reaction was completed, as detected by LC-MS, the reaction solution was concentrated under reduced pressure. The crude product was purified by silica gel column chromatography (MeOH:DCM=1:50) to give the product (1.0 g, yield: 84%).

Step 3: Synthesis of (E)-2-(2-((5-cyclopropyl-4-oxo-4,5-dihydro-2H-pyrazolo[4,3-c]pyridin-2-yl)methyl)-3-fluoroallyl)isoindolin-1,3-dione and (E)-2-(2-((5-cyclopropyl-4-oxo-4,5-dihydro-1H-pyrazolo[4,3-c]pyridin-1-yl)methyl)-3-fluoroallyl)isoindolin-1,3-dione Step 4: Synthesis of (E)-2-(2-(aminomethyl)-3-fluoroallyl)-5-cyclopropyl-2,5-dihydro-4H-pyrazolo[4,3-c]pyridin-4-one and (E)-1-(2-(aminomethyl)-3-fluoroallyl)-5-cyclopropyl-1,5-dihydro-4H-pyrazolo[4,3-c]pyridin-4-one hydrochloride

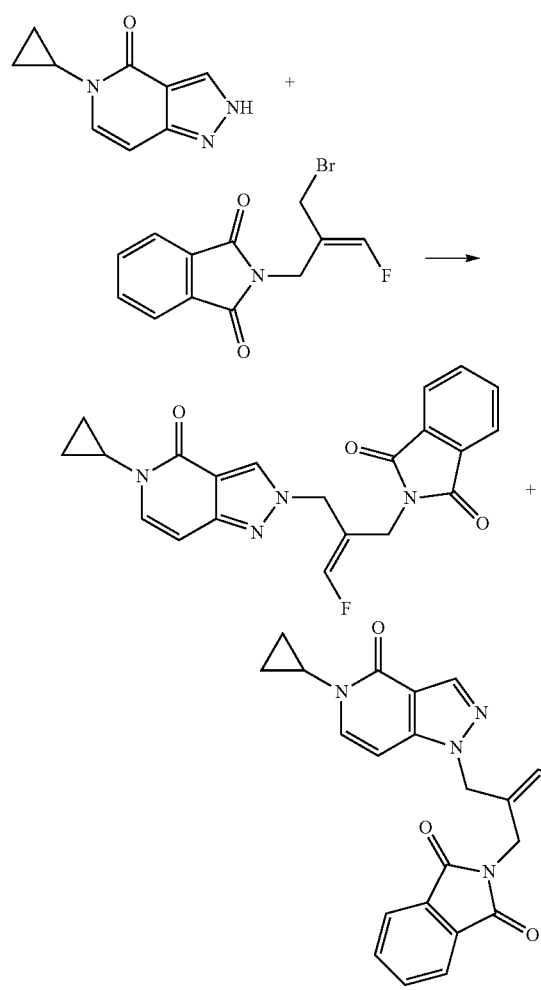

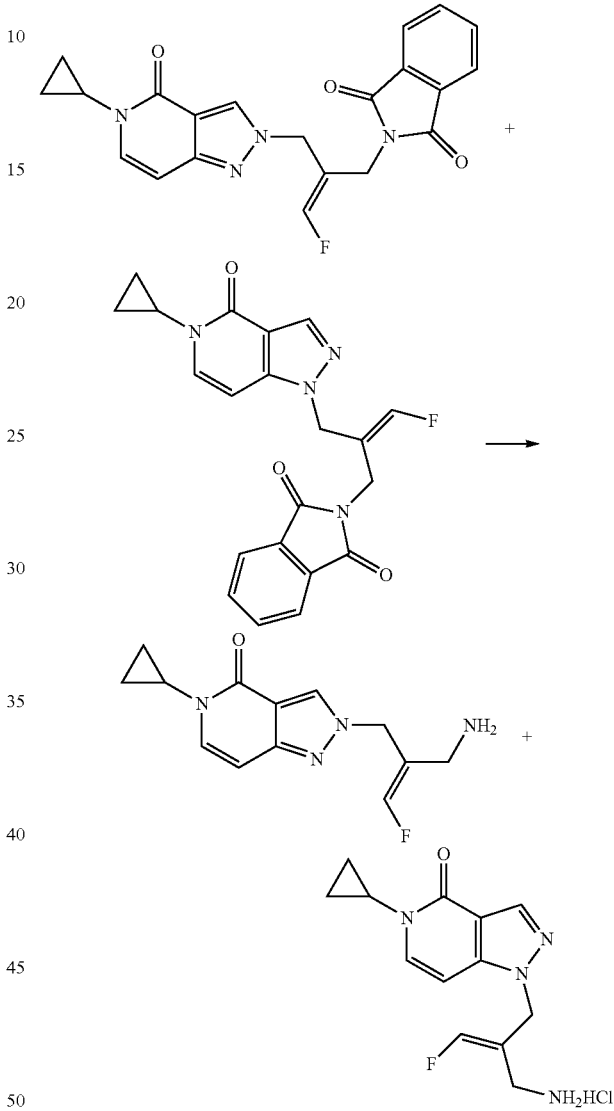

5-cyclopropyl-2,5-dihydro-4H-pyrazolo[4,3-c]pyridin-4-one (1.0 g, 5.71 mmol, 1.0 eq.), (E)-2-(2-(bromomethyl)-3-fluoroallyl)isoindolin-1,3-dione (1.87 g, 6.28 mmol, 1.1 eq.), potassium carbonate (867 mg, 6.28 mmol, 1.1 eq.) and TBAB (184 mg, 0.57 mmol, 0.1 eq.) were dissolved in absolute ethanol (8 mL) to react for 19 h. After the reaction was completed, as detected by TLC, the reaction solution was concentrated under reduced pressure. The crude product was purified by silica gel column chromatography (PE:EA=1:1) to give a mixture of (E)-2-(2-((5-cyclopropyl-4-oxo-4,5-dihydro-2H-pyrazolo[4,3-c]pyridin-2-yl)methyl)-3-fluoroallyl)isoindolin-1,3-dione and (E)-2-(2-((5-cyclopropyl-4-oxo-4,5-dihydro-1H-pyrazolo[4,3-c]pyridin-1-yl)methyl)-3-fluoroallyl)isoindolin-1,3-dione (1.8 g, yield: 80%).

The mixture (1.4 g, 3.57 mmol, 1.0 eq.) obtained in the previous step and hydrazine hydrate (335 mg, 5.35 mmol, 1.5 eq.) were dissolved in EtOH (20 mL) to react at 80° C. for 20 min. After the reaction was completed, as detected by TLC, the reaction solution was cooled to room temperature and filtered under vacuum, and the filtrate was concentrated under reduced pressure. The crude product was dissolved in dichloromethane, the solution was filtered under vacuum, and the filtrate was concentrated under reduced pressure. The crude product was purified by preparative thin-layer chromatography (dichloromethane:isopropanol:ammonia=10:1:0.5) to give (E)-2-(2-(aminomethyl)-3-fluoroallyl)-5-cyclopropyl-2,5-dihydro-4H-pyrazolo[4,3-c]pyridin-4-one with a low Rf value (350 mg, yield: 37%), which is compound A41.

¹H NMR (400 MHz, DMSO-d₆) δ (ppm): 8.55 (s, 1H), 6.87-7.02 (d, 1H), 4.91 (s, 2H), 3.18 (s, 1H), 3.05 (s, 2H), 1.60 (s, 2H), 0.96-0.97 (d, 2H), 0.79 (s, 2H).

Molecular formula: $C_{13}H_{15}FN_4O$, molecular weight: 262.29, LC-MS (Pos, m/z)=263.13[M+H]⁺.

The one with a high Rf value was dissolved in ethanol. The solution was added with hydrogen chloride ethanol solution, concentrated under reduced pressure and lyophilized to give (E)-1-(2-(aminomethyl)-3-fluoroallyl)-5-cyclopropyl-1,5-dihydro-4H-pyrazolo[4,3-c]pyridin-4-one hydrochloride (220 mg, yield: 20%), which is compound A44.

¹H NMR (300 MHz, DMSO-d₆) δ (ppm): 8.48 (s, 3H), 8.08 (s, 1H), 7.44-7.46 (d, 1H), 7.35 (s, 0.5H), 7.08 (s, 0.5H), 6.86-6.88 (d, 1H), 5.10-5.11 (d, 2H), 3.36 (s, 2H), 3.22-3.26 (m, 1H), 0.98-1.00 (d, 2H), 0.81-0.84 (m, 2H).

Molecular formula: $C_{13}H_{15}FN_4O$, molecular weight: 262.29, LC-MS (Pos, m/z)=263.10[M+H]⁺.

Example 37: Synthesis of (E)-(1-(2-(aminomethyl)-3-fluoroallyl)-1H-indol-5-yl)(morpholino)methanone (Compound C1)

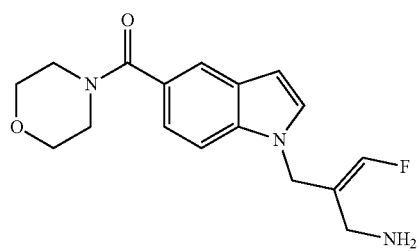 [SMILES: NC/C(=C\F)Cn1ccc2cc(C(=O)N3CCOCC3)ccc21]

Step 1: Synthesis of (Z)-2-(3-fluoro-2-((5-(morpholine-4-carbonyl)-1H-indol-1-yl)methyl)allyl)isoindoline-1,3-dione

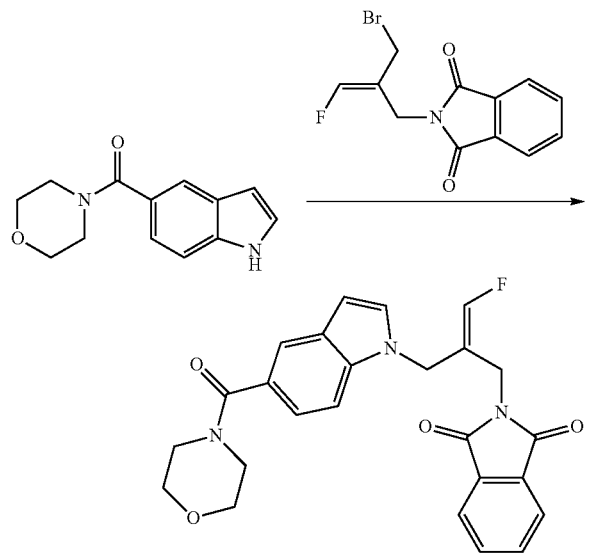

(1H-indol-5-yl)(morpholino)methanone (1.00 g, 4.34 mmol, 1 eq.) was dissolved in DMF (10 mL), and the solution was cooled to 0° C. The solution was added with NaH (mass fraction: 60%, 0.19 g, 4.77 mmol, 1.1 eq.) in nitrogen atmosphere, and was stirred for 30 min in N₂ atmosphere. The solution was added with a solution of (E)-2-(2-(bromomethyl)-3-fluoroallyl)isoindolin-1,3-dione (1.55 g, 5.21 mmol, 1.2 eq.) in DMF (10 mL) dropwise, and incubate at room temperature overnight. After the reaction was completed, as detected by TLC, the reaction solution was added with water (60 mL) and extracted with EA (80 mL×3). The organic phases were combined, backwashed with water, dried over anhydrous sodium sulfate and filtered, and the filtrate was concentrated under reduced pressure. The crude product was purified by silica gel column chromatography (DCM:MeOH=150:1) to give the product (1.42 g, yield: 73.2%).

Step 2: Synthesis of (E)-(1-(2-(aminomethyl)-3-fluoroallyl)-1H-indol-5-yl)(morpholino)methanone

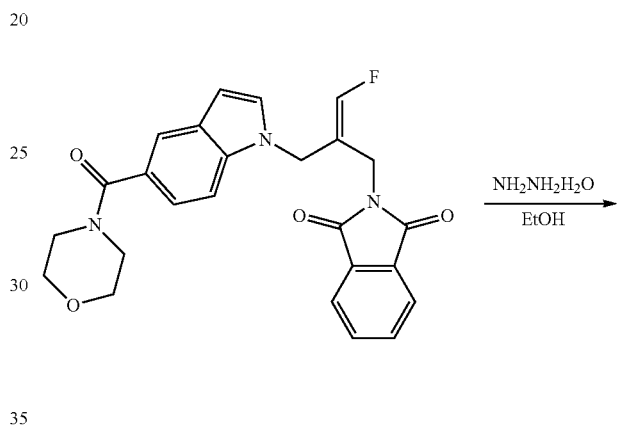

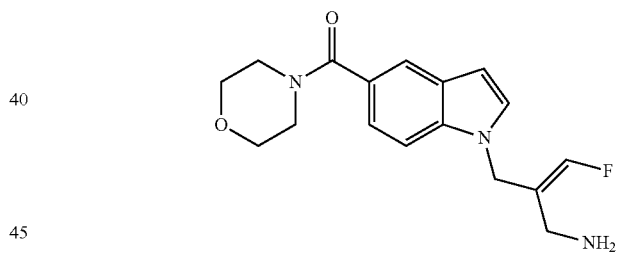

The intermediate (Z)-2-(3-fluoro-2-((5-(morpholine-4-carbonyl)-1H-indol-1-yl)methyl)allyl)isoindoline-1,3-dione (1.42 g, 3.17 mmol, 1 eq.) was dissolved in EtOH (35 mL). The solution was added with 85% of hydrazine hydrate (0.65 g, 11.08 mmol, 3.5 eq.) and reacted at reflux for 2 h. After the reaction was completed, as detected by TLC, filtration under vacuum and concentration were carried out. The crude product was purified by preparative thin-layer chromatography (DCM:MeOH=10:1) to give the product (0.13 g, yield: 13.1%).

¹H-NMR (400 MHz, DMSO-d₆) δ(ppm): 7.64-7.65 (t, 2H), 7.59-7.60 (d, 1H), 7.20-7.22 (m, 1H), 7.04-7.25 (d, J=84 Hz, 1H), 6.55-6.56 (d, 1H), 4.96 (d, 2H), 3.60 (s, 4H), 3.52 (s, 4H), 3.17 (s, 2H), 3.12 (d, 2H).

Molecular formula: $C_{17}H_{20}FN_3O_2$, molecular weight: 317.36, LC-MS (Pos, m/z)=318.19 [M+H]⁺.

Example 38: Synthesis of (E)-(1-(2-(aminomethyl)-3-fluoroallyl)-1H-indol-5-yl)(azetidin-1-yl)methanone (Compound C13) Hydrochloride

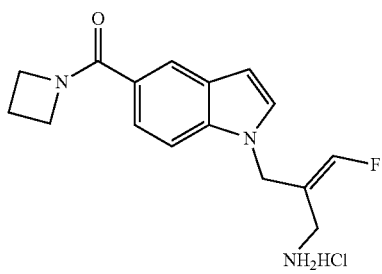

Step 1: Synthesis of azetidin-1-yl(1H-indol-5-yl)methanone

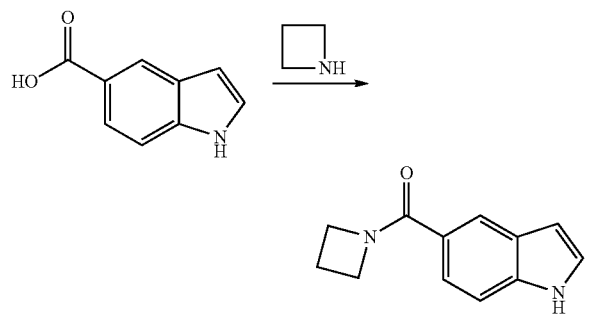

Materials 1H-indole-5-carboxylic acid (1 g, 6.2 mmol, 1.0 eq.) and DIPEA (2.4 g, 18.6 mmol, 3.0 eq.) were dissolved in N,N-dimethylacetamide (5 mL), and nitrogen was charged to replace by evacuation. The solution was cooled to 0° C., and added with HATU (3.5 g, 9.3 mmol, 1.5 eq.) to react for 0.5 h. The reaction solution was added with azetidine (708.6 mg, 12.41 mmol, 2.0 eq.) to react for 1 h. After no materials were left, as detected by TLC, the reaction solution was added with water (50 mL) and extracted with ethyl acetate (50 mL×3). The organic phases were combined, dried over anhydrous magnesium sulfate and filtered, and the filtrate was concentrated under reduced pressure. The crude product was purified by silica gel column chromatography (MeOH:DCM=1:100-1:50). The obtained solid was added with a small amount of ethyl acetate and filtered, and the filter cake was dried to give the product (1.1 g, yield: 88.7%).

Step 2: Synthesis of (Z)-2-(2-((5-(azetidine-1-carbonyl)-1H-indol-1-yl) methyl)-3-fluoroallyl)isoindoline-1,3-dione

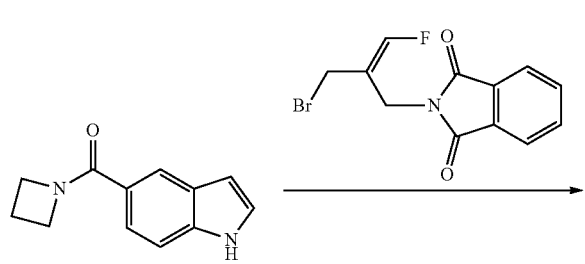

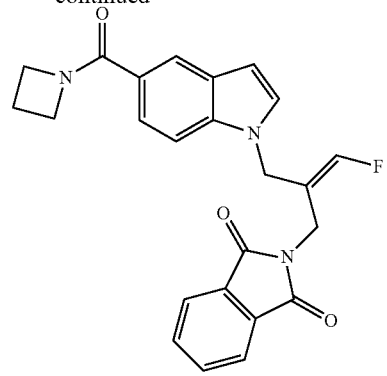

The intermediate azetidin-1-yl(1H-indol-5-yl)methanone (500 mg, 2.5 mmol, 1.0 eq.) was dissolve in N,N-dimethylacetamide (5 mL). Nitrogen was charged to replace by evacuation, and the solution was cooled to 0° C., added with sodium hydride (mass fraction: 60%, 109.8 mg, 2.75 mmol, 1.1 eq.) and stirred for 0.5 h. The mixture was added with (E)-2-(2-(bromomethyl)-3-fluoroallyl)isoindoline-1,3-dione (894.3 mg, 3 mmol, 1.2 eq.) to react for 1 h. After no materials were left, as detected by TLC, the reaction solution was added with saturated aqueous ammonium chloride solution (50 mL) and water (50 mL), stirred for 10 min and extracted with ethyl acetate (50 mL×3). The organic phases were combined, washed with water (50 mL), dried over anhydrous magnesium sulfate and filtered. The filtrate was concentrated under reduced pressure, and the crude product was purified by silica gel column chromatography (MeOH:DCM=1:100-1:60) to give the product (643 mg, yield: 64.3%).

Step 3: Synthesis of (E)-(1-(2-(aminomethyl)-3-fluoroallyl)-1H-indol-5-yl)(azetidin-1-yl)methanone hydrochloride

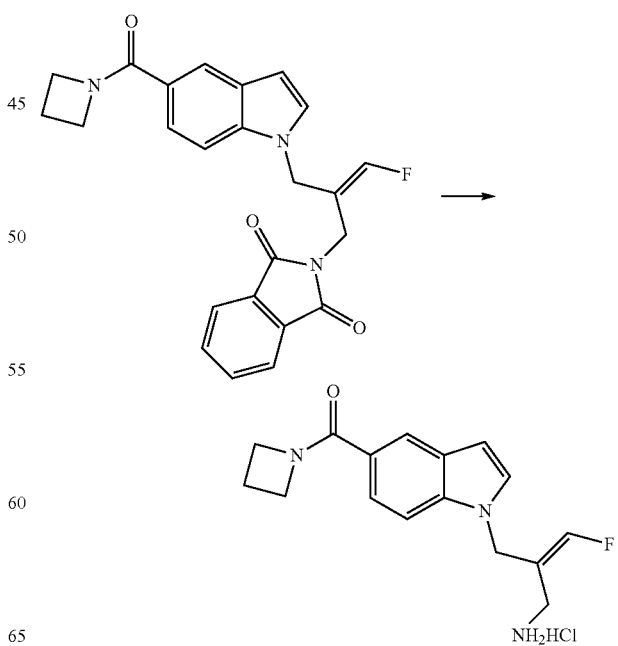

The intermediate (Z)-2-(2-((5-(azetidine-1-carbonyl)-1H-indol-1-yl) methyl)-3-fluoroallyl)isoindoline-1,3-dione (643 mg, 1.59 mmol, 1.0 eq.) was dissolved in EtOH (10 mL). The solution was added with 80% hydrazine hydrate (348 mg, 5.56 mmol, 3.5 eq.) to react at 80° C. for 1 h. After the reaction was completed, as detected by TLC, the reaction solution was cooled to room temperature and filtered under vacuum. The filtrate was concentrated, slurried with dichloromethane (10 mL) and filtered, and the filtrate obtained therefrom was concentrated under reduced pressure. The crude product was purified by preparative thin-layer chromatography (DCM:MeOH=10:1) to give an oily liquid (260 mg). The oily liquid was added with dichloromethane (5 mL). The mixture was added with 20% hydrogen chloride ethanol solution (104 mg) dropwise, stirred for 10 min and concentrated under reduced pressure to give the product (238 mg, yield: 46.2%).

$^1$H-NMR (400 MHz, DMSO-d$_6$) δ(ppm): 7.88 (d, 1H), 7.67-7.64 (d, 2H), 7.47-7.43 (d, 1H), 7.38 (s, 0.5H), 7.11 (s, 0.5H), 6.60-6.59 (s, 1H), 5.04-5.03 (s, 2H), 4.34 (m, 2H), 4.06 (m, 2H), 3.23-3.17 (m, 4H), 2.31-2.21 (m, 2H).

Molecular formula: C$_{16}$H$_{19}$ClFN$_3$O, molecular weight: 323.8, LC-MS (Pos, n/z)=287.65[M+H]$^+$.

Example 39: Synthesis of (E)-(1-(2-(aminomethyl)-3-fluoroallyl)-1H-indol-5-yl)(4-methoxypiperidin-1-yl)methanone (Compound C14) Hydrochloride

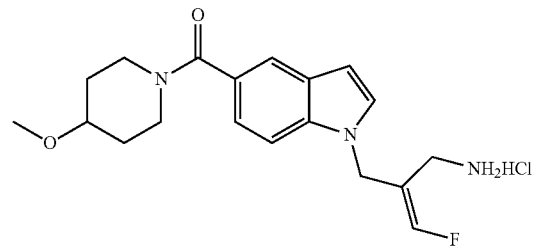

Step 1: Synthesis of (1H-indol-5-yl)(4-methoxypiperidin-1-yl)methanone

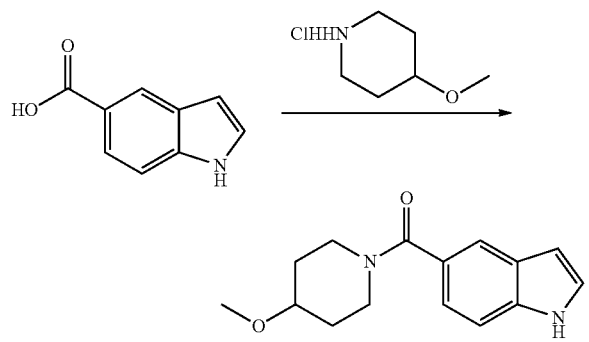

Materials 1H-indole-5-carboxylic acid (1 g, 6.2 mmol, 1.0 eq.) an DIPEA (2.4 g, 18.6 mmol, 3.0 eq.) were dissolved in N,N-dimethylacetamide (5 mL), and nitrogen was charged to replace by evacuation. The solution was cooled to 0° C., and added with HATU (3.5 g, 9.3 mmol, 1.5 eq.) to react for 0.5 h. The reaction solution was added with 4-methoxypiperidine hydrochloride (1.88 g, 12.41 mmol, 2.0 eq.) to react for 1 h. After no materials were left, as detected by TLC, the reaction solution was added with saturated ammonium chloride (50 mL) and water (50 mL), stirred for 10 min and extracted with ethyl acetate (50 mL×3). The organic phases were combined, washed with water (50 mL), dried over anhydrous magnesium sulfate and filtered, and the filtrate was concentrated under reduced pressure to give the product (1.6 g, yield: 100%).

Step 2: Synthesis of (Z)-2-(3-fluoro-2-((5-(4-methoxypiperidine-1-carbonyl)-1H-indol-1-yl) methyl)allyl)isoindoline-1,3-dione

The intermediate (1H-indol-5-yl)(4-methoxypiperidin-1-yl)methanone (500 mg, 1.94 mmol, 1.0 eq.) was dissolve in N,N-dimethylacetamide (5 mL). Nitrogen was charged to replace by evacuation, and the solution was cooled to 0° C., added with sodium hydride (mass fraction: 60%, 85.2 mg, 2.13 mmol, 1.1 eq.) and stirred for 0.5 h. The mixture was added with (E)-2-(2-(bromomethyl)-3-fluoroallyl)isoindoline-1,3-dione (694 mg, 2.33 mmol, 1.2 eq.) to react for 18 h. When there were a small amount of materials left, as detected by TLC, the reaction solution was added with saturated aqueous ammonium chloride solution (50 mL) and water (20 mL), stirred for 10 min and extracted with ethyl acetate (50 mL×3). The organic phases were combined, washed with water (50 mL), dried over anhydrous magnesium sulfate and filtered. The filtrate was concentrated under reduced pressure, and the crude product was purified by preparative thin-layer chromatography (MeOH:DCM=1:20) to give the product (431 mg, yield: 48.1%).

Step 3: Synthesis of (E)-(1-(2-(aminomethyl)-3-fluoroallyl)-1H-indol-5-yl)(4-methoxypiperidin-1-yl)methanone hydrochloride

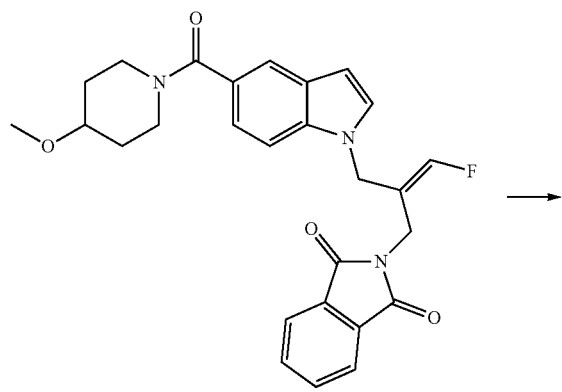

The intermediate (Z)-2-(3-fluoro-2-((5-(4-methoxypiperidine-1-carbonyl)-1H-indol-1-yl)methyl)allyl)isoindoline-1,3-dione (431 mg, 0.93 mmol, 1.0 eq.) was dissolved in EtOH (10 mL). The solution was added with 80% hydrazine hydrate (204.5 mg, 3.26 mmol, 3.5 eq.) to react at 80° C. for 1 h. After the reaction was completed, as detected by TLC, the reaction solution was cooled to room temperature and filtered under vacuum. The filtrate was concentrated, slurried with dichloromethane (10 mL) and filtered, and the filtrate obtained therefrom was concentrated under reduced pressure. The crude product was purified by preparative thin-layer chromatography (DCM:MeOH=10:1) to give an oily liquid (86 mg). The oily liquid was added with dichloromethane (5 mL). The mixture was added with 20% hydrogen chloride ethanol solution (45 mg) dropwise, stirred for 10 min and concentrated under reduced pressure to give the product (84 mg, yield: 23.6%).

$^1$H-NMR (400 MHz, DMSO-$d_6$) δ(ppm): 8.44 (s, 3H), 7.67-7.63 (d, 3H), 7.40 (s, 0.5H), 7.27-7.18 (d, 1H), 7.13 (s, 0.5H), 6.57-6.56 (d, 1H), 5.04 (m, 2H), 3.76 (m, 2H), 3.21-3.21 (m, 7H), 1.84 (m, 2H), 1.44-1.40 (m, 2H).

Molecular formula: $C_{19}H_{25}ClFN_3O_2$, molecular weight: 381.88, LC-MS (Pos, m/z)=346.17[M+H]$^+$.

Example 40: Synthesis of (E)-(1-(2-(aminomethyl)-3-fluoroallyl)-1H-indol-5-yl)(4-methoxy-4-methylpiperidin-1-yl)methanone (Compound C15) Hydrochloride

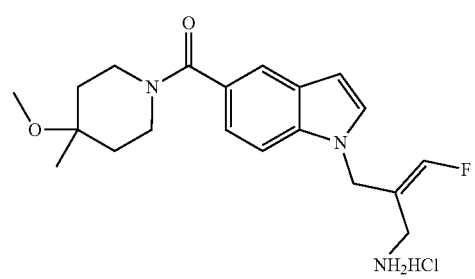

Step 1: Synthesis of (1H-indol-5-yl)(4-methoxy-4-methylpiperidin-1-yl) methanone

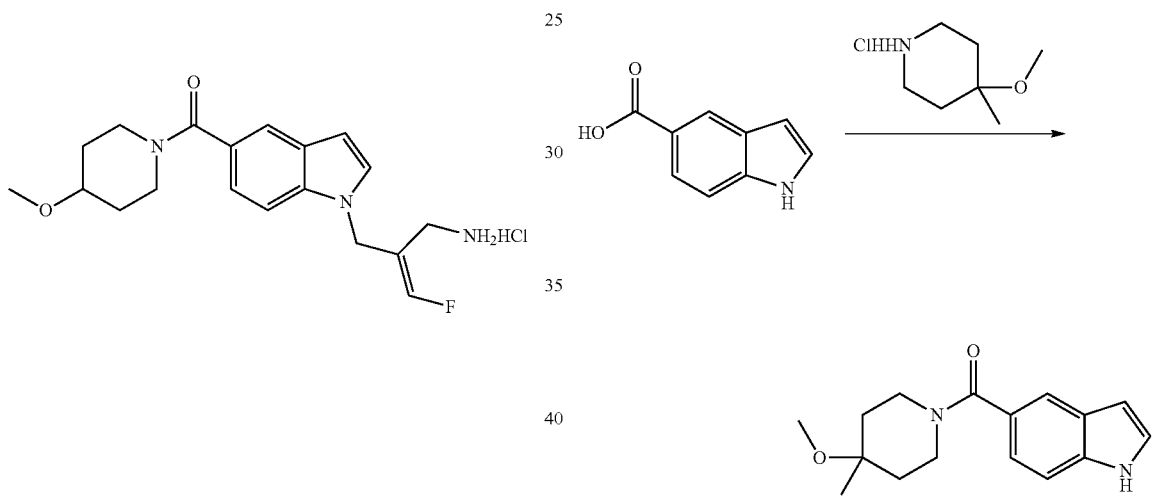

Materials 1H-indole-5-carboxylic acid (1 g, 6.2 mmol, 1.0 eq.) and DIPEA (2.4 g, 18.6 mmol, 3.0 eq.) were dissolved in N,N-dimethylacetamide (5 mL), and nitrogen was charged to replace by evacuation. The solution was cooled to 0° C., and added with HATU (3.5 g, 9.3 mmol, 1.5 eq.) to react for 0.5 h. The reaction solution was added with 4-methoxy-4-methylpiperidine hydrochloride (1.88 g, 12.41 mmol, 2.0 eq.) to react for 1 h. After no materials were left, as detected by TLC, the reaction solution was added with water (50 mL), stirred for 10 min and extracted with ethyl acetate (50 mL×3), followed by liquid separation. The organic phases were combined, washed with water (50 mL), dried over anhydrous magnesium sulfate and filtered, and the filtrate was concentrated under reduced pressure to give the product (1.68 g, yield: 100%).

Step 2: Synthesis of (Z)-2-(3-fluoro-2-((5-(4-methoxy-4-methylpiperidine-1-carbonyl)-1H-indol-1-yl)methyl)allyl)isoindoline-1,3-dione

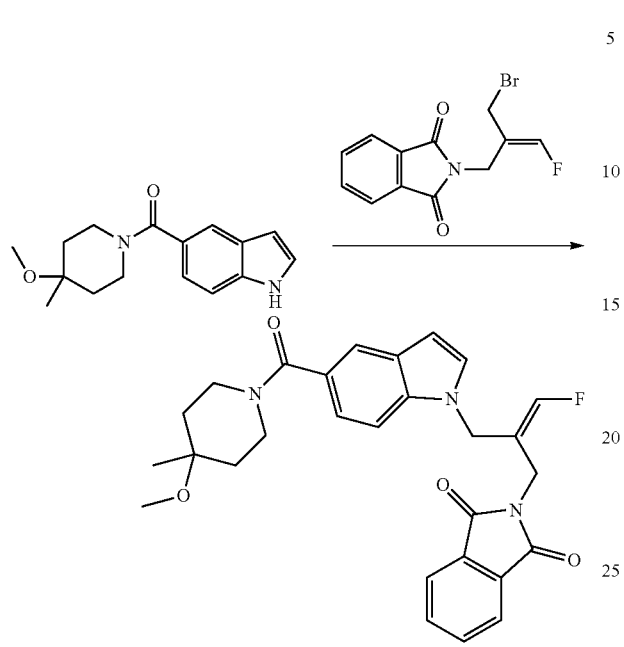

The intermediate (1H-indol-5-yl)(4-methoxy-4-methylpiperidin-1-yl) methanone (500 mg, 1.84 mmol, 1.0 eq.) was dissolve in N,N-dimethylacetamide (5 mL). Nitrogen was charged to replace by evacuation, and the solution was cooled to 0° C., added with sodium hydride (mass fraction: 60%, 80.9 mg, 2.13 mmol, 1.1 eq.) and stirred for 0.5 h. The mixture was added with (E)-2-(2-(bromomethyl)-3-fluoroallyl)isoindoline-1,3-dione (658.2 mg, 2.20 mmol, 1.2 eq.) to react for 1 h. When there were a small amount of materials left, as detected by TLC, the reaction solution was added with saturated aqueous ammonium chloride solution (50 mL) and water (50 mL), stirred overnight and extracted with ethyl acetate (50 mL×3). The organic phases were combined, washed with water (50 mL), dried over anhydrous magnesium sulfate and filtered, and the filtrate was concentrated under reduced pressure to give an oily liquid. The oily liquid was purified by preparative thin-layer chromatography (MeOH:DCM=1:20) to give the product (421 mg, yield: 48.1%).

Step 3: Synthesis of (E)-(1-(2-(aminomethyl)-3-fluoroallyl)-1H-indol-5-yl)(4-methoxy-4-methylpiperidin-1-yl)methanone hydrochloride

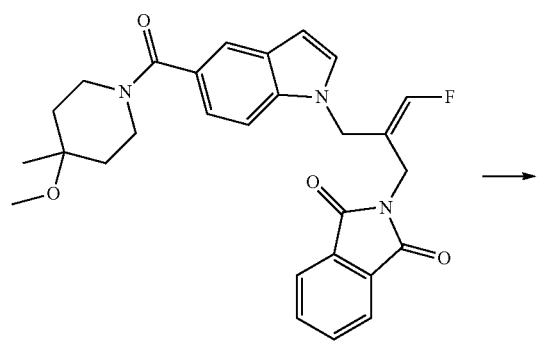

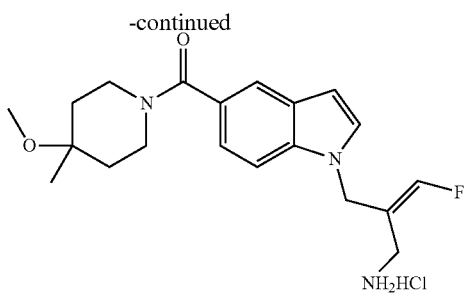

The intermediate (Z)-2-(3-fluoro-2-((5-(4-methoxy-4-methylpiperidine-1-carbonyl)-1H-indol-1-yl)methyl)allyl) isoindoline-1,3-dione (421 mg, 0.88 mmol, 1.0 eq.) was dissolved in EtOH (15 mL). The solution was added with 80% hydrazine hydrate (193.9 mg, 3.10 mmol, 3.5 eq.) to react at 80° C. for 1 h. After the reaction was completed, as detected by TLC, the reaction solution was cooled to room temperature and filtered under vacuum. The filtrate was concentrated to give a white solid. Dichloromethane (10 mL) was added for slurrying, followed by filtration. The mother liquor was concentrated under reduced pressure. The crude product was purified by preparative thin-layer chromatography (DCM:MeOH=10-15:1) to give a product (200 mg). Dichloromethane (5 mL) was added, 20% hydrogen chloride ethanol solution (102 mg) was added dropwise, and stirring was carried out for 10 min. The product (200 mg, yield: 57%) was obtained by concentration under reduced pressure.

$^1$H-NMR (400 MHz, DMSO-d$_6$) δ(ppm): 8.46 (s, 3H), 7.66-7.62 (d, 3H), 7.41 (s, 0.5H), 7.21-7.18 (d, 1H), 7.13 (s, 0.5H), 6.56-6.55 (s, 1H), 5.04-5.04 (m, 2H), 3.43 (m, 2H), 3.26-3.20 (m, 4H), 3.12 (s, 3H), 1.67 (m, 2H), 1.49-1.42 (m, 2H), 1.14 (s, 3H).

Molecular formula: C$_{20}$H$_{27}$ClFN$_3$O$_2$, molecular weight: 395.9, LC+MS (Pos, n/z)=360.14[M+H]$^+$.

Example 41: Synthesis of (E)-2-(2-(aminomethyl)-3-fluoroallyl)-5-neopentyl-2,5,6,7-tetrahydro-4H-pyrazolo[4,3-c]pyridin-4-one (Compound A37) Hydrochloride

Step 1: Synthesis of ethyl 3-(neopentylamino)propionate

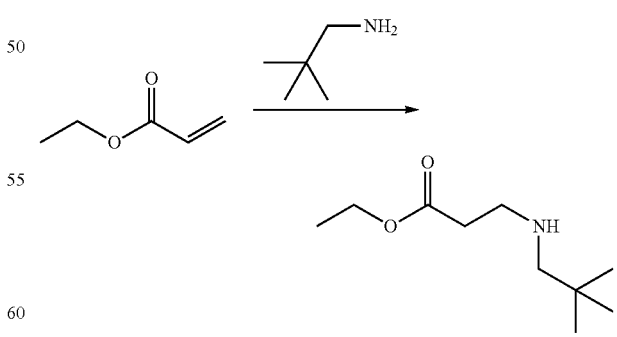

Neopentylamine (31.38 g, 0.36 mol, 1.2 eq.) was dissolved in ethanol (100 mL). Ethyl acrylate (30 g, 0.3 mol, 1.0 eq.) was slowly added dropwise at 10° C., and after the addition was completed, reaction was carried out at 20° C. for 3 h. After no materials were left, as detected by TLC, the reaction solution was concentrated under reduced pressure to give the product (56.18 g, yield: 100%).

Step 2: Synthesis of ethyl 3-((3-ethoxy-3-oxopropyl)(neopentyl)amino)-3-oxopropanoate

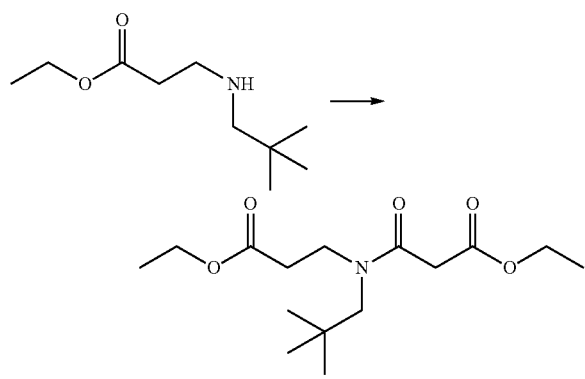

The intermediate ethyl 3-(neopentylamino)propionate (56.18 g, 0.3 mol, 1.0 eq.), ethyl potassium malonate (61.27 g, 0.36 mol, 1.2 eq.), 4-dimethylaminopyridine (7.33 g, 0.06 mol, 0.2 eq.) and triethylamine (39.46 g, 0.39 mol, 1.3 eq.) were dissolved in dichloromethane (300 mL) and the solution was stirred for 5 min. The solution was added with 1-(3-dimethylaminopropyl)-3-ethylcarbodiimide hydrochloride (69.01 g, 0.36 mol, 1.2 eq.) under an ice bath batch by batch to react for 15 h. After the reaction was completed, as detected by TLC, the reaction solution was added with water (200 mL), followed by liquid separation. The aqueous phase was extracted with dichloromethane (200 mL). The organic phases were combined and concentrated under reduced pressure. The crude product was dissolved in ethyl acetate (200 mL), the pH was adjusted to 5 with hydrochloric acid, and liquid separation was performed. The organic phase was washed with saturated aqueous sodium bicarbonate solution (200 mL), dried over anhydrous sodium sulfate and filtered, and concentration under reduced pressure was performed to give the product (85 g, yield: 94%).

Step 3: Synthesis of ethyl 1-neopentyl-2,4-dioxopiperidine-3-carboxylate

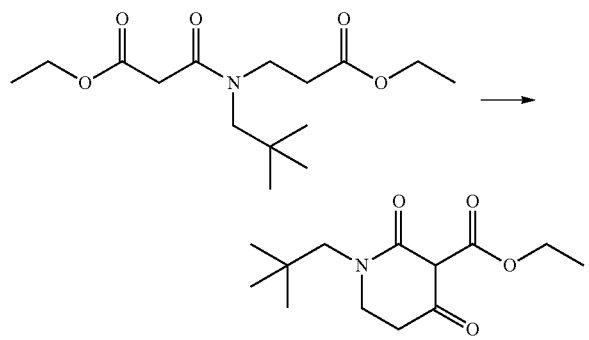

The intermediate ethyl 3-((3-ethoxy-3-oxopropyl)neopentyl)amino)-3-oxopropionate (85 g, 0.282 mmol, 1.0 eq.) and sodium tert-butoxide (32.48 g, 0.338 mol, 1.2 eq.) were dissolved in ethanol (400 mL) to react at 60° C. for 30 min. After the reaction was completed, as detected by TLC, the reaction solution was concentrated under reduced pressure to give the product, which was directly used in the next step.

Step 4: Synthesis of 1-neopentylpiperidine-2,4-dione

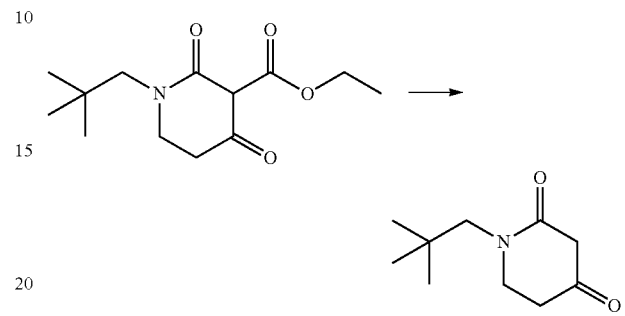

The crude product obtained in the previous step was dissolved in water. The pH was adjusted to 3, and the solution was heated to 90° C. to react for 3 h. After the reaction was completed, as detected by TLC, the reaction solution was cooled to room temperature and added with sodium chloride solid until saturated. Extraction was performed with ethyl acetate (300 mL×3), and the organic phase was dried and concentrated. The crude product was slurried with MTBE:PE (1:1), and filtration under vacuum was performed. The filter cake was dried to give the product (42 g, two-step yield: 81%).

Step 5: Synthesis of 3-((dimethylamino)methylene)-1-neopentylpiperidine-2,4-dione

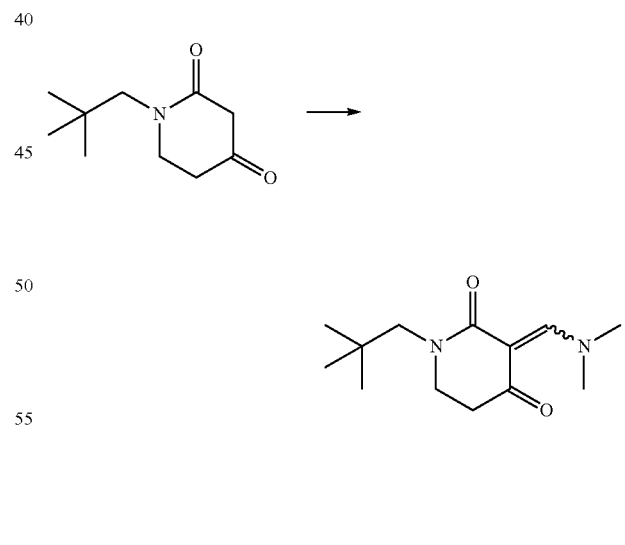

1-neopentylpiperidine-2,4-dione (5 g, 27.28 mmol, 1.0 eq.) was added into N,N-dimethylformamide dimethyl acetal (3.58 g, 30 mmol, 1.1 eq.) batch by batch to react for 30 min. After the reaction was completed, as detected by TLC, concentration under reduced pressure was performed, and the crude product was treated with isopropanol to give the product (6.5 g, yield: 100%).

Step 6: Synthesis of 5-neopentyl-2,5,6,7-tetrahydro-4H-pyrazolo[4,3-c]pyridin-4-one

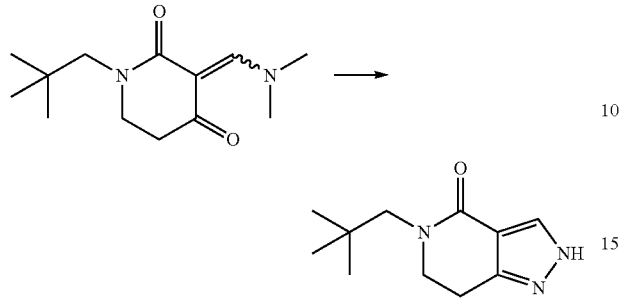

The intermediate 3-((dimethylamino)methylene)-1-neopentylpiperidine-2,4-dione (6.5 g, 27.28 mmol, 1.0 eq.) and hydrazine hydrate (1.77 g, 30 mmol, 1.1 eq.) were dissolved in isopropanol (30 mL) to react at 80° C. for 1 h. After the reaction was completed, as detected by TLC, the reaction solution was concentrated under reduced pressure, and the crude product was purified by silica gel column chromatography (ethyl acetate) to give the product (4.4 g, yield: 77%).

Step 7: Synthesis of (E)-2-(3-fluoro-2-((5-neopentyl-4-oxo-4,5,6,7-tetrahydro-2H-pyrazolo[4,3-c]pyridin-2-yl)methyl)allyl)isoindoline-1,3-dione

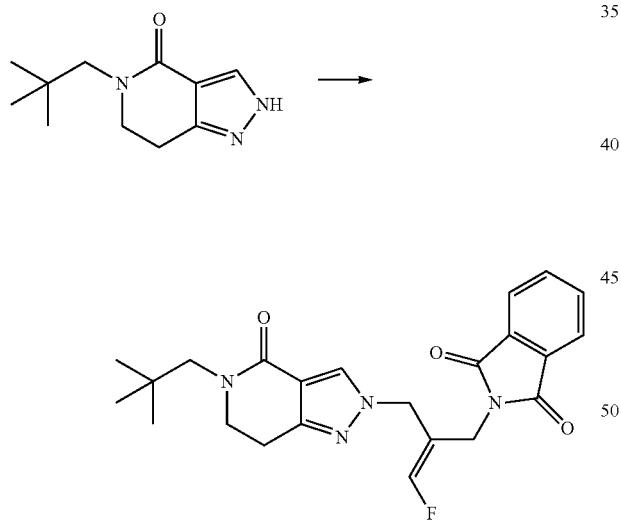

5-neopentyl-2,5,6,7-tetrahydro-4H-pyrazolo[4,3-c]pyridin-4-one (4.4 g, 21.22 mmol, 1.0 eq.), (E)-2-(2-(bromomethyl)-3-fluoroallyl)isoindoline-1,3-dione (6.96 g, 23.34 mmol, 1.1 eq.), potassium carbonate (3.22 g, 23.34 mmol, 1.1 eq.) and TBAB (684 mg, 2.12 mmol, 0.1 eq.) were dissolved in absolute ethanol (50 mL) to react for 17 h. After the reaction was completed, as detected by TLC, the reaction solution was concentrated under reduced pressure. The crude product was purified by silica gel column chromatography (PE:EA=1:1) to give the product (4.0 g, yield: 44%).

Step 8: Synthesis of (E)-2-(2-(aminomethyl)-3-fluoroallyl)-5-neopentyl-2,5,6,7-tetrahydro-4H-pyrazolo[4,3-c]pyridin-4-one hydrochloride

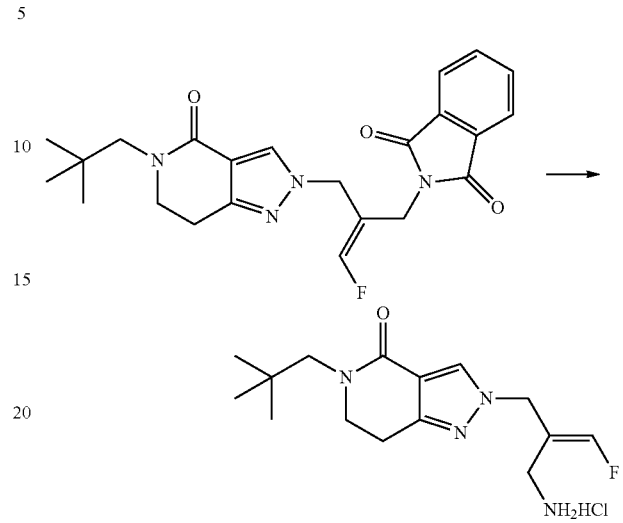

The intermediate (E)-2-(3-fluoro-2-((5-neopentyl-4-oxo-4,5,6,7-tetrahydro-2H-pyrazolo[4,3-c]pyridin-2-yl)methyl)allyl)isoindoline-1,3-dione (4.0 mg, 9.42 mmol, 1.0 eq.) and hydrazine hydrate (884 mg, 14.13 mmol, 1.5 eq.) were dissolved in EtOH (40 mL) to react at 80° C. for 1 h. After the reaction was completed, as detected by LC-MS, the reaction solution was cooled to room temperature and filtered under vacuum. The filtrate was concentrated under reduced pressure. The crude product was slurried with isopropyl acetate (20 mL) and filtered under vacuum. 20% hydrogen chloride ethanol solution (2.06 g, 1.2 eq.) was then added to the filtrate under an ice bath and the mixture was stirred for 10 min. A large amount of white solid was precipitated. Filtration under vacuum was performed, and the filter cake was dried at 40° C. to give the product (2.32 g, yield: 74%).

$^1$HNMR (300 MHz, DMSO-$d_6$) δ(ppm): 8.49 (s, 3H), 8.27 (s, 1H), 7.41 (s, 0.5H), 7.13 (s, 0.5H), 4.94 (d, 2H), 3.55-3.59 (t, 2H), 3.34-3.35 (d, 2H), 3.20 (s, 2H) 2.81-2.85 (t, 2H), 0.91 (s, 9H).

Molecular formula: $C_{15}H_{24}ClFN_4O$, molecular weight: 330.83, LC-MS (Pos, m/z)=295.12[M+H]$^+$.

Example 42: Synthesis of (E)-(1-(2-(aminomethyl)-3-fluoroallyl)-1H-indole-5-yl)(pyrrolidin-1-yl)methanone (Compound C7) Hydrochloride

Step 1: Synthesis of (Z)-2-(3-fluoro-2-((5-(pyrrolidine-1-carbonyl)-1H-indol-1-yl)methyl)allyl)isoindoline-1,3-dione

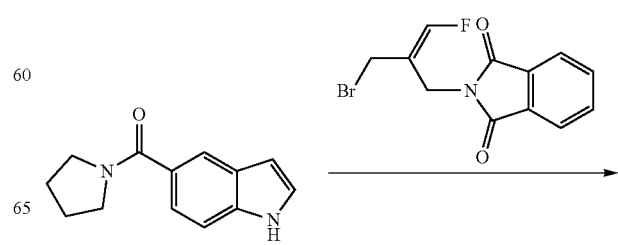

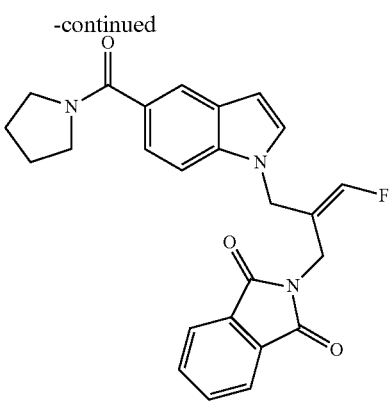

The intermediate (1H-indol-5-yl)(pyrrolidin-1-yl)methanone (500 mg, 2.33 mmol, 1.0 eq.) was dissolve in N,N-dimethylacetamide (3 mL). Nitrogen was charged to replace by evacuation, and the solution was cooled to 0° C., added with sodium hydride (mass fraction: 60%, 102.6 mg, 2.56 mmol, 1.1 eq.) and stirred for 0.5 h. The mixture was added with a solution of (E)-2-(2-(bromomethyl)-3-fluoroallyl)isoindoline-1,3-dione (833.5 mg, 2.80 mmol, 1.2 eq.) in N,N-dimethylacetamide (2 mL) dropwise to react for 1 h. When less than 10% of materials were left, as detected by LC-MS, the reaction solution was added with saturated aqueous ammonium chloride solution (50 mL), stirred for 10 min and extracted with ethyl acetate (50 mL×3). The organic phases were combined and washed with water (50 mL), liquid separation was performed, and drying was performed with anhydrous magnesium sulfate, followed by filtration. The filtrate was concentrated under reduced pressure, and the crude product was purified by preparative thin-layer chromatography (DCM:MeOH=20:1) to give the product (755 mg, yield: 77.8%).

Step 2: Synthesis of (E)-(1-(2-(aminomethyl)-3-fluoroallyl)-1H-indol-5-yl)(pyrrolidin-1-yl)methanone hydrochloride

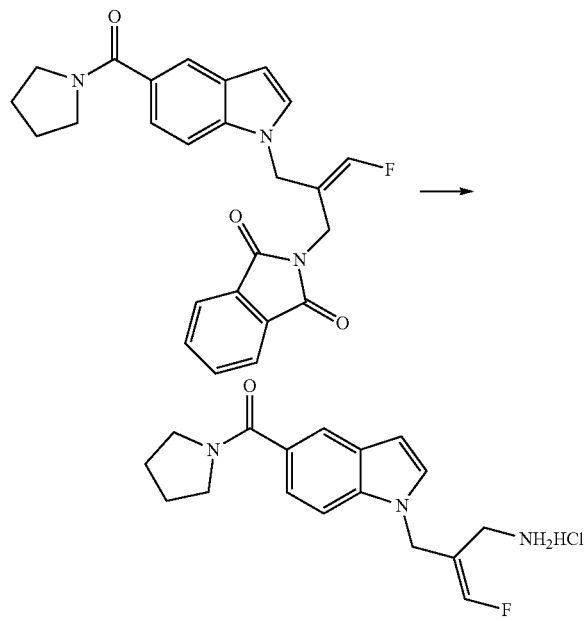

The intermediate (Z)-2-(3-fluoro-2-((5-(pyrrolidine-1-carbonyl)-1H-indol-1-yl)methyl)allyl)isoindoline-1,3-dione (755 mg, 1.81 mmol, 1.0 eq.) was dissolved in EtOH (10 mL), and the solution was added with hydrazine hydrate (mass fraction: 80%, 397 mg, 6.34 mmol, 3.5 eq.) to react at 80° C. for 2 h. After no materials were left, as detected by TLC, the reaction solution was cooled to room temperature, filtered under vacuum and rinsed with ethanol. The filtrate was concentrated to give a white solid, which was slurried with dichloromethane (10 mL) for 5 min and filtered. The filter cake was rinsed with DCM. The filtrates were combined and concentrated under reduced pressure to give an oily liquid (487 mg), which was purified by thin-layer chromatography (DCM:MeOH=10:1) to give an oily liquid (357 mg). The oily liquid was added with dichloromethane (5 mL) for dissolution. The solution was added with 20% hydrogen chloride ethanol solution (104.2 mg), stirred for 10 min and concentrated under reduced pressure to give a light yellow solid (325 mg). The solid was purified by preparative HPLC (0.05% hydrochloric acid:water:acetonitrile) to give the product (120 mg, yield: 19.6%).

$^1$H-NMR (300 MHz, DMSO-$d_6$) δ(ppm): 8.58 (s, 3H), 7.78-7.77 (s, 1H), 7.70-7.64 (d, 2H), 7.41 (s, 0.5H), 7.35-7.32 (d, 1H), 7.13 (s, 0.5H), 6.56-6.55 (d, 1H), 5.08-5.07 (d, 2H), 3.47 (m, 4H), 3.24-3.23 (d, 2H), 1.85-1.82 (m, 4H).

Molecular formula: $C_{17}H_{21}ClFN_3O$, molecular weight: 337.82, LC-MS (Pos, m/z)=302.10 [M+H$^+$]

Example 43: Synthesis of (E)-2-(2-(aminomethyl)-3-fluoroallyl)-5-cyclopropyl-6,7-dihydroisoxazolo[4,5-c]pyridine-3,4(2H,5H)-dione (Compound A18) Hydrochloride

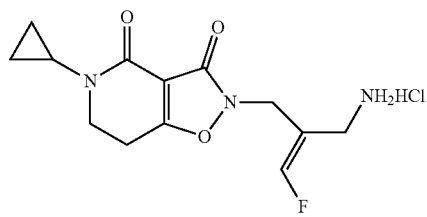

Step 1: Synthesis of 5-cyclopropyl-6,7-dihydroisoxazolo[4,5-c]pyridine-3,4(2H,5H)-dione

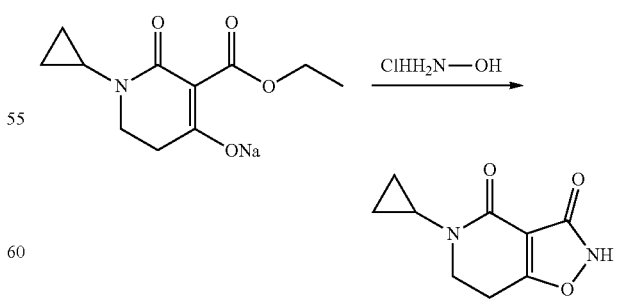

Sodium 1-cyclopropyl-5-(ethoxycarbonyl)-6-oxo-1,2,3,6-tetrahydropyridin-4-olate (10.0 g, 0.040 mol, 1.0 eq.), sodium hydroxide (19.4 g, 0.485 mol, 12 eq.), hydroxylamine hydrochloride (30.9 g, 0.444 mol, 11 eq.) were added into ethanol (100 mL) and water (10 mL), with the pH adjusted to 7-8 at room temperature, and reaction was carried out at 50° C. for 17 h. After the reaction was completed, as detected by LC-MS, the reaction solution was cooled to room temperature and filtered. The filtrate was concentrated under reduced pressure, added with ethanol (100 mL), heated to 60° C. for dissolution and filtered while hot. The filtrate was concentrated under reduced pressure to give the product (5.1 g, yield: 64.97%).

Step 2: Synthesis of (E)-5-cyclopropyl-2-(2-((1,3-dioxoisoindolin-2-yl) methyl)-3-fluoroallyl)-6,7-dihydroisoxazolo[4,5-c]pyridine-3,4(2H,5H)-dione

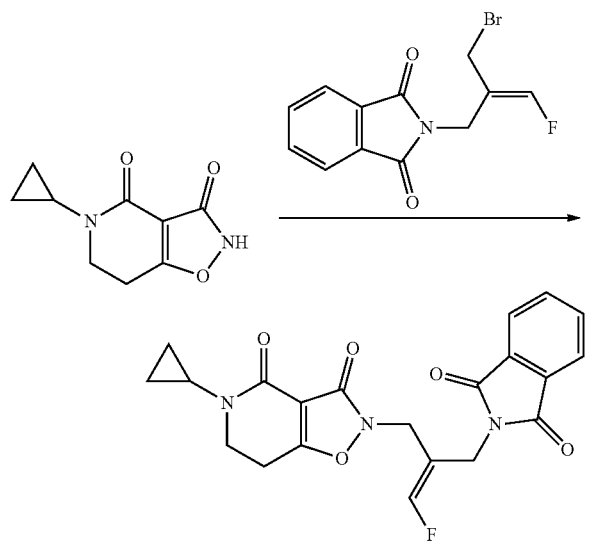

The intermediate 5-cyclopropyl-6,7-dihydroisoxazolo[4,5-c]pyridine-3,4(2H,5H)-dione (1.00 g, 5.15 mmol, 1 eq.) was dissolved in DMF (15 mL). The solution was added with sodium hydride (mass fraction: 60%, 0.25 g, 6.18 mmol, 1.2 eq.) at 0° C. and stirred for 15 min while temperature was kept. The mixture was added with (E)-2-(2-(bromomethyl)-3-fluoroallyl)isoindoline-1,3-dione (1.84 g, 6.18 mmol, 1.2 eq.) to react at 60° C. for 17 h. The reaction solution was cooled, added with water (15 mL) and extracted with dichloromethane (30 mL×3), followed by liquid separation. The organic phase was dried over anhydrous sodium sulfate and concentrated under reduced pressure, and the crude product was separated by silica gel column chromatography (DCM:MeOH=200:1) to give the product (688 mg, yield: 32.4%).

Step 3: Synthesis of (E)-2-(2-(aminomethyl)-3-fluoroallyl)-5-cyclopropyl-6,7-dihydroisoxazolo[4,5-c]pyridine-3,4(2H,5H)-dione hydrochloride

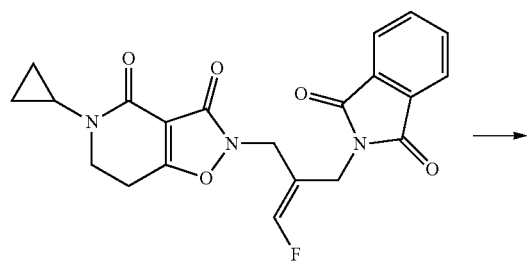

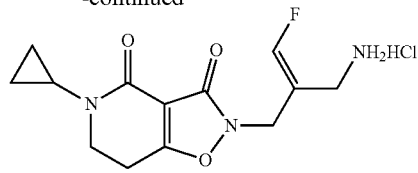

The intermediate (E)-5-cyclopropyl-2-(2-((1,3-dioxoisoindolin-2-yl) methyl)-3-fluoroallyl)-6,7-dihydroisoxazolo[4,5-c]pyridine-3,4(2H,5H)-dione (545 mg, 1.32 mmol, 1.0 eq.) was dissolved in absolute ethanol (20 mL). The solution was added with hydrazine hydrate (85%, 273 mg, 4.64 mmol, 3.5 eq.) and refluxed for 2 h until the reaction was completed. The reaction solution was thermally filtered. The filtrate was cooled and then filtered under vacuum. The filtrate was concentrated under reduced pressure, added with EA (20 mL), refluxed at 85° C. and filtered while hot. The filtrate was cooled and then filtered again, and the filtrate obtained therefrom was concentrated under reduced pressure. The crude product was separated by preparative thin-layer chromatography (DCM:MeOH=10:1) to give an oily product. The oily product was added with a small amount of ethanol for dissolution, hydrogen chloride ethanol solution was added dropwise, and white solid was precipitated. Filtration under vacuum was carried out to give the product (62.92 mg, yield: 16.9%).

$^1$HNMR (400 MHz, DMSO-d$_6$) δ(ppm): 8.40 (s, 3H), 7.22-7.42 (d, J=80 Hz, 1H), 4.74 (s, 2H), 3.53-3.56 (t, 2H), 3.49 (s, 2H), 3.05-3.08 (t, 2H), 2.53-2.57 (m, 1H), 0.70-0.74 (m, 2H), 0.54-0.58 (m, 2H).

Molecular formula: $C_{13}H_{17}ClFN_3O_3$, molecular weight: 317.75, LC-MS (Pos, m/z)=282.15[M+H]$^+$.

Example 44: Synthesis of (E)-2-(2-(aminomethyl)-3-fluoroallyl)-5-cyclopropyl-3-phenyl-2,5,6,7-tetrahydro-4H-pyrazolo[4,3-c]pyridin-4-one (Compound A45)

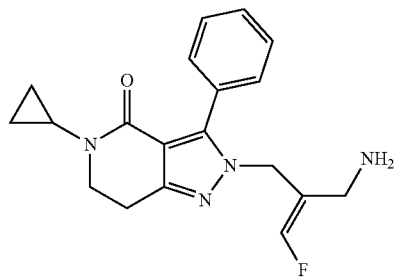 [SMILES: NC/C(=C\F)Cn1nc2c(c1-c1ccccc1)C(=O)N(C1CC1)CC2]

Step 1: Synthesis of 3-benzoyl-1-cyclopropylpiperidine-2,4-dione

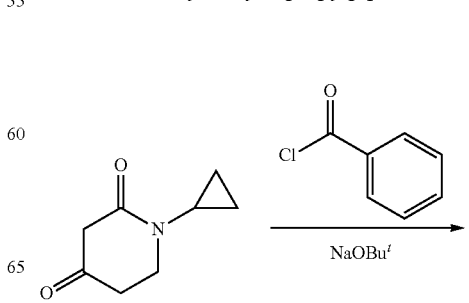

-continued

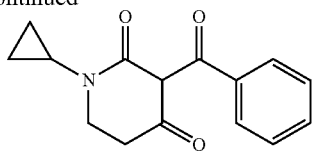

1-cyclopropylpiperidine-2,4-dione (50.00 g, 0.33 mol, 1.0 eq.) was added to a reaction flask, and THF (500 mL) was added. The materials were cooled to 0° C., added with sodium tert-butoxide (66.60 g, 0.69 mol, 2.1 eq.) and stirred for 30 min. Benzoyl chloride (55.06 g, 0.39 mol, 1.2 eq.) was slowly added dropwise at 0° C. After addition, the mixture was incubate at room temperature for 5 h. After the reaction was completed, as detected by TLC, the reaction solution was added with water for dilution, the pH was adjusted to 3, and EA (100 mL×3) was added for extraction. Drying was performed with anhydrous sodium sulfate, followed by concentration under reduced pressure. The crude product was separated by silica gel column chromatography (DCM:MeOH=100:1-50:1) to give the product (28.3 g, yield: 33.7%).

Step 2: Synthesis of 5-cyclopropyl-3-phenyl-2,5,6,7-tetrahydro-4H-pyrazolo[4,3-c]pyridin-4-one

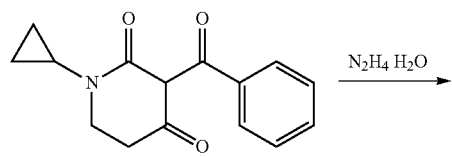

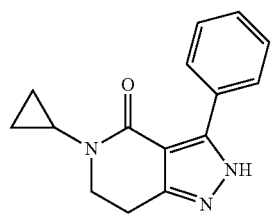

Hydrazine hydrate (85%, 9.72 g, 0.16 mol, 1.5 eq.) was dissolved in ethanol (100 mL), and hydrochloric acid was added to adjust the pH to 3,3-benzoyl-1-cyclopropylpiperidine-2,4-dione (28.30 g, 0.11 mol, 1.0 eq.) was added, and the pH was adjusted to 6. The mixture was heated to reflux for 2 h. After the reaction was completed, as detected by TLC, the reaction solution was concentrated under reduced pressure. The crude product was first separated by silica gel column chromatography (DCM:MeOH=50:1) and then recrystallized with absolute ethanol (50 mL) to give the product (8.0 g, yield: 28.7%).

Step 3: Synthesis of (E)-2-(2-((5-cyclopropyl-4-oxo-3-phenyl-4,5,6,7-tetrahydro-2H-pyrazolo[4,3-c]pyridin-2-yl)methyl)-3-fluoroallyl)isoindoline-1,3-dione

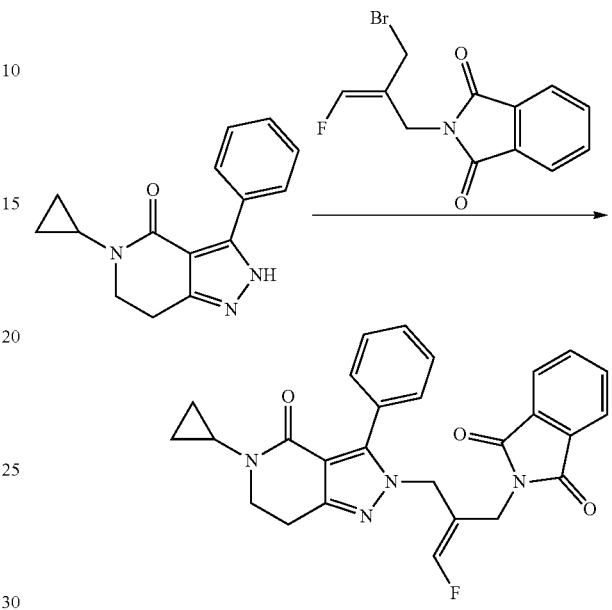

The intermediate 5-cyclopropyl-3-phenyl-2,5,6,7-tetrahydro-4H-pyrazolo [4,3-c]pyridin-4-one (3.00 g, 0.012 mol, 1 eq.), (E)-2-(2-(bromomethyl)-3-fluoroallyl)isoindoline-1,3-dione (3.89 g, 0.013 mol, 1.1 eq.), potassium carbonate (1.80 g, 0.013 mol, 1.1 eq.) and tetrabutylammonium bromide (0.39 g, 0.001 mol, 0.1 eq.) were added into absolute ethanol (30 mL) and the mixture was stirred at room temperature for 72 h. When there was a small amount of pyrazole material left, as detected by TLC, the reaction solution was filtered under vacuum. The filter cake was washed with ethanol. The filtrates were combined, added with MTBE (5 mL), concentrated to half the volume under reduced pressure and cooled to room temperature, and a large amount of white solid was precipitated. Filtration under vacuum was performed, followed by drying. The crude product was recrystallized with ethanol (15 mL) to give the product (1.8 g, yield: 32.1%).

Step 4: Synthesis of (E)-2-(2-(aminomethyl)-3-fluoroallyl)-5-cyclopropyl-3-phenyl-2,5,6,7-tetrahydro-4H-pyrazolo[4,3-c]pyridin-4-one

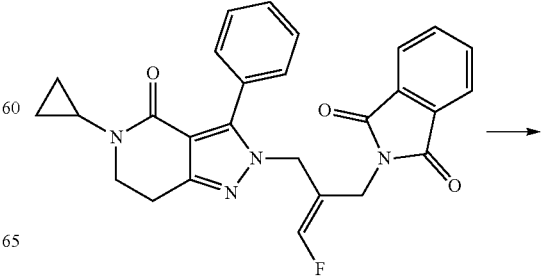

-continued

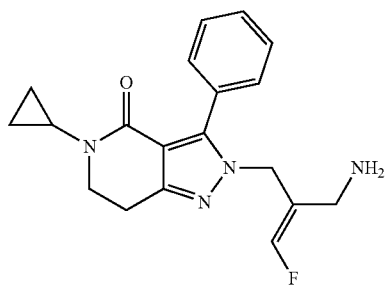

(E)-2-(2-((5-cyclopropyl-4-oxo-3-phenyl-4,5,6,7-tetrahydro-2H-pyrazolo[4,3-c]pyridin-2-yl)methyl)-3-fluoroallyl)isoindoline-1,3-dione (1.80 g, 3.83 mmol, 1.0 eq.) was dissolved in EtOH (18 mL), and the solution was added with hydrazine hydrate (85%, 0.34 g, 5.74 mmol, 1.5 eq.) and reacted at reflux for 1 h. When the reaction was completed, filtration under vacuum was performed. The filtrate was concentrated under reduced pressure, added with isopropyl acetate (30 mL), heated to reflux for 30 min and cooled to room temperature, and a small amount of solid was precipitated. Then filtration under vacuum was performed, the filtrate was concentrated under reduced pressure and a large amount of solid was precipitated. Filtration under vacuum was performed, and the filter cake was washed with a small amount of isopropyl acetate, concentrated and dried to give the product (850 mg, yield: 65.4%).

$^1$HNMR (400 MHz, DMSO-$d_6$) δ(ppm): 8.06-8.08 (m, 2H), 7.32-7.40 (m, 3H), 6.82-7.04 (d, J=84 Hz, 1H), 4.76-4.77 (d, 2H), 3.57-3.60 (t, 2H), 3.32 (brs, 2H), 3.12-3.13 (d, 2H), 2.98-3.02 (t, 2H), 2.60-2.67 (m, 1H), 0.74-0.79 (m, 2H), 0.66-0.72 (m, 2H).

Molecular formula: $C_{19}H_{21}FN_4O$, molecular weight: 340.40, LC-MS (Pos, m/z)=341.12[M+H]$^+$.

Example 45: Synthesis of (E)-2-(2-(aminomethyl)-3-fluoroallyl)-5-cyclopropyl-1-(3-fluorophenyl)-2,5,6,7-tetrahydro-4H-pyrrolo[3,4c]pyridin-4-one (Compound A46) Hydrochloride Synthesis of intermediate tert-butyl (E)-(2-((5-cyclopropyl-1-(3-fluorophenyl)-4-oxo-4,5,6,7-tetrahydro-2H-pyrrolo[3,4-c]pyridin-2-yl)methyl)-3-fluoroallyl)carbamate

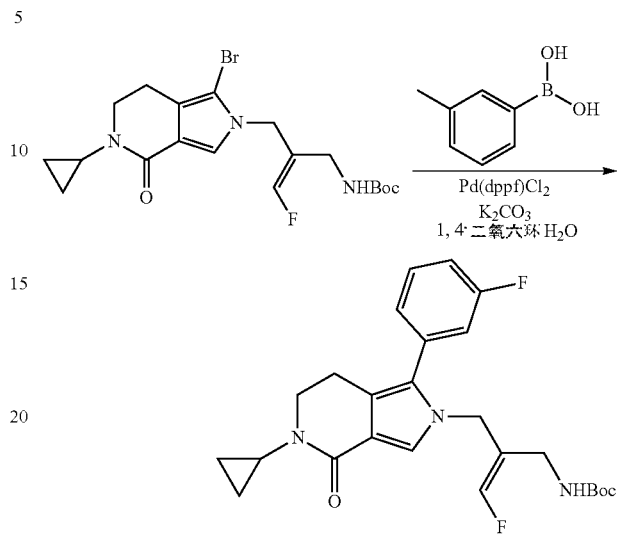

Tert-butyl (E)-(2-((1-bromo-5-cyclopropyl-4-oxo-4,5,6,7-tetrahydro-2H-pyrrolo[3,4-c]pyridin-2-yl)methyl)-3-fluoroallyl)carbamate (150 mg, 0.339 mmol, 1 eq.) and m-fluorophenylboronic acid (72 mg, 0.509 mmol, 1.5 eq.) were dissolved in 1,4-dioxane (5 mL). The solution was added with an aqueous solution (1 mL) of potassium carbonate (118 mg, 0.848 mmol, 2.5 eq.), and Pd(dppf)Cl$_2$ (28 mg, 0.0339 mmol, 0.1 eq.) was added in N$_2$ atmosphere. After addition, reaction was carried out at 90° C. for 17 h. After the reaction was completed, as detected by TLC, the reaction solution was filtered through celite. The filtrate was added with ethyl acetate (20 mL), washed with water (20 mL) and saturated brine (20 mL) in sequence, dried over anhydrous Na$_2$SO$_4$ and filtered. The filtrate was concentrated to give a crude product (190 mg), which was purified by preparative thin-layer chromatography (PE:EA=1:1) to give the product (70 mg, yield: 45%).

Step 2: Synthesis of Compound (E)-2-(2-(aminomethyl)-3-fluoroallyl)-5-cyclopropyl-1-(3-fluorophenyl)-2,5,6,7-tetrahydro-4H-pyrrolo[3,4-c]pyridin-4-one hydrochloride

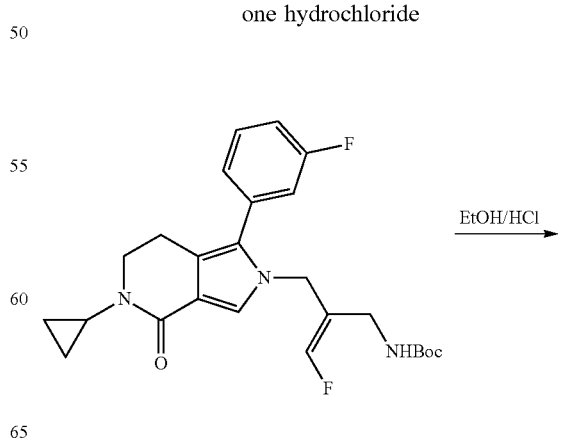

-continued

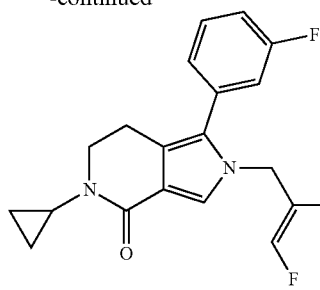

Tert-butyl (E)-(2-((5-cyclopropyl-1-(3-fluorophenyl)-4-oxo-4,5,6,7-tetrahydro-2H-pyrrolo[3,4-c]pyridin-2-yl)methyl)-3-fluoroallyl)carbamate (70 mg, 0.153 mmol, 1 eq.) was dissolved in hydrogen chloride ethanol solution (5 mL) and the solution was stirred for 3 h. After the reaction was completed, as detected by LC-MS, the reaction solution was concentrated and lyophilized to give the product (28 mg, yield: 51%).

$^1$H-NMR (300 MHz, DMSO-d$_6$) δ(ppm): 8.32 (brs, 3H), 7.46-7.52 (m, 2H), 7.19-7.22 (m, 3H), 6.36-6.63 (d, 1H), 4.81 (s, 2H), 3.40-3.44 (t, 2H), 3.12-3.13 (m, 2H), 2.59-2.67 (m, 3H), 0.72-0.78 (m, 2H), 0.58-0.60 (m, 2H).

Molecular formula: $C_{20}H_{21}F_2N_3O$, molecular weight: 357.17, LC-MS (n/z)=358.12 [M+H]$^+$.

Example 46: Synthesis of (E)-2-(2-(aminomethyl)-3-fluoroallyl)-5-(2-methoxyethyl)-2,5,6,7-tetrahydro-4H-pyrazolo[4,3-c]pyridin-4-one (Compound A47) Hydrochloride

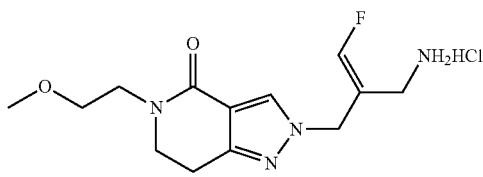

Step 1: Synthesis of ethyl 3-((2-methoxyethyl)amino)propionate

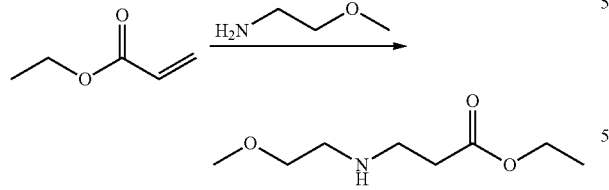

The material 2-methoxyethan-1-amine (10 g, 133.14 mmol, 1.0 eq.) was dissolved in absolute ethanol (100 mL). Ethyl acrylate (11.32 g, 113.06 mmol, 0.85 eq.) was slowly added dropwise under an ice bath. After addition, reaction was carried out for 2 h. After no materials were left, as detected by TLC, the reaction solution was concentrated under reduced pressure at 80° C. to give a crude product, which was used in the next step according to a theoretical amount.

Step 2: Synthesis of ethyl 3-((3-ethoxy-3-oxopropyl)(2-methoxyethyl) amino)-3-oxopropionate

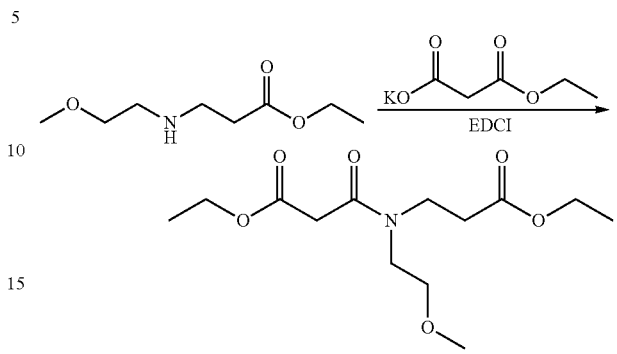

The intermediate ethyl 3-((2-methoxyethyl)amino)propionate (133.14 mmol, 1.0 eq.) was dissolved in dichloromethane (100 mL). The solution was cooled to 0° C. with ice water and sequentially added with ethyl potassium malonate (19.2 g, 133.14 mmol, 1.0 eq.), 1-(3-dimethylaminopropyl)-3-ethylcarbodiimide hydrochloride (26 g, 135.63 mmol, 1.2 eq.), 4-dimethylaminopyridine (1.38 g, 11.32 mmol, 0.1 eq.) and triethylamine (17.2 g, 169.98 mmol, 1.5 eq.). After addition, the materials were incubate at room temperature for 16 h. After no materials were left, as detected by TLC, water (200 mL) was added, concentrated hydrochloric acid (20 mL) was added dropwise, the pH was adjusted to about 5, and liquid separation was performed. The aqueous phase was extracted with dichloromethane (100 mL). The organic phases were combined, washed with 5% aqueous sodium bicarbonate solution (100 mL) and water (100 mL) in sequence, dried over anhydrous magnesium sulfate and filtered. The filtrate was concentrated under reduced pressure to give a yellow oily liquid (26.2 g, two-step yield: 80.3%).

Step 3: Synthesis of ethyl 1-(2-methoxyethyl)-2,4-dioxopiperidine-3-carboxylate

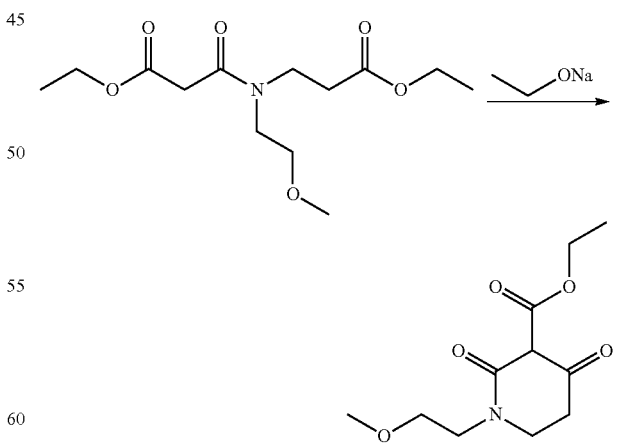

The intermediate ethyl 3-((3-ethoxy-3-oxopropyl)(2-methoxyethyl) amino)-3-oxopropionate (26.2 g, 90.55 mmol, 1.0 eq.) was dissolved in absolute ethanol (100 mL). The solution was added with sodium ethoxide (15.4 g, 226.38 mmol, 2.5 eq.) to react at 80° C. for 1 h. After no materials were left, as detected by TLC, the reaction solution was concentrated under reduced pressure to give the product.

Step 4: Synthesis of 1-(2-methoxyethyl)piperidine-2,4-dione

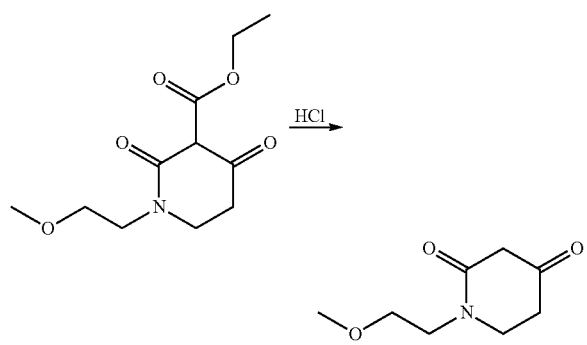

The intermediate ethyl 1-(2-methoxyethyl)-2,4-dioxopiperidine-3-carboxylate (90.55 mmol, 1.0 eq.) was dissolved in water (50 mL). The solution was added with concentrated hydrochloric acid (20 mL) dropwise and heated to 80 to react for 3 h. After no materials were left, as detected by TLC, the reaction solution was cooled to room temperature and extracted with dichloromethane (100 mL×3). The organic phases were combined, dried over anhydrous magnesium sulfate and filtered. The filtrate was concentrated to give the product, which was used in the next step according to a theoretical amount.

Step 5: Synthesis of 3-((dimethylamino)methylene)-1-(2-methoxyethyl) piperidine-2,4-dione

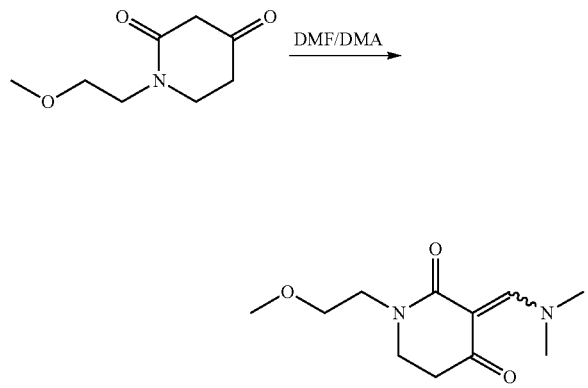

N,N-dimethylformamide dimethyl acetal (11.8 g, 99.60 mmol, 1.1 eq.) was added dropwise into the intermediate 1-(2-methoxyethyl)piperidine-2,4-dione (90.55 mmol, 1.0 eq.), releasing intense heat. After addition, reaction was carried out at room temperature for 1 h. After no materials were left, as detected by TLC, the reaction solution was concentrated under reduced pressure to give the product, which was used in the next step according to a theoretical amount.

Step 6: Synthesis of 5-(2-methoxyethyl)-2,5,6,7-tetrahydro-4H-pyrazolo [4,3-c]pyridin-4-one

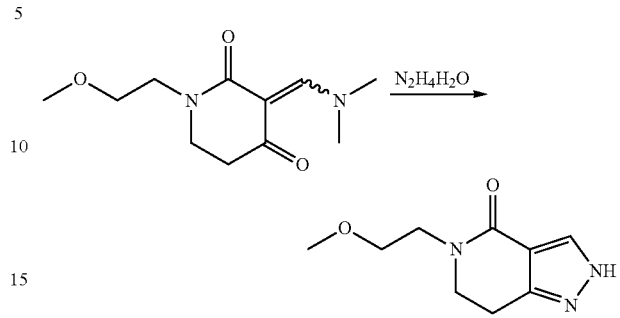

The intermediate 3-((dimethylamino)methylene)-1-(2-methoxyethyl) piperidine-2,4-dione (20.4 g, 90.55 mmol, 1.0 eq.) and hydrazine hydrate (mass fraction: 80%, 6.23 g, 99.60 mmol, 1.1 eq.) were dissolved in methanol (20 mL). The solution was heated to 70° C. to react for 0.5 h. After no materials were left, as detected by TLC, the reaction solution was concentrated under reduced pressure. The crude product was purified by silica gel column chromatography (DCM: MeOH=100:1-60:1) to give the product (10.6 g, four-step yield: 60.2%).

Step 7: Synthesis of (E)-2-(3-fluoro-2-((5-(2-methoxyethyl)-4-oxo-4,5,6,7-tetrahydro-2H-pyrazolo[4,3-c]pyridin-2-yl)methyl)allyl)isoindoline-1,3-dione

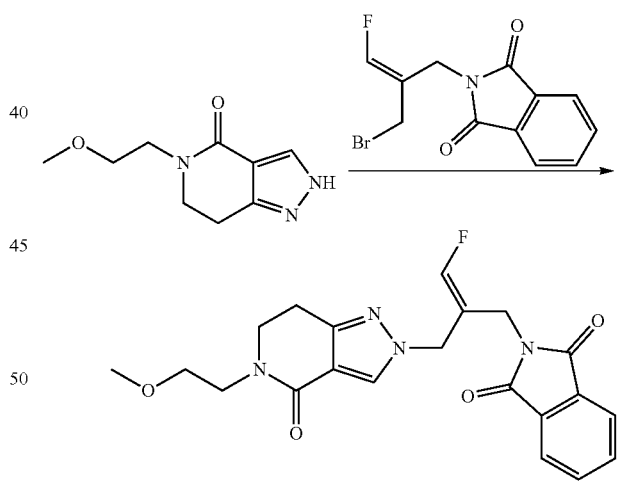

The intermediate 5-(2-methoxyethyl)-2,5,6,7-tetrahydro-4H-pyrazolo[4,3-c]pyridin-4-one (5.0 g, 25.61 mmol, 1.0 eq.), (E)-2-(2-(bromomethyl)-3-fluoroallyl)isoindoline-1,3-dione (8.4 g, 28.17 mmol, 1.1 eq.), anhydrous potassium carbonate (3.9 g, 28.17 mmol, 1.1 eq.) and tetrabutylammonium bromide (825.6 mg, 2.56 mmol, 0.1 eq.) were added to absolute ethanol (50 mL) and the solution was stirred at room temperature for 20 h. When there were a small amount of materials left, as detected by TLC, filtration was performed. The filter cake was rinsed with ethyl acetate. The filtrate was concentrated under reduced pressure, added with ethyl acetate (50 mL) and filtered. The filtrate obtained therefrom was concentrated under reduced pressure to give a crude product (11 g). Part of the crude product (2 g) was purified by preparative thin-layer chromatography (DCM:MeOH=60:1) to give the product (907 mg).

Step 8: Synthesis of (E)-2-(2-(aminomethyl)-3-fluoroallyl)-5-(2-methoxyethyl)-2,5,6,7-tetrahydro-4H-pyrazolo[4,3-c]pyridin-4-one hydrochloride

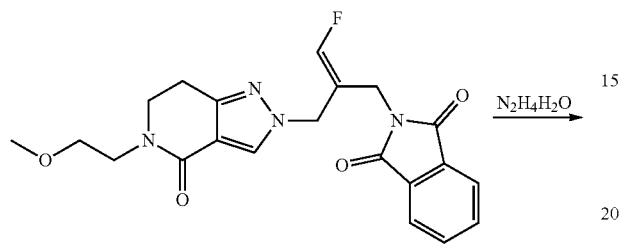

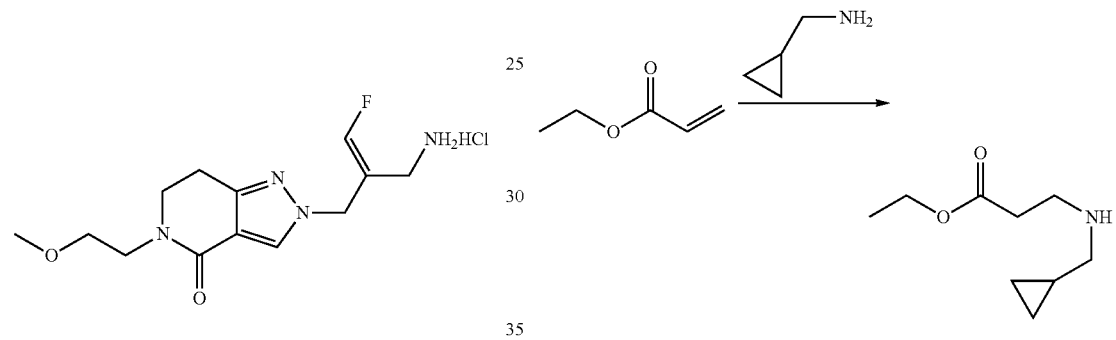

The intermediate (E)-2-(3-fluoro-2-((5-(2-methoxyethyl)-4-oxo-4,5,6,7-tetrahydro-2H-pyrazolo[4,3-c]pyridin-2-yl)methyl)allyl)isoindoline-1,3-dione (900 mg, 2.18 mmol, 1.0 eq.) was dissolved in ethanol (10 mL). The mixture was heated for dissolution and added with hydrazine hydrate (mass fraction: 85%, 128.3 mg, 3.27 mmol, 1.5 eq.) to react at 80° C. for 3 h. When there were a small amount of materials left, as detected by TLC, the reaction solution was cooled to room temperature and filtered under vacuum. The filter cake was rinsed with dichloromethane. The filtrate was concentrated, slurried with dichloromethane (10 mL) and filtered, and the filtrate obtained therefrom was concentrated under reduced pressure. The crude product was purified by preparative thin-layer chromatography (DCM:MeOH=10:1) to give a product (338 mg). Dichloromethane (5 mL) was added. The mixture was added with hydrogen chloride ethanol solution (mass fraction: 20%, 218 mg) dropwise, stirred for 10 min and concentrated under reduced pressure to give the product (317 mg, yield: 45.6%).

$^1$HNMR (300 MHz, DMSO-$d_6$) δ (ppm): 8.34 (s, 3H), 8.10 (s, 1H), 7.40 (s, 0.5H), 7.13 (s, 0.5H), 4.90-4.89 (d, 2H), 3.62-3.54 (m, 4H), 3.48-3.45 (m, 2H), 3.39 (m, 2H), 3.25 (s, 3H), 2.84-2.79 (m, 2H).

Molecular formula: $C_{13}H_{20}ClFN_4O_2$, molecular weight: 318.78, LC-MS (Pos, m/z)=283.07 $[M+H]^+$.

Example 47: Synthesis of (E)-2-(2-(aminomethyl)-3-fluoroallyl)-5-(cyclopropylmethyl)-2,5,6,7-tetrahydro-4H-pyrazolo[4,3-c]pyridin-4-one (Compound A48) Hydrochloride

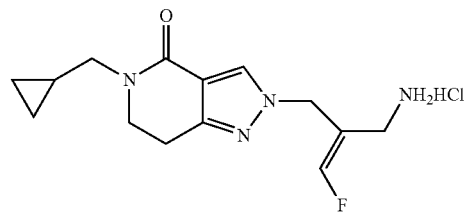

Step 1: Synthesis of ethyl 3-((cyclopropylmethyl)amino)propionate

The material cyclopropanemethanamine (10 g, 99.88 mmol, 1.0 eq.) was dissolved in ethanol (30 mL). The solution was added with ethyl acrylate (12.67 g, 89.89 mmol, 0.9 eq.) dropwise in a slow manner under an ice bath, and after addition, reaction was carried out at room temperature for 16 h. After no materials were left, as detected by TLC, the reaction solution was concentrated under reduced pressure to give the product (15.39 g, yield: 100%).

Step 2: Synthesis of ethyl 3-((cyclopropylmethyl)(3-ethoxy-3-oxopropyl) amino)-3-oxopropionate

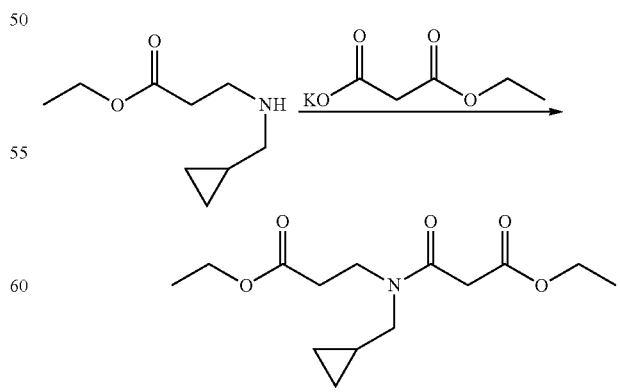

The intermediate ethyl 3-((cyclopropylmethyl)amino)propionate (15.39 g, 89.89 mmol, 1.0 eq.), ethyl potassium malonate (18.36 g, 107.87 mmol, 1.2 eq.), 4-dimethylaminopyridine (2.2 g, 17.98 mmol, 0.2 eq.) and triethylamine (11.83 g, 116.83 mmol, 1.3 eq.) were dissolved in dichloromethane (150 mL). The solution was added with 1-(3-dimethylaminopropyl)-3-ethylcarbodiimide hydrochloride (20.68 g, 107.87 mmol, 1.2 eq.) batch by batch to react for 23 h. After the reaction was completed, as detected by TLC, the reaction solution was added with water (100 mL) and hydrochloric acid (50 mL), followed by liquid separation. The aqueous phase was extracted with dichloromethane (200 mL). The organic phases were combined and concentrated under reduced pressure to give the product (21 g, yield: 81.8%).

Step 3: Synthesis of ethyl 1-(cyclopropylmethyl)-2,4-dioxopiperidine-3-carboxylate

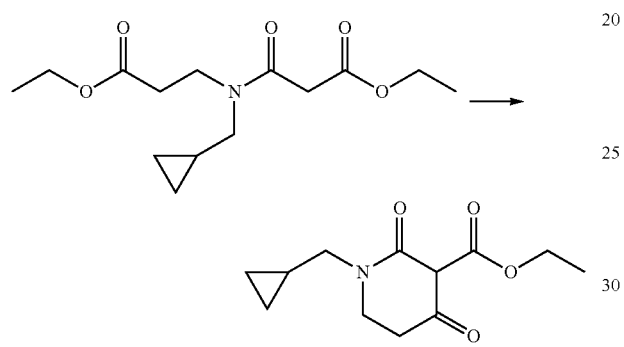

The intermediate ethyl 3-((cyclopropylmethyl)(3-ethoxy-3-oxopropyl) amino)-3-oxopropionate (21 g, 73.59 mmol, 1.0 eq.) and sodium tert-butoxide (8.49 g, 88.3 mmol, 1.2 eq.) were dissolved in ethanol (100 mL) to react at 80° C. for 20 min. After the reaction was completed, as detected by TLC, the reaction solution was concentrated under reduced pressure to give the product (17.6 g, yield: 100%).

Step 4: Synthesis of 1-(cyclopropylmethyl)piperidine-2,4-dione

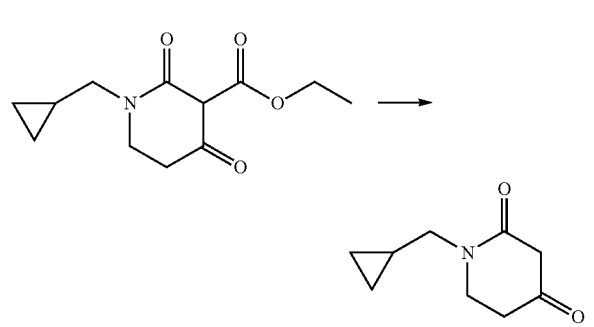

The intermediate ethyl 1-(cyclopropylmethyl)-2,4-dioxopiperidine-3-carboxylate (17.6 g, 73.59 mmol, 1.0 eq.) was dissolved in hydrochloric acid (10 mL) and water (100 mL) to react at 80° C. for 3 h. After the reaction was completed, as detected by LC-MS, the reaction solution was cooled to room temperature and added with sodium chloride solid until saturated. Extraction was performed with dichloromethane (100 mL×3), and the organic phase was dried and concentrated to give the product (11 g, yield: 89%).

Step 5: Synthesis of 1-(cyclopropylmethyl)-3-((dimethylamino)methylene) piperidine-2,4-dione

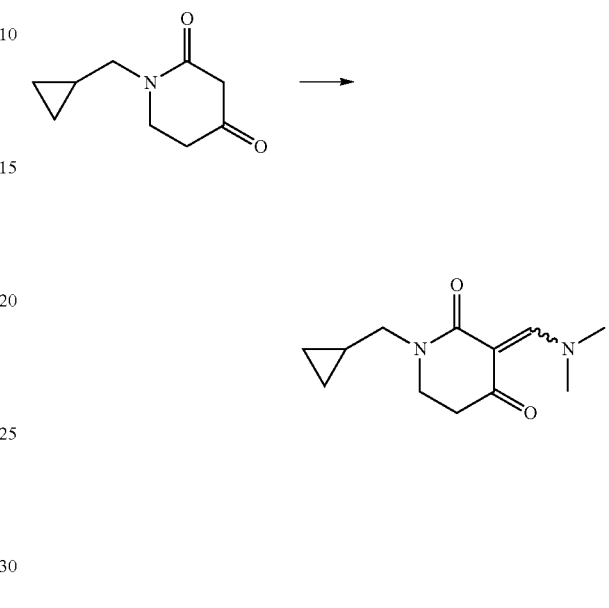

The intermediate 1-(cyclopropylmethyl)piperidine-2,4-dione (11 g, 65.78 mmol, 1.0 eq.) was dissolved in N,N-dimethylformamide dimethyl acetal (8.62 g, 72.36 mmol, 1.1 eq.) to react at room temperature for 40 min. After the reaction was completed, as detected by TLC, the reaction solution was concentrated under reduced pressure to give the product (15.08 g, yield: 100%).

Step 6: Synthesis of 5-(cyclopropylmethyl)-2,5,6,7-tetrahydro-4H-pyrazolo [4,3-c]pyridin-4-one

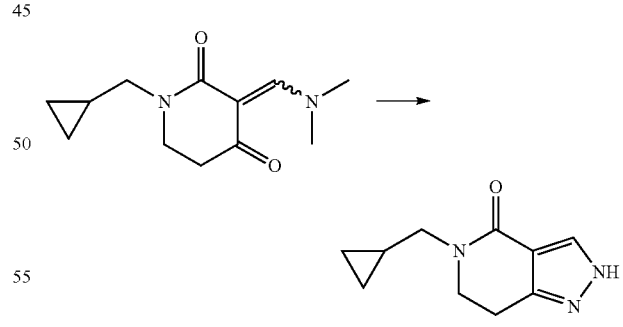

The intermediate 1-(cyclopropylmethyl)-3-((dimethylamino)methylene) piperidine-2,4-dione (15.08 g, 65.78 mmol, 1.0 eq.) and hydrazine hydrate (4.26 g, 72.36 mmol, 1.1 eq.) were dissolved in isopropanol (100 mL) to react at 80° C. for 30 min. After the reaction was completed, as detected by TLC, the reaction solution was concentrated under reduced pressure. The crude product was purified by silica gel column chromatography (MeOH:DCM=1:40) to give the product (8.2 g, yield: 65%).

Step 7: Synthesis of (E)-2-(2-((5-(cyclopropylmethyl)-4-oxo-4,5,6,7-tetrahydro-2H-pyrazolo[4,3-c]pyridin-2-yl)methyl)-3-fluoroallyl)isoindoline-1,3-dione

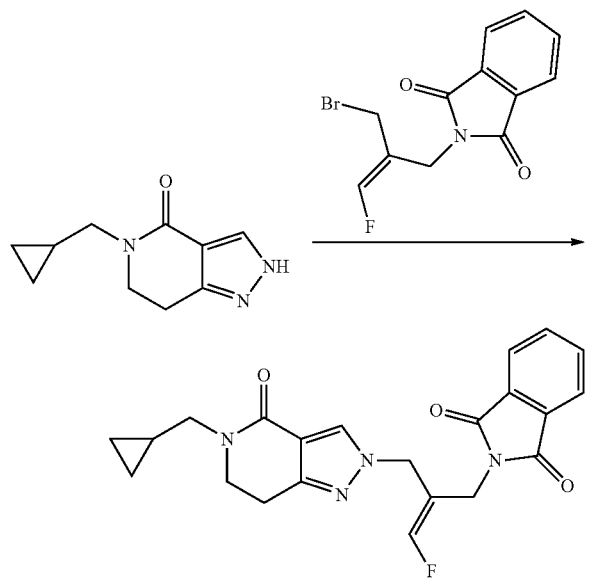

The intermediate 5-(cyclopropylmethyl)-2,5,6,7-tetrahydro-4H-pyrazolo [4,3-c]pyridin-4-one (4.2 g, 21.96 mmol, 1.0 eq), (E)-2-(2-(bromomethyl)-3-fluoroallyl)isoindoline-1,3-dione (7.18 g, 24.16 mmol, 1.1 eq.), potassium carbonate (3.34 g, 24.16 mmol, 1.1 eq.) and tetrabutylammonium bromide (709 mg, 2.2 mmol, 0.1 eq.) were added in absolute ethanol (30 mL) to react for 15 h. After the reaction was completed, as detected by TLC, the reaction solution was concentrated under reduced pressure, and ethanol was removed. DCM (50 mL) was added, stirring was performed for 30 min, and filtration under vacuum was performed. The mother liquor was concentrated under reduced pressure to give 8.0 g of crude yellow oil droplets. 2.0 g of the crude yellow oil droplets were purified by preparative thin-layer chromatography (MeOH:DCM=1:20) to give the product (1.3 g, yield: 56%).

Step 8: Synthesis of (E)-2-(2-(aminomethyl)-3-fluoroallyl)-5-(cyclopropylmethyl)-2,5,6,7-tetrahydro-4H-pyrazolo[4,3-c]pyridin-4-one hydrochloride

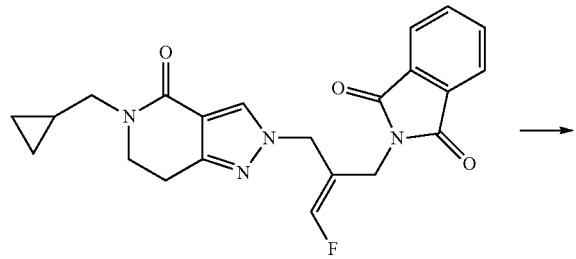

-continued

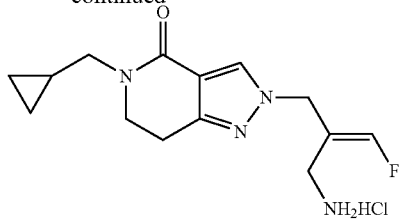

The intermediate (E)-2-(2-((5-(cyclopropylmethyl)-4-oxo-4,5,6,7-tetrahydro-2H-pyrazolo[4,3-c]pyridin-2-yl)methyl)-3-fluoroallyl)isoindoline-1,3-dione (1.3 g, 3.18 mmol, 1.0 eq.) and hydrazine hydrate (281 mg, 4.77 mmol, 1.5 eq.) were dissolved in EtOH (20 mL) to react at 80° C. for 1 h. After the reaction was completed, as detected by LC-MS, the reaction solution was cooled to room temperature and filtered under vacuum. The filtrate was concentrated under reduced pressure. The crude product was dissolved in isopropyl acetate and the solution was stirred for 30 min and filtered under vacuum. The filtrate was added with hydrogen chloride ethanol solution under an ice bath and concentrated. The crude product was purified by silica gel column chromatography (MeOH:DCM=1:15) to give the product (800 mg, yield: 80%).

$^1$HNMR (300 MHz, DMSO-$d_6$) δ(ppm): 8.47 (s, 3H), 8.28 (s, 1H), 7.40 (s, 0.5H), 7.13 (s, 0.5H), 4.93-4.94 (d, 2H), 3.61-3.65 (m, 2H), 3.33-3.34 (d, 2H), 3.27-3.29 (d, 2H), 2.82-2.86 (m, 2H), 0.96-1.00 (m, 1H), 0.40-0.50 (m, 2H), 0.20-0.30 (m, 2H).

Molecular formula: $C_{14}H_{20}ClFN_4O$, molecular weight: 314.79, LC-MS (Pos, m/z)=279.11[M+H]$^+$.

Example 48: Synthesis of (E)-2-(2-(aminomethyl)-3-fluoroallyl)-5-(tert-pentyl)-2,5,6,7-tetrahydro-4H-pyrazolo[4,3-c]pyridin-4-one (Compound A49) Hydrochloride

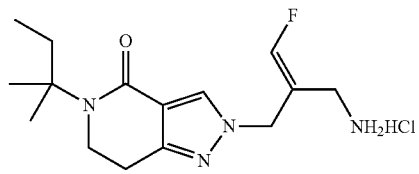

Step 1: Synthesis of ethyl 3-(tert-pentylamino)propanoate

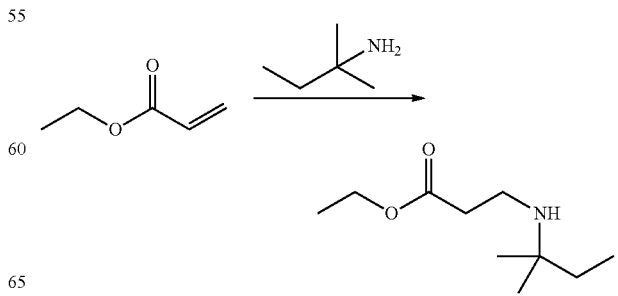

The material 2-methylbutyl-2-amine (7.44 g, 85.35 mmol, 1.0 eq.) was dissolved in absolute ethanol (75 mL). Ethyl acrylate (7.26 g, 72.54 mmol, 0.85 eq.) was slowly added dropwise under an ice bath. After addition, the mixture was incubate at room temperature for 9 h. After no materials were left, as detected by TLC, the reaction solution was concentrated under reduced pressure at 80° C. to give the product, which was used in the next step according to a theoretical amount.

Step 2: Synthesis of ethyl 3-((3-ethoxy-3-oxopropyl)(tert-pentyl)amino)-3-oxopropanoate

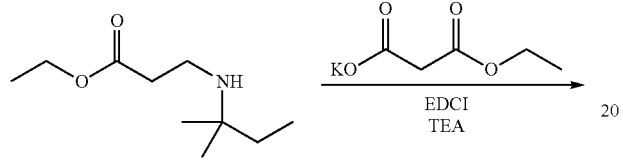

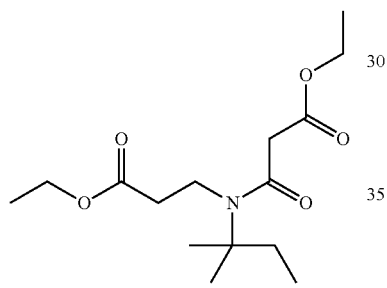

The intermediate ethyl 3-(tert-pentylamino)propanoate (85.35 mmol, 1.0 eq.) was dissolved in dichloromethane (150 mL). The solution was added with ethyl potassium malonate (14.5 g, 85.35 mmol, 1.0 eq.), triethylamine (12.9 g, 128 mmol, 1.5 eq.) and 4-dimethylaminopyridine (1 g, 8.53 mmol, 0.1 eq.) in sequence, cooled to 0° C. with ice water and added with 1-(3-dimethylaminopropyl)-3-ethylcarbodiimide hydrochloride (19.6 g, 102.42 mmol, 1.2 eq.). After addition, the mixture was incubate at room temperature for 15 h. After no materials were left, as detected by TLC, the reaction solution was added with water (100 mL), cooled with ice water, and added with concentrated hydrochloric acid (20 mL, in mass fraction) dropwise to adjust the pH to about 4-5, followed by liquid separation. The aqueous phase was extracted with dichloromethane (100 mL). The organic phases were combined and added with water (100 mL), sodium carbonate was added to adjust the pH to about 8-9, and liquid separation was performed. The organic phase was washed with water (100 mL), dried over anhydrous magnesium sulfate and filtered, and the filtrate was concentrated under reduced pressure to give the product (14.5 g, two-step yield: 56.4%).

Step 3: Synthesis of ethyl 2,4-dioxo-1-(tert-pentyl)piperidine-3-carboxylate

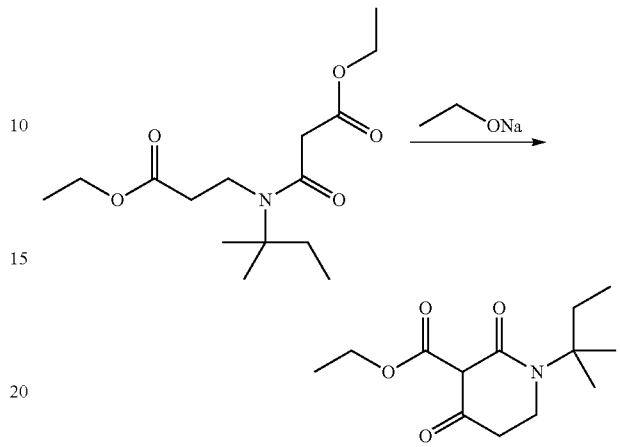

The intermediate ethyl 3-((3-ethoxy-3-oxopropyl)(tert-pentyl)amino)-3-oxopropanoate (14.5 g, 48.11 mmol, 1.0 eq.) was dissolved in absolute ethanol (100 mL). The solution was added with sodium ethoxide (8.2 g, 120.2 mmol, 2.5 eq.) to react at 80° C. for 1 h. After no materials were left, as detected by TLC, the reaction solution was concentrated under reduced pressure to give the product, which was used in the next step according to a theoretical amount.

Step 4: Synthesis of 1-(tert-pentyl)piperidine-2,4-dione

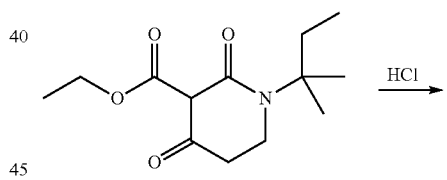

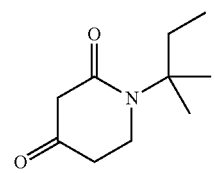

The intermediate ethyl 2,4-dioxo-1-(tert-pentyl)piperidine-3-carboxylate (48.11 mmol, 1.0 eq.) was dissolved in water (100 mL). The solution was added with concentrated hydrochloric acid (10 mL, in mass fraction) dropwise to react at 80° C. for 3 h. After no materials were left, as detected by TLC, the reaction solution was cooled to 0° C. and extracted with dichloromethane (100 mL×3). The organic phases were combined, dried over anhydrous magnesium sulfate and filtered. The filtrate was concentrated to give the product (8.4 g, two-step yield: 95.5%).

Step 5: Synthesis of 3-((dimethylamino)methylene)-1-(tert-pentyl) piperidine-2,4-dione

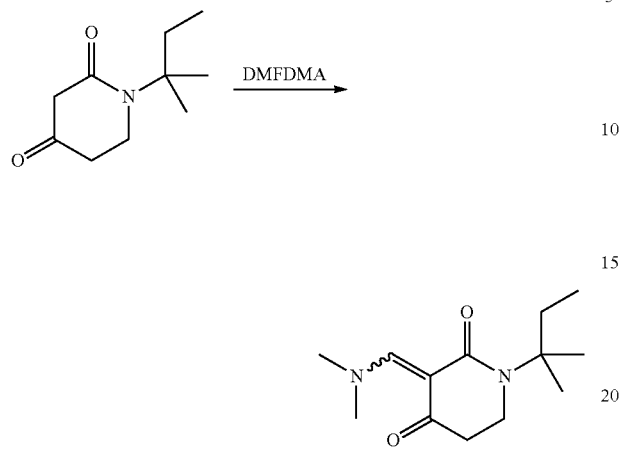

N,N-dimethylformamide dimethyl acetal (6.0 g, 50.42 mmol, 1.1 eq.) was added dropwise into the intermediate 1-(tert-pentyl)piperidine-2,4-dione (8.4 g, 45.84 mmol, 1.0 eq.), releasing intense heat. After addition, reaction was carried out at room temperature for 1 h. After no materials were left, as detected by TLC, the reaction solution was concentrated under reduced pressure to give the product, which was used in the next step according to a theoretical amount.

Step 6: Synthesis of 5-(tert-pentyl)-2,5,6,7-tetrahydro-4H-pyrazolo[4,3-c]pyridin-4-one

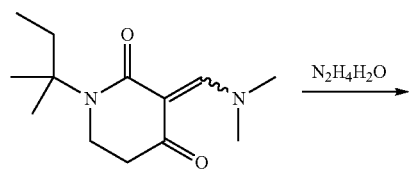

The intermediate 3-((dimethylamino)methylene)-1-(tert-pentyl)piperidine-2,4-dione (45.84 mmol, 1.0 eq.) and hydrazine hydrate (mass fraction: 80%, 3.15 g, 50.42 mmol, 1.1 eq.) were dissolved in isopropanol (100 mL). The solution was heated to reflux for 0.5 h. After no materials were left, as detected by TLC, the reaction solution was concentrated under reduced pressure. The crude product was purified by silica gel column chromatography (DCM: MeOH=100:1-50:1) to give the product (4.29 g, two-step yield: 45.2%).

Step 7: Synthesis of (E)-2-(3-fluoro-2-((4-oxo-5-(tert-pentyl)-4,5,6,7-tetrahydro-2H-pyrazolo[4,3-c]pyridin-2-yl)methyl)allyl)isoindoline-1,3-dione

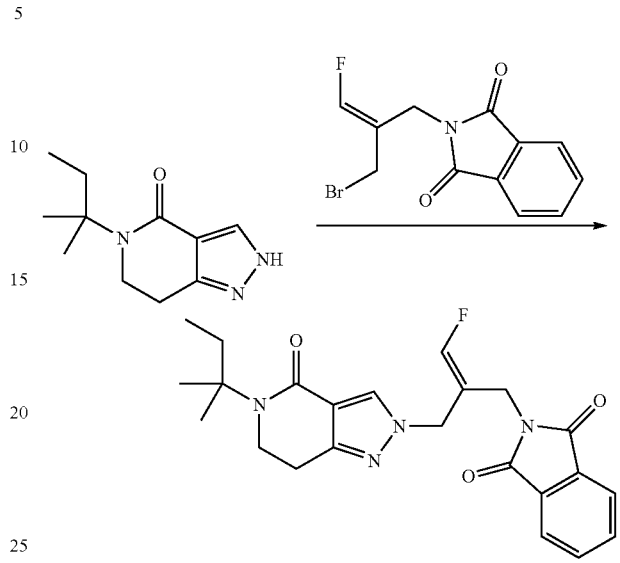

The intermediate 5-(tert-pentyl)-2,5,6,7-tetrahydro-4H-pyrazolo[4,3-c]pyridin-4-one (2.0 g, 9.65 mmol, 1.0 eq.), (E)-2-(2-(bromomethyl)-3-fluoroallyl) isoindoline-1,3-dione (3.16 g, 10.61 mmol, 1.1 eq.), anhydrous potassium carbonate (1.46 g, 10.61 mmol, 1.1 eq.) and tetrabutylammonium bromide (341.7 mg, 1.06 mmol, 0.1 eq.) were added to absolute ethanol (20 mL) and the mixture was stirred at room temperature for 48 h. When there were a small amount of materials left, as detected by TLC, filtration was performed. The filter cake was rinsed with ethyl acetate. The filtrate was concentrated under reduced pressure to give a crude product (4.9 g). The crude product (2 g) was purified by preparative thin-layer chromatography (DCM: MeOH=60:1) to give an oily liquid (821 mg).

Step 8: Synthesis of (E)-2-(2-(aminomethyl)-3-fluoroallyl)-5-(tert-pentyl)-2,5,6,7-tetrahydro-4H-pyrazolo[4,3-c]pyridin-4-one hydrochloride

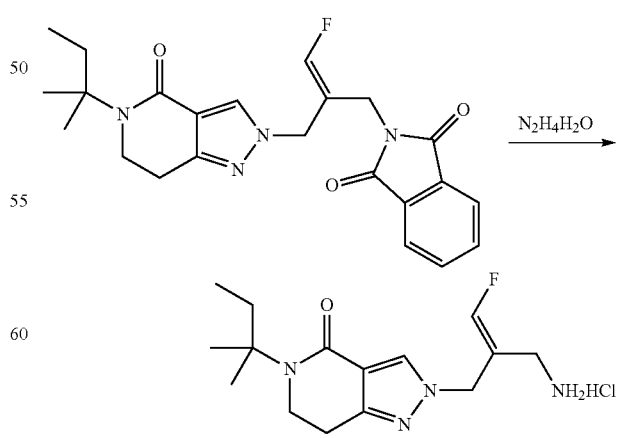

The intermediate (E)-2-(3-fluoro-2-((4-oxo-5-(tert-pentyl)-4,5,6,7-tetrahydro-2H-pyrazolo[4,3-c]pyridin-2-yl)

methyl)allyl)isoindoline-1,3-dione (821 mg, 1.93 mmol, 1.0 eq.) was dissolved in ethanol (10 mL). The solution was added with hydrazine hydrate (mass fraction: 85%, 398.6 mg, 6.77 mmol, 3.5 eq.) to react at 80° C. for 1 h. After no materials were left, as detected by TLC, the reaction solution was cooled to room temperature and filtered under vacuum. The filter cake was rinsed with ethanol. The filtrate was concentrated, slurried with dichloromethane (10 mL) and filtered, and the filtrate obtained therefrom was concentrated under reduced pressure. The crude product was purified by preparative thin-layer chromatography (DCM:MeOH=10:1) to give a product (329 mg). The product was dissolved in dichloromethane (10 mL). The solution was added with hydrogen chloride ethanol solution (mass fraction: 20%, 200 mg) dropwise and stirred for 5 min. Concentration under reduced pressure was performed to give the product (352 mg, yield: 61.9%).

$^1$HNMR (300 MHz, DMSO-$d_6$) δ (ppm): 8.38 (s, 3H), 8.17 (s, 1H), 7.40 (s, 0.5H), 7.13 (s, 0.5H), 4.89-4.88 (d, 2H), 3.54-3.50 (m, 2H), 3.36-3.35 (m, 2H), 2.76-2.71 (m, 2H), 1.94-1.87 (m, 2H), 1.38 (s, 6H), 0.79-0.74 (m, 3H).

Molecular formula: $C_{15}H_{24}ClFN_4O$, molecular weight: 330.83, LC-MS (Pos, m/z)=295.11 $[M+H]^+$.

In the following biological examples of the present invention, all dosages are expressed as free body compounds.

Biological Example 1: Enzymatic Activity Assay

Samples: The compounds of the present invention shown in Table 1, which were prepared according to exemplary methods 1. Inhibitory Activity of Compounds Against rhVAP-1 Enzyme
(1) Instrument, Consumable and Reagent
Multifunctional microplate reader (MD, FlexStation3), black unclear-bottom 96-well plate (Corning), and rhVAP-1 (PeproTech)
(2) Preparation of Concentration Gradient Compound Solutions
An appropriate amount of the compound to be tested was taken, dissolved in DMSO to 10 mM and then stored. Before the study, an appropriate amount of mother liquor of the 10 mM compound to be tested was diluted with DMSO, so that 1 mM solution was obtained. The solution was then gradiently diluted 3-fold with DMSO, 10 concentration gradients in total. PBS was then used to carry out 100-fold dilution, so that compound solutions of 10× series of concentrations were prepared.
(3) Preparation of Enzyme Solutions
An appropriate amount of protein diluent was added into rhVAP-1 powder, obtaining 1 mg/mL of mother liquor for storage. Before the study, PBS was used to carry out dilution to obtain enzyme solutions of 4× concentrations.
(4) Preparation of Substrate Mixtures of 2× Concentrations
An appropriate amount of benzylamine was weighed and dissolved with PBS to obtain 200 mM of benzylamine solution. The benzylamine solution was added with 2 mM of Amplex Red mother liquor and 500 U/mL of HRP mother liquor and diluted with PBS to obtain substrate mixtures of 2× concentrations.
(5) Study Method
10 μL compound solutions of different concentrations, 25 μL rhVAP-1 enzyme solutions of 4× concentrations and 15 μL of PBS were first added into a 96-well plate, shaken to be mixed uniformly and then incubated at 37° C. for 30 min. 50 μL substrate mixtures of 2× concentrations were then added into each well, and the microplate reader was immediately used to detect fluorescence intensity of each well with 565 nm exciting light and 590 nm emission light for 5 min each time, 25 min in total. The inhibition rate was calculated according to the following formula:

$$V \text{ (RFU/min)}=(F_t \text{ (RFU)}-F_0 \text{ (RFU)})/(\text{time(min)})$$

$$\text{Inhibition rate (\%)}=100\%-V_{cmpd} \text{ (RFU/min)}/V_{max} \text{ (RFU/min)}\times 100\%$$

V: fluorescence change rate; $F_t$: fluorescence reading at time point t; $F_0$: initial fluorescence reading; Time: duration t; $V_{cmpd}$: fluorescence change rate of tested compound; $V_{max}$: Max hole fluorescence change rate.
(6) Fitting of Dose-Response Curve
With the log value of concentration as the X axis and the percent inhibition rate as the Y axis, the log (inhibitor) vs. response-variable slope of analysis software GraphPad Prism 5 was used to fit a dose-response curve, thus obtaining the $IC_{50}$ value of activity of each compound against the enzyme.

2. Selectivity of Compounds Against rhAOC1 Enzyme
(1) Instrument, Consumable and Reagent
Microplate reader (Perkin Elmer, Nivo 5S), black unclear-bottom 96-well plate (Corning) and rhAOC1 (R&D)
(2) Preparation of Concentration Gradient Compound Solutions
An appropriate amount of the compound to be tested was taken, dissolved in DMSO to 10 mM and then stored. Before the study, an appropriate amount of mother liquor of the 10 mM compound to be tested was taken and gradiently diluted 3-fold with DMSO, 10 concentration gradients in total. Each concentration gradient was then diluted 10-fold with 0.1 M of PBS.
(3) Preparation of Enzyme Solutions
An appropriate amount of rhAOC1 mother liquor with a concentration of 0.441 mg/mL was taken and diluted with an appropriate amount of 50 mM HEPES buffer solution to obtain enzyme solutions of 4× concentrations.
(4) Preparation of Substrate Mixtures of 2× Concentrations
An appropriate amount of histamine was weighed and dissolved with 50 mM of HEPES buffer solution to obtain 20 mM of histamine solution. The histamine solution was added with 2 mM of Amplex Red mother liquor and 500 U/mL of HRP mother liquor and diluted with 50 mM of HEPES buffer solution to obtain substrate mixtures of 2× concentrations.
(5) Study Method
10 μL compound solutions of different concentrations, 25 μL rhAOC1 enzyme solutions of 4× concentrations and 15 μL of 50 mM HEPES buffer solution were first added into a 96-well plate, shaken to be mixed uniformly and then incubated at 37° C. for 30 min. 50 μL substrate mixtures of 2× concentrations were then added into each well, and the microplate reader was immediately used to detect fluorescence intensity of each well with 580 nm (20 nm) exciting light and 620 nm (10 nm) emission light for 5 min each time, 30 min in total. The inhibition rate was calculated according to the following formula:

$$V \text{ (RFU/min)}=(F_t \text{ (RFU)}-F_0 \text{ (RFU)})/(\text{time(min)})$$

$$\text{Inhibition rate (\%)}=100\%-V_{cmpd} \text{ (RFU/min)}/V_{max} \text{ (RFU/min)}\times 100\%$$

V: fluorescence change rate; $F_t$: fluorescence reading at time point t; $F_0$: initial fluorescence reading; Time: duration t; $V_{cmpd}$: fluorescence change rate of tested compound; $V_{max}$: Max hole fluorescence change rate.

(6) Fitting of Dose-Response Curve

With the log value of concentration as the X axis and the percent inhibition rate as the Y axis, the log (inhibitor) vs. response-variable slope of analysis software GraphPad Prism 5 was used to fit a dose-response curve, thus obtaining the IC50 value of activity of each compound against the enzyme.

3. Study Results Shown as Table 1

TABLE 1

| Samples | rhVAP-1 IC$_{50}$(nM) | rhAOC1 IC$_{50}$(nM) |
|---|---|---|
| Compound A1 | 38 | 22067 |
| Compound A2 hydrochloride | 73 | >10000 |
| Compound C1 | 79 | 26884 |

It can be seen from the table above that the compounds of the present invention show excellent inhibition on rhVAP-1 enzyme and show excellent selectivity against rhAOC1 enzyme. This indicates that the compounds of the present invention can be applied in the prevention and/or treatment of diseases related to an increase in expression or an increase in activity of VAP-1 enzyme. Moreover, because the compounds of the present invention have excellent inhibition on VAP-1 enzyme and show excellent selectivity against rhAOC1 enzyme, side effects caused by inhibition of rhAOC1 enzyme will not occur.

Biological Example 2: Enzymatic Activity Assay

Samples: The compounds of the present invention shown in Table 2, which were prepared according to exemplary methods 1. Inhibitory Activity of Compounds Against rhVAP-1 Enzyme (1) Instrument, Consumable and Reagent Microplate reader (Perkin Elmer, Nivo 5S), black unclear-bottom 96-well plate (Corning) and rhVAP-1 (PeproTech)

(2) Preparation of Concentration Gradient Compound Solutions

An appropriate amount of the compound to be tested was taken, dissolved in DMSO to 10 mM and then stored. Before the study, an appropriate amount of mother liquor of the 10 mM compound to be tested was taken and gradiently diluted 3-fold with DMSO, 10 concentration gradients in total. Each concentration gradient was then diluted 100-fold with 0.1 M of PBS.

(3) Preparation of Enzyme Solutions

An appropriate amount of protein diluent was added into rhVAP-1 powder, obtaining 1 mg/mL of mother liquor for storage. Before the study, PBS was used to carry out dilution to obtain enzyme solutions of 4× concentrations.

(4) Preparation of Substrate Mixtures of 2× Concentrations

An appropriate amount of benzylamine was weighed and dissolved with PBS to obtain 200 mM of benzylamine solution. The benzylamine solution was added with 2 mM of Amplex Red mother liquor and 500 U/mL of HRP mother liquor and diluted with PBS to obtain substrate mixtures of 2× concentrations.

(5) Study Method

10 µL compound solutions of different concentrations, 25 µL rhVAP-1 enzyme solutions of 4× concentrations and 15 µL of PBS were first added into a 96-well plate, shaken to be mixed uniformly and then incubated at 37° C. for 30 min. 50 µL substrate mixtures of 2× concentrations were then added into each well, and the microplate reader was immediately used to perform detection with 580 nm (20 nm) exciting light and 620 nm (10 nm) emission light for 5 min each time, 30 min in total. The inhibition rate was calculated according to the following formula:

$V$ (RFU/min)=($F_t$ (RFU)–$F_0$ (RFU))/(time(min))

Inhibition rate (%)=100%–$V_{cmpd}$ (RFU/min)/$V_{max}$ (RFU/min)×100%

V: fluorescence change rate; $F_t$: fluorescence reading at time point t; $F_0$: initial fluorescence reading; Time: duration t; $V_{cmpd}$: fluorescence change rate of tested compound; $V_{max}$: Max hole fluorescence change rate.

(6) Fitting of Dose-Response Curve

With the log value of concentration as the X axis and the percent inhibition rate as the Y axis, the log (inhibitor) vs. response-variable slope of analysis software GraphPad Prism 5 was used to fit a dose-response curve, thus obtaining the IC50 value of activity of each compound against the enzyme.

2. Selectivity of Compounds Against rhAOC1 Enzyme (1) Instrument, Consumable and Reagent Microplate reader (Perkin Elmer, Nivo 5S), black unclear-bottom 96-well plate (Corning) and rhAOC1 (R&D)

(2) Preparation of Concentration Gradient Compound Solutions

An appropriate amount of the compound to be tested was taken, dissolved in DMSO to 10 mM and then stored. Before the study, an appropriate amount of mother liquor of the 10 mM compound to be tested was taken and gradiently diluted 3-fold with DMSO, 10 concentration gradients in total. Each concentration gradient was then diluted 10-fold with 0.1 M of PBS.

(3) Preparation of Enzyme Solutions

An appropriate amount of rhAOC1 mother liquor with a concentration of 0.441 mg/mL was taken and diluted with an appropriate amount of 50 mM HEPES buffer solution to obtain enzyme solutions of 4× concentrations.

(4) Preparation of Substrate Mixtures of 2× Concentrations

An appropriate amount of histamine was weighed and dissolved with 50 mM of HEPES buffer solution to obtain 20 mM of histamine solution. The histamine solution was added with 2 mM of Amplex Red mother liquor and 500 U/mL of HRP mother liquor and diluted with 50 mM of HEPES buffer solution to obtain substrate mixtures of 2× concentrations.

(5) Study Method

10 µL compound solutions of different concentrations, 25 µL rhAOC1 enzyme solutions of 4× concentrations and 15 µL of 50 mM HEPES buffer solution were first added into a 96-well plate, shaken to be mixed uniformly and then incubated at 37° C. for 30 min. 50 µL substrate mixtures of 2× concentrations were then added into each well, and the microplate reader was immediately used to detect fluorescence intensity of each well with 580 nm (20 nm) exciting light and 620 nm (10 nm) emission light for 5 min each time, 30 min in total. The inhibition rate was calculated according to the following formula:

$V$ (RFU/min)=($F_t$ (RFU)–$F_0$ (RFU))/(time(min))

Inhibition rate (%)=100%–$V_{cmpd}$ (RFU/min)/$V_{max}$ (RFU/min)×100%

V: fluorescence change rate; $F_t$: fluorescence reading at time point t; $F_0$: initial fluorescence reading; Time: duration t; $V_{cmpd}$: fluorescence change rate of tested compound; $V_{max}$: Max hole fluorescence change rate.

(6) Fitting of Dose-Response Curve

With the log value of concentration as the X axis and the percent inhibition rate as the Y axis, the log (inhibitor) vs. response-variable slope of analysis software GraphPad Prism 5 was used to fit a dose-response curve, thus obtaining the IC50 value of activity of each compound against the enzyme.

3. Study Results Shown as Table 2

TABLE 2

| Samples | rhVAP-1 IC$_{50}$(nM) | rhAOC1 IC$_{50}$(nM) |
|---|---|---|
| Compound A6 hydrochloride | 23 | 8946 |
| Compound A7 hydrochloride | 46 | 50000 |
| Compound A9 hydrochloride | 37 | 911 |
| Compound A10 hydrochloride | 40 | 1237 |
| Compound A13 | 58 | 4181 |
| Compound A21 | 96 | 4051 |
| Compound A22 | 44 | 14799 |
| Compound A23 | 39 | NA |
| Compound A24 hydrochloride | 54 | 4719 |
| Compound A25 | 45 | 11535 |
| Compound A27 hydrochloride | 112 | 9652 |
| Compound A28 hydrochloride | 33 | 4058 |
| Compound A29 hydrochloride | 60 | 674 |
| Compound A31 hydrochloride | 53 | 8281 |
| Compound A32 hydrochloride | 15 | 23618 |
| Compound A33 hydrochloride | 23 | >100000 |
| Compound A35 hydrochloride | 24 | 7035 |
| Compound A37 hydrochloride | 8 | NA |
| Compound A42 hydrochloride | 17 | 28909 |
| Compound A41 | 8 | 9646 |
| Compound A44 hydrochloride | 13 | NA |
| Compound A47 hydrochloride | 20 | NA |
| Compound A48 hydrochloride | 12 | NA |
| Compound A49 hydrochloride | 17 | NA |
| Compound B1 | 40 | 3177 |
| Compound B2 | 55 | 5385 |
| Compound B3 | 89 | 12520 |
| Compound B4 hydrochloride | 51 | 5930 |
| Compound B12 | 83 | 8581 |
| Compound B28 | 14 | NA |
| Compound B29 | 70 | 10763 |
| Compound C7 hydrochloride | 96 | 13426 |
| Compound C13 hydrochloride | 67 | 1085 |
| Compound C14 hydrochloride | 50 | 13108 |
| Compound C15 hydrochloride | 63 | 8382 |

NA represents untested.

It can be seen from the table above that the compounds of the present invention show excellent inhibition on rhVAP-1 enzyme and show excellent selectivity against rhAOC1 enzyme. This indicates that the compounds of the present invention can be applied in the prevention and/or treatment of diseases related to an increase in expression or an increase in activity of VAP-1 enzyme. Moreover, because the compounds of the present invention have excellent inhibition on VAP-1 enzyme and show excellent selectivity against rhAOC1 enzyme, side effects caused by inhibition of rhAOC1 enzyme will not occur.

Biological Example 3: Selectivity of the Compounds of the Present Invention against MAO-A/B Enzyme (1) Instrument, Consumable and Reagent Microplate reader (Perkin Elmer, EnVision), 384-well plate (Perkin Elmer), centrifuge (Eppendorf), MAO-Glo™ (Promega), MAO-A (Active Motif) and MAO-B (Active Motif).

(2) Preparation of Concentration Gradient Compound Solutions

An appropriate amount of the compound to be tested was taken, dissolved in DMSO to 10 mM and then stored. The solution was then gradiently diluted 4-fold with DMSO, 6 concentration gradients in total.

(3) Preparation of Enzyme Solutions

MAO-A/B mother liquor was diluted with the experimental buffer for MAO-A/B to obtain enzyme solutions of 2× concentrations.

(4) Preparation of Substrate Mixtures of 2× Concentrations

The mother liquor of MAO-A/B substrate mixture was diluted with the experimental buffer for MAO-A/B to obtain substrate mixtures of 2× concentrations.

(5) Study Method 200 nL compound solutions or solvents of different concentrations and 10 µL MAO-A/B enzyme solutions of 2× concentrations were added into a 384-well plate, centrifuged at 1,000 rpm for 60 s, shaken to be mixed uniformly and then incubated at room temperature for 15 min. 10 µL substrate mixtures of 2× concentrations were then added into each well, and reaction was initiated. The 384-well plate was centrifuged at 1,000 rpm for 60 s, shaken for a uniform mixing and then incubated at room temperature for 60 min. 20 µL of test stop solution was added to stop reaction. Centrifugation was performed at 1,000 rpm for 60 s, and shaking was performed for uniform mixing. After 30 min of standing, the microplate reader was used to perform reading.

The inhibition rate was calculated according to the following formula:

Inhibition rate (%)=(Signal_Max-Signal_sample)/(Signal_Max-Signal_min)×100

(6) Fitting of Dose-Response Curve

With the log value of concentration as the X axis and the percent inhibition rate as the Y axis, the log (inhibitor) vs. response-variable slope of analysis software GraphPad Prism 5 was used to fit a dose-response curve, thus obtaining the IC50 value of activity of each compound against the enzyme.

3. Study Results Shown as Table 3

TABLE 3

| Samples | MAO-A IC$_{50}$(nM) | MAO-B IC$_{50}$(nM) |
|---|---|---|
| Compound A1 | 67000 | >100000 |
| Compound A2 hydrochloride | >100000 | >100000 |
| Compound A6 hydrochloride | 89120 | >100000 |
| Compound A7 hydrochloride | >100000 | >100000 |
| Compound A22 | >100000 | >100000 |
| Compound A25 | >100000 | >100000 |
| Compound A28 hydrochloride | >100000 | >100000 |
| Compound A29 hydrochloride | 87730 | >100000 |
| Compound A32 hydrochloride | 60970 | >100000 |
| Compound A33 hydrochloride | 55940 | >100000 |
| Compound A35 hydrochloride | 8809 | 92740 |
| Compound A37 hydrochloride | >100000 | >100000 |
| Compound A41 | >100000 | >100000 |
| Compound A42 hydrochloride | 47600 | >100000 |
| Compound A44 hydrochloride | 77430 | 88900 |
| Compound B1 | >100000 | >100000 |

It can be seen from Table 3 above that the compounds of the present invention have good inhibitory activity on rhVAP-1 enzyme, and show excellent selectivity against monoamine oxidase (MAO). To sum up, it can be seen from Table 1, Table 2 and Table 3 above that while treating and/or preventing diseases related to SSAO/VAP-1 enzyme, the compounds of the present invention do not have side effects caused by inhibition of rhAOC1 enzyme and MAO enzyme.

Biological Example 4: Rat Blood-Brain Barrier Evaluation of the Compounds of the Present Invention (1) Animal Administration and Sampling Method:

The study compound A1, the compound A41 and PXS-4728 were dissolved in normal saline to prepare solutions. The prepared solutions were separately administered by intragastric administration to SD rats at a dose of 10 mg/kg. Time points for blood and brain tissue sampling were: 0.0167 h, 1 h and 6 h. At each time point, samples were collected from three SD rats.

(2) Sample Collection:

On the day of the study, the animals were fixed to collect 0.15 mL of blood from the jugular vein at each set time point, and the whole blood samples were put into anticoagulation tubes containing EDTA-K$_2$. After blood sampling was completed, heart perfusion was immediately performed for the animals, and following the heart perfusion, brain tissue samples were collected.

(3) Sample Treatment:

After the whole blood samples were centrifuged under the condition of 1,524 g for 10 min, top plasma samples were collected into sample tubes. The tissue samples were weighed, added with 20% of aqueous methanol solution at a weight-to-volume ratio of 1:5 (tissue:homogenate) and homogenized. The biological samples were stored at −40° C. to −20° C. for analysis.

(4) Sample Analysis Method:

Plasma sample: The samples to be tested were taken out of the refrigerator, naturally thawed at room temperature and then swirled for 5 min, and 20 μL of plasma sample was accurately pipetted into 1.5 mL centrifuge tubes. 100 μL of internal standard working solution (solution of 5 ng/mL verapamil and 50 ng/mL glibenclamide in acetonitrile) was added, and uniform mixing was performed. After 1 min of swirling, centrifugation was performed at 13,000 rpm for 8 min. 40 μL of supernate was accurately pipetted into a 96-well plate added with 160 μL water/well in advance. Uniform mixing was performed by swirling for 10 min, followed by LC-MS/MS assay.

Brain tissue sample: The samples to be tested were taken out of the refrigerator, naturally thawed at room temperature and then swirled for 5 min, and 50 μL of plasma sample was accurately pipetted into 1.5 mL centrifuge tubes. 250 μL of internal standard working solution (solution of 5 ng/mL verapamil and 50 ng/mL glibenclamide in acetonitrile) was added, and uniform mixing was performed. After 1 min of swirling, centrifugation was performed at 13,000 rpm for 8 min. 30 μL of supernate was accurately pipetted into a 96-well plate added with 150 μL water/well in advance. Uniform mixing was performed by swirling for 10 min, followed by LC-MS/MS assay.

(5) Data Processing Method:

Analyst 1.6.2 from AB Sciex was used to output concentration results of tested compounds. Microsoft Excel was used to calculate parameters such as mean value, standard deviation and variation coefficient (excluding those outputted directly by Analyst 1.6.2).

(6) Results Shown as Table 4

TABLE 4

| Samples | Time (h) | Average concentration (N= 3) | | Mean brain tissue/plasma concentration ratio |
|---|---|---|---|---|
| | | Plasma concentration (ng/mL) | Brain tissue concentration (ng/g) | |
| Compound A1 | 0.167 | 158 | BLOQ | 0← |
| | 1 | 1300 | 39.1 | 0.030 |
| | 6 | 80.7 | 31.3 | 0.39 |
| Compound A41 | 0.167 | 624 | BLOQ | NA |
| | 1 | 1753 | BLOQ | NA |
| | 6 | 39.7 | BLOQ | NA |
| PXS-4728 | 0.167 | 373 | 337 | 0.89 |
| | 1 | 1043 | 1400 | 1.34 |
| | 6 | 175 | 311 | 1.89 |

BLOQ means that the concentration is below the limit of quantification; and NA represents incalculable It can be seen from Table 4 above that the compounds A1 and A41 of the present invention, even over time, have such low concentrations in brain tissues that the compounds are below the limit of detection. This indicates that the compounds of the present invention can hardly pass through the blood-brain barrier, so the toxic risk of the compounds of the present invention to the nervous system is very low.

Biological Example 5: Rat PK Evaluation of the Compounds

Animal Administration and Sample Collection:

The study compounds A1, A6, A32, A41 and A42 were each dissolved in normal saline to prepare solutions. The solutions of the compounds were separately administered to SD rats by intragastric administration at a dose of 5.0 mg/kg. Time points for blood collection were 15 min, 30 min, 1 h, 2 h, 4 h, 6 h, 8 h and 24 h.

The study compounds A1, A6, A32, A41 and A42 were each dissolved in normal saline to prepare solutions. The solutions of the compounds were separately administered to SD rats by intravenous push at a dose of 1.0 mg/kg. Time points for blood collection were 5 min, 15 min, 30 min, 1 h, 2 h, 4 h, 6 h, 8 h and 24 h.

Venous catheterization was performed the day before the administration. Subsequent to the administration, about 300 μL of blood was collected from the jugular vein and put into anticoagulation tubes containing EDTA-$K_2$. Preparation was performed within 30 min after the blood collection. Plasma samples were obtained by centrifugation at 8,000 rpm for 6 min at 4° C., and were stored in a –80° C. refrigerator before plasma testing.

Sample Analysis Method:

(1) the samples to be tested were taken out of the –80° C. refrigerator, naturally thawed at room temperature and then swirled for 5 min;

(2) 20 μL of plasma sample was accurately pipetted into a 1.5 mL centrifuge tube;

(3) 200 μL of internal standard working solution (solution of tolbutamide in methanol) with a concentration of 100 ng/mL was added, and uniform mixing was performed;

(4) after 5 min of swirling, centrifugation was performed at 12,000 rpm for 5 min;

(5) 50 μL of supernate was accurately pipetted into a 96-well plate added with 150 μL water/well in advance;

(6) uniform mixing was performed by swirling for 5 min, followed by LC-MS/MS assay.

Data Processing Method:

Analyst 1.6.3 from AB Sciex was used to output concentration results of tested compounds. Microsoft Excel was used to calculate parameters such as mean value, standard deviation and variation coefficient (excluding those outputted directly by Analyst 1.6.3). Pharsight Phoenix 6.1 software NCA was adopted to calculate PK parameters ($T_{max}$ was median).

Results:

TABLE 5

PK Parameters of Compounds in SD Rats
(IV: 1 mg/kg, PO: 5 mg/kg, n = 3)

| Compound | $t_{z1/2}$ iv/po (h) | $V_{z\_obs}$ iv (L/kg) | $Cl_{obs}$ iv (L/h/kg) | $T_{max}$ po (h) | $AUC_{inf}$ iv/po (h * ng/mL) | F % |
|---|---|---|---|---|---|---|
| A1 | 0.87/1.17 | 2.31 | 1.85 | 2.00 | 545/2371 | 87.0 |
| A6 (hydrochloride) | 0.73/1.09 | 2.38 | 2.27 | 0.50 | 445/1697 | 76.3 |
| A32 (hydrochloride) | 0.48/0.75 | 1.20 | 1.75 | 0.25 | 572/4950 | 173 |
| A41 | 0.56/1.79 | 1.53 | 1.89 | 1.00 | 531/1643 | 61.9 |
| A42 (hydrochloride) | 0.53/1.33 | 1.29 | 1.77 | 1.00 | 591/4477 | 151 |

Note:
$T_{z1/2}$: terminal half-life;
$Cl_{obs}$: clearance rate;
$V_{z\_obs}$: apparent volume of distribution;
$T_{max}$: time of maximum observed plasma concentration;
$AUC_{inf}$: area under plasma concentration-time curve 0-∞;
F %: absolute bioavailability It can be seen from the results in Table 5 that the compounds of the present invention have low clearance rates and excellent oral absolute bioavailability, which indicates that the compounds of the present invention have excellent pharmacokinetic properties.

INDUSTRIAL APPLICABILITY

The halo-allylamine compound of the present invention can be used to prevent and/or treat diseases related to or mediated by the SSAO/VAP-1 protein. Moreover, the compound of the present invention shows excellent selective inhibitory activity on VAP-1 enzyme relative to rhAOC1 enzyme and MAO enzyme, and can hardly cause other side effects. In addition, compared with existing medicament, the compound of the present invention can hardly penetrate the blood-brain barrier, so the compound of the present invention has a very low toxic risk to the nervous system, that is, the safety of the compound of the present invention is excellent.

The invention claimed is:

1. A compound of formula I, or a pharmaceutically acceptable salt, an ester, a stereoisomer or a tautomer thereof,

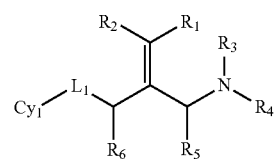

I wherein $R_1$ and $R_2$ are each independently selected from hydrogen and halogen, and $R_1$ and $R_2$ are not both hydrogen;

$R_3$ and $R_4$ are each independently selected from hydrogen and $C_{1-6}$ alkyl, or form a 5-10 membered nitrogen containing heterocycle optionally substituted by a substituent along with a N atom connected thereto;

$R_5$ and $R_6$ are each independently selected from hydrogen and $C_{1-6}$ alkyl;

$L_1$ is absent, or is —CR'R"—, —N—, —O—, —S—, —$SO_2$—, S (O), —SONR'—, —$SO_2$NR'— or —NR'CONR'—, and R' and R" are each independently selected from hydrogen and $C_{1-6}$ alkyl;

$Cy_1$ is a group that is unsubstituted or substituted by one or more $R^a$ shown in general formula (A-1), (A-2), (A-3), (a), (b) or (c-2) below:

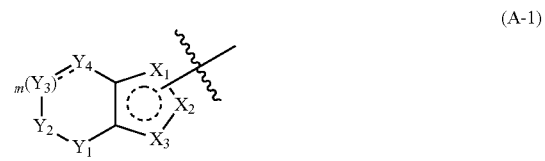

(A-1)

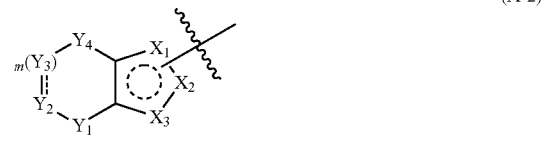

(A-2)

(A-3)

-continued (a)

(b)

(c-2)

m is an integer from 0 to 3;
$Y_1$, $Y_2$, $Y_3$ and $Y_4$ are each independently selected from $CH_2$, NH, O, S and C=O;
$X_1$, $X_2$, $X_3$, $X_4$, $X_9$ and $X_{10}$ are each independently selected from $CH_2$, CH, N, O, S, NH and C=O, and at least one of $X_1$, $X_2$ and $X_3$ is N;
each $R^a$ is independently selected from hydroxyl, amino, carboxyl, cyano, nitro, halogen, and $C_{1-6}$ alkyl, $C_{2-6}$ alkenyl, $C_{2-6}$ alkynyl, $C_{1-6}$ alkoxy, $C_{1-6}$ alkoxy $C_{1-6}$ alkyl, $C_{1-6}$ alkoxy $C_{1-6}$ alkoxy, $C_{1-6}$ alkylthio, $C_{1-6}$ alkylthio $C_{1-6}$ alkyl, $C_{1-6}$ alkylamino, ($C_{1-6}$ alkyl) 2 amino, $C_{1-6}$ alkylamino $C_{1-6}$ alkyl, $C_{1-6}$ alkylaminocarbonyl, $C_{1-6}$ alkylaminocarbonyl $C_{1-6}$ alkyl, $C_{1-6}$ alkylcarbonylamino, $C_{1-6}$ alkylcarbonylamino $C_{1-6}$ alkyl, ($C_{1-6}$ alkyl) 2 amino $C_{1-6}$ alkyl, $C_{1-6}$ alkylcarbonyl, $C_{1-6}$ alkylcarbonyl $C_{1-6}$ alkyl, $C_{1-6}$ alkylaminosulfonyl, $C_{1-6}$ alkylaminosulfonyl $C_{1-6}$ alkyl, $C_{1-6}$ alkylsulfonylamino, $C_{1-6}$ alkylsulfonylamino $C_{1-6}$ alkyl, $C_{1-6}$ alkylsulfonyl, $C_{1-6}$ alkylsulfonyl $C_{1-6}$ alkyl, $Cy_2$-, $Cy_2$-$C_{1-6}$ alkyl, $Cy_2$-$C_{1-6}$ alkoxy, $Cy_2$-carbonyl and $Cy_2$-aminocarbonyl unsubstituted or substituted by one or more Rb,
$Cy_2$ is 3-12 membered cycloalkyl, 3-12 membered cycloalkenyl, 3-12 membered heterocyclyl, aryl or 5-14 membered heteroaryl;
each $R^b$ is independently selected from amino, carboxyl, cyano, nitro, halogen, $C_{1-6}$ alkyl, $C_{2-6}$ alkenyl, $C_{2-6}$ alkynyl, $C_{1-6}$ alkoxy, $C_{1-6}$ alkoxy $C_{1-6}$ alkyl, $C_{1-6}$ alkoxy $C_{1-6}$ alkoxy, $C_{1-6}$ alkylthio, $C_{1-6}$ alkylamino, ($C_{1-6}$ alkyl)$_2$ amino, $C_{1-6}$ alkylaminocarbonyl, $C_{1-6}$ alkylcarbonylamino, $C_{1-6}$ alkylcarbonyl, $C_{1-6}$ alkylaminosulfonyl, $C_{1-6}$ alkylsulfonylamino and $C_{1-6}$ alkylsulfonyl;
with the proviso that when $Cy_1$ is formula (c-2), formula (c-2) is substituted by one or more $R^a$;
with the proviso that when $Cy_1$ is formula (b), $X_1$, $X_2$, $X_3$, $X_9$ and $X_{10}$ are not C=O;
=== represents a single bond or a double bond; and
⟨⟩ represents a double bond optionally present in the ring structure.

2. The compound, or the pharmaceutically acceptable salt, the ester, the stereoisomer or the tautomer thereof according to claim 1,
wherein $R_1$ and $R_2$ are each independently selected from hydrogen and halogen, and $R_1$ and $R_2$ are not both hydrogen;

$R_3$ and $R_4$ are each independently selected from hydrogen and $C_{1-6}$ alkyl;
$R_5$ and $R_6$ are each independently selected from hydrogen and $C_{1-6}$ alkyl;
$L_1$ is absent, or is —CR'R"—, —N—, —O— or —S—, and R' and R" are each independently selected from hydrogen and $C_{1-6}$ alkyl;
$Cy_1$ is a group that is unsubstituted or substituted by one or more $R^a$ shown in general formula (A-1), (A-2), (A-3), (a), (b) or (c-2) below:

(A-1)

(A-2)

(A-3)

(a)

(b)

(c-2)

m is an integer from 0 to 3;
$Y_1$, $Y_2$, $Y_3$ and $Y_4$ are each independently selected from $CH_2$, NH and C=O;
$X_1$, $X_2$, $X_3$, $X_4$, $X_9$ and $X_{10}$ are each independently selected from $CH_2$, CH, N, NH and C=O, and at least one of $X_1$, $X_2$ and $X_3$ is N;
each $R^a$ is independently selected from hydroxyl, amino, carboxyl, cyano, nitro, halogen, and $C_{1-6}$ alkyl, $C_{1-6}$ alkoxy, $C_{1-6}$ alkoxy $C_{1-6}$ alkyl, $C_{1-6}$ alkoxy $C_{1-6}$ alkoxy, $C_{1-6}$ alkylthio, $C_{1-6}$ alkylthio $C_{1-6}$ alkyl, $C_{1-6}$ alkylamino, $C_{1-6}$ alkylamino $C_{1-6}$ alkyl, $C_{1-6}$ alkylaminocarbonyl, $C_{1-6}$ alkylaminocarbonyl $C_{1-6}$ alkyl, $C_{1-6}$ alkylcarbonylamino, $C_{1-6}$ alkylcarbonylamino $C_{1-6}$ alkyl, $C_{1-6}$ alkylcarbonyl, $C_{1-6}$ alkylcarbonyl $C_{1-6}$ alkyl, $Cy_2$, $Cy_2$-$C_{1-6}$ alkyl, $Cy_2$-$C_{1-6}$ alkoxy, $Cy_2$-carbonyl and $Cy_2$-aminocarbonyl unsubstituted or substituted by one or more substituents $R^b$,
$Cy_2$ is 3-8 membered cycloalkyl, 5-10 membered heterocyclyl, phenyl or 5-10 membered heteroaryl;

each $R^b$ is independently selected from amino, carboxyl, cyano, nitro, halogen, $C_{1-6}$ alkyl, $C_{1-6}$ alkoxy, $C_{1-6}$ alkoxy $C_{1-6}$ alkyl, $C_{1-6}$ alkoxy $C_{1-6}$ alkoxy, $C_{1-6}$ alkylthio, $C_{1-6}$ alkylamino, $C_{1-6}$ alkylaminocarbonyl, $C_{1-6}$ alkylcarbonylamino and $C_{1-6}$ alkylcarbonyl;

with the proviso that when $Cy_1$ is formula (c-2), formula (c-2) is substituted by one or more $R^a$;

with the proviso that when $Cy_1$ is formula (b), $X_1, X_2, X_3, X_9$ and $X_{10}$ are not C=O; and ⟨⟩ represents a double bond optionally present in the ring structure.

3. The compound, or the pharmaceutically acceptable salt, the ester, the stereoisomer or the tautomer thereof according to claim 1, wherein $Cy_1$ is a group that is unsubstituted or substituted by one or more $R^a$ shown in general formula (A-11), (a-1), (a-2), (b-1), or (c-2) below:

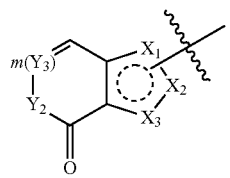

(A-11)

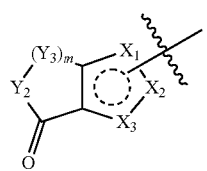

(a-1)

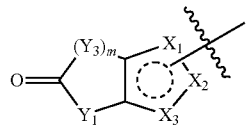

(a-2)

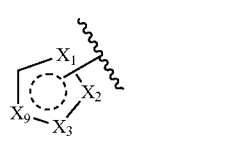

(b-1)

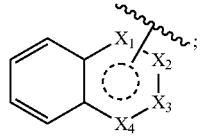

(c-2)

m is an integer that is 1 or 2;
$Y_1, Y_2$ and $Y_3$ are each independently selected from $CH_2$ and NH;
$X_1, X_2, X_3, X_4$ and $X_9$ are each independently selected from $CH_2$, CH, N, NH and C=O, and at least one of $X_1, X_2$ and $X_3$ is N;
with the proviso that when $Cy_1$ is formula (c-2), formula or (c-2) is substituted by one or more $R^a$;
with the proviso that when $Cy_1$ is formula (b-1), $X_1, X_2, X_3$ and $X_9$ are not C=O; and
represents a double bond optionally present in the ring structure.

4. The compound, or the pharmaceutically acceptable salt, the ester, the stereoisomer or the tautomer thereof according to claim 3, wherein $Cy_1$ is a group that is unsubstituted or substituted by one or more $R^a$ shown in general formula (A-11) or (a-1) below:

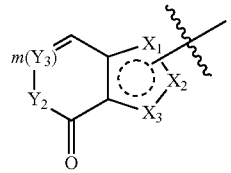

(A-11)

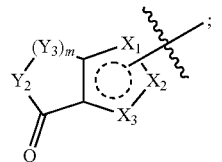

(a-1)

m is an integer that is 1 or 2;
$Y_2$ and $Y_3$ are each independently selected from $CH_2$ and NH;
$X_1, X_2$ and $X_3$ are each independently selected from $CH_2$, CH, N and NH, and at least one of $X_1, X_2$ and $X_3$ is N; and ⟨⟩ represents a double bond optionally present in the ring structure.

5. The compound, or the pharmaceutically acceptable salt, the ester, the stereoisomer or the tautomer thereof according to claim 4, wherein $R_1$ and $R_2$ are each independently selected from hydrogen and halogen, and $R_1$ and $R_2$ are not both hydrogen;
$R_3$ and $R_4$ are each independently selected from hydrogen and $C_{1-6}$ alkyl;
$R_5$ and $R_6$ are each independently selected from hydrogen and $C_{1-6}$ alkyl;
$L_1$ is absent;
$Cy_1$ is one of the following groups unsubstituted or substituted by one or more $R^a$:

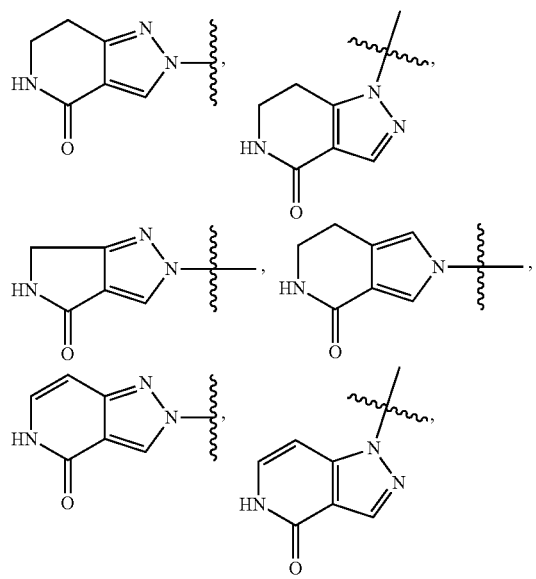

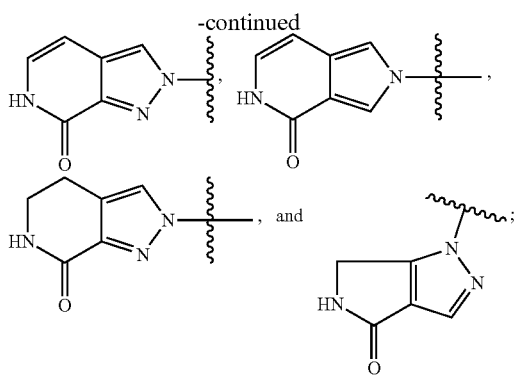

each $R^a$ is independently selected from hydroxyl, amino, carboxyl, cyano, nitro, halogen, and $C_{1-6}$ alkyl, $C_{1-6}$ alkoxy, $C_{1-6}$ alkoxy $C_{1-6}$ alkyl, $C_{1-6}$ alkoxy $C_{1-6}$ alkoxy, $C_{1-6}$ alkylamino, $C_{1-6}$ alkylamino $C_{1-6}$ alkyl, $C_{1-6}$ alkylaminocarbonyl, $C_{1-6}$ alkylaminocarbonyl $C_{1-6}$ alkyl, $C_{1-6}$ alkylcarbonylamino, $C_{1-6}$ alkylcarbonylamino $C_{1-6}$ alkyl, $C_{1-6}$ alkylcarbonyl, $C_{1-6}$ alkylcarbonyl $C_{1-6}$ alkyl, $Cy_2$, $Cy_2$-$C_{1-6}$ alkyl, $Cy_2$-$C_{1-6}$ alkoxy, $Cy_2$-carbonyl and $Cy_2$-aminocarbonyl unsubstituted or substituted by one or more substituents $R^b$, $Cy_2$ is 3-8 membered cycloalkyl, 5-10 membered heterocyclyl, phenyl or 5-10 membered heteroaryl;

each $R^b$ is independently selected from amino, carboxyl, cyano, nitro, halogen, $C_{1-6}$ alkyl, $C_{1-6}$ alkoxy, $C_{1-6}$ alkoxy $C_{1-6}$ alkyl, $C_{1-6}$ alkoxy $C_{1-6}$ alkoxy, $C_{1-6}$ alkylthio, $C_{1-6}$ alkylamino, $C_{1-6}$ alkylaminocarbonyl, $C_{1-6}$ alkylcarbonylamino and $C_{1-6}$ alkylcarbonyl;

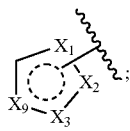 represents a double bond optionally present in the ring structure.

6. The compound, or the pharmaceutically acceptable salt, the ester, the stereoisomer or the tautomer thereof according to claim 3,
wherein $Cy_1$ is a group that is unsubstituted or substituted by one or more $R^a$ shown in general formula (b-1) below:

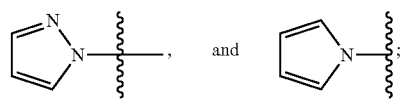 (b-1)

$X_1$, $X_2$, $X_3$ and $X_9$ are each independently selected from $CH_2$, CH, N and NH, and at least one of $X_1$, $X_2$ and $X_3$ is N; and

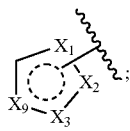 represents a double bond optionally present in the ring structure;
with the proviso that in general formula (b-1), $X_1$, $X_2$, $X_3$ and $X_9$ are not C=O.

7. The compound, or the pharmaceutically acceptable salt, the ester, the stereoisomer or the tautomer thereof according to claim 6,
wherein $R_1$ and $R_2$ are each independently selected from hydrogen and halogen, and $R_1$ and $R_2$ are not both hydrogen;
$R_3$ and $R_4$ are each independently selected from hydrogen and $C_{1-6}$ alkyl;

$R_5$ and $R_6$ are each independently selected from hydrogen and $C_{1-6}$ alkyl;

$L_1$ is absent;

$Cy_1$ is one of the following groups unsubstituted or substituted by one or more $R^a$:

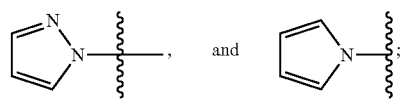 [SMILES: *n1cccn1 ; *n1cccc1]

each $R^a$ is independently selected from hydroxyl, amino, carboxyl, cyano, nitro, halogen, and $C_{1-6}$ alkyl, $C_{1-6}$ alkoxy, $C_{1-6}$ alkoxy $C_{1-6}$ alkyl, $C_{1-6}$ alkoxy $C_{1-6}$ alkoxy, $C_{1-6}$ alkylamino, $C_{1-6}$ alkylamino $C_{1-6}$ alkyl, $C_{1-6}$ alkylaminocarbonyl, $C_{1-6}$ alkylaminocarbonyl $C_{1-6}$ alkyl, $C_{1-6}$ alkylcarbonylamino, $C_{1-6}$ alkylcarbonylamino $C_{1-6}$ alkyl, $C_{1-6}$ alkylcarbonyl, $C_{1-6}$ alkylcarbonyl $C_{1-6}$ alkyl, $Cy_2$, $Cy_2$-$C_{1-6}$ alkyl, $Cy_2$-$C_{1-6}$ alkoxy, $Cy_2$-carbonyl and $Cy_2$-aminocarbonyl unsubstituted or substituted by one or more substituents $R^b$, $Cy_2$ is 3-8 membered cycloalkyl, 5-10 membered heterocyclyl, phenyl or 5-10 membered heteroaryl; and each $R^b$ is independently selected from amino, carboxyl, cyano, nitro, halogen, $C_{1-6}$ alkyl, $C_{1-6}$ alkoxy, $C_{1-6}$ alkoxy $C_{1-6}$ alkyl, $C_{1-6}$ alkoxy $C_{1-6}$ alkoxy, $C_{1-6}$ alkylthio, $C_{1-6}$ alkylamino, $C_{1-6}$ alkylaminocarbonyl, $C_{1-6}$ alkylcarbonylamino and $C_{1-6}$ alkylcarbonyl.

8. The compound, or the pharmaceutically acceptable salt, the ester, the stereoisomer or the tautomer thereof according to claim 1,
wherein, $Cy_1$ is one of the following groups unsubstituted or substituted by one or more $R^a$:

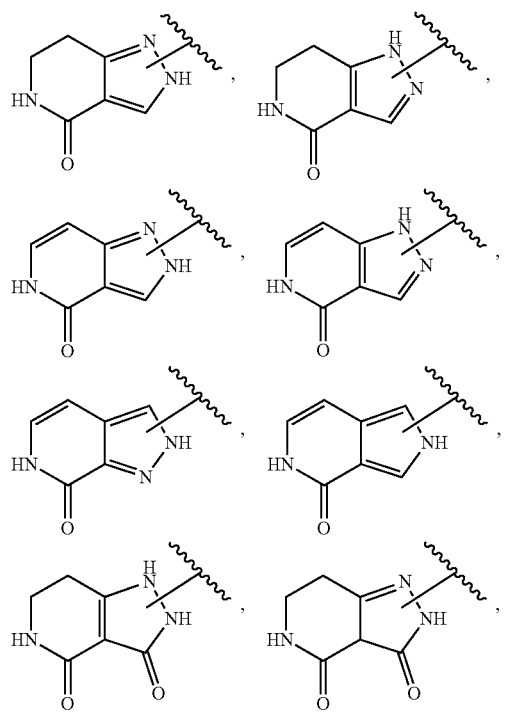

237
-continued

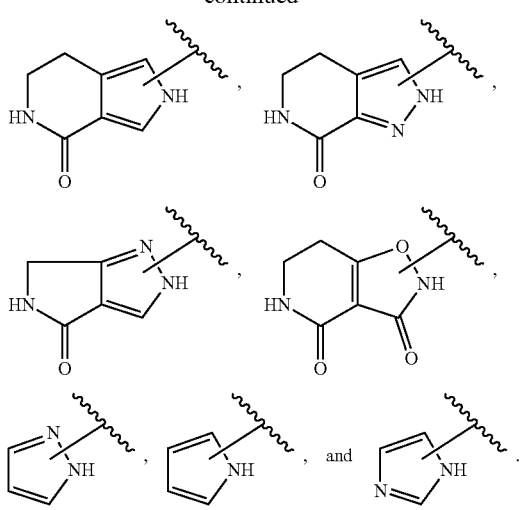

9. The compound, or the pharmaceutically acceptable salt, the ester, the stereoisomer or the tautomer thereof according to claim 8, wherein $R_1$ and $R_2$ are each independently selected from hydrogen and fluorine, and $R_1$ and $R_2$ are not both hydrogen;

$R_3$ and $R_4$ are each independently selected from hydrogen and $C_{1-6}$ alkyl;

$R_5$ and $R_6$ are hydrogen;

L is absent;

$Cy_1$ is one of the following groups unsubstituted or substituted by one or substituent more substituents $R^a$:

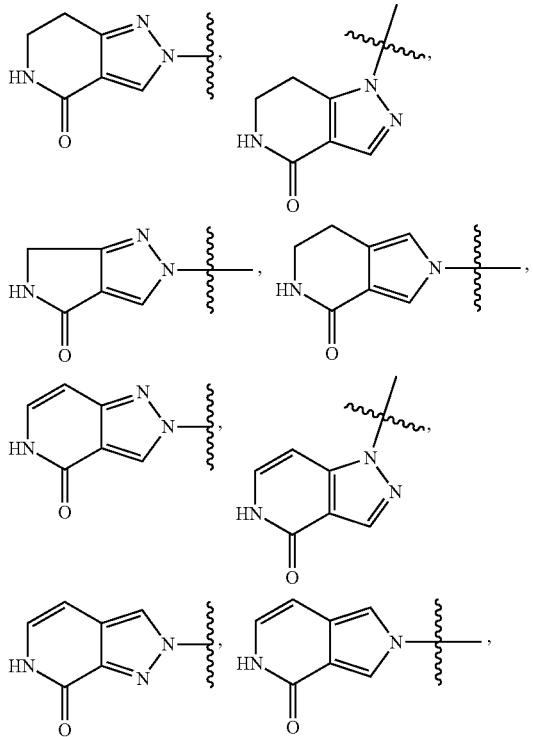

238
-continued

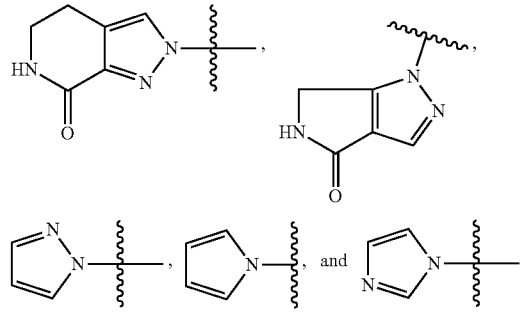

each $R^a$ is independently selected from hydroxyl, amino, carboxyl, cyano, nitro, halogen and $C_{1-6}$ alkyl, $C_{1-6}$ alkoxy, $C_{1-6}$ alkylaminocarbonyl, $Cy_2$, $Cy_2$-carbonyl and $Cy_2$-aminocarbonyl unsubstituted or substituted by one or more substituents $R^b$, $Cy_2$ is 3-6 membered cycloalkyl, 5-6 membered heterocyclyl, phenyl or 5-6 membered heteroaryl;

each $R^b$ is independently selected from amino, carboxyl, cyano, nitro, halogen, $C_{1-6}$ alkyl and $C_{1-6}$ alkoxy.

10. A compound, or the pharmaceutically acceptable salt, the ester, the stereoisomer or the tautomer thereof wherein the compound is selected from:

| Serial number | Structural formula |
|---|---|
| A1 | |
| A2 | |
| A3 | |
| A4 | |

| Serial number | Structural formula |
|---|---|
| A5 | 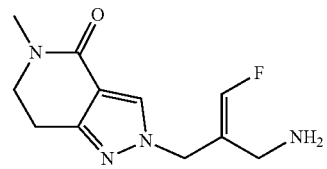 [SMILES: CN1CCc2nn(C/C(=C/F)CN)cc2C1=O] |
| A6 | 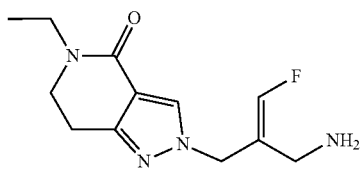 [SMILES: CCN1CCc2nn(C/C(=C/F)CN)cc2C1=O] |
| A7 | 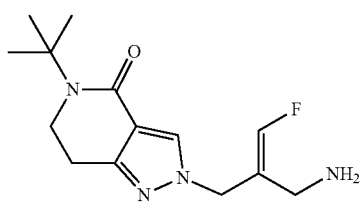 [SMILES: CC(C)(C)N1CCc2nn(C/C(=C/F)CN)cc2C1=O] |
| A9 | 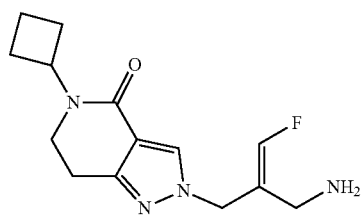 [SMILES: NC/C(=C\F)Cn1cc2c(n1)CCN(C1CCC1)C2=O] |
| A10 | 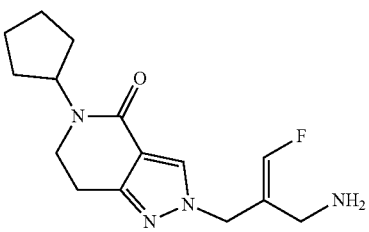 [SMILES: NC/C(=C\F)Cn1cc2c(n1)CCN(C1CCCC1)C2=O] |
| A11 | 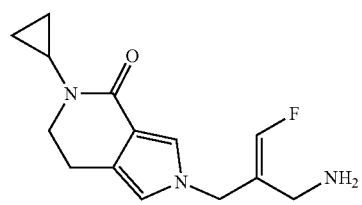 [SMILES: NC/C(=C\F)Cn1cc2c(c1)C(=O)N(C1CC1)CC2] |
| A12 | 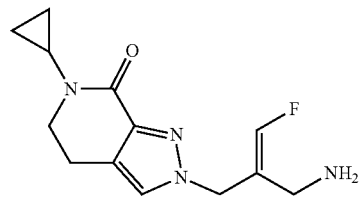 [SMILES: NC/C(=C\F)Cn1cc2c(n1)C(=O)N(C1CC1)CC2] |
| A13 | 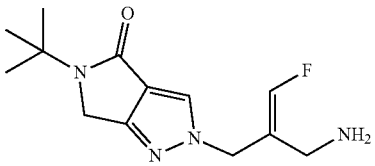 [SMILES: CC(C)(C)N1Cc2nn(C/C(=C/F)CN)cc2C1=O] |
| A14 | 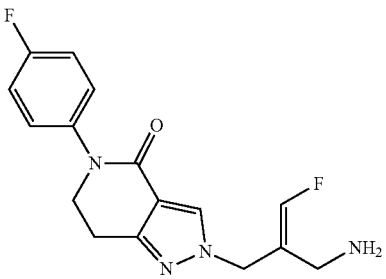 [SMILES: NC/C(=C\F)Cn1cc2c(n1)CCN(c1ccc(F)cc1)C2=O] |
| A15 | 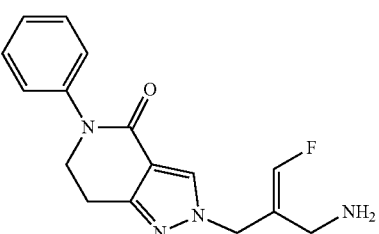 |
| A16 | 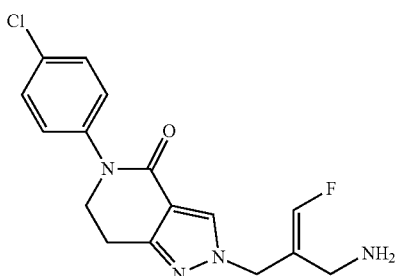 |
| A17 | 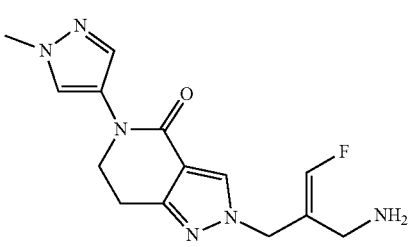 [SMILES: Cn1cc(N2CCc3nn(C/C(=C/F)CN)cc3C2=O)cn1] |
| A18 | 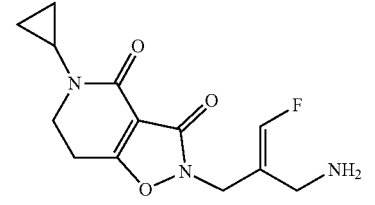 [SMILES: NC/C(=C\F)Cn1oc2c(c1=O)C(=O)N(C1CC1)CC2] |

| Serial number | Structural formula |
|---|---|
| A19 | 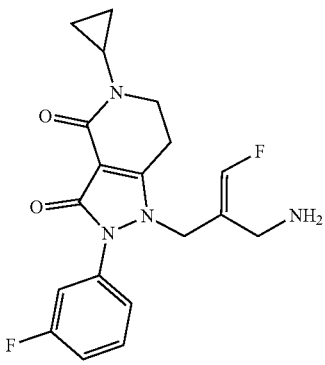 [SMILES: NC/C(=C\F)Cn1c2c(c(=O)n1-c1cccc(F)c1)C(=O)N(C1CC1)CC2] |
| A20 | 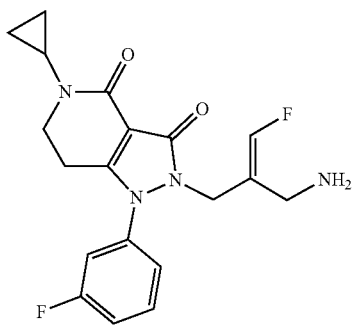 [SMILES: NC/C(=C\F)Cn1c(=O)c2c(n1-c1cccc(F)c1)CCN(C1CC1)C2=O] |
| A21 | 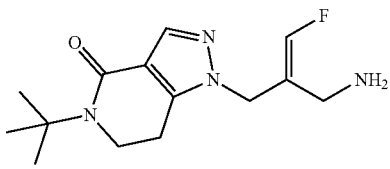 [SMILES: CC(C)(C)N1CCc2c(cnn2C/C(=C/F)CN)C1=O] |
| A22 | 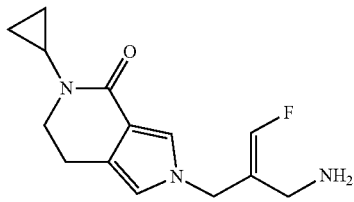 [SMILES: NC/C(=C\F)Cn1cc2c(c1)C(=O)N(C1CC1)CC2] |
| A23 | 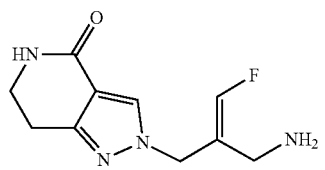 [SMILES: NC/C(=C\F)Cn1cc2c(n1)CCNC2=O] |
| A24 | 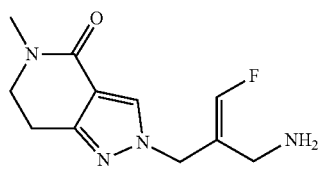 [SMILES: CN1CCc2nn(C/C(=C/F)CN)cc2C1=O] |
| Serial number | Structural formula |
|---|---|
| A25 | 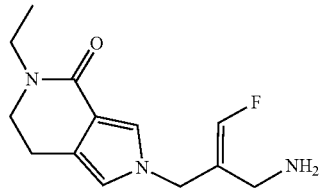 [SMILES: CCN1CCc2cn(C/C(=C/F)CN)cc2C1=O] |
| A26 | 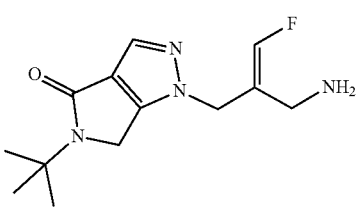 [SMILES: CC(C)(C)N1Cc2c(cnn2C/C(=C/F)CN)C1=O] |
| A27 | 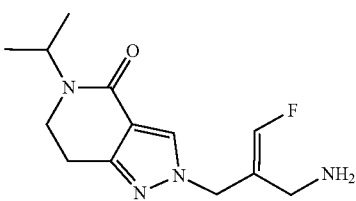 [SMILES: CC(C)N1CCc2nn(C/C(=C/F)CN)cc2C1=O] |
| A28 | 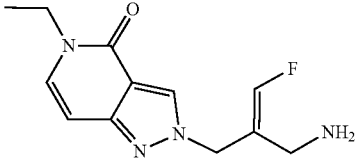 [SMILES: CCn1ccc2nn(C/C(=C/F)CN)cc2c1=O] |
| A29 | 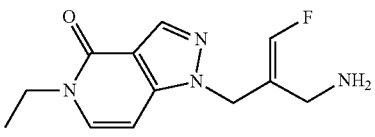 |
| A30 | 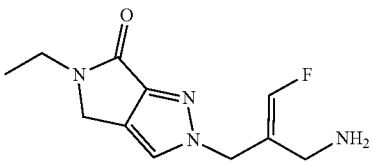 [SMILES: CCN1Cc2cn(C/C(=C/F)CN)nc2C1=O] |
| A31 | 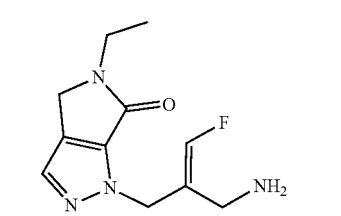 [SMILES: CCN1Cc2cnn(C/C(=C/F)CN)c2C1=O] |
| A32 | 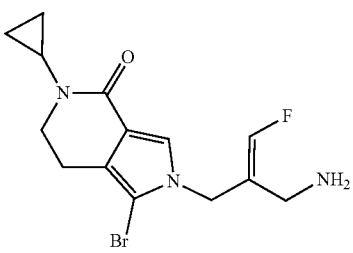 [SMILES: NC/C(=C\F)Cn1cc2c(c1Br)CCN(C1CC1)C2=O] |

| Serial number | Structural formula |
|---|---|
| A33 | 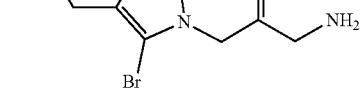 |
| A34 | |
| A35 | |
| A36 | |
| A37 | |
| A38 | |
| Serial number | Structural formula |
|---|---|
| A39 | 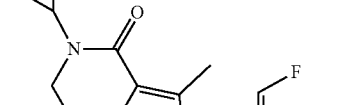 |
| A40 | |
| A41 | |
| A42 | |
| A44 | |
| A45 | |

| Serial number | Structural formula |
|---|---|
| A46 | 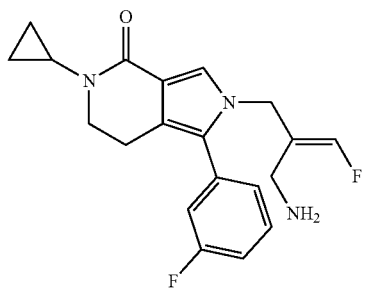 [SMILES: NC/C(=C\F)Cn1cc2c(c1-c1cccc(F)c1)CCN(C1CC1)C2=O] |
| A47 | 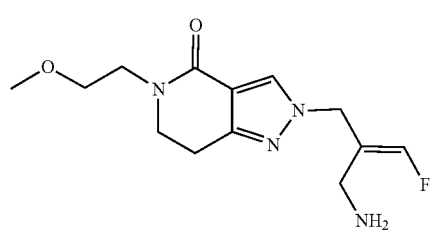 [SMILES: COCCN1CCc2nn(C/C(=C/F)CN)cc2C1=O] |
| A48 | 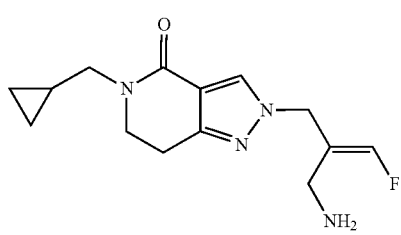 [SMILES: NC/C(=C\F)Cn1cc2c(n1)CCN(CC1CC1)C2=O] |
| A49 | 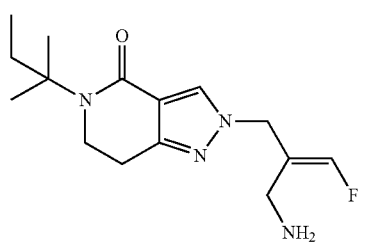 [SMILES: CCC(C)(C)N1CCc2nn(C/C(=C/F)CN)cc2C1=O] |
| A50 | 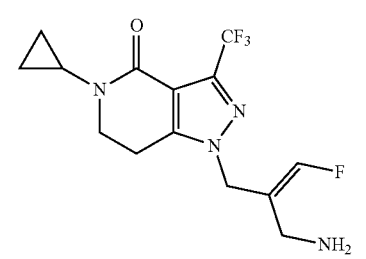 [SMILES: NC/C(=C\F)Cn1nc(C(F)(F)F)c2c1CCN(C1CC1)C2=O] |
| A51 | 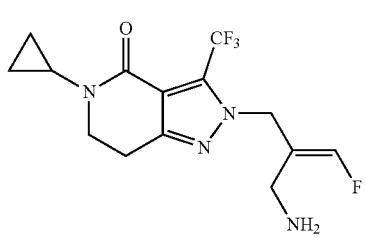 [SMILES: NC/C(=C\F)Cn1nc2c(c1C(F)(F)F)C(=O)N(C1CC1)CC2] |
| A52 | 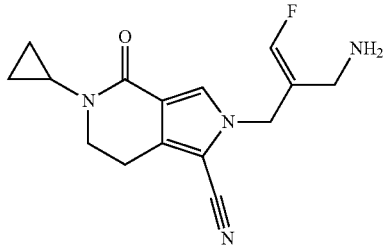 [SMILES: N#Cc1c2c(cn1C/C(=C/F)CN)C(=O)N(C1CC1)CC2] |
| B1 | 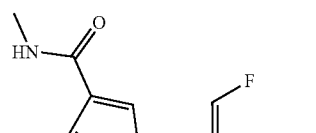 |
| B2 | 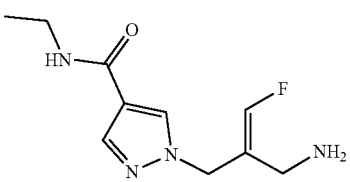 [SMILES: CCNC(=O)c1cnn(C/C(=C/F)CN)c1] |
| B3 | 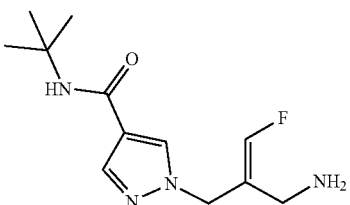 |
| B4 | 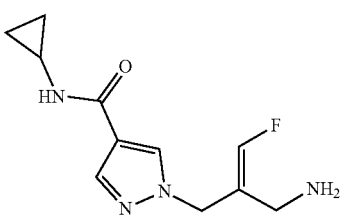 [SMILES: NC/C(=C\F)Cn1cc(C(=O)NC2CC2)cn1] |
| B5 | 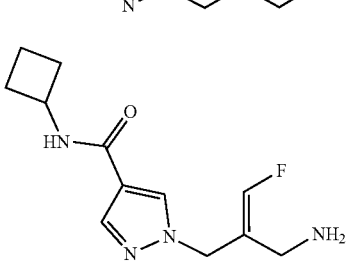 |
| B6 | 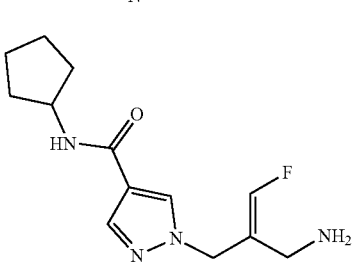 |

| Serial number | Structural formula |
|---|---|
| B7 | 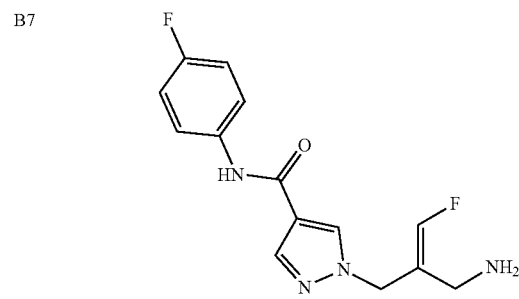 |
| B8 | 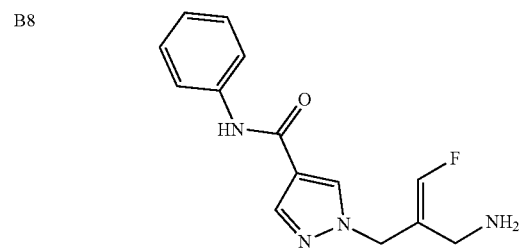 |
| B9 | 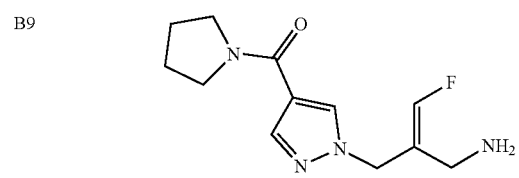 |
| B10 | 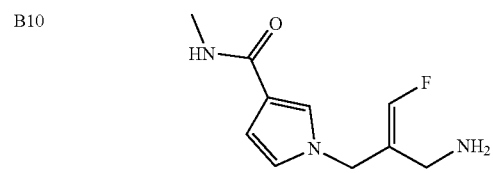 |
| B11 | 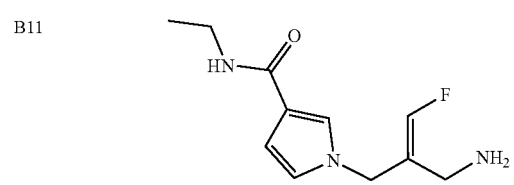 |
| B12 | 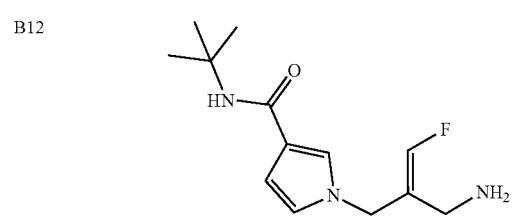 |
| B13 | 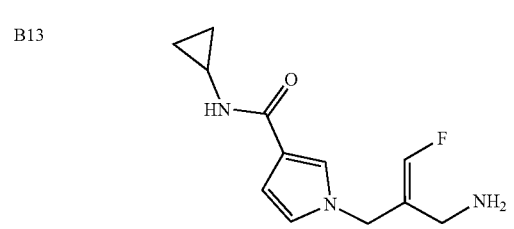 |
| Serial number | Structural formula |
|---|---|
| B14 | 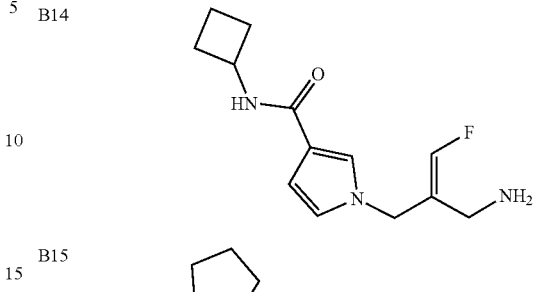 |
| B15 | 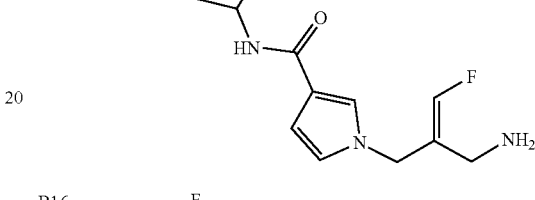 |
| B16 | 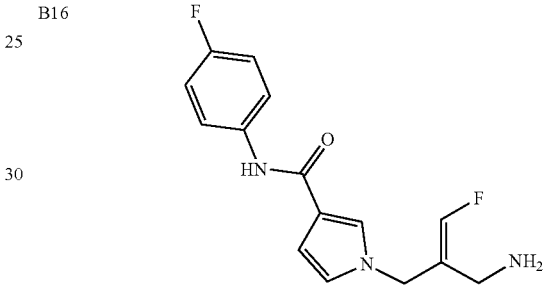 |
| B17 | 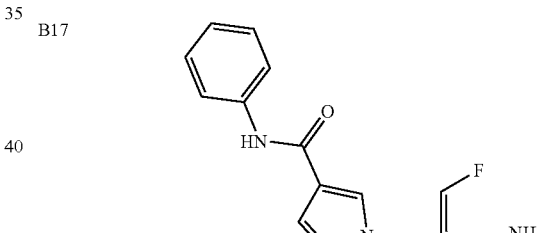 |
| B18 | 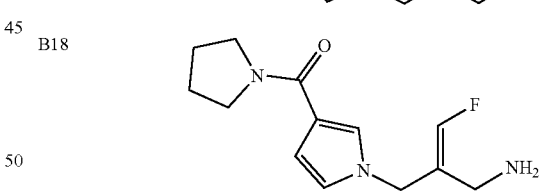 |
| B19 | 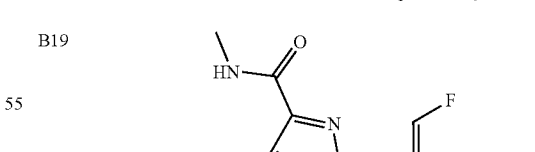 |
| B20 | 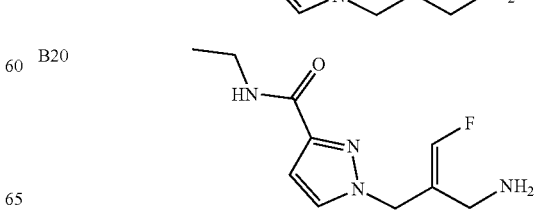 |

| Serial number | Structural formula |
|---|---|
| B21 | 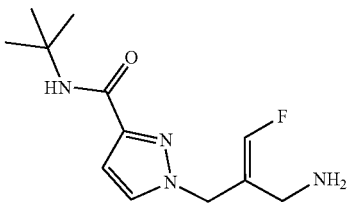 [SMILES: CC(C)(C)NC(=O)c1ccn(C/C(=C/F)CN)n1] |
| B22 | 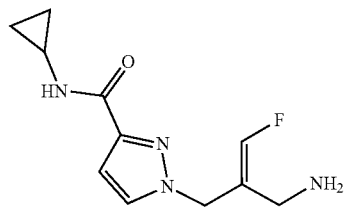 [SMILES: NC/C(=C\F)Cn1ccc(C(=O)NC2CC2)n1] |
| B23 | 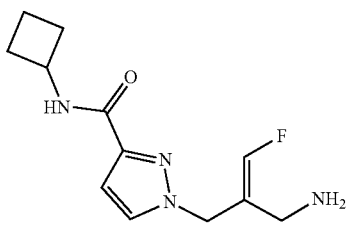 [SMILES: NC/C(=C\F)Cn1ccc(C(=O)NC2CCC2)n1] |
| B24 | 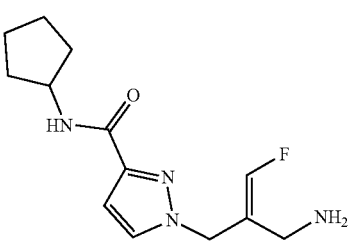 [SMILES: NC/C(=C\F)Cn1ccc(C(=O)NC2CCCC2)n1] |
| B25 | 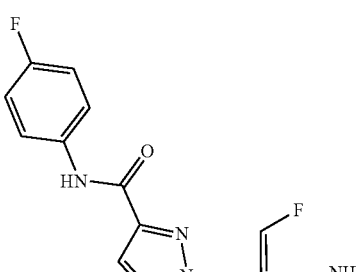 |
| B26 | 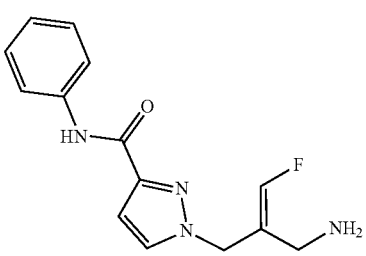 [SMILES: NC/C(=C\F)Cn1ccc(C(=O)Nc2ccccc2)n1] |
| B27 | 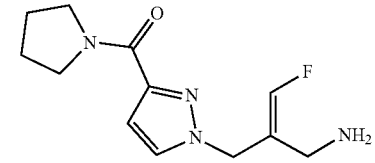 [SMILES: NC/C(=C\F)Cn1ccc(C(=O)N2CCCC2)n1] |
| B28 | 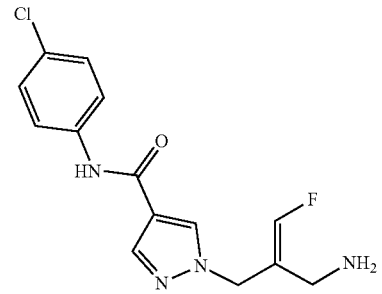 [SMILES: NC/C(=C\F)Cn1cc(C(=O)Nc2ccc(Cl)cc2)cn1] |
| B29 | 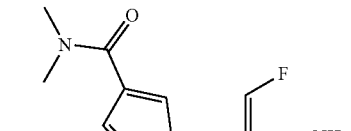 |
| B30 | 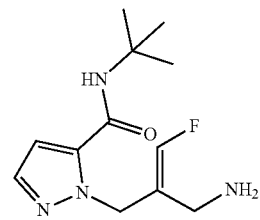 [SMILES: CC(C)(C)NC(=O)c1ccnn1C/C(=C/F)CN] |
| B31 | 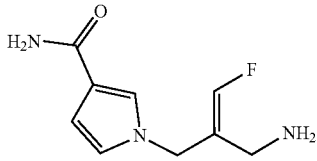 [SMILES: NC/C(=C\F)Cn1ccc(C(N)=O)c1] |
| C1 | 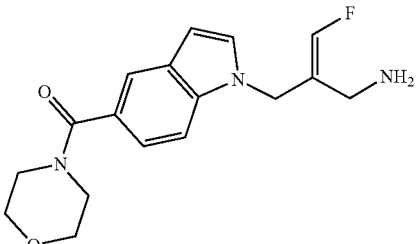 |
| C2 | 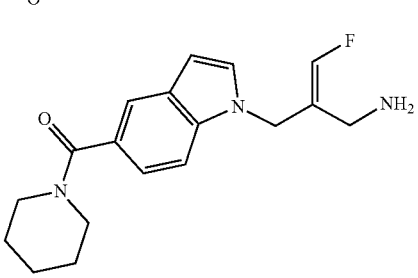 |

251
-continued

| Serial number | Structural formula |
|---|---|
| C4 |  |
| C5 | |
| C6 | |
| C7 | |
| C8 | |
| C9 | |
| C10 | |

252
-continued

| Serial number | Structural formula |
|---|---|
| C11 |  |
| C12 | |
| C13 | |
| C14 | |
| C15 | |

11. A pharmaceutical composition comprising the compound or the pharmaceutically acceptable salt, the ester, the stereoisomer or the tautomer thereof according to claim 1, wherein the pharmaceutical composition optionally comprises one or more pharmaceutically acceptable carriers.

12. The compound, or the pharmaceutically acceptable salt, the ester, the stereoisomer or the tautomer thereof according to claim 3, wherein Cy$_1$ is a group that is unsubstituted or substituted by one or more R$^a$ shown in general formula (A-11), (a-1), (a-2), (b-1), or (c-2) below:

(A-11)

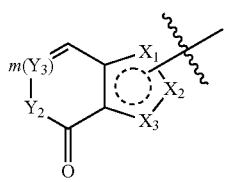

(a-1)

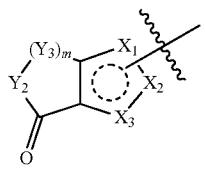

(a-2)

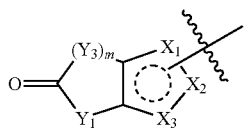

(b-1)

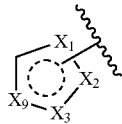

(c-2)

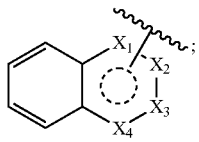;

m is an integer that is 1 or 2;

Y₁, Y₂ and Y₃ are each independently selected from CH₂ and NH;

X₁, X₂, X₃, X₄ and X₉ are each independently selected from CH₂, CH, N, NH and C=O, and at least one of X₁, X₂ and X₃ is N;

with the proviso that when Cy₁ is formula of (c-2), formula of (c-2) is substituted by one or more $R^a$;

with the proviso that when Cy₁ is formula (b-1), X₁, X₂, X₃ and X₉ are not C=O; and ⋯ represents a double bond optionally present in the ring structure.

13. The compound, or the pharmaceutically acceptable salt, the ester, the stereoisomer or the tautomer thereof according to claim 12, wherein Cy₁ is a group that is unsubstituted or substituted by one or more $R^a$ shown in general formula (A-11) or (a-1) below:

(A-11)

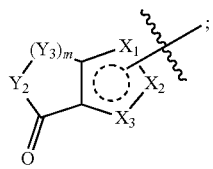

-continued (a-1)

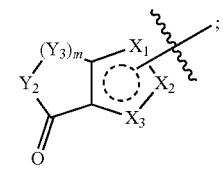

m is an integer that is 1 or 2;

Y₂ and Y₃ are each independently selected from CH₂ and NH;

X₁, X₂ and X₃ are each independently selected from CH₂, CH, N and NH, and at least one of X₁, X₂ and X₃ is N; and ⋯ represents a double bond optionally present in the ring structure.

14. The compound, or the pharmaceutically acceptable salt, the ester, the stereoisomer or the tautomer thereof according to claim 13, wherein R₁ and R₂ are each independently selected from hydrogen and halogen, and R₁ and R₂ are not both hydrogen;

R₃ and R₄ are each independently selected from hydrogen and $C_{1-6}$ alkyl;

R₅ and R₆ are each independently selected from hydrogen and $C_{1-6}$ alkyl;

L₁ is absent;

Cy is one of the following groups unsubstituted or substituted by one or more $R^a$:

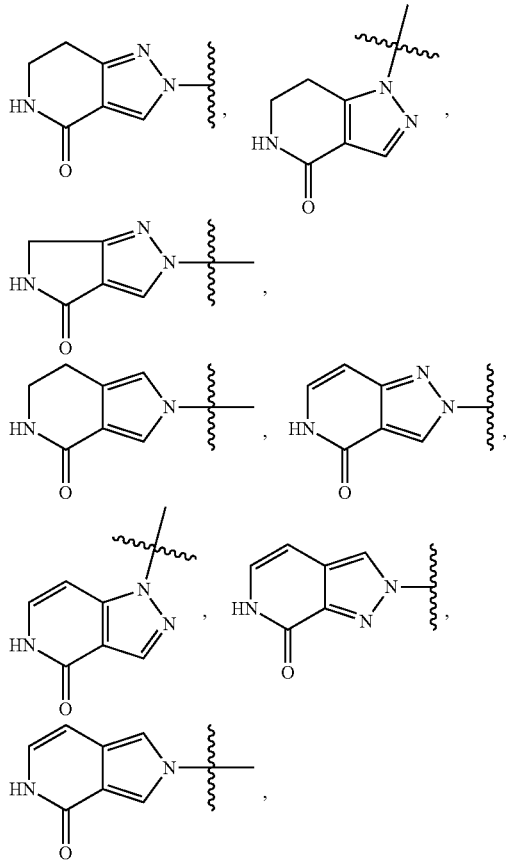

-continued

[chemical structures]

, and ;

each $R^a$ is independently selected from hydroxyl, amino, carboxyl, cyano, nitro, halogen, and $C_{1-6}$ alkyl, $C_{1-6}$ alkoxy, $C_{1-6}$ alkoxy $C_{1-6}$ alkyl, $C_{1-6}$ alkoxy $C_{1-6}$ alkoxy, $C_{1-6}$ alkylamino, $C_{1-6}$ alkylamino $C_{1-6}$ alkyl, $C_{1-6}$ alkylaminocarbonyl, $C_{1-6}$ alkylaminocarbonyl $C_{1-6}$ alkyl, $C_{1-6}$ alkylcarbonylamino, $C_{1-6}$ alkylcarbonylamino $C_{1-6}$ alkyl, $C_{1-6}$ alkylcarbonyl, $C_{1-6}$ alkylcarbonyl $C_{1-6}$ alkyl, $Cy_2$, $Cy_2$-$C_{1-6}$ alkyl, $Cy_2$-$C_{1-6}$ alkoxy, $Cy_2$-carbonyl and $Cy_2$-aminocarbonyl unsubstituted or substituted by one or more substituents $R^b$, $Cy_2$ is 3-8 membered cycloalkyl, 5-10 membered heterocyclyl, phenyl or 5-10 membered heteroaryl;

each $R^b$ is independently selected from hydroxyl, amino, carboxyl, cyano, nitro, halogen, $C_{1-6}$ alkyl, $C_{1-6}$ alkoxy, $C_{1-6}$ alkoxy $C_{1-6}$ alkyl, $C_{1-6}$ alkoxy $C_{1-6}$ alkoxy, $C_{1-6}$ alkylthio, $C_{1-6}$ alkylamino, $C_{1-6}$ alkylaminocarbonyl, $C_{1-6}$ alkylcarbonylamino and $C_{1-6}$ alkylcarbonyl;

⊙ represents a double bond optionally present in the ring structure.

15. The compound, or the pharmaceutically acceptable salt, the ester, the stereoisomer or the tautomer thereof according to claim 12, wherein $Cy_1$ is a group that is unsubstituted or substituted by one or more $R^a$ shown in general formula (b-1) below:

(b-1)

[structure]

$X_1$, $X_2$, $X_3$ and $X_9$ are each independently selected from $CH_2$, CH, N and NH, and at least one of $X_1$, $X_2$ and $X_3$ is N; and ⊙ represents a double bond optionally present in the ring structure;

with the proviso that in general formula (b-1), $X_1$, $X_2$, $X_3$ and $X_9$ are not C═O.

16. The compound, or the pharmaceutically acceptable salt, the ester, the stereoisomer or the tautomer thereof according to claim 15, wherein $R_1$ and $R_2$ are each independently selected from hydrogen and halogen, and $R_1$ and $R_2$ are not both hydrogen;

$R_3$ and $R_4$ are each independently selected from hydrogen and $C_{1-6}$ alkyl;

$R_5$ and $R_6$ are each independently selected from hydrogen and $C_{1-6}$ alkyl;

$L_1$ is absent;

$Cy_1$ is one of the following groups unsubstituted or substituted by one or more $R^a$:

each $R^a$ is independently selected from hydroxyl, amino, carboxyl, cyano, nitro, halogen, and $C_{1-6}$ alkyl, $C_{1-6}$ alkoxy, $C_{1-6}$ alkoxy $C_{1-6}$ alkyl, $C_{1-6}$ alkoxy $C_{1-6}$ alkoxy, $C_{1-6}$ alkylamino, $C_{1-6}$ alkylamino $C_{1-6}$ alkyl, $C_{1-6}$ alkylaminocarbonyl, $C_{1-6}$ alkylaminocarbonyl $C_{1-6}$ alkyl, $C_{1-6}$ alkylcarbonylamino, $C_{1-6}$ alkylcarbonylamino $C_{1-6}$ alkyl, $C_{1-6}$ alkylcarbonyl, $C_{1-6}$ alkylcarbonyl $C_{1-6}$ alkyl, $Cy_2$, $Cy_2$-$C_{1-6}$ alkyl, $Cy_2$-$C_{1-6}$ alkoxy, $Cy_2$-carbonyl and $Cy_2$-aminocarbonyl unsubstituted or substituted by one or more substituents $R^b$, $Cy_2$ is 3-8 membered cycloalkyl, 5-10 membered heterocyclyl, phenyl or 5-10 membered heteroaryl; and each $R^b$ is independently selected from amino, carboxyl, cyano, nitro, halogen, $C_{1-6}$ alkyl, $C_{1-6}$ alkoxy, $C_{1-6}$ alkoxy $C_{1-6}$ alkyl, $C_{1-6}$ alkoxy $C_{1-6}$ alkoxy, $C_{1-6}$ alkylthio, $C_{1-6}$ alkylamino, $C_{1-6}$ alkylaminocarbonyl, $C_{1-6}$ alkylcarbonylamino and $C_{1-6}$ alkylcarbonyl.

17. The compound, or the pharmaceutically acceptable salt, the ester, the stereoisomer or the tautomer thereof according to claim 4, wherein $Cy_2$ is 3-6 membered cycloalkyl, 5-6 membered heterocyclyl, phenyl or 5-6 membered heteroaryl.

18. The compound, or the pharmaceutically acceptable salt, the ester, the stereoisomer or the tautomer thereof according to claim 9, wherein $Cy_1$ is one of the following groups substituted by one or more substituents $R^a$:

[chemical structures]

, and ;

each $R^a$ is independently selected from hydroxyl, amino, carboxyl, cyano, nitro, halogen, and $C_{1-6}$ alkyl or 3-6 membered cycloalkyl unsubstituted or substituted by one or more substituents $R^b$; and each $R^b$ is independently selected from amino, cyano, nitro and halogen.

19. The compound, or the pharmaceutically acceptable salt, the ester, the stereoisomer or the tautomer thereof according to claim 18, $Cy_2$ is 3-6 membered cycloalkyl, 5-6 membered heterocyclyl, phenyl or 5-6 membered heteroaryl.

* * * * *